(12) United States Patent
Elbaz et al.

(10) Patent No.: US 9,970,040 B2
(45) Date of Patent: May 15, 2018

(54) ENGINEERING DNA ASSEMBLY IN VIVO AND METHODS OF MAKING AND USING THE REVERSE TRANSCRIPTASE TECHNOLOGY

(71) Applicant: Massachusetts Institute of Technology, Cambridge, MA (US)

(72) Inventors: Johann Elbaz, Brookline, MA (US); Christopher Voigt, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days. days.

(21) Appl. No.: 14/498,116

(22) Filed: Sep. 26, 2014

(65) Prior Publication Data
US 2015/0184213 A1 Jul. 2, 2015

Related U.S. Application Data

(60) Provisional application No. 62/013,305, filed on Jun. 17, 2014, provisional application No. 61/882,871, filed on Sep. 26, 2013.

(51) Int. Cl.
| | |
|---|---|
| *C12P 19/34* | (2006.01) |
| *C12N 9/12* | (2006.01) |
| *C12P 21/06* | (2006.01) |
| *C07H 21/02* | (2006.01) |
| *C12N 15/10* | (2006.01) |
| *C07H 21/00* | (2006.01) |

(52) U.S. Cl.
CPC .............. *C12P 19/34* (2013.01); *C07H 21/00* (2013.01); *C12N 15/1096* (2013.01); *C12N 9/1276* (2013.01)

(58) Field of Classification Search
None
See application file for complete search history.

(56) References Cited

PUBLICATIONS

Hayafune et al. HIV gene therapy unsing RNA virus systems. Nucleic Acids Symposium Series No. 50 79-80.*
Kim. Human immunodeficiency virus reverse transcriptase substitutes for DNA polymerase I in *Escherichia coli*. Proc. Natl. Acad. Sci. USA. vol. 92, pp. 684-688, Jan. 1995.*
Durfee. The Complete Genome Sequence of *Escherichia coli* DH10B: Insights into the Biology of a Laboratory Workhorse. Journal of Bacteriology, Apr. 2008, p. 2597-2606.*
MAX Efficiency DH10B Competent Cells. Invitrogen Catalog. 2006.*
Hayafune et al., HIV gene therapy using RNA virus systems. Nucleic Acids Symp Ser (Oxf). 2006;(50):79-80.
Kusunoki et al., A novel single-stranded DNA enzyme expression system using HIV-1 reverse transcriptase. Biochem Biophys Res Commun. Feb. 7, 2003;301(2):535-9.
Sugiyama et al., HIV-1 RT-dependent DNAzyme expression inhibits HIV-1 replication without the emergence of escape viruses. Nucleic Acids Res. Jan. 2011;39(2):589-98. doi: 10.1093/nar/gkq794. Epub Sep. 9, 2010.
[No Author Listed] PrimerQuest® program, IDT, Coralville, USA. Retrieved Dec. 12, 2012. http://www.idtdna.com/Scitools.
Abbondanzieri et al. Dynamic binding orientations direct activity of HIV reverse transcriptase. Nature 184-189 (2008).
Aiyar et al., Interaction between retroviral US RNA and the TC loop of the tRNATrp primer is required for efficient initiation of reverse transcription. J. Virol. 66:2464-2472 (1992).
Amir et al., Universal computing by DNA origami robots in a living animal. Nature Nanotechnology 353-357 (2014).
Conrado et al., DNA-guided assembly of biosynthetic pathways promotes improved catalytic efficiency. Nucl. Acids Res 40:1879-1889 (2012).
Davis et al., Design, construction and characterization of a set of insulated bacterial promoters. Nucleic Acids Res. 39:1131-1141 (2011).
Douglas et al., Self Assembly of DNA into Nanoscale Three-Dimensional Shapes. Nature 2009, 459:414-418.
Elbaz et al., Powering the programmed nanostructure and function of gold nanoparticles with catenated DNA machines. Nat. Commun. Jun. 13, 2013;4:2000. dx.doi.org/10.1038/ncomms3000.
Elbaz et al., Genetic encoding of DNA nanostructures and their self-assembly in living bacteria. Nat Commun. Apr. 19, 2016;7:11179. doi:10.1038/ncomms11179.
Engler et al., A one pot, one step, precision cloning method with high throughput capability. PLoS ONE. 2008. doi:10.1371/joumal.pone.0003647.
Gradisar et al., Design of a single-chain polypeptide tetrahedron assembled from coiled-coil segments. Nature Chemical Biology 362-366 (2013).
Gu et al., A proximity-based programmable DNA nanoscale assembly line. Nature 465:202-205 (2010).
He et al., Autonomous Multistep Organic Synthesis in a Single Isothermal 25 Solution Mediated by a DNA Walker. Nat. Nanotech. 5:778-782 (2010).
Jacobo-Molina et al., Crystal structure of human immunodeficiency virus type 1 reverse transcriptase complexed with double-stranded DNA at 3.0 A resolution shows bent DNA. Proc. Natl. Acad. Sci. U.S.A. 90:6320 (1993).
Jiang et al., Ellington Coupling two different nucleic acid circuits in an enzyme-free amplifier. Molecules 17:13211-13220. (2012).
Ke et al., Three-dimensional structures self-assembled from DNA bricks Science 338:1177-1183 (2012).
Kleiman, tRNA(Lys3): the primer tRNA for reverse transcription in HIV-1. IUBMB Life. Feb. 2002;53(2):107-14.
Lanchy et al., Binding and kinetic propeliies of HIV-1 reverse transcriptase markedly differ during initiation and elongation of reverse transcription. EMBO J. 15:7178-7187 ( 1996).
Lee et al., Molecularly self-assembled nucleic acid nanoparticles for targeted in vivo siRNA delivery Nature Nanotech. 7:389-393 (2012).

(Continued)

*Primary Examiner* — Yong D Pak
(74) *Attorney, Agent, or Firm* — Wolf, Greenfield & Sacks, P.C.

(57) ABSTRACT

Cells that can synthesize oligonucleotides in vivo to produce a nucleic acid nanostructure are described. Methods for producing oligonucleotide nanostructures for use in regulating gene expression and altering biological pathways are provided. Methods of performing multiplex automated genome editing (MAGE) are also provided.

15 Claims, 29 Drawing Sheets

(56) References Cited

PUBLICATIONS

Leis et al., RNA-dependent DNA polymerase activity of RNA tumor viruses. 5. Mechanism of action of ribonuclease H isolated from avian myeloblastosis virus and *Escherichia coli*. Proc. Natl Acad. Sci. USA 70:466-470 (1973).
Lim et al., Crystal Structure of the Moloney Murine Leukemia Virus RNase H Domain. J. VIROL 80:8379-8389 (2006).
Lin et al., In vivo cloning of artificial DNA nanostructures. Proc. Natl. Acad. Sci. U.S.A. 105:17626-17631(2008).
Mak et al., Primer tRNAs for reverse transcription. J Virol. Nov. 1997;71(11):8087-95.
Mastroianni et al., Pyramidal and chiral groupings of gold nanocrystals assembled using DNA scaffolds. J. Am. Chem. Soc. 131:8455-8459 (2009).
Moon et al., Genetic programs constructed from layered logic gates in single cells. Nature 491:249-253 (2012).
Omabegho et al., A bipedal DNA Brownian motor with coordinated legs. Science 324:67-71 (2009).
Pinheiro et al., Challenges and opportunities for structural DNA nanotechnology. Nature Nanotech. 6:763-772 (2011).
Wang et al., *Bacillus subtilis* genome editing using ssDNA with short homology regions. Nucleic Acids Res. Jul. 2012;40(12):e91. doi: 10.1093/nar/gks248. Epub Mar. 15, 2012.
Wang et al., Programming cells by multiplex genome engineering and accelerated evolution. Nature 460:894-898 (2009).
Yeates et al., The protein shells of bacterial microcompartment organelles. Curr. Opin. Struct. Biol. 21:223-231 (2011).
Arnold et al., Structure of HIV-1 reverse transcriptase/DNA complex at 7 A resolution showing active site locations. Nature. May 7, 1992;357:85-89.
Baltimore, Viral RNA-dependent DNA polymerase: RNA-dependent DNA polymerase in virions of RNA tumour viruses. Nature. Jun. 27, 1970;226:1209-1211.
Bath et al., DNA nanomachines. Nat. Nanotech. May 2007;2:275-284.
Carr, Church Genome engineering. Nat. Biotech. Dec. 2009;27:1151-1162.
Chen et al. Characterization of 582 natural and synthetic terminators and quantification of their design constraints. Nature Methods. Jul. 2013;10(7):659-664. Online Methods.
Chen et al., Rich, Crystal structure of a four-stranded intercalated DNA: d(C4)Biochemistry 1994;33:13540-.
Delebecque et al., Organization of Intracellular Reactions with Rationally Designed RNA Assemblies. Science. 2011;333:470-474.
Douglas et al., A Logic-Gated Nanorobot for Targeted Transport of Molecular Payloads. Science. 2012;335:831-834.
Ducani et al., Hogberg Enzamatic production of monoclonal stoichiometric single-stranded DNA oligonucleotides. Nat. Methods 2013;10:647-652.
Dueber et al., Synthetic protein scaffolds provide modular control over metabolic flux. Nat. Biotechnol. 2009;27:753-759. Online Methods.
Elbaz et al., DNA computing circuits using libraries of DNAzyme subunits. Nat. Nanotech. 2010;5:417-422. Corrigendum.
Elbaz et al., pH-stimulated concurrent mechanical activation of two DNA 'tweezers'. A 'Setreset' logic gate system. Nano Lett. 2009;9:4510-4514.
Ellington, Szostak In vitro selection of RNA molecules that bind specific ligands. Nature. 1990;346:818-822.
Freeman et al., Quantitative RT-PCR: pitfalls and potential. BioTechniques 1999;26:112-122.
Fu et al., DNA Double-crossover Molecules. Biochemistry 1993;32:3211-3220.
Gibson et al. Enzymatic assembly of DNA molecules up to several hundred kilobases. Nat. Methods. 2009;6:343-345.
Gibson et al., Chemical synthesis of the mouse mitochondrial genome. Nat. Methods. 2010;7:901-903. Online Methods.
Goodman et al., Rapid Chiral Assembly of Rigid DNA Building Blocks for Molecular Nanofablication. Science 2005;310:1661-1665.
Gwinn et al., Sequence-Dependent Fluorescence of DNA-Hosted Silver Nanoclusters. Adv. Mater. 2008;20:279-283.
Han et al., DNA Origami with Complex Curvatures in Three-Dimensional Space. Science 2011;332:343-346.
Harris et al., The p51 subunit of human immunodeficiency virus type 1 reverse transcriptase is essential in loading the p66 subunit on the template primer, Biochemistry. 1998;37:5903-5908.
He et al., Hierarchical self-assembly of DNA into symmetric supramolecular polyhedra. Nature. 2008;452:198-201. Methods.
Krishnan et al., Nucleic acid based molecular devices. Angew. Chem. Int. Ed. 2011;50:3124-3156.
Le et al., DNA-Templated Self-Assembly of Metallic Nanocomponent Arrays on a Surface. Nano Lett. 2004;4:2343-2347.
Li et al., Antiparallel DNA Double Crossover Molecules As Components for Nanoconstruction. J. Am. Chem. Soc. 1996;118:6131-6140.
Marquet et al., tRNAs as primer of reverse transcriptases. Biochimie. 1995;77(1-2):113-24.
Modi et al., A DNA Nanomachine that Maps Spatial and Temporal pH Changes Inside Living Cells. Nat. Nanotechnol. 2009;4:325-330.
Mutalik et al., Precise and reliable gene expression via standard transcription and translation initiation elements. Nat. Methods. 2013;10:354-360. Online Methods.
Nam et al., Peptide-Mediated Reduction of Silver Ions on Engineered Biological Scaffolds ACS Nano. 2008;2:1480-1486.
Pei et al., Stojanovic Training a molecular automaton to play a game. Nature Nanotechnology. Oct. 24, 2010;5:773-777.
Petty et al., DNA-Templated Ag Nanocluster Formation J. Am. Chem. Soc. 2004;126:5207-5212.
Qian et al., Scaling Up Digital Circuit Computation with DNA Strand Displacement Cascades Science. 2011;332:1196-1201.
Rothemund, Folding DNA to Create Nanoscale Shapes and Patterns. Nature. 2006;440:297-302.
Seelig et al., Enzyme-free nucleic acid logic circuits. Science. 2006;314:1585-1588.
Shin et al., A Synthetic DNA Walker for Molecular Transport. J. Am. Chem. Soc. 2004;126:10834-10835.
Telesnitsky et al., Reverse transcriptase and the generation of retroviral DNA Retroviruses, 1977;121-160.
Temin et al., Viral RNA-dependent DNA polymerase: RNAdependent DNA polymerase in virions of Rous sarcoma virus. Nature. 1970;226:1211-1213.
Tian et al., Molecular gears: a pair of DNA circles continuously rolls against each other. J. Am. Chem. Soc. 2004;126:11410-11411.
Voigt et al. Single-molecule chemical reactions on DNA origami. Nature Nanotechnology. 2010;5:200-203.
Wang et al., DNA machines: bipedal walker and stepper. Nano Lett. 2011;11:304-309.
Wilner et al., Enzyme cascades activated on topologically programmed DNA scaffolds. Nat. Nanotech. 2009;4:249-254.
Winfree et al., Design and Self-assembly of Two-dimensional DNA Crystals. Nature 1998;394:539-544.
Yin et al., Programming DNA tube circumferences. Science. 2008;321:824-826.
Yurke et al., A DNA-Fuelled Molecular Machine made of DNA. Nature. Aug. 2000;406:605-608.
Zadeh et al., NUPACK: Analysis and design of nucleic acid systems. J Comput Chem, 2010;32:170-173.
PCT/US2014/057695, dated Dec. 10, 2014, International Search Report and Written Opinion.
PCT/US2014/057695, dated Oct. 21, 2014, Invitation to Pay Additional Fes.
PCT/US2014/057695, dated Apr. 7, 2016, International Preliminary Report on Patentability.

\* cited by examiner

Gene Regulation

Reverse transcriptase Translation Regulation

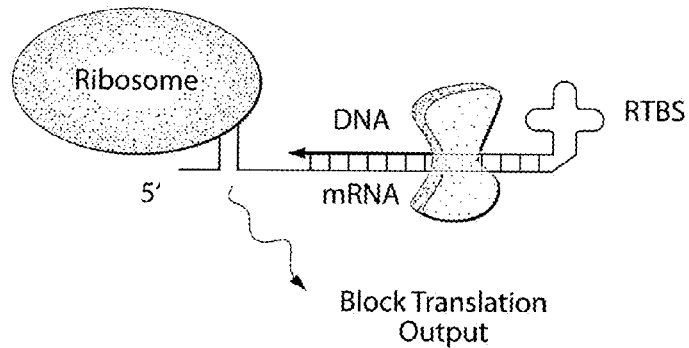

Block Translation
Output

Advantages:
- Selectivity: no cross talk with other mRNA
- Stoichiometry
- Minimize circuitry parts: both terminator and functional part
- Easy to incorporate to optimize circuits: RTBS is conjugated to the 3' ends of the mRNA (No interaction with the RBS part)
- Large level of regulation: control of the RT velocity (RBS mimicking behavior)

Fig. 4

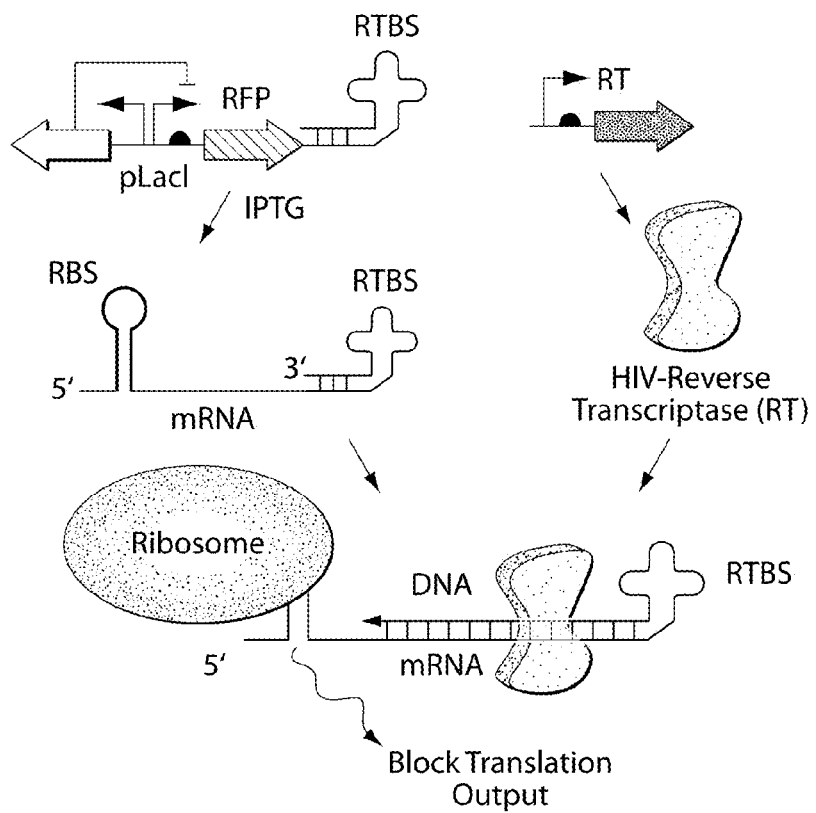
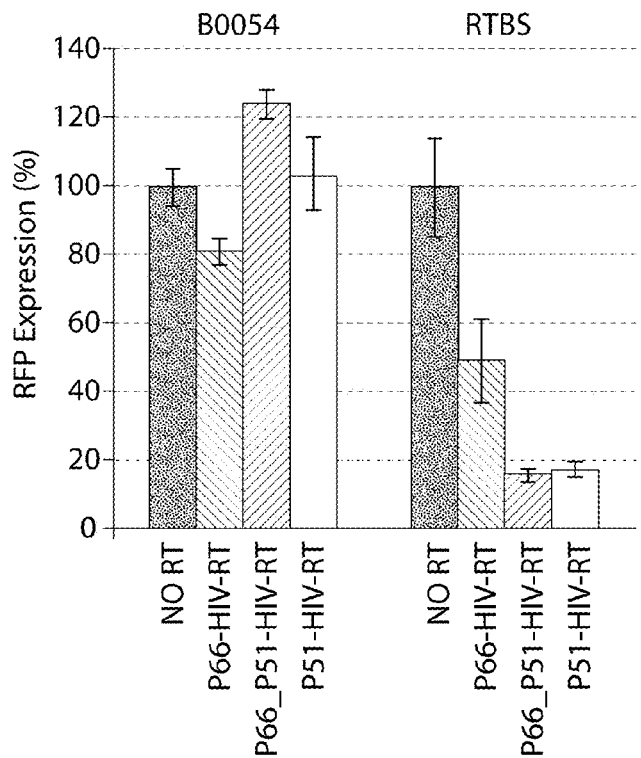
Fig. 5

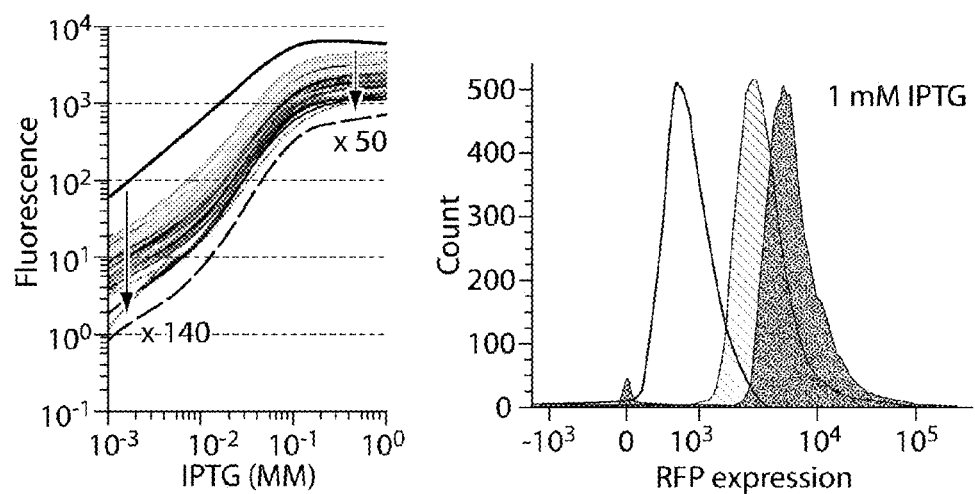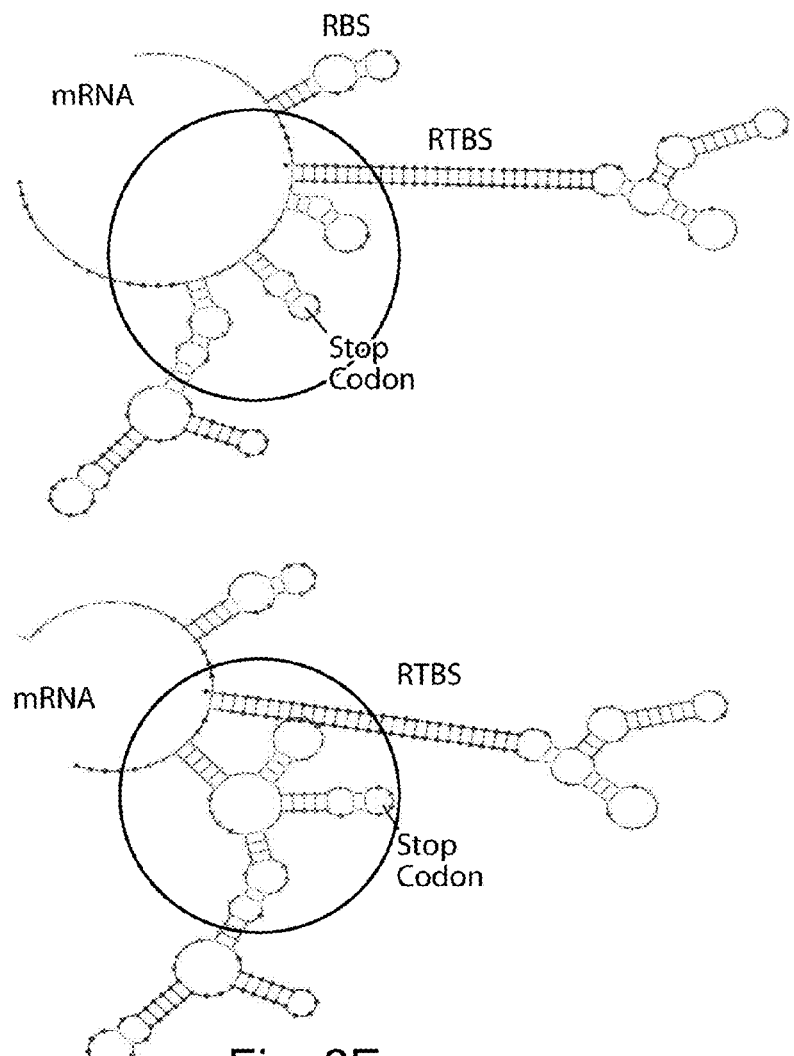
Fig. 6E

SEQUENCE LISTING

```
<160> NUMBER OF SEQ ID NOS: 39

<210> SEQ ID NO 1
<211> LENGTH: 1686
<212> TYPE: DNA
<213> ORGANISM: Artificial Sequence
<220> FEATURE:
<223> OTHER INFORMATION: Synthetic Polynucleotide

<400> SEQUENCE: 1
atgccgatta gcccgattga aaccgttccg gttaaactga aaccgggtat ggatggtccg      60
aaagttaaac agtggcctct gaccgaagaa aaaatcaaag cactggttga aatctgcacc     120
gagatggaaa aagaaggcaa aattagcaaa atcggtccgg aaaatccgta taatacaccg     180 gttttttgcca ttaagaaaaa agatagcacc aaatggcgca aactggtgga ttttcgtgaa     240
ctgaataaac gcacccagga ttttgggaa gttcagctgg gtattccgca tccggcaggt     300
ctgaaacaga aaaaaagcgt taccgttctg gatgttggtg atgcatattt tagcgttccg     360
ctggataaag atttccgtaa atataccgca tttaccatcc cgagcattaa taacgaaaca     420
ccgggtattc gctatcagta taatgttctg ccgcagggtt ggaaaggtag tccggcaatt     480
tttcagtgta gcatgaccaa aattctggaa ccgtttcgta aacagaatcc ggatattgtg     540
atctaccagt atatggatga tctgtatgtt ggtagcgatc tggaaattgg tcagcatcgt     600
accaaaattg aagaactgcg tcagcatctg ctgcgttggg gttttaccac accggataaa     660
aaacatcaga aagaaccgcc ttttctgtgg atgggttatg aactgcatcc ggataaatgg     720
accgttcagc cgattgttct gccggaaaaa gatagctgga ccgttaatga tattcagaaa     780
ctggtgggta aactgaattg ggcaagccag atttatgccg gtattaaagt tcgtcagctg     840
tgtaaactgc tgcgtggcac caaagcactg accgaagttg ttccgctgac agaagaagca     900
```

| | |
|---|---|
| gaactggaac tggcagaaaa tcgtgaaatt ctgaaagaac cggttcacgg cgtttattat | 960 |
| gatccgagca agatctgat tgccgaaatt cagaaacagg gtcagggtca gtggacctat | 1020 |
| cagatttatc aagaaccgtt taaaaacctg aaaaccggca atatgcacg tatgaaaggt | 1080 |
| gcacatacca acgatgttaa acagctgacc gaagcagttc agaaaattgc aaccgaaagc | 1140 |
| attgtgattt ggggtaaaac cccgaaattc aaactgccga ttcagaaaga aacctgggaa | 1200 |
| gcatggtgga ccgaatattg caggcaacc tggattccgg aatgggaatt tgttaatacc | 1260 |
| cctccgctgg ttaaactgtg gtatcagctg aaaaagaac cgattattgg tgccgaaacc | 1320 |
| ttttatgttg atggtgcagc caatcgtgaa accaaactgg gtaaagcagg ttatgttacc | 1380 |
| gatcgtggtc gtcagaaagt ggtgccgctg accgatacca ccaatcagaa aaccgaactg | 1440 |
| caggcaattc atctggcact gcaggatagc ggtctggaag ttaatattgt taccgatagc | 1500 |
| cagtatgccc tgggtattat tcaggcacag ccggataaaa gcgaaagcga actggttagc | 1560 |
| cagattattg aacagctgat caaaaaagaa aaagtgtacc tggcatgggt tccggcacat | 1620 |
| aaaggtattg gtgttaatga acaggttgat ggtctggtta cgcaggtat tcgtaaagtt | 1680 |
| ctgtaa | 1686 |

<210> SEQ ID NO 2
<211> LENGTH: 1326
<212> TYPE: DNA
<213> ORGANISM: Artificial Sequence
<220> FEATURE:
<223> OTHER INFORMATION: Synthetic Polynucleotide

<400> SEQUENCE: 2

| | |
|---|---|
| atgccgatta gcccgattga aaccgttccg gttaaactga accgggtat ggatggtccg | 60 |
| aaagttaaac agtggcctct gaccgaagaa aaatcaaag cactggttga aatctgcacc | 120 |
| gagatggaaa agaaggcaa aattagcaaa atcggtccgg aaaatccgta taatacaccg | 180 |
| gtttttgcca ttaagaaaaa agatagcacc aaatggcgca aactggtgga ttttcgtgaa | 240 |
| ctgaataaac gcacccagga ttttttggga gttcagctgg gtattccgca tccggcaggt | 300 |
| ctgaaacaga aaaaagcgt taccgttctg gatgttggtg atgcatattt tagcgttccg | 360 |
| ctggataaag atttccgtaa atataccgca tttaccatcc cgagcattaa taacgaaaca | 420 |
| ccgggtattc gctatcagta taatgttctg ccgcagggtt ggaaaggtag tccggcaatt | 480 |
| tttcagtgta gcatgaccaa aattctggaa ccgtttcgta acagaatcc ggatattgtg | 540 |
| atctaccagt atatggatga tctgtatgtt ggtagcgatc tggaaattgg tcagcatcgt | 600 |
| accaaaattg aagaactgcg tcagcatctg ctgcgttggg ttttaccac accggataaa | 660 |
| aaacatcaga agaaccgcc ttttctgtgg atgggttatg aactgcatcc ggataaatgg | 720 |
| accgttcagc cgattgttct gccggaaaaa gatagctgga ccgttaatga tattcagaaa | 780 |
| ctggtgggta actgaattg gcaagccag atttatgccg gtattaaagt tcgtcagctg | 840 |
| tgtaaactgc tgcgtggcac caaagcactg accgaagttg ttccgctgac agaagaagca | 900 |
| gaactggaac tggcagaaaa tcgtgaaatt ctgaaagaac cggttcacgg cgtttattat | 960 |
| gatccgagca agatctgat tgccgaaatt cagaaacagg gtcagggtca gtggacctat | 1020 |
| cagatttatc aagaaccgtt taaaaacctg aaaaccggca atatgcacg tatgaaaggt | 1080 |
| gcacatacca acgatgttaa acagctgacc gaagcagttc agaaaattgc aaccgaaagc | 1140 |
| attgtgattt ggggtaaaac cccgaaattc aaactgccga ttcagaaaga aacctgggaa | 1200 |
| gcatggtgga ccgaatattg caggcaacc tggattccgg aatgggaatt tgttaatacc | 1260 |

| | |
|---|---|
| cctccgctgg ttaaactgtg gtatcagctg gaaaagaac cgattattgg tgccgaaacc | 1320 |
| ttttaa | 1326 |

<210> SEQ ID NO 3
<211> LENGTH: 2001
<212> TYPE: DNA
<213> ORGANISM: Artificial Sequence
<220> FEATURE:
<223> OTHER INFORMATION: Synthetic Polynucleotide

<400> SEQUENCE: 3

| | |
|---|---|
| atgggtcata atcataatca taatcataat cataatcaca acggtggaga tgacgatgac | 60 |
| aagggtggtc gacaagcttg gatccctgca ggcctcaggg cccgatcgat gggaccaatg | 120 |
| gggcagcccc tgcaagtgtt gaccctaaat atagaagatg agtatcggct acatgagacc | 180 |
| tcaaaagagc cagatgtttc tctagggtcc acatggctgt ctgattttcc tcaggcctgg | 240 |
| gcggaaaccg ggggcatggg actggcagtt cgccaagctc ctctgatcat acctctgaaa | 300 |
| gcaacctcta cccccgtgtc cataaaacaa taccccatgt cacaagaagc cagactgggg | 360 |
| atcaagcccc acatacagag actgttggac cagggaatac tggtaccctg ccagtccccc | 420 |
| tggaacacgc cctgctacc cgttaagaaa ccagggacta atgattatag gcctgtccag | 480 |
| gatctgagag aagtcaacaa gcgggtggaa gacatccacc ccaccgtgcc caaccttac | 540 |
| aacctcttga gcgggctccc accgtccac cagtggtaca ctgtgcttga tttaaaggat | 600 |
| gccttttttct gcctgagact ccacccacc agtcagcctc tcttcgcctt tgagtggaga | 660 |
| gatccagaga tgggaatctc aggacaattg acctggacca gactcccaca gggttttcaaa | 720 |
| aacagtccca ccctgtttga tgaggcactg cacagagacc tagcagactt ccggatccag | 780 |
| cacccagact tgatcctgct acagtacgtg gatgacttac tgctggccgc cacttctgag | 840 |
| ctagactgcc aacaaggtac tcgggccctg ttacaaaccc tagggaacct cgggtatcgg | 900 |
| gcctcggcca agaaagccca aatttgccag aaacaggtca agtatctggg gtatcttcta | 960 |
| aaagagggtc agagatggct gactgaggcc agaaaagaga ctgtgatggg gcagcctact | 1020 |
| ccgaagaccc ctcgacaact aagggagttc ctagggacgg caggcttctg tcgcctctgg | 1080 |
| atccctgggt tgcagaaaat ggcagccccc ttgtaccctc tcaccaaaac ggggactctg | 1140 |
| tttaattggg gccagaccca acaaaaggc tatcaagaaa tcaagcaagc tcttctaact | 1200 |
| gccccagccc tgggggttgcc agatttgact aagcccttg aactctttgt cgacgagaag | 1260 |
| cagggctacg ccaaaggtgt cctaacgcaa aaactgggac cttggcgtcg gccggtggcc | 1320 |
| tacctgtcca aaaagctaga cccagtagca gctgggtggc ccccttgcct acggatggta | 1380 |
| gcagccattg ccgtactgac aaaggatgca ggcaagctaa ccatgggaca gccactagtc | 1440 |
| attctggccc ccatgcagt agaggcacta gtcaaacaac ccccgaccg ctggctttcc | 1500 |
| aacgcccgga tgactcacta tcaggccttg ctttttggaca cggaccgggt ccagttcgga | 1560 |
| ccggtggtag ccctgaaccc ggctacgctg ctcccactgc tgaggaagg gctgcaacac | 1620 |
| aactgccttg atatcctggc cgaagcccac ggaacccgac ccgacctaac ggaccagccg | 1680 |
| ctcccagacg ccgaccacac ctggtacacg gatggaagca gtcttcttaca agagggacag | 1740 |
| cgtaaggcgg gagctgcggt gaccaccgag accgaggtaa tctgggctaa agccctgcca | 1800 |
| gccgggacat ccgctcagcg ggctgaactg atagcactca cccaggccct aaagatggca | 1860 |
| gaaggtaaga agctaaatgt ttatactgat agccgttatg cttttgctac tgcccatatc | 1920 |

```
catggagaaa tatacagaag gcgtgggttg ctcacatcag aaggcaaaga gatcaaaaat    1980
aaagacgaga tctttaaatg a                                              2001

<210> SEQ ID NO 4
<211> LENGTH: 111
<212> TYPE: DNA
<213> ORGANISM: Artificial Sequence
<220> FEATURE:
<223> OTHER INFORMATION: Synthetic Polynucleotide

<400> SEQUENCE: 4
aaaaaaaaac gtggcgcccg aacagggacg gatagctcag tcggtagagc atcagacttt     60
taatctgagg gtccagggtt caagtccctg ttcgggcgcc acgttttttt t             111

<210> SEQ ID NO 5
<211> LENGTH: 3988
<212> TYPE: DNA
<213> ORGANISM: Artificial Sequence
<220> FEATURE:
<223> OTHER INFORMATION: Synthetic Polynucleotide

<400> SEQUENCE: 5
ttgacagcta gctcagtcct aggtactgtg ctagctacta gtgaaagagg agaaatacta     60
gatgccgatt agcccgattg aaaccgttcc ggttaaactg aaaccgggta tggatggtcc    120
gaaagttaaa cagtggcctc tgaccgaaga aaaaatcaaa gcactggttg aaatctgcac    180
cgagatggaa aagaaggca aattagcaa atcggtccg gaaatccgt ataatacacc       240 ggtttttgcc attaagaaaa aagatagcac caaatggcgc aaactggtgg attttcgtga    300
actgaataaa cgcacccagg attttgggga agttcagctg gtattccgc atccggcagg    360 tctgaaacag aaaaaagcg ttaccgttct ggatgttggt gatgcatatt ttagcgttcc    420
gctggataaa gatttccgta atataccgc atttaccatc ccgagcatta taacgaaac    480 accgggtatt cgctatcagt ataatgttct gccgcagggt tggaaaggta gtccggcaat    540 tttttcagtgt agcatgacca aaattctgga accgtttcgt aaacagaatc ggatattgt    600 gatctaccag tatatggatg atctgtatgt tggtagcgat ctggaaattg gtcagcatcg    660
taccaaaatt gaagaactgc gtcagcatct gctgcgttgg ggttttacca caccggataa    720
aaaacatcag aaagaaccgc ctttctgtg gatgggttat gaactgcatc cggataaatg    780
gaccgttcag ccgattgttc tgccggaaaa agatagctgg accgttaatg atattcagaa    840
actggtgggt aaactgaatt gggcaagcca gatttatgcc ggtattaaag ttcgtcagct    900
gtgtaaactg ctgcgtggca ccaaagcact gaccgaagtt gttccgctga cagaagaagc    960
agaactggaa ctggcagaaa tcgtgaat tctgaaagaa ccggttcacg gcgtttatta    1020
tgatccgagc aaagatctga ttgccgaaat tcagaaacag ggtcagggtc agtggaccta   1080
tcagatttat caagaaccgt taaaaaacct gaaaaccggc aaatatgcac gtatgaaagg   1140
tgcacatacc aacgatgtta aacagctgac cgaagcagtt cagaaaattg caaccgaaag   1200
cattgtgatt tggggtaaaa ccccgaaatt caaactgccg attcagaaag aaacctggga   1260
agcatggtgg accgaatatt ggcaggcaac ctggattccg gaatgggaat tgttaatac   1320 cctccgctg gttaaactgt ggtatcagct ggaaaagaa ccgattattg gtgccgaaac   1380
cttttatgtt gatggtgcag ccaatcgtga aaccaaactg ggtaaagcag gttatgttac   1440
cgatcgtggt cgtcagaaag tggtgccgct gaccgatacc accaatcaga aaaccgaact   1500
gcaggcaatt catctggcac tgcaggatag cggtctggaa gttaatattg ttaccgatag   1560
```

```
ccagtatgcc ctgggtatta ttcaggcaca gccggataaa agcgaaagcg aactggttag    1620
ccagattatt gaacagctga tcaaaaaaga aaaagtgtac ctggcatggg ttccggcaca    1680
taaaggtatt ggtggtaatg aacaggttga tggtctggtt agcgcaggta ttcgtaaagt    1740
tctgtaacgc tgatagtgct agtgtagatc gctactagag ccaggcatca aataaaacga    1800
aaggctcagt cgaaagactg ggcctttcgt tttatctgtt gtttgtcggt gaacgctctc    1860
tactagagtc acactggctc accttcgggt gggcctttct gcgtttatat actagaagcg    1920
gccgctgcag gcttcctcgc tcactgactc gctgcgctcg gtcgttcggc tgcggcgagc    1980
ggtatcagct cactcaaagg cggtaatacg gttatccaca gaatcagggg ataacgcagg    2040
aaagaacatg tgagcaaaag gccagcaaaa ggccaggaac cgtaaaaagg ccgcgttgct    2100
ggcgtttttc cataggctcc gcccccctga cgagcatcac aaaaatcgac gctcaagtca    2160
gaggtggcga aacccgacag gactataaag ataccaggcg tttccccctg gaagctccct    2220
cgtgcgctct cctgttccga ccctgccgct taccggatac ctgtccgcct ttctcccttc    2280
gggaagcgtg gcgctttctc atagctcacg ctgtaggtat ctcagttcgg tgtaggtcgt    2340
tcgctccaag ctgggctgtg tgcacgaacc ccccgttcag cccgaccgct gcgccttatc    2400
cggtaactat cgtcttgagt ccaacccggt aagacacgac ttatcgccac tggcagcagc    2460
cactggtaac aggattagca gagcgaggta tgtaggcggt gctacagagt tcttgaagtg    2520
gtggcctaac tacggctaca ctagaaggac agtatttggt atctgcgctc tgctgaagcc    2580
agttaccttc ggaaaaagag ttggtagctc ttgatccggc aaacaaacca ccgctggtag    2640
cggtggtttt tttgtttgca agcagcagat tacgcgcaga aaaaaaggat ctcaagaaga    2700
tcctttgatc ttttctacgg ggtctgacgc tcagtggaac gaaaactcac gttaagggat    2760
tttggtcatg agattatcaa aaaggatctt cacctagatc cttttaaatt aaaaatgaag    2820
ttttaaatca atctaaagta tatatgagta aacttggtct gacagttacc aatgcttaat    2880
cagtgaggca cctatctcag cgatctgtct atttcgttca tccatagttg cctgactccc    2940
cgtcgtgtag ataactacga tacgggaggg cttaccatct ggccccagtg ctgcaatgat    3000
accgcgagac ccacgctcac cggctccaga tttatcagca ataaaccagc cagccggaag    3060
ggccgagcgc agaagtggtc ctgcaacttt atccgcctcc atccagtcta ttaattgttg    3120
ccgggaagct agagtaagta gttcgccagt taatagtttg cgcaacgttg ttgccattgc    3180
tacaggcatc gtggtgtcac gctcgtcgtt tggtatggct tcattcagct ccggttccca    3240
acgatcaagg cgagttacat gatcccccat gttgtgcaaa aaagcggtta gctccttcgg    3300
tcctccgatc gttgtcagaa gtaagttggc cgcagtgtta tcactcatgg ttatggcagc    3360
actgcataat tctcttactg tcatgccatc cgtaagatgc ttttctgtga ctggtgagta    3420
ctcaaccaag tcattctgag aatagtgtat gcggcgaccg agttgctctt gcccggcgtc    3480
aatacgggat aataccgcgc cacatagcag aactttaaaa gtgctcatca ttggaaaacg    3540
ttcttcgggg cgaaaactct caaggatctt accgctgttg agatccagtt cgatgtaacc    3600
cactcgtgca cccaactgat cttcagcatc ttttactttc accagcgttt ctgggtgagc    3660
aaaaacagga aggcaaaatg ccgcaaaaaa gggaataagg gcgacacgga aatgttgaat    3720
actcatactc ttcctttttc aatattattg aagcatttat cagggttatt gtctcatgag    3780
cggatacata tttgaatgta tttagaaaaa taaacaaata ggggttccgc gcacatttcc    3840
ccgaaaagtg ccacctgacg tctaagaaac cattattatc atgacattaa cctataaaaa    3900
```

```
taggcgtatc acgaggcaga atttcagata aaaaaaatcc ttagctttcg ctaaggatga    3960
tttctggaat tcgcggccgc atctagag                                       3988

<210> SEQ ID NO 6
<211> LENGTH: 5321
<212> TYPE: DNA
<213> ORGANISM: Artificial Sequence
<220> FEATURE:
<223> OTHER INFORMATION: Synthetic Polynucleotide

<400> SEQUENCE: 6
ttgacagcta gctcagtcct aggtactgtg ctagctacta gtgaaagagg agaaatacta      60
gatgccgatt agcccgattg aaaccgttcc ggttaaactg aaaccgggta tggatggtcc     120
gaaagttaaa cagtgcctc tgaccgaaga aaaaatcaaa gcactggttg aaatctgcac     180
cgagatggaa aaagaaggca aaattagcaa atcggtccg gaaaatccgt ataatacacc     240 ggttttgcc attaagaaaa aagatagcac caaatggcgc aaactggtgg attttcgtga     300
actgaataaa cgcacccagg attttgggg agttcagctg gtattccgc atccggcagg     360 tctgaaacag aaaaaagcg ttaccgttct ggatgttggt gatgcatatt ttagcgttcc     420
gctggataaa gatttccgta atataccgc atttaccatc ccgagcatta ataacgaaac     480
accgggtatt cgctatcagt ataatgttct gccgcagggt tggaaaggta gtccggcaat     540
ttttcagtgt agcatgacca aaattctgga accgttcgt aaacagaatc cggatattgt     600
gatctaccag tatatggatg atctgtatgt tggtagcgat ctggaaattg gtcagcatcg     660
taccaaaatt gaagaactgc gtcagcatct gctgcgttgg ggttttacca caccggataa     720
aaaacatcag aaagaaccgc cttttctgtg gatgggttat gaactgcatc cggataaatg     780
gaccgttcag ccgattgttc tgccggaaaa agatagctgg accgttaatg atattcagaa     840
actggtgggt aaactgaatt gggcaagcca gatttatgcc ggtattaaag ttcgtcagct     900
gtgtaaactg ctgcgtggca ccaaagcact gaccgaagtt gttccgctga cagaagaagc     960
agaactggaa ctggcagaaa atcgtgaaat tctgaaagaa ccggttcacg gcgtttatta    1020
tgatccgagc aaagatctga ttgccgaaat tcagaaacag ggtcagggtc agtggaccta    1080
tcagatttat caagaaccgt ttaaaaacct gaaaccggc aaatatgcac gtatgaaagg    1140
tgcacatacc aacgatgtta aacagctgac cgaagcagtt cagaaaattg caaccgaaag    1200
cattgtgatt tggggtaaaa ccccgaaatt caaactgccg attcagaaag aaacctggga    1260
agcatggtgg accgaatatt ggcaggcaac ctggattccg aatgggaat tgttaatac    1320 ccctccgctg gttaaactgt ggtatcagct ggaaaaagaa ccgattattg gtgccgaaac    1380 ctttatgtt gatggtgcag ccaatcgtga accaaactg gtaaagcag ttatgttac    1440 cgatcgtggt cgtcagaaag tggtgccgct gaccgatacc accaatcaga aaccgaact    1500 gcaggcaatt catctggcac tgcaggatag cggtctggaa gttaatattg ttaccgatag    1560
ccagtatgcc ctgggtatta ttcaggcaca gccggataaa agcgaaagcg aactggttag    1620
ccagattatt gaacagctga tcaaaaaaga aaagtgtac ctggcatggg ttccggcaca    1680
taaaggtatt ggtggtaatg aacaggttga tggtctggtt agcgcaggta ttcgtaaagt    1740
tctgtaatac tagtgaaaga ggagaaatac tagatgccga ttagcccgat tgaaaccgtt    1800
ccggttaaac tgaaaccggg tatggatggt ccgaaagtta acagtgcc tctgaccgaa    1860 gaaaaaatca aagcactggt tgaaatctgc accgagatgg aaaaagaagg caaaattagc    1920 aaatcggtc cggaaaatcc gtataataca ccggttttg ccattaagaa aaagatagc    1980
```

```
accaaatggc gcaaactggt ggattttcgt gaactgaata aacgcaccca ggattttgg        2040 gaagttcagc tgggtattcc gcatccggca ggtctgaaac agaaaaaaag cgttaccgtt      2100
ctggatgttg gtgatgcata ttttagcgtt ccgctggata agatttccg taaatatacc       2160 gcatttacca tcccgagcat taataacgaa acaccgggta ttcgctatca gtataatgtt      2220
ctgccgcagg gttggaaagg tagtccggca atttttcagt gtagcatgac caaaattctg      2280
gaaccgtttc gtaaacagaa tccggatatt gtgatctacc agtatatgga tgatctgtat      2340
gttggtagcg atctggaaat tggtcagcat cgtaccaaaa ttgaagaact gcgtcagcat      2400
ctgctgcgtt ggggttttac cacaccggat aaaaaacatc agaaagaacc gccttttctg     2460
tggatgggtt atgaactgca tccggataaa tggaccgttc agccgattgt tctgccggaa     2520
aaagatagct ggaccgttaa tgatattcag aaactggtgg gtaaactgaa ttgggcaagc     2580
cagatttatg ccggtattaa agttcgtcag ctgtgtaaac tgctgcgtgg caccaaagca     2640
ctgaccgaag ttgttccgct gacagaagaa gcagaactgg aactggcaga aaatcgtgaa     2700
attctgaaag aaccggttca cggcgtttat tatgatccga gcaaagatct gattgccgaa     2760
attcagaaac agggtcaggg tcagtggacc tatcagattt atcaagaacc gtttaaaaac     2820
ctgaaaaccg gcaaatatgc acgtatgaaa ggtgcacata ccaacgatgt taaacagctg     2880
accgaagcag ttcagaaaat tgcaaccgaa agcattgtga tttggggtaa accccgaaa     2940 ttcaaactgc cgattcagaa agaaacctgg gaagcatggt ggaccgaata ttggcaggca     3000
acctggattc cggaatggga atttgttaat acccctccgc tggttaaact gtggtatcag     3060
ctggaaaaag aaccgattat tggtgccgaa acctttaag atcgctacta gagccaggca      3120
tcaaataaaa cgaaaggctc agtcgaaaga ctgggccttt cgttttatct gttgtttgtc     3180
ggtgaacgct ctctactaga gtcacactgg ctcaccttcg ggtgggcctt tctgcgttta     3240
tatactagaa gcggccgctg caggcttcct cgctcactga ctcgctgcgc tcggtcgttc     3300
ggctgcggcg agcggtatca gctcactcaa aggcggtaat acggttatcc acagaatcag    3360
gggataacgc aggaaagaac atgtgagcaa aaggccagca aaaggccagg aaccgtaaaa    3420
aggccgcgtt gctggcgttt ttccataggc tccgcccccc tgacgagcat cacaaaaatc    3480
gacgctcaag tcagaggtgg cgaaacccga caggactata aagataccag gcgtttcccc   3540
ctggaagctc cctcgtgcgc tctcctgttc cgaccctgcc gcttaccgga tacctgtccg    3600
cctttctccc ttcgggaagc gtggcgcttt ctcatagctc acgctgtagg tatctcagtt    3660
cggtgtaggt cgttcgctcc aagctgggct gtgtgcacga accccccgtt cagcccgacc    3720
gctgcgcctt atccggtaac tatcgtcttg agtccaaccc ggtaagacac gacttatcgc   3780
cactggcagc agccactggt aacaggatta gcagagcgag gtatgtaggc ggtgctacag    3840
agttcttgaa gtggtggcct aactacggct acactagaag gacagtattt ggtatctgcg    3900
ctctgctgaa gccagttacc ttcggaaaaa gagttggtag ctcttgatcc ggcaaacaaa    3960
ccaccgctgg tagcggtggt ttttttgttt gcaagcagca gattacgcgc agaaaaaaag    4020
gatctcaaga agatcctttg atcttttcta cggggtctga cgctcagtgg aacgaaaact    4080
cacgttaagg gattttggtc atgagattat caaaaaggat cttcacctag atccttttaa    4140
attaaaaatg aagttttaaa tcaatctaaa gtatatatga gtaaacttgg tctgacagtt    4200
accaatgctt aatcagtgag gcacctatct cagcgatctg tctatttcgt tcatccatag    4260
ttgcctgact ccccgtcgtg tagataacta cgatacggga gggcttacca tctggcccca   4320
gtgctgcaat gataccgcga gacccacgct caccggctcc agatttatca gcaataaacc   4380
```

```
agccagccgg aagggccgag cgcagaagtg gtcctgcaac tttatccgcc tccatccagt    4440
ctattaattg ttgccgggaa gctagagtaa gtagttcgcc agttaatagt ttgcgcaacg    4500
ttgttgccat tgctacaggc atcgtggtgt cacgctcgtc gtttggtatg gcttcattca    4560
gctccggttc ccaacgatca aggcgagtta catgatcccc catgttgtgc aaaaaagcgg    4620
ttagctcctt cggtcctccg atcgttgtca gaagtaagtt ggccgcagtg ttatcactca    4680
tggttatggc agcactgcat aattctctta ctgtcatgcc atccgtaaga tgcttttctg    4740
tgactggtga gtactcaacc aagtcattct gagaatagtg tatgcggcga ccgagttgct    4800
cttgcccggc gtcaatacgg gataataccg cgccacatag cagaacttta aaagtgctca    4860
tcattggaaa acgttcttcg ggcgaaaac tctcaaggat cttaccgctg ttgagatcca    4920
gttcgatgta acccactcgt gcacccaact gatcttcagc atctttact ttcaccagcg    4980
tttctgggtg agcaaaaaca ggaaggcaaa atgccgcaaa aagggaata agggcgacac    5040
ggaaatgttg aatactcata ctcttccttt tcaatatta ttgaagcatt tatcagggtt    5100
attgtctcat gagcggatac atatttgaat gtatttagaa aaataaacaa ataggggttc    5160
cgcgcacatt tccccgaaaa gtgccacctg acgtctaaga accattatt atcatgacat    5220
taacctataa aaataggcgt atcacgaggc agaatttcag ataaaaaaaa tccttagctt    5280
tcgctaagga tgatttctgg aattcgcggc cgcatctaga g                        5321
```

<210> SEQ ID NO 7
<211> LENGTH: 6621
<212> TYPE: DNA
<213> ORGANISM: Artificial Sequence
<220> FEATURE:
<223> OTHER INFORMATION: Synthetic Polynucleotide

<400> SEQUENCE: 7

```
aaaaataaac aaataggggt tccgcgcaca tttccccgaa aagtgccacc tgacgtctaa      60
gaaaaggaat attcagcaat ttgcccgtgc cgaagaaagg cccacccgtg aaggtgagcc     120
agtgagttga ttgctacgta atgtcggcca attcgcgcta acttacatta attgcgttgc     180
gctcactgcc cgctttccag tcgggaaacc tgtcgtgcca gctgcattaa tgaatcggcc     240
aacgcgcggg gagaggcggt ttgcgtattg ggcgccaggg tggttttct tttcaccagt     300
gagactggca acagctgatt gcccttcacc gcctggccct gagagagttg cagcaagcgg     360
tccacgctgg tttgccccag caggcgaaaa tcctgtttga tggtggttaa cggcgggata     420
taacatgagc tatcttcggt atcgtcgtat cccactaccg agatatccgc accaacgcgc     480
agcccggact cggtaatggc gcgcattgcg cccagcgcca tctgatcgtt ggcaaccagc     540
atcgcagtgg gaacgatgcc ctcattcagc atttgcatgg tttgttgaaa accggacatg     600
gcactccagt cgccttcccg ttccgctatc ggctgaattt gattgcgagt gagatattta     660
tgccagccag ccagacgcag acgcgccgag acagaactta atgggcccgc taacagcgcg     720
atttgctggt gacccaatgc gaccagatgc tccacgccca gtcgcgtacc gtcctcatgg     780
gagaaaataa tactgttgat gggtgtctgg tcagagacat caagaaataa cgccggaaca     840
ttagtgcagg cagcttccac agcaatggca tcctggtcat ccagcggata gttaatgatc     900
agcccactga cgcgttgcgc gagaagattg tgcaccgccg ctttacaggc ttcgacgccg     960
cttcgttcta ccatcgacac caccacgctg gcacccagtt gatcggcgcg agatttaatc    1020
gccgcgacaa tttgcgacgg cgcgtgcagg gccagactgg aggtggcaac gccaatcagc    1080
aacgactgtt tgcccgccag ttgttgtgcc acgcggttgg gaatgtaatt cagctccgcc    1140
```

```
atcgccgctt ccactttttc ccgcgttttc gcagaaacgt ggctggcctg gttcaccacg      1200
cgggaaacgg tctgataaga gacaccggca tactctgcga catcgtataa cgttactggt      1260
ttcatattca ccaccctgaa ttgactctct tccgggcgct atcatgccat accgcgaaag      1320
gttttgcgcc attcgatggc gcgccgcttc gtcaggccac atagctttct gttctgatc      1380
ggaacgatcg ttggctgtgt tgacaattaa tcatcggctc gtataatgtg tggaattgtg      1440
agcgctcaca attctatgga ctatgttct gtcaccggat gtgctttccg gtctgatgag      1500
tccgtgagga cgaaacagta ctagtgaaag aggagaaata ctagatgccg attagcccga      1560
ttgaaaccgt tccggttaaa ctgaaaccgg gtatggatgg tccgaaagtt aaacagtggc      1620
ctctgaccga agaaaaaatc aaagcactgg ttgaaatctg caccgagatg gaaaaagaag      1680
gcaaaattag caaatcggt ccggaaaatc cgtataatac accggttttt gccattaaga      1740
aaaagatag caccaaatgg cgcaaactgg tggattttcg tgaactgaat aaacgcaccc      1800
aggattttg gaagttcag ctgggtattc cgcatccggc aggtctgaaa cagaaaaaaa      1860
gcgttaccgt tctggatgtt ggtgatgcat attttagcgt tccgctggat aaagatttcc      1920
gtaaatatac cgcatttacc atcccgagca ttaataacga aacaccgggt attcgctatc      1980
agtataatgt tctgccgcag ggttggaaag gtagtccggc aattttttcag tgtagcatga      2040
ccaaaattct ggaaccgttt cgtaaacaga tccggatat tgtgatctac cagtatatgg      2100
atgatctgta tgttggtagc gatctggaaa ttggtcagca tcgtaccaaa attgaagaac      2160
tgcgtcagca tctgctgcgt tggggttta ccacaccgga taaaaaacat cagaagaac      2220
cgccttttct gtgatgggt tatgaactgc atccggataa atggaccgtt cagccgattg      2280
ttctgccgga aaagatagc tggaccgtta atgatattca gaaactggtg gtaaactga      2340
attgggcaag ccagatttat gccggtatta agttcgtca gctgtgtaaa ctgctgcgtg      2400
gcaccaaagc actgaccgaa gttgttccgc tgacagaaga agcagaactg gaactggcag      2460
aaaatcgtga aattctgaaa gaaccggttc acggcgttta ttatgatccg agcaaagatc      2520
tgattgccga aattcagaaa cagggtcagg gtcagtggac ctatcagatt tatcaagaac      2580
cgtttaaaaa cctgaaaacc ggcaaatatg cacgtatgaa aggtgcacat accaacgatg      2640
ttaaacagct gaccgaagca gttcagaaaa ttgcaaccga aagcattgtg atttggggta      2700
aaaccccgaa attcaaactg ccgattcaga agaaacctg ggaagcatgg tggaccgaat      2760
attggcaggc aacctggatt ccggaatggg aatttgttaa taccccctccg ctggttaaac      2820
tgtggtatca gctggaaaaa gaaccgatta ttggtgccga aaccttttat gttgatggtg      2880
cagccaatcg tgaaaccaaa ctgggtaaag caggttatgt taccgatcgt ggtcgtcaga      2940
aagtggtgcc gctgaccgat accaccaatc agaaaaccga actgcaggca attcatctgg      3000
cactgcagga tagcggtctg gaagttaata ttgttaccga tagccagtat gccctgggta      3060
ttattcaggc acagccggat aaaagcgaaa gcgaactggt tagccagatt attgaacagc      3120
tgatcaaaaa agaaaaagtg tacctggcat gggttccggc acataaaggt attggtggta      3180
atgaacaggt tgatggtctg gttagcgcag gtattcgtaa agttctgtaa tactagtgaa      3240
agaggagaaa tactagatgc cgattagccc gattgaaacc gttccggtta aactgaaacc      3300
gggtatggat ggtccgaaag ttaaacagtg gcctctgacc gaagaaaaaa tcaaagcact      3360
ggttgaaatc tgcaccgaga tggaaaaaga aggcaaaatt agcaaaatcg gtccggaaaa      3420
tccgtataat acaccggttt ttgccattaa gaaaaaagat agcaccaaat ggcgcaaact      3480
ggtggatttt cgtgaactga ataaacgcac ccaggatttt tgggaagttc agctgggtat      3540
```

```
tccgcatccg gcaggtctga aacagaaaaa aagcgttacc gttctggatg ttggtgatgc    3600
atattttagc gttccgctgg ataaagattt ccgtaaatat accgcattta ccatcccgag    3660
cattaataac gaaacaccgg gtattcgcta tcagtataat gttctgccgc agggttggaa    3720
aggtagtccg gcaattttc agtgtagcat gaccaaaatt ctggaaccgt ttcgtaaaca    3780
gaatccggat attgtgatct accagtatat ggatgatctg tatgttggta gcgatctgga    3840
aattggtcag catcgtacca aaattgaaga actgcgtcag catctgctgc gttgggttt    3900 taccacaccg gataaaaaac atcagaaaga accgcctttt ctgtggatgg gttatgaact    3960
gcatccggat aaatggaccg ttcagccgat tgttctgccg gaaaaagata gctggaccgt    4020
taatgatatt cagaaactgg tgggtaaact gaattgggca agccagattt atgccggtat    4080
taaagttcgt cagctgtgta aactgctgcg tggcaccaaa gcactgaccg aagttgttcc    4140
gctgacagaa gaagcagaac tggaactggc agaaaatcgt gaaattctga agaaccggt    4200 tcacggcgtt tattatgatc cgagcaaaga tctgattgcc gaaattcaga acagggtca    4260 gggtcagtgg acctatcaga tttatcaaga accgtttaaa aacctgaaaa ccggcaaata    4320
tgcacgtatg aaaggtgcac ataccaacga tgttaaacag ctgaccgaag cagttcagaa    4380
aattgcaacc gaaagcattg tgatttgggg taaaaccccg aaattcaaac tgccgattca    4440
gaaagaaacc tgggaagcat ggtggaccga atattggcag gcaacctgga ttccggaatg    4500
ggaatttgtt aatacccctc cgctggttaa actgtggtat cagctggaaa agaaccgat    4560 tattggtgcc gaaaccttt aagatcgcta ctagagccag gcatcaaata aaacgaaagg    4620
ctcagtcgaa agactgggcc tttcgtttta tctgttgttt gtcggtgaac gctctctact    4680
agagtcacac tggctcacct tcgggtgggc ctttctgcgt ttatatacta gaagcggccg    4740
ctgcaggctt cctcgctcac tgactcgctg cgctcggtcg ttcggctgcg cgagcggta    4800 tcagctcact caaaggcggt aatacggtta tccacagaat caggggataa cgcaggaag    4860 aacatgtgag caaaaggcca gcaaaaggcc aggaaccgta aaaaggccgc gttgctggcg    4920
tttttccata ggctccgccc ccctgacgag catcacaaaa atcgacgctc aagtcagagg    4980
tggcgaaacc cgacaggact ataaagatac caggcgtttc cccctggaag ctccctcgtg    5040
cgctctcctg ttccgaccct gccgcttacc ggatacctgt ccgcctttct cccttcggga    5100
agcgtggcgc tttctcatag ctcacgctgt aggtatctca gttcggtgta ggtcgttcgc    5160
tccaagctgg gctgtgtgca cgaacccccc gttcagcccg accgctgcgc cttatccggt    5220
aactatcgtc ttgagtccaa cccggtaaga cacgacttat cgccactggc agcagccact    5280
ggtaacagga ttagcagagc gaggtatgta ggcggtgcta cagagttctt gaagtggtgg    5340
cctaactacg gctacactag aaggacagta tttggtatct gcgctctgct gaagccagtt    5400
accttcggaa aaagagttgg tagctcttga tccggcaaac aaaccaccgc tggtagcggt    5460 ggttttttg tttgcaagca gcagattacg cgcagaaaaa aaggatctca agaagatcct    5520
ttgatctttt ctacggggtc tgacgctcag tggaacgaaa actcacgtta agggattttg    5580
gtcatgagat tatcaaaaag gatcttcacc tagatccttt taaattaaaa atgaagttt    5640 aaatcaatct aaagtatata tgagtaaact tggtctgaca gttaccaatg cttaatcagt    5700
gaggcaccta tctcagcgat ctgtctattt cgttcatcca tagttgcctg actccccgtc    5760
gtgtagataa ctacgatacg ggagggctta ccatctggcc ccagtgctgc aatgataccg    5820
cgagacccac gctcaccggc tccagattta tcagcaataa accagccagc cggaagggcc    5880
gagcgcagaa gtggtcctgc aactttatcc gcctccatcc agtctattaa ttgttgccgg    5940
```

| | |
|---|---:|
| gaagctagag taagtagttc gccagttaat agtttgcgca acgttgttgc cattgctaca | 6000 |
| ggcatcgtgg tgtcacgctc gtcgtttggt atggcttcat tcagctccgg ttcccaacga | 6060 |
| tcaaggcgag ttacatgatc ccccatgttg tgcaaaaaag cggttagctc cttcggtcct | 6120 |
| ccgatcgttg tcagaagtaa gttggccgca gtgttatcac tcatggttat ggcagcactg | 6180 |
| cataattctc ttactgtcat gccatccgta agatgctttt ctgtgactgg tgagtactca | 6240 |
| accaagtcat tctgagaata gtgtatgcgg cgaccgagtt gctcttgccc ggcgtcaata | 6300 |
| cgggataata ccgcgccaca tagcagaact ttaaaagtgc tcatcattgg aaaacgttct | 6360 |
| tcggggcgaa aactctcaag gatcttaccg ctgttgagat ccagttcgat gtaacccact | 6420 |
| cgtgcaccca actgatcttc agcatctttt actttcacca gcgtttctgg gtgagcaaaa | 6480 |
| acaggaaggc aaaatgccgc aaaaaaggga taagggcga cacggaaatg ttgaatactc | 6540 |
| atactcttcc ttttcaata ttattgaagc atttatcagg gttattgtct catgagcgga | 6600 |
| tacatatttg aatgtattta g | 6621 |

<210> SEQ ID NO 8
<211> LENGTH: 5742
<212> TYPE: DNA
<213> ORGANISM: Artificial Sequence
<220> FEATURE:
<223> OTHER INFORMATION: Synthetic Polynucleotide

<400> SEQUENCE: 8

| | |
|---|---:|
| ttcaggtttg ccggctgaaa gcgctatttc ttccagaatt gccatgattt ttccccacg | 60 |
| ggaggcgtca ctggctcccg tgttgtcggc agctttgatt cgataagcag catcgcctgt | 120 |
| ttcaggctgt ctatgtgtga ctgttgagct gtaacaagtt gtctcaggtg ttcaatttca | 180 |
| tgttctagtt gctttgtttt actggtttca cctgttctat taggtgttac atgctgttca | 240 |
| tctgttacat tgtcgatctg ttcatggtga acagctttaa atgcaccaaa aactcgtaaa | 300 |
| agctctgatg tatctatctt ttttacaccg ttttcatctg tgcatatgga cagttttccc | 360 |
| tttgatatct aacggtgaac agttgttcta cttttgtttg ttagtcttga tgcttcactg | 420 |
| atagatacaa gagccataag aacctcagat ccttccgtat ttagccagta tgttctctag | 480 |
| tgtggttcgt tgttttttgcg tgagccatga gaacgaacca ttgagatcat gcttactttg | 540 |
| catgtcactc aaaaattttg cctcaaaact ggtgagctga attttgcag ttaaagcatc | 600 |
| gtgtagtgtt tttcttagtc cgttacgtag gtaggaatct gatgtaatgg ttgttggtat | 660 |
| tttgtcacca ttcatttta tctggttgtt ctcaagttcg gttacgagat ccatttgtct | 720 |
| atctagttca acttggaaaa tcaacgtatc agtcgggcgg cctcgcttat caaccaccaa | 780 |
| tttcatattg ctgtaagtgt ttaaatcttt acttattggt ttcaaaaccc attggttaag | 840 |
| ccttttaaac tcatggtagt tattttcaag cattaacatg aacttaaatt catcaaggct | 900 |
| aatctctata tttgccttgt gagttttctt ttgtgttagt tcttttaata accactcata | 960 |
| aatcctcata gagtatttgt tttcaaaaga cttaacatgt tccagattat attttatgaa | 1020 |
| ttttttaac tggaaaagat aaggcaatat ctcttcacta aaaactaatt ctaatttttc | 1080 |
| gcttgagaac ttggcatagt ttgtccactg gaaaatctca aagcctttaa ccaaaggatt | 1140 |
| cctgatttcc acagttctcg tcatcagctc tctggttgct ttagctaata caccataagc | 1200 |
| atttcccta ctgatgttca tcatctgagc gtattggtta taagtgaacg ataccgtccg | 1260 |
| ttctttcctt gtagggtttt caatcgtggg gttgagtagt gccacacagc ataaaattag | 1320 |
| cttggtttca tgctccgtta agtcatagcg actaatcgct agttcatttg ctttgaaaac | 1380 |

```
aactaattca gacatacatc tcaattggtc taggtgattt taatcactat accaattgag    1440
atgggctagt caatgataat tactagtcct tttcctttga gttgtgggta tctgtaaatt    1500
ctgctagacc tttgctggaa aacttgtaaa ttctgctaga ccctctgtaa attccgctag    1560
acctttgtgt gttttttttg tttatattca agtggttata atttatagaa taaagaaaga    1620
ataaaaaaag ataaaaagaa tagatcccag ccctgtgtat aactcactac tttagtcagt    1680
tccgcagtat tacaaaagga tgtcgcaaac gctgtttgct cctctacaaa acagacctta    1740
aaaccctaaa ggcttaagta gcaccctcgc aagctcgggc aaatcgctga atattccttt    1800
tgtctccgac catcaggcac ctgagtcgct gtctttttcg tgacattcag ttcgctgcgc    1860
tcacggctct ggcagtgaat gggggtaaat ggcactacag gcgcctttta tggattcatg    1920
caaggaaact acccataata caagaaaagc ccgtcacggg cttctcaggg cgttttatgg    1980
cgggtctgct atgtggtgct atctgacttt ttgctgttca gcagttcctg ccctctgatt    2040
ttccagtctg accacttcgg attatcccgt gacaggtcat tcagactggc taatgcaccc    2100
agtaaggcag cggtatcatc aacaggctta cccgtcttac tgtccctagt gcttggattc    2160
tcaccaataa aaacgcccg gcggcaaccg agcgttctga acaaatccag atggagttct    2220
gaggtcatta ctggatctat caacaggagt ccaagcgagc tctcgaaccc cagagtcccg    2280
ctcagaagaa ctcgtcaaga aggcgataga aggcgatgcg ctgcgaatcg ggagcggcga    2340
taccgtaaag cacgaggaag cggtcagccc attcgccgcc aagctcttca gcaatatcac    2400
gggtagccaa cgctatgtcc tgatagcggt ccgccacacc cagccggcca cagtcgatga    2460
atccagaaaa gcggccattt tccaccatga tattcggcaa gcaggcatcg ccatgggtca    2520
cgacgagatc ctcgccgtcg ggcatgcgcg ccttgagcct ggcgaacagt tcggctggcg    2580
cgagcccctg atgctcttcg tccagatcat cctgatcgac aagaccggct tccatccgag    2640
tacgtgctcg ctcgatgcga tgtttcgctt ggtggtcgaa tgggcaggta gccggatcaa    2700
gcgtatgcag ccgccgcatt gcatcagcca tgatggatac tttctcggca ggagcaaggt    2760
gagatgacag gagatcctgc cccggcactt cgcccaatag cagccagtcc cttcccgctt    2820
cagtgacaac gtcgagcaca gctgcgcaag gaacgcccgt cgtggccagc cacgatagcc    2880
gcgctgcctc gtcctgcagt tcattcaggg caccggacag gtcggtcttg acaaaaagaa    2940
ccgggcgccc ctgcgctgac agccggaaca cggcggcatc agagcagccg attgtctgtt    3000
gtgcccagtc atagccgaat agcctctcca cccaagcggc cggagaacct gcgtgcaatc    3060
catcttgttc aatcatgcga aacgatcctc atcctgtctc ttgatcagat cttgatcccc    3120
tgcgccatca gatccttggc ggcaagaaag ccatccagtt tactttgcag gcttcccaa    3180 ccttaccaga gggcgcccca gctggcaatt ccgacgtcta agaaaccatt attatcatga    3240
cattaaccta taaaaatagg cgtatcacga ggccctttcg tcttcacctc gagttgacag    3300
ctagctcagt cctaggtact gtgctagcgg aattcattaa agaggagaaa ggtaccatgg    3360
gtcataatca taatcataat cataatcata atcacaacgg tggagatgac gatgacaagg    3420
gtggtcgaca agcttggatc cctgcaggcc tcagggcccg atcgatggga ccaatggggc    3480
agcccctgca agtgttgacc ctaaatatag aagatgagta tcggctacat gagacctcaa    3540
aagagccaga tgtttctcta gggtccacat ggctgtctga ttttcctcag gcctgggcgg    3600
aaaccggggg catgggactg gcagttcgcc aagctcctct gatcatacct ctgaaagcaa    3660
cctctacccc cgtgtccata aaacaatacc ccatgtcaca agaagccaga ctggggatca    3720
agccccacat acagagactg ttggaccagg gaatactggt accctgccag tccccctgga    3780
```

```
acacgcccct gctacccgtt aagaaaccag ggactaatga ttataggcct gtccaggatc    3840
tgagagaagt caacaagcgg gtggaagaca tccaccccac cgtgcccaac ccttacaacc    3900
tcttgagcgg gctcccaccg tcccaccagt ggtacactgt gcttgattta aaggatgcct    3960
ttttctgcct gagactccac cccaccagtc agcctctctt cgcctttgag tggagagatc    4020
cagagatggg aatctcagga caattgacct ggaccagact cccacagggt ttcaaaaaca    4080
gtcccaccct gtttgatgag gcactgcaca gagacctagc agacttccgg atccagcacc    4140
cagacttgat cctgctacag tacgtggatg acttactgct ggccgccact tctgagctag    4200
actgccaaca aggtactcgg gccctgttac aaaccctagg gaacctcggg tatcgggcct    4260
cggccaagaa agcccaaatt tgccagaaac aggtcaagta tctggggtat cttctaaaag    4320
agggtcagag atggctgact gaggccagaa aagagactgt gatggggcag cctactccga    4380
agacccctcg acaactaagg gagttcctag ggacggcagg cttctgtcgc ctctggatcc    4440
ctgggtttgc agaaatggca gcccccttgt accctctcac caaaacgggg actctgttta    4500 attgggccc agaccaacaa aaggcctatc aagaaatcaa gcaagctctt ctaactgccc    4560
cagccctggg gttgccagat ttgactaagc cctttgaact ctttgtcgac gagaagcagg    4620
gctacgccaa aggtgtccta acgcaaaaac tgggaccttg gcgtcggccg gtggcctacc    4680
tgtccaaaaa gctagaccca gtagcagctg ggtggccccc ttgcctacgg atggtagcag    4740
ccattgccgt actgacaaag gatgcaggca agctaaccat gggacagcca ctagtcattc    4800
tggcccccca tgcagtagag gcactagtca acaaccccc cgaccgctgg ctttccaacg    4860
cccggatgac tcactatcag gccttgcttt tggacacgga ccgggtccag ttcggaccgg    4920
tggtagccct gaacccggct acgctgctcc cactgcctga ggaagggctg caacacaact    4980
gccttgatat cctggccgaa gcccacggaa cccgacccga cctaacggac cagccgctcc    5040
cagacgccga ccacacctgg tacacggatg gaagcagtct cttacaagag ggacagcgta    5100
aggcgggagc tgcggtgacc accgagaccg aggtaatctg ggctaaagcc ctgccagccg    5160
ggacatccgc tcagcgggct gaactgatag cactcaccca ggccctaaag atggcagaag    5220
gtaagaagct aaatgtttat actgatagcc gttatgcttt tgctactgcc catatccatg    5280
gagaaatata cagaaggcgt gggttgctca catcagaagg caaagagatc aaaaataaag    5340
acgagatctt aaatgacgc tgatagtgct agtgtagatc gctactagag ccaggcatca    5400
aataaaacga aaggctcagt cgaaagactg ggcctttcgt tttatctgtt gtttgtcggt    5460
gaacgctctc tactagagtc acactggctc accttcgggt gggcctttct gcgtttatat    5520
ataataaatg tccagacctg caggcatgca agcctctaga ggcatcaaat aaaacgaaag    5580
gctcagtcga aagactgggc ctttcgtttt atctgttgtt tgtcggtgaa cgctctcctg    5640
agtaggacaa atccgccgcc ctagacctag gtacgggtt ttgctgcccg caaacgggct    5700
gttctggtgt tgctagtttg ttatcagaat cgcagatccg gc                     5742

<210> SEQ ID NO 9
<211> LENGTH: 4421
<212> TYPE: DNA
<213> ORGANISM: Artificial Sequence
<220> FEATURE:
<223> OTHER INFORMATION: Synthetic Polynucleotide

<400> SEQUENCE: 9
tgccacctga cgtctaagaa aaggaatatt cagcaatttg cccgtgccga agaaaggccc      60
acccgtgaag gtgagccagt gagttgattg ctacgtaatg tcggccaatt cgcgctaact     120
```

```
tacattaatt gcgttgcgct cactgcccgc tttccagtcg ggaaacctgt cgtgccagct    180
gcattaatga atcggccaac gcgcggggag aggcggtttg cgtattgggc gccaggtgg    240 tttttctttt caccagtgag actggcaaca gctgattgcc cttcaccgcc tggccctgag    300
agagttgcag caagcggtcc acgctggttt gccccagcag gcgaaaatcc tgtttgatgg    360
tggttaacgg cgggatataa catgagctat cttcggtatc gtcgtatccc actaccgaga    420
tatccgcacc aacgcgcagc ccggactcgg taatggcgcg cattgcgccc agcgccatct    480
gatcgttggc aaccagcatc gcagtgggaa cgatgccctc attcagcatt tgcatggttt    540
gttgaaaacc ggacatggca ctccagtcgc cttcccgttc cgctatcggc tgaatttgat    600
tgcgagtgag atatttatgc cagccagcca gacgcagacg cgccgagaca gaacttaatg    660
ggcccgctaa cagcgcgatt tgctggtgac ccaatgcgac cagatgctcc acgcccagtc    720
gcgtaccgtc ctcatgggag aaaataatac tgttgatggg tgtctggtca gagacatcaa    780
gaaataacgc cggaacatta gtgcaggcag cttccacagc aatggcatcc tggtcatcca    840
gcggatagtt aatgatcagc ccactgacgc gttgcgcgag aagattgtgc accgccgctt    900
tacaggcttc gacgccgctt cgttctacca tcgacaccac cacgctggca cccagttgat    960
cggcgcgaga tttaatcgcc gcgacaattt gcgacgcgcg gtgcagggcc agactggagg    1020 tgcaacgcc aatcagcaac gactgtttgc ccgccagttg ttgtgccacg cggttgggaa    1080
tgtaattcag ctccgccatc gccgcttcca ctttttcccg cgtttcgca gaaacgtggc    1140 tggcctggtt caccacgcgg gaaacggtct gataagagac accggcatac tctgcgacat    1200
cgtataacgt tactggttc atattcacca ccctgaattg actctcttcc gggcgctatc    1260
atgccatacc gcgaaaggtt ttgcgccatt cgatggcgcg ccgcttcgtc aggccacata    1320
gctttcttgt tctgatcgga acgatcgttg gctgtgttga caattaatca tcggctcgta    1380
taatgtgtgg aattgtgagc gctcacaatt cttgggactc gttgtagcta gcctcctgtc    1440
cggttccgtt aacggtcacg agttcgaaat cgaaggtgaa ggtgaaggtc gtccgtacga    1500
aggtacccag accgctaaac tgaaagttac caaaggtggt ccgctgccgt cgcttggga    1560 catcctgtcc ccgcagttcc agtacggttc caaagcttaa aaacgtggtg cccgaacagg    1620
gacggatccg cccggatagc tcagtcggta gagcatcaga cttttaatct gagggtccag    1680
ggttcaagtc cctgttcggg cgccacgttt ttcgctgcag gagtcactaa gggttagtta    1740
gttagattag cagaaagtca aaagcctccg accggaggct tttgactaaa acttcccttg    1800
gggttatcat tggggctcac tcaaaggcgg taatcagata aaaaaaatcc ttagctttcg    1860
ctaaggatga tttctgctag agatggaata gactggatgg aggcggataa agttgcagga    1920
ccacttctgc gctcggccct tccggctggc tggtttattg ctgataaatc tggagccggt    1980
gagcgtgggt ctcgcggtat cattgcagca ctggggccag atggtaagcc ctcccgtatc    2040
gtagttatct acacgacggg gagtcaggca actatggatg aacgaaatag acagatcgct    2100
gagataggtg cctcactgat taagcattgg taactgtcag accaagttta ctcatatata    2160
ctttagattg atttaaaact tcatttttaa tttaaaagga tctaggtgaa gatcctttt    2220 gataatctca tgaccaaaat cccttaacgt gagttttcgt tccactgagc gtcagacccc    2280
ttaataagat gatcttcttg agatcgtttt ggtctgcgcg taatctcttg ctctgaaaac    2340 gaaaaaccg ccttgcaggg cggttttcg aaggttctct gagctaccaa ctctttgaac    2400
cgaggtaact ggcttggagg agcgcagtca ccaaaacttg tcctttcagt ttagccttaa    2460
ccggcgcatg acttcaagac taactcctct aaatcaatta ccagtggctg ctgccagtgg    2520
```

| | |
|---|---|
| tgcttttgca tgtctttccg ggttggactc aagacgatag ttaccggata aggcgcagcg | 2580 |
| gtcggactga acgggggtt cgtgcataca gtccagcttg gagcgaactg cctacccgga | 2640 |
| actgagtgtc aggcgtggaa tgagacaaac gcggccataa cagcggaatg acaccggtaa | 2700 |
| accgaaaggc aggaacagga gagcgcacga gggagccgcc aggggaaacg cctggtatct | 2760 |
| ttatagtcct gtcgggtttc gccaccactg atttgagcgt cagatttcgt gatgcttgtc | 2820 |
| aggggggcgg agcctatgga aaaacggctt tgccgcggcc ctctcacttc cctgttaagt | 2880 |
| atcttcctgg catcttccag gaaatctccg ccccgttcgt aagccatttc cgctcgccgc | 2940 |
| agtcgaacga ccgagcgtag cgagtcagtg agcgaggaag cggaatatat cctgtatcac | 3000 |
| atattctgct gacgcaccgg tgcagccttt tttctcctgc cacatgaagc acttcactga | 3060 |
| caccctcatc agtgccaaca tagtaagcca gtatacactc cgctagcgct gaggtctgcc | 3120 |
| tcgtgaagaa ggtgttgctg actcatacca ggcctgaatc gccccatcat ccagccagaa | 3180 |
| agtgagggag ccacggttga tgagagcttt gttgtaggtg gaccagttgg tgattttgaa | 3240 |
| cttttgcttt gccacggaac ggtctgcgtt gtcgggaaga tgcgtgatct gatccttcaa | 3300 |
| ctcagcaaaa gttcgattta ttcaacaaag ccacgttgtg tctcaaaatc tctgatgtta | 3360 |
| cattgcacaa gataaaaata tatcatcatg aacaataaaa ctgtctgctt acataaacag | 3420 |
| taatacaagg ggtgtttact agaggttgat cgggcacgta agaggttcca actttcacca | 3480 |
| taatgaaata agatcactac cgggcgtatt ttttgagtta tcgagatttt caggagctaa | 3540 |
| ggaagctaaa atgagggaag cggtgatcgc cgaagtatcg actcaactat cagaggtagt | 3600 |
| tggcgtcatc gagcgccatc tcgaaccgac gttgctggcc gtacatttgt acggctccgc | 3660 |
| agtggatggc ggcctgaagc cacacagtga tattgatttg ctggttacgg tgaccgtaag | 3720 |
| gcttgatgaa acaacgcggc gagctttgat caacgacctt ttggaaactt cggcttcccc | 3780 |
| tggagagagc gagattctcc gcgctgtaga agtcaccatt gttgtgcacg acgacatcat | 3840 |
| tccgtggcgt tatccagcta agcgcgaact gcaatttgga gaatggcagc gcaatgacat | 3900 |
| tcttgcaggt atcttcgagc cagccacgat cgacattgat ctggctatct tgctgacaaa | 3960 |
| agcaagagaa catagcgttg ccttggtagg tccagcggcg gaggaactct ttgatccggt | 4020 |
| tcctgaacag gatctatttg aggcgctaaa tgaaacctta acgctatgga actcgccgcc | 4080 |
| cgactgggct ggcgatgagc gaaatgtagt gcttacgttg tcccgcattt ggtacagcgc | 4140 |
| agtaaccggc aaaatcgcgc cgaaggatgt cgctgccgac tgggcaatgg agcgcctgcc | 4200 |
| ggcccagtat cagcccgtca tacttgaagc tagacaggct tatcttggac aagaagaaga | 4260 |
| tcgcttggcc tcgcgcgcag atcagttgga agaatttgtc cactacgtga aaggcgagat | 4320 |
| caccaaggta gtcggcaaat aatactagct ccggcaaaaa aacgggcaag gtgtcaccac | 4380 |
| cctgcccttt ttctttaaaa ccgaaaagat tacttcgcgt t | 4421 |

<210> SEQ ID NO 10
<211> LENGTH: 4247
<212> TYPE: DNA
<213> ORGANISM: Artificial Sequence
<220> FEATURE:
<223> OTHER INFORMATION: Synthetic Polynucleotide

<400> SEQUENCE: 10

| | |
|---|---|
| aggtcccaat gataacccca agggaagttt tagtcaaaag cctccggtcg gaggcttttg | 60 |
| actttctgct aatctaacta actaaccctt agtgactcct gcagcgaaaa aaaacgtggc | 120 |
| gcccgaacag ggacttgaac cctggaccct cagattaaaa gtctgatgct ctaccgactg | 180 |

```
agctatccgt ccctgttcgg gcgccacgtt ttttttcggt gatgttcagc catagtagcg      240
ggtgcgccga atgctctatt taaagttaaa caaaattatt tgtagaggga aaccgttgtg      300
gtctccctga atatattata cgagccttat gcatgcccgt aaagttatcc agcaaccact      360
catagaccta gggcagcaga tagggacgac gtggtgttag ctgtgagcgg cgtgtcattg      420
ggggcttata caggcgtaga ctacaatggg cccaactcac acagctaaca ccacgtcgtc      480
cctatctgct gccctaggtc tatgagtggt tgctggataa ctttacgggc atgcataagg      540
ctcgtataat atattcaggg agaccacaac ggtttccctc tacaaataat tttgtttaac      600
tttaaatacg gtgatgttgg cgtgctcaag cgggtgcggg attgcgcaaa aaaaaacgtg      660
gcgcccgaac agggacggat agctcagtcg gtagagcatc agacttttaa tctgagggtc      720
cagggttcaa gtccctgttc gggcgccacg ttttttttcg ctgcaggagt cataagggtt      780
agttagttag attagcagaa agtcaaaagc ctccgaccgg aggcttttga ctaaaacttc      840
ccttggggtt atcattgggc tccgctagag atggaataga ctggatggag gcggataaag      900
ttgcaggacc acttctgcgc tcggcccttc cggctggctg gtttattgct gataaatctg      960
gagccggtga gcgtgggtct cgcggtatca ttgcagcact ggggccagat ggtaagccct     1020
cccgtatcgt agttatctac acgacgggga gtcaggcaac tatggatgaa cgaaatagac     1080
agatcgctga gataggtgcc tcactgatta agcattggta actgtcagac caagtttact     1140
catatatact ttagattgat ttaaaacttc attttttaatt taaaaggatc taggtgaaga     1200
tcctttttga taatctcatg accaaaatcc cttaacgtga gttttcgttc cactgagcgt     1260
cagacccctt aataagatga tcttcttgag atcgttttgg tctgcgcgta atctcttgct     1320
ctgaaaacga aaaaaccgcc ttgcagggcg ttttttcgaa ggttctctga gctaccaact     1380
ctttgaaccg aggtaactgg cttggaggag cgcagtcacc aaaacttgtc ctttcagttt     1440
agccttaacc ggcgcatgac ttcaagacta actcctctaa atcaattacc agtggctgct     1500
gccagtggtg cttttgcatg tctttccggg ttggactcaa gacgatagtt accggataag     1560
gcgcagcggt cggactgaac ggggggttcg tgcatacagt ccagcttgga gcgaactgcc     1620
tacccggaac tgagtgtcag gcgtggaatg agacaaacgc ggccataaca gcggaatgac     1680
accggtaaac cgaaaggcag gaacaggaga gcgcacgagg gagccgccag gggaaacgcc     1740
tggtatcttt atagtcctgt cgggtttcgc caccactgat ttgagcgtca gatttcgtga     1800
tgcttgtcag gggggcggag cctatggaaa aacggctttg ccgcggccct ctcacttccc     1860
tgttaagtat cttcctggca tcttccagga aatctccgcc ccgttcgtaa gcctatttccg     1920 ctcgccgcag tcgaacgacc gagcgtagcg agtcagtgag cgaggaagcg gaatatatcc     1980
tgtatcacat attctgctga cgcaccggtg cagcctttttt tctcctgcca catgaagcac     2040
ttcactgaca ccctcatcag tgccaacata gtaagccagt atacactccg ctagcgctga     2100
ggtctgcctc gtgaagaagg tgttgctgac tcataccagg cctgaatcgc ccatcatcc      2160 agccagaaag tgagggagcc acggttgatg agagctttgt tgtaggtgga ccagttggtg     2220
attttgaact tttgctttgc cacggaacgg tctgcgttgt cgggaagatg cgtgatctga     2280
tccttcaact cagcaaaagt tcgatttatt caacaaagcc acgttgtgtc tcaaaatctc     2340
tgatgttaca ttgcacaaga taaaaatata tcatcatgaa caataaaact gtctgcttac     2400
ataaacagta atacaagggg tgtttactag aggcttccca atgataaccc caagggaagt     2460
tttagtcaaa agcctccggt cggaggcttt tgactttctg ctaatctaac taactaactg     2520
cagcgaaaaa aaacgtggcg cccgaacagg gacttgaacc ctggaccctc agattaaaag     2580
```

```
tctgatgctc taccgactga gctatccgtc cctgttcggg cgccacgttt tttttgcggc    2640
tagcagagca ttcgggaaag gtgtgactat ggctgtattt aaagttaaac aaaattattt    2700
gtagagggaa accgttgtgg tctccctgaa tatattatac gagccttatg catgcccgta    2760
aagttatcca gcaaccactc atagacctag ggcagcagat agggacgacg tggtgttagc    2820
tgtgagtaat cacagctcga gcgccttgaa taacatactc atctctatac attctcgaca    2880
cagctaacac cacgtcgtcc ctatctgctg ccctaggtct atgagtggtt gctggataac    2940
tttacgggca tgcataaggc tcgtataata tattcaggga ccacaacg gtttccctct      3000 acaaataatt ttgtttaact ttaaatagcg gctagcatgc gcaatccgaa aggtgtgtga    3060
gcacgccaaa aaaacgtgg cgcccgaaca gggacggata gctcagtcgg tagagcatca     3120
gacttttaat ctgagggtcc agggttcaag tccctgttcg ggcgccacgt tttttttcgc    3180
tgcagttagt tagttagatt agcagaaagt caaaagcctc cgaccggagg cttttgacta    3240
aaacttccct tggggttatc attgggcatt gttgatcggg cacgtaagag gttccaactt    3300
tcaccataat gaaataagat cactaccggg cgtattttt gagttatcga gattttcagg     3360
agctaaggaa gctaaaatga gggaagcggt gatcgccgaa gtatcgactc aactatcaga    3420
ggtagttggc gtcatcgagc gccatctcga accgacgttg ctggccgtac atttgtacgg    3480
ctccgcagtg gatggcggcc tgaagccaca cagtgatatt gatttgctgg ttacggtgac    3540
cgtaaggctt gatgaaacaa cgcggcgagc tttgatcaac gaccttttgg aaacttcggc    3600
ttcccctgga gagagcgaga ttctccgcgc tgtagaagtc accattgttg tgcacgacga    3660
catcattccg tggcgttatc cagctaagcg cgaactgcaa tttggagaat ggcagcgcaa    3720
tgacattctt gcaggtatct tcgagccagc cacgatcgac attgatctgg ctatcttgct    3780
gacaaaagca agagaacata gcgttgcctt ggtaggtcca gcggcggagg aactctttga    3840
tccggttcct gaacaggatc tatttgaggc gctaaatgaa accttaacgc tatggaactc    3900
gccgcccgac tgggctggcg atgagcgaaa tgtagtgctt acgttgtccc gcatttggta    3960
cagcgcagta accggcaaaa tcgcgccgaa ggatgtcgct gccgactggg caatggagcg    4020
cctgccggcc cagtatcagc ccgtcatact tgaagctaga caggcttatc ttggacaaga    4080
agaagatcgc ttggcctcgc gcgcagatca gttggaagaa tttgtccact acgtgaaagg    4140
cgagatcacc aaggtagtcg gcaaataata ctagctccgg caaaaaaacg ggcaaggtgt    4200
caccaccctg cccttttttct ttaaaaccga aaagattact tcgcgtt                 4247
```

<210> SEQ ID NO 11
<211> LENGTH: 3944
<212> TYPE: DNA
<213> ORGANISM: Artificial Sequence
<220> FEATURE:
<223> OTHER INFORMATION: Synthetic Polynucleotide

<400> SEQUENCE: 11

```
aggtcccaat gataacccca agggaagttt tagtcaaaag cctccggtcg gaggcttttg     60
actttctgct aatctaacta actaaccctt agtgactcct gcagcggcgt gtcattgggg    120
gcttatacag gcgtagacta caatgggccc aactcacaca gctaacacca cgtcgtccct    180
atctgctgcc ctaggtctat gagtggttgc tggataactt tacgggcatg cataaggctc    240
gtataatata ttcagggaga ccacaacggt ttccctctac aaataatttt gtttaacttt    300
aaatacggtg atgttggcgt gctcaagcgg gtgcggatt gcgcaaaaaa aaacgtggcg     360
cccgaacagg gacggatagc tcagtcggta gagcatcaga cttttaatct gagggtccag    420
```

```
ggttcaagtc cctgttcggg cgccacgttt tttttcgctg caggagtcat aagggttagt    480
tagttagatt agcagaaagt caaaagcctc cgaccgagg cttttgacta aaacttccct    540
tggggttatc attgggctcc gctagagatg aatagactg gatggaggcg ataaagttg     600 caggaccact tctgcgctcg gcccttccgg ctggctggtt tattgctgat aaatctggag    660
ccggtgagcg tgggtctcgc ggtatcattg cagcactggg gccagatggt aagccctccc    720
gtatcgtagt tatctacacg acggggagtc aggcaactat ggatgaacga atagacaga    780 tcgctgagat aggtgcctca ctgattaagc attggtaact gtcagaccaa gtttactcat    840
atatacttta gattgattta aaacttcatt tttaatttaa aaggatctag gtgaagatcc    900
tttttgataa tctcatgacc aaaatccctt aacgtgagtt ttcgttccac tgagcgtcag    960 acccccttaat aagatgatct tcttgagatc gttttggtct gcgcgtaatc tcttgctctg   1020
aaaacgaaaa aaccgccttg cagggcggtt tttcgaaggt tctctgagct accaactctt   1080
tgaaccgagg taactggctt ggaggagcgc agtcaccaaa acttgtcctt tcagtttagc   1140
cttaaccggc gcatgacttc aagactaact cctctaaatc aattaccagt ggctgctgcc   1200
agtggtgctt ttgcatgtct ttccggttg gactcaagac gatagttacc ggataaggcg    1260
cagcggtcgg actgaacggg gggttcgtgc atacagtcca gcttggagcg aactgcctac   1320
ccggaactga gtgtcaggcg tggaatgaga caaacgcggc cataacagcg gaatgacacc   1380
ggtaaaccga aaggcaggaa caggagagcg cacgagggag ccgccagggg aaacgcctgg   1440
tatctttata gtcctgtcgg gtttcgccac cactgatttg agcgtcagat ttcgtgatgc    1500
ttgtcagggg ggcggagcct atggaaaaac ggctttgccg cggccctctc acttccctgt   1560
taagtatctt cctggcatct tccaggaaat ctccgccccg ttcgtaagcc atttccgctc   1620
gccgcagtcg aacgaccgag cgtagcgagt cagtgagcga ggaagcggaa tatatcctgt   1680
atcacatatt ctgctgacgc accggtgcag cctttttct cctgccacat gaagcacttc    1740
actgacaccc tcatcagtgc caacatagta agccagtata cactccgcta gcgctgaggt   1800
ctgcctcgtg aagaaggtgt tgctgactca taccaggcct gaatcgcccc atcatccagc   1860
cagaaagtga gggagccacg gttgatgaga gctttgttgt aggtggacca gttggtgatt   1920
ttgaactttt gctttgccac ggaacggtct gcgttgtcgg gaagatgcgt gatctgatcc   1980
ttcaactcag caaagttcg atttattcaa caaagccacg ttgtgtctca aaatctctga    2040
tgttacattg cacaagataa aaatatatca tcatgaacaa taaaactgtc tgcttacata    2100
aacagtaata caagggggtgt ttactagagg cttcccaatg ataaccccaa gggaagtttt   2160
agtcaaaagc ctccggtcgg aggcttttga cttctgcta atctaactaa ctaactgcag    2220
cgaaaaaaaa cgtggcgccc gaacagggac ttgaaccctg gaccctcaga ttaaaagtct   2280
gatgctctac cgactgagct atccgtccct gttcgggcgc cacgttttt ttgcggctag    2340 cagagcattc gggaaaggtg tgactatggc tgtatttaaa gttaaacaaa attatttgta   2400
gagggaaacc gttgtggtct ccctgaatat attatacgag ccttatgcat gcccgtaaag   2460
ttatccagca accactcata gacctagggc agcagatagg gacgacgtgg tgttagctgt   2520
gagtaatcac agctcgagcg ccttgaataa catactcatc tctatacatt ctcgacacag   2580
ctaacaccac gtcgtccta tctgctgccc taggtctatg agtggttgct ggataacttt   2640
acgggcatgc ataaggctcg tataatatat tcagggagac cacaacggtt tccctctaca   2700
aataattttg tttaacttta aatagcggct agcatgcgca atccgaaagg tgtgtgagca   2760
cgccaaaaaa aacgtggcgc ccgaacaggg acggatagct cagtcggtag agcatcagac   2820
```

```
ttttaatctg agggtccagg gttcaagtcc ctgttcgggc gccacgtttt ttttcgctgc    2880
agttagttag ttagattagc agaaagtcaa aagcctccga ccggaggctt ttgactaaaa    2940
cttcccttgg ggttatcatt gggcattgtt gatcgggcac gtaagaggtt ccaactttca    3000
ccataatgaa ataagatcac taccgggcgt attttttgag ttatcgagat tttcaggagc    3060
taaggaagct aaaatgaggg aagcggtgat cgccgaagta tcgactcaac tatcagaggt    3120
agttggcgtc atcgagcgcc atctcgaacc gacgttgctg gccgtacatt tgtacggctc    3180
cgcagtggat ggcggcctga agccacacag tgatattgat ttgctggtta cggtgaccgt    3240
aaggcttgat gaaacaacgc ggcgagcttt gatcaacgac cttttggaaa cttcggcttc    3300
ccctggagag agcgagattc tccgcgctgt agaagtcacc attgttgtgc acgacgacat    3360
cattccgtgg cgttatccag ctaagcgcga actgcaattt ggagaatggc agcgcaatga    3420
cattcttgca ggtatcttcg agccagccac gatcgacatt gatctggcta tcttgctgac    3480
aaaagcaaga gaacatagcg ttgccttggt aggtccagcg gcggaggaac tctttgatcc    3540
ggttcctgaa caggatctat ttgaggcgct aaatgaaacc ttaacgctat ggaactcgcc    3600
gcccgactgg gctggcgatg agcgaaatgt agtgcttacg ttgtcccgca tttggtacag    3660
cgcagtaacc ggcaaaatcg cgccgaagga tgtcgctgcc gactgggcaa tggagcgcct    3720
gccggcccag tatcagcccg tcatacttga agctagacag gcttatcttg acaagaaga    3780 agatcgcttg gcctcgcgcg cagatcagtt ggaagaattt gtccactacg tgaaaggcga    3840
gatcaccaag gtagtcggca ataatacta gctccggcaa aaaacgggc aaggtgtcac    3900 caccctgccc ttttttctttа aaaccgaaaa gattacttcg cgtt                   3944
```

<210> SEQ ID NO 12
<211> LENGTH: 3388
<212> TYPE: DNA
<213> ORGANISM: Artificial Sequence
<220> FEATURE:
<223> OTHER INFORMATION: Synthetic Polynucleotide

<400> SEQUENCE: 12

```
aggtgctaga gatggaatag actggatgga ggcggataaa gttgcaggac cacttctgcg     60
ctcggccctt ccggctggct ggtttattgc tgataaatct ggagccggtg agcgtgggtc    120
tcgcggtatc attgcagcac tggggccaga tggtaagccc tcccgtatcg tagttatcta    180
cacgacgggg agtcaggcaa ctatggatga acgaaataga cagatcgctg ataggtgc     240 ctcactgatt aagcattggt aactgtcaga ccaagtttac tcatatatac tttagattga    300
tttaaaactt cattttttaat ttaaaaggat ctaggtgaag atccttttg ataatctcat    360 gaccaaaatc ccttaacgtg agttttcgtt ccactgagcg tcagaccccct taataagatg    420 atcttcttga tcgttttg gtctgcgcgt aatctcttgc tctgaaaacg aaaaaaccgc    480
cttgcagggc ggtttttcga aggttctctg agctaccaac tctttgaacc gaggtaactg    540
gcttggagga gcgcagtcac caaaacttgt cctttcagtt tagccttaac cggcgcatga    600
cttcaagact aactcctcta aatcaattac cagtggctgc tgccagtggt gcttttgcat    660
gtctttccgg gttggactca agacgatagt taccggataa ggcgcagcgg tcggactgaa    720
cggggggttc gtgcatacag tccagcttgg agcgaactgc ctacccggaa ctgagtgtca    780
ggcgtggaat gagacaaacg cggccataac agcggaatga caccggtaaa ccgaaaggca    840
ggaacaggag agcgcacgag ggagccgcca ggggaaacgc ctggtatctt tatagtcctg    900
tcgggtttcg ccaccactga tttgagcgtc agatttcgtg atgcttgtca ggggggcgga    960
```

```
gcctatggaa aaacggcttt gccgcggccc tctcacttcc ctgttaagta tcttcctggc    1020
atcttccagg aaatctccgc cccgttcgta agccatttcc gctcgccgca gtcgaacgac    1080
cgagcgtagc gagtcagtga gcgaggaagc ggaatatatc ctgtatcaca tattctgctg    1140
acgcaccggt gcagccttt ttctcctgcc acatgaagca cttcactgac accctcatca    1200
gtgccaacat agtaagccag tatacactcc gctagcgctg aggtctgcct cgtgaagaag    1260
gtgttgctga ctcataccag gcctgaatcg ccccatcatc cagccagaaa gtgagggagc    1320
cacggttgat gagagctttg ttgtaggtgg accagttggt gattttgaac ttttgctttg    1380
ccacggaacg gtctgcgttg tcgggaagat gcgtgatctg atccttcaac tcagcaaaag    1440
ttcgatttat tcaacaaagc cacgttgtgt ctcaaaatct ctgatgttac attgcacaag    1500
ataaaaatat atcatcatga acaataaaac tgtctgctta cataaacagt aatcaagggg    1560
gtgtttacta gaggcttccc aatgataacc ccaagggaag ttttagtcaa aagcctccgg    1620
tcggaggctt ttgactttct gctaatctaa ctaactaact gcagcgaaaa aaaacgtggc    1680
gcccgaacag ggacttgaac cctggaccct cagattaaaa gtctgatgct ctaccgactg    1740
agctatccgt ccctgttcgg gcgccacgtt ttttttgcgg ctagcagagc attcgggaaa    1800
ggtgtgacta tggctgtatt taagttaaa caaaattatt tgtagaggga aaccgttgtg    1860
gtctccctga atatattata cgagccttat gcatgcccgt aaagttatcc agcaaccact    1920
catagaccta gggcagcaga tagggacgac gtggtgttag ctgtgagtaa tcacagctcg    1980
agcgccttga ataacatact catctctata cattctcgac acagctaaca ccacgtcgtc    2040
cctatctgct gccctaggtc tatgagtggt tgctggataa cttttacggg catgcataagg    2100 ctcgtataat atattcaggg agaccacaac ggtttccctc tacaaataat tttgtttaac    2160
tttaaatagc ggctagcatg cgcaatccga aaggtgtgtg agcacgccaa aaaaaacgtg    2220
gcgcccgaac agggacggat agctcagtcg gtagagcatc agacttttaa tctgagggtc    2280
cagggttcaa gtccctgttc gggcgccacg tttttttcg ctgcagttag ttagttagat    2340
tagcagaaag tcaaaagcct ccgaccggag gcttttgact aaaacttccc ttggggttat    2400
cattgggcat tgttgatcgg gcacgtaaga ggttccaact ttcaccataa tgaaataaga    2460
tcactaccgg gcgtattttt tgagttatcg agattttcag gagctaagga agctaaaatg    2520
agggaagcgg tgatcgccga agtatcgact caactatcag aggtagttgg cgtcatcgag    2580
cgccatctcg aaccgacgtt gctggccgta catttgtacg gctccgcagt ggatggcggc    2640
ctgaagccac acagtgatat tgatttgctg gttacggtga ccgtaaggct tgatgaaaca    2700
acgcggcgag ctttgatcaa cgaccttttg gaaacttcgg cttcccctgg agagagcgag    2760
attctccgcg ctgtagaagt caccattgtt gtgcacgacg acatcattcc gtggcgttat    2820
ccagctaagc gcgaactgca atttggagaa tggcagcgca atgacattct tgcaggtatc    2880
ttcgagccag ccacgatcga cattgatctg gctatcttgc tgacaaaagc aagagaacat    2940
agcgttgcct tggtaggtcc agcggcggag gaactctttg atccggttcc tgaacaggat    3000
ctatttgagg cgctaaatga aaccttaacg ctatggaact cgccgcccga ctgggctggc    3060
gatgagcgaa atgtagtgct tacgttgtcc cgcatttggt acagcgcagt aaccggcaaa    3120
atcgcgccga aggatgtcgc tgccgactgg gcaatggagc gcctgccggc ccagtatcag    3180
cccgtcatac ttgaagctag acaggcttat cttggacaag aagaagatcg cttgcctcg    3240 cgcgcagatc agttggaaga atttgtccac tacgtgaaag gcgagatcac caaggtagtc    3300
```

```
ggcaaataat actagctccg gcaaaaaaac gggcaaggtg tcaccaccct gcccttttc      3360 tttaaaaccg aaaagattac ttcgcgtt                                         3388

<210> SEQ ID NO 13
<211> LENGTH: 3056
<212> TYPE: DNA
<213> ORGANISM: Artificial Sequence
<220> FEATURE:
<223> OTHER INFORMATION: Synthetic Polynucleotide

<400> SEQUENCE: 13
accctgccct ttttctttaa aaccgaaaag attacttcgc gtttgccacc tgacgtctaa       60
gaacacagct aacaccacgt cgtccctatc tgctgcccta ggtctatgag tggttgctgg      120
ataactttac gggcatgcat aaggctcgta atatattc agggagacca caacggtttc       180
cctctacaaa taattttgtt taacttttgc gcaatccgaa aggtgtgtga gcacgccaaa     240
aaaaaacgtg gcgcccgaac agggacggat agctcagtcg gtagagcatc agacttttaa     300
tctgagggtc caggggttcaa gtccctgttc gggcgccacg ttttttttcg ctgcagttag     360
gagtcataag ggttagttag attagcagaa agtcaaaagc ctccgaccgg aggcttttga     420
ctaaaacttc ccttgggggtt atcattgggg ctcactcaaa ggcggtaatc agataaaaaa     480
aatccttagc tttcgctaag gatgatttct gctagagatg aatagactg atggaggcg       540 gataaagttg caggaccact tctgcgctcg gcccttccgg ctggctggtt tattgctgat     600
aaatctggag ccggtgagcg tgggtctcgc ggtatcattg cagcactggg gccagatggt     660
aagccctccc gtatcgtagt tatctacacg acggggagtc aggcaactat ggatgaacga     720
aatagacaga tcgctgagat aggtgcctca ctgattaagc attggtaact gtcagaccaa     780
gtttactcat atatacttta gattgattta aaacttcatt tttaatttaa aaggatctag     840
gtgaagatcc ttttttgataa tctcatgacc aaaatccctt aacgtgagtt ttcgttccac     900
tgagcgtcag accccttaat aagatgatct tcttgagatc gttttggtct gcgcgtaatc     960
tcttgctctg aaaacgaaaa aaccgccttg caggggcggtt tttcgaaggt tctctgagct    1020
accaactctt tgaaccgagg taactggctt ggaggagcgc agtcaccaaa acttgtcctt    1080
tcagtttagc cttaaccggc gcatgacttc aagactaact cctctaaatc aattaccagt    1140
ggctgctgcc agtggtgctt ttgcatgtct ttccggggttg gactcaagac gatagttacc    1200
ggataaggcg cagcggtcgg actgaacggg gggttcgtgc atacagtcca gcttggagcg    1260
aactgcctac ccggaactga gtgtcaggcg tggaatgaga caaacgcggc cataacagcg    1320
gaatgacacc ggtaaaccga aaggcaggaa caggagagcg cacgagggag ccgccagggg    1380
aaacgcctgg tatctttata gtcctgtcgg gtttcgccac cactgatttg agcgtcagat    1440
ttcgtgatgc ttgtcagggg ggcggagcct atggaaaaac ggctttgccg cggccctctc    1500
acttccctgt taagtatctt cctggcatct tccaggaaat ctccgccccg ttcgtaagcc    1560
atttccgctc gccgcagtcg aacgaccgag cgtagcgagt cagtgagcga ggaagcggaa    1620
tatatcctgt atcacatatt ctgctgacgc accggtgcag cctttttttct cctgccacat    1680 gaagcacttc actgacaccc tcatcagtgc caacatagta agccagtata cactccgcta    1740
gcgctgaggt ctgcctcgtg aagaaggtgt tgctgactca taccaggcct gaatcgcccc    1800
atcatccagc cagaaagtga gggagccacg gttgatgaga gctttgttgt aggtggacca    1860
gttggtgatt ttgaactttt gctttgccac ggaacggtct gcgttgtcgg aagatgcgt     1920 gatctgatcc ttcaactcag caaaagttcg atttattcaa caaagccacg ttgtgtctca    1980
```

| | |
|---|---|
| aaatctctga tgttacattg cacaagataa aatatatca tcatgaacaa taaaactgtc | 2040 |
| tgcttacata acagtaata caaggggtgt ttactagagg ttgatcgggc acgtaagagg | 2100 |
| ttccaacttt caccataatg aaataagatc actaccgggc gtattttttg agttatcgag | 2160 |
| attttcagga gctaaggaag ctaaaatgag ggaagcggtg atcgccgaag tatcgactca | 2220 |
| actatcagag gtagttggcg tcatcgagcg ccatctcgaa ccgacgttgc tggccgtaca | 2280 |
| tttgtacggc tccgcagtgg atggcggcct gaagccacac agtgatattg atttgctggt | 2340 |
| tacggtgacc gtaaggcttg atgaaacaac gcggcgagct ttgatcaacg acctttttgga | 2400 |
| aacttcggct tcccctggag agagcgagat tctccgcgct gtagaagtca ccattgttgt | 2460 |
| gcacgacgac atcattccgt ggcgttatcc agctaagcgc gaactgcaat ttggagaatg | 2520 |
| gcagcgcaat gacattcttg caggtatctt cgagccagcc acgatcgaca ttgatctggc | 2580 |
| tatcttgctg acaaaagcaa gagaacatag cgttgccttg gtaggtccag cggcggagga | 2640 |
| actctttgat ccggttcctg aacaggatct atttgaggcg ctaaatgaaa ccttaacgct | 2700 |
| atggaactcg ccgcccgact gggctggcga tgagcgaaat gtagtgctta cgttgtcccg | 2760 |
| catttggtac agcgcagtaa ccggcaaaat cgcgccgaag gatgtcgctg ccgactgggc | 2820 |
| aatggagcgc ctgccggccc agtatcagcc cgtcatactt gaagctagac aggcttatct | 2880 |
| tggacaagaa gaagatcgct tggcctcgcg cgcagatcag ttggaagaat ttgtccacta | 2940 |
| cgtgaaaggc gagatcacca aggtagtcgg caaataatac tagctccggc aaaaaaacgg | 3000 |
| gcaaggtgtc accaccctgc cctttttctt taaaaccgaa aagattactt cgcgtt | 3056 |

<210> SEQ ID NO 14
<211> LENGTH: 5204
<212> TYPE: DNA
<213> ORGANISM: Artificial Sequence
<220> FEATURE:
<223> OTHER INFORMATION: Synthetic Polynucleotide

<400> SEQUENCE: 14

| | |
|---|---|
| aggtcccaat gataacccca agggaagttt tagtcaaaag cctccggtcg gaggcttttg | 60 |
| actttctgct aatctaacta actaaccctt agtgactcct gcagcgaaaa aaaacgtggc | 120 |
| gcccgaacag ggacttgaac cctggaccct cagattaaaa gtctgatgct ctaccgactg | 180 |
| agctatccgt ccctgttcgg cgccacgtt tttttcggt gatgttcagc catagtagcg | 240 |
| ggtgcgccga atgctcggag aaacagtaga gagttgcgat aaaaagcgtc aggtaggatc | 300 |
| cgctaatctt atggataaaa atgctatggc atagcaaagt gtgacgccgt gcaaataatc | 360 |
| aatgtagcgg cgtgtcattg ggggcttata caggcgtaga ctacaatggg cccaactcac | 420 |
| acagctaaca ccacgtcgtc cctatctgct gccctaggtc tatgagtggt tgctggataa | 480 |
| ctttacgggc atgcataagg ctcgtataat atattcaggg agaccacaac ggtttccctc | 540 |
| tacaaataat tttgtttaac tttaaatacg gtgatgttgg cgtgctcaag cgggtgcggg | 600 |
| attgcgcaaa aaaaacgtg gcgcccgaac agggacggat agctcagtcg gtagagcatc | 660 |
| agacttttaa tctgagggtc cagggttcaa gtccctgttc gggcgccacg tttttttcg | 720 |
| ctgcaggagt cataagggtt agttagttag attagcagaa agtcaaaagc ctccgaccgg | 780 |
| aggctttga ctaaaacttc ccttgggtt atcattgggc tccgctagag atggaataga | 840 |
| ctggatggag gcggataaag ttgcaggacc acttctgcgc tcggcccttc cggctggctg | 900 |
| gtttattgct gataaatctg gagccggtga gcgtgggtct cgcggtatca ttgcagcact | 960 |
| ggggccagat ggtaagccct cccgtatcgt agttatctac acgacgggga gtcaggcaac | 1020 |

```
tatggatgaa cgaaatagac agatcgctga gataggtgcc tcactgatta agcattggta    1080
actgtcagac caagtttact catatatact ttagattgat ttaaaacttc atttttaatt    1140
taaaaggatc taggtgaaga tccttttga taatctcatg accaaaatcc cttaacgtga     1200
gttttcgttc cactgagcgt cagacccctt aataagatga tcttcttgag atcgttttgg    1260
tctgcgcgta atctcttgct ctgaaaacga aaaaaccgcc ttgcagggcg ttttttcgaa    1320
ggttctctga gctaccaact cttttgaaccg aggtaactgg cttggaggag cgcagtcacc   1380
aaaacttgtc ctttcagttt agccttaacc ggcgcatgac ttcaagacta actcctctaa    1440
atcaattacc agtggctgct gccagtggtg cttttgcatg tctttccggg ttggactcaa    1500
gacgatagtt accggataag gcgcagcggt cggactgaac ggggggttcg tgcatacagt    1560
ccagcttgga gcgaactgcc tacccggaac tgagtgtcag gcgtggaatg agacaaacgc    1620
ggccataaca gcggaatgac accggtaaac cgaaaggcag gaacaggaga gcgcacgagg    1680
gagccgccag gggaaacgcc tggtatcttt atagtcctgt cgggtttcgc caccactgat    1740
ttgagcgtca gatttcgtga tgcttgtcag ggggcggag cctatggaaa aacgctttg     1800
ccgcggccct ctcacttccc tgttaagtat cttcctggca tcttccagga aatctccgcc    1860
ccgttcgtaa gccatttccg ctcgccgcag tcgaacgacc gagcgtagcg agtcagtgag    1920
cgaggaagcg gaatatatcc tgtatcacat attctgctga cgcaccggtg cagccttttt    1980
tctcctgcca catgaagcac ttcactgaca ccctcatcag tgccaacata gtaagccagt    2040
atacactccg ctagcgctga ggtctgcctc gtgaagaagg tgttgctgac tcataccagg    2100
cctgaatcgc cccatcatcc agccagaaag tgagggagcc acggttgatg agagctttgt    2160
tgtaggtgga ccagttggtg attttgaact tttgctttgc cacggaacgg tctgcgttgt    2220
cgggaagatg cgtgatctga tccttcaact cagcaaaagt tcgatttatt caacaaagcc    2280
acgttgtgtc tcaaaatctc tgatgttaca ttgcacaaga taaaaatata tcatcatgaa    2340
caataaaact gtctgcttac ataaacagta atacaagggg tgtttactag aggcttccca    2400
atgataaccc caagggaagt tttagtcaaa agcctccggt cggaggcttt tgactttctg    2460
ctaatctaac taactaactg cagcgaaaaa aaacgtggcg cccgaacagg gacttgaacc    2520
ctggaccctc agattaaaag tctgatgctc taccgactga gctatccgtc cctgttcggg    2580
cgccacgttt ttttgcggc tagcagagca ttcgggaaag gtgtgactat ggctgtattt     2640
aaagttaaac aaaattattt gtagagggaa accgttgtgg tctccctgaa tatattatac    2700
gagccttatg catgcccgta aagttatcca gcaaccactc atagacctag gcagcagat     2760
agggacgacg tggtgttagc tgtgagtata ctagagttat gacaacttga cggctacatc    2820
attcactttt tcttcacaac cggcacggaa ctcgctcggg ctggccccgg tgcatttttt    2880
aaatacccgc gagaaataga gttgatcgtc aaaaccaaca ttgcgaccga cggtggcgat    2940
aggcatccgg gtggtgctca aaagcagctt cgcctggctg atacgttggt cctcgcgcca    3000
gcttaagacg ctaatcccta actgctgcg gaaaagatgt gacagacgcg acggcgacaa     3060
gcaaacatgc tgtgcgacgc tggcgatatc aaaattgctg tctgccaggt gatcgctgat    3120
gtactgacaa gcctcgcgta cccgattatc catcggtgga tggagcgact cgttaatcgc    3180
ttccatgcgc cgcagtaaca attgctcaag cagatttatc gccagcagct ccgaatagcg    3240
cccttcccct tgcccggcgt taatgatttg cccaaacagg tcgctgaaat gcggctggtg    3300
cgcttcatcc gggcgaaaga accccgtatt ggcaaatatt gacggccagt taagccattc    3360
atgccagtag gcgcgcggac gaaagtaaac ccactggtga taccattcgc gagcctccgg    3420
```

| | |
|---|---|
| atgacgaccg tagtgatgaa tctctcctgg cgggaacagc aaaatatcac ccggtcggca | 3480 |
| aacaaattct cgtccctgat ttttcaccac ccctgaccg cgaatggtga gattgagaat | 3540 |
| ataacctttc attcccagcg gtcggtcgat aaaaaaatcg agataaccgt tggcctcaat | 3600 |
| cggcgttaaa cccgccacca gatgggcatt aaacgagtat cccggcagca ggggatcatt | 3660 |
| ttgcgcttca gccatacttt tcatactccc gccattcaga aagaaacca attgtccata | 3720 |
| ttgcatcaga cattgccgtc actgcgtctt ttactggctc ttctcgctaa ccaaaccggt | 3780 |
| aaccccgctt attaaaagca ttctgtaaca aagcgggacc aaagccatga caaaaacgcg | 3840 |
| taacaaaagt gtctataatc acggcagaaa agtccacatt gattatttgc acggcgtcac | 3900 |
| actttgctat gccatagcat ttttatccat aagattagcg gatcctacct gacgcttttt | 3960 |
| atcgcaactc tctactgttt ctccgcggct agcatgcgca atccgaaagg tgtgtgagca | 4020 |
| cgccaaaaaa aacgtggcgc ccgaacaggg acggatagct cagtcggtag agcatcagac | 4080 |
| ttttaatctg agggtccagg gttcaagtcc ctgttcgggc gccacgtttt ttttcgctgc | 4140 |
| agttagttag ttagattagc agaaagtcaa aagcctccga ccggaggctt ttgactaaaa | 4200 |
| cttcccttgg ggttatcatt gggcattgtt gatcgggcac gtaagaggtt ccaactttca | 4260 |
| ccataatgaa ataagatcac taccgggcgt atttttgag ttatcgagat tttcaggagc | 4320 |
| taaggaagct aaaatgaggg aagcggtgat cgccgaagta tcgactcaac tatcagaggt | 4380 |
| agttggcgtc atctcgagcgcc atctcgaacc gacgttgctg gccgtacatt tgtacggctc | 4440 |
| cgcagtggat ggcggcctga agccacacag tgatattgat ttgctggtta cggtgaccgt | 4500 |
| aaggcttgat gaaacaacgc ggcgagcttt gatcaacgac cttttggaaa cttcggcttc | 4560 |
| ccctggagag agcgagattc tccgcgctgt agaagtcacc attgttgtgc acgacgacat | 4620 |
| cattccgtgg cgttatccag ctaagcgcga actgcaattt ggagaatggc agcgcaatga | 4680 |
| cattcttgca ggtatcttcg agccagccac gatcgacatt gatctggcta tcttgctgac | 4740 |
| aaaagcaaga gaacatagcg ttgccttggt aggtccagcg gcggaggaac tctttgatcc | 4800 |
| ggttcctgaa caggatctat ttgaggcgct aaatgaaacc ttaacgctat ggaactcgcc | 4860 |
| gcccgactgg gctggcgatg agcgaaatgt agtgcttacg ttgtcccgca tttggtacag | 4920 |
| cgcagtaacc ggcaaaatcg cgccaagga tgtcgctgcc gactgggcaa tggagcgcct | 4980 |
| gccggcccag tatcagcccg tcatacttga agctagacag gcttatcttg acaagaaga | 5040 |
| agatcgcttg gcctcgcgcg cagatcagtt ggaagaattt gtccactacg tgaaaggcga | 5100 |
| gatcaccaag gtagtcggca aataatacta gctccggcaa aaaacgggc aaggtgtcac | 5160 |
| caccctgccc ttttcttta aaaccgaaaa gattacttcg cgtt | 5204 |

```
<210> SEQ ID NO 15
<211> LENGTH: 104
<212> TYPE: RNA
<213> ORGANISM: Artificial Sequence
<220> FEATURE:
<223> OTHER INFORMATION: Synthetic Polynucleotide

<400> SEQUENCE: 15
```

| | |
|---|---|
| aaaaaaaacg uggcgcccga acagggacgg auccgcccgg auaaucagac uuuuaaucug | 60 |
| agggguccagg guucaagucc cuguucgggc gccacguuuu uuuu | 104 |

```
<210> SEQ ID NO 16
<211> LENGTH: 105
<212> TYPE: RNA
<213> ORGANISM: Artificial Sequence
```

```
<220> FEATURE:
<223> OTHER INFORMATION: Synthetic Polynucleotide

<400> SEQUENCE: 16
aaaaaaaacg uggcgcccga acagggacgg auccgcccgg auagcucagu cgguagagca    60
ucagacuuuu aaucugaguc ccguucggg cgccacguuu uuuuu                    105

<210> SEQ ID NO 17
<211> LENGTH: 65
<212> TYPE: RNA
<213> ORGANISM: Artificial Sequence
<220> FEATURE:
<223> OTHER INFORMATION: Synthetic Polynucleotide

<400> SEQUENCE: 17
aaaaaaaacg uggcgcccga acagggacuc guggaauguc ccguucggg cgccacguuu    60 uuuuu                                                                65

<210> SEQ ID NO 18
<211> LENGTH: 110
<212> TYPE: RNA
<213> ORGANISM: Artificial Sequence
<220> FEATURE:
<223> OTHER INFORMATION: Synthetic Polynucleotide

<400> SEQUENCE: 18
aaaaaaaacg uggcgcccga acagggacgg auagcucagu cgguagagca ucagacuuuu    60
aaucugaggg uccaggguuc aagucccugu ucgggcgcca cguuuuuuuu              110

<210> SEQ ID NO 19
<211> LENGTH: 112
<212> TYPE: RNA
<213> ORGANISM: Artificial Sequence
<220> FEATURE:
<223> OTHER INFORMATION: Synthetic Polynucleotide

<400> SEQUENCE: 19
aaaaaaaacg uggcgcccga acagggacgg auccgcccgg auagcucagu cgguagagca    60
ucagacuuuu aaucugaggg uccagggyuc aagucccugu ucgggcgcca cg           112

<210> SEQ ID NO 20
<211> LENGTH: 114
<212> TYPE: RNA
<213> ORGANISM: Artificial Sequence
<220> FEATURE:
<223> OTHER INFORMATION: Synthetic Polynucleotide

<400> SEQUENCE: 20
aaaaacgugg cgcccgaaca gggacggauc cgcccggaua gcucagucgg uagagcauca    60
gacuuuuaau cugagggucc aggguucaag cccuguucg gcgccacgu uuuu           114

<210> SEQ ID NO 21
<211> LENGTH: 120
<212> TYPE: RNA
<213> ORGANISM: Artificial Sequence
<220> FEATURE:
<223> OTHER INFORMATION: Synthetic Polynucleotide

<400> SEQUENCE: 21
aaaaaaaacg uggcgcccga acagggacgg auccgcccgg auagcucagu cgguagagca    60
ucagacuuuu aaucugaggg uccagggyuc aagucccugu ucgggcgcca cguuuuuuuu   120
```

<210> SEQ ID NO 22
<211> LENGTH: 122
<212> TYPE: RNA
<213> ORGANISM: Artificial Sequence
<220> FEATURE:
<223> OTHER INFORMATION: Synthetic Polynucleotide

<400> SEQUENCE: 22
aaaaaaaaac guggcgcccg aacagggacg gauccgcccg gauagcucag ucgguagagc    60
aucagacuuu uaaucugagg guccagggüu caaguccccug uucgggcgcc acguuuuuu   120 uu                                                                 122

<210> SEQ ID NO 23
<211> LENGTH: 189
<212> TYPE: DNA
<213> ORGANISM: Artificial Sequence
<220> FEATURE:
<223> OTHER INFORMATION: Synthetic Polynucleotide

<400> SEQUENCE: 23
taagctttgg aaccgtactg gaactgcggg gacaggatgt cccaagcgaa cggcagcgga    60
ccacctttgg taactttcag tttagcggtc tgggtaccct cgtacggacg accttcacct   120
tcaccttcga tttcgaactc gtgaccgtta acggaaccgg acaggaggct agctacaacg   180
agtcccaag                                                          189

<210> SEQ ID NO 24
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 24
aacggaaccg gacaggaggc tagctacaac gagtcccaag                          40

<210> SEQ ID NO 25
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 25
tgcgcaatcc cgcacccgct tgagcacgcc aacatcaccg tattt                    45

<210> SEQ ID NO 26
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 26
gcggctagca gagcattcgg gaaaggtgtg actatggctg tattt                    45

<210> SEQ ID NO 27
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 27
ggcgtgctca cacacctttc ggattgcgca tgctagccgc tattt 45

<210> SEQ ID NO 28
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 28
cggtgatgtt cagccatagt agcgggtgcg ccgaatgctc tattt 45

<210> SEQ ID NO 29
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 29
ttgacagcta gctcagtcct aggtactgtg ctagc 35

<210> SEQ ID NO 30
<211> LENGTH: 144
<212> TYPE: DNA
<213> ORGANISM: Artificial Sequence
<220> FEATURE:
<223> OTHER INFORMATION: Synthetic Polynucleotide

<400> SEQUENCE: 30
cacagctaac accacgtcgt ccctatctgc tgccctaggt ctatgagtgg ttgctggata 60
actttacggg catgcataag gctcgtataa tatattcagg gagaccacaa cggtttccct 120
ctacaaataa ttttgtttaa cttt 144

<210> SEQ ID NO 31
<211> LENGTH: 82
<212> TYPE: DNA
<213> ORGANISM: Artificial Sequence
<220> FEATURE:
<223> OTHER INFORMATION: Synthetic Polynucleotide

<400> SEQUENCE: 31
gcggcgcgcc atcgaatggc gcaaaacctt tcgcggtatg gcatgatagc gcccggaaga 60
gagtcaattc agggtggtga at 82

<210> SEQ ID NO 32
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 32
tgttgacaat taatcatcgg ctcgtataat gtgtggaatt gtgagcgctc acaatt 56

<210> SEQ ID NO 33
<211> LENGTH: 1123
<212> TYPE: DNA
<213> ORGANISM: Artificial Sequence
<220> FEATURE:
<223> OTHER INFORMATION: Synthetic Polynucleotide

<400> SEQUENCE: 33

```
atgaaaccag taacgttata cgatgtcgca gagtatgccg gtgtctctta tcagaccgtt      60
tcccgcgtgg tgaaccaggc cagccacgtt tctgcgaaaa cgcgggaaaa agtggaagcg     120
gcgatggcgc agctgaatta cattcccaac cgcgtggcac aacaactggc gggcaaacag     180
tcgttgctga ttggcgttgc cacctccagt ctggccctgc acgcgccgtc gcaaattgtc     240
gcggcgatta atctcgcgc cgatcaactg ggtgccagcg tggtggtgtc gatggtagaa      300
cgaagcggcg tcgaagcctg taaagcggcg gtgcacaatc ttctcgcgca acgcgtcagt     360
gggctgatca ttaactatcc gctggatgac caggatgcca ttgctgtgga agctgcctgc     420
actaatgttc cggcgttatt tcttgatgtc tctgaccaga cacccatcaa cagtattatt     480
ttctcccatg aggacggtac gcgactgggc gtggagcatc tggtcgcatt gggtcaccag     540
caaatcgcgc tgttagcggg cccattaagt tctgtctcgg cgcgtctgcg tctggctggc     600
tggcataaat atctcactcg caatcaaatt cagccgatag cggaacggga aggcgactgg     660
agtgccatgt ccggttttca acaaaccatg caaatgctga atgagggcat cgttcccact     720
gcgatgctgg ttgccaacga tcagatggcg ctgggcgcaa tgcgcgccat taccgagtcc     780
gggctgcgcg ttggtgcgga tatctcggta gtgggatacg acgataccga agatagctca     840
tgttatatcc cgccgttaac caccatcaaa caggattttc gcctgctggg gcaaaccagc     900
gtggaccgct gctgcaact ctctcagggc caggcggtga agggcaatca gctgttgcca      960
gtctcactgg tgaaaagaaa aaccaccctg gcgcccaata cgcaaaccgc ctctccccgc    1020
gcgttggccg attcattaat gcagctggca cgacaggttt cccgactgga aagcgggcag    1080
tgagcgcaac gcaattaatg taagttagcg cgaattggcc gac                     1123
```

<210> SEQ ID NO 34
<211> LENGTH: 1190
<212> TYPE: DNA
<213> ORGANISM: Artificial Sequence
<220> FEATURE:
<223> OTHER INFORMATION: Synthetic Polynucleotide

<400> SEQUENCE: 34

```
agttatgaca acttgacggc tacatcattc acttttcctt cacaaccggc acggaactcg      60
ctcgggctgg ccccggtgca ttttttaaat acccgcgaga aatagagttg atcgtcaaaa     120
ccaacattgc gaccgacggt ggcgataggc atccgggtgg tgctcaaaag cagcttcgcc     180
tggctgatac gttggtcctc gcgccagctt aagacgctaa tccctaactg ctggcggaaa     240
agatgtgaca gacgcgacgg cgacaagcaa acatgctgtg cgacgctggc gatatcaaaa     300
ttgctgtctg ccaggtgatc gctgatgtac tgacaagcct cgcgtacccg attatccatc     360
ggtggatgga gcgactcgtt aatcgcttcc atgcgccgca gtaacaattg ctcaagcaga     420
tttatcgcca gcagctccga atagcgccct tccccttgcc cggcgttaat gatttgccca     480
aacaggtcgc tgaaatgcgg ctggtgcgct tcatccgggc gaaagaaccc cgtattggca     540
aatattgacg gccagttaag ccattcatgc cagtaggcgc gcggacgaaa gtaaacccac     600
tggtgatacc attcgcgagc ctccggatga cgaccgtagt gatgaatctc tcctggcggg     660
aacagcaaaa tatcacccgg tcggcaaaca aattctcgtc cctgattttt caccaccccc     720
tgaccgcgaa tggtgagatt gagaatataa cctttcattc ccagcggtcg gtcgataaaa     780
aaatcgagat aaccgttggc ctcaatcggg gttaaacccg ccaccagatg ggcattaaac     840
gagtatcccg gcagcagggg atcattttgc gcttcagcca tactttcat actcccgcca      900
```

```
ttcagagaag aaaccaattg tccatattgc atcagacatt gccgtcactg cgtctttttac    960 tggctcttct cgctaaccaa accggtaacc ccgcttatta aaagcattct gtaacaaagc   1020
gggaccaaag ccatgacaaa aacgcgtaac aaaagtgtct ataatcacgg cagaaaagtc   1080
cacattgatt atttgcacgg cgtcacactt tgctatgcca tagcattttt atccataaga   1140
ttagcggatc ctacctgacg ctttttatcg caactctcta ctgtttctcc              1190

<210> SEQ ID NO 35
<211> LENGTH: 129
<212> TYPE: DNA
<213> ORGANISM: Artificial Sequence
<220> FEATURE:
<223> OTHER INFORMATION: Synthetic Polynucleotide

<400> SEQUENCE: 35
ccaggcatca aataaaacga aaggctcagt cgaaagactg ggcctttcgt tttatctgtt     60
gtttgtcggt gaacgctctc tactagagtc acactggctc accttcgggt gggcctttct    120
gcgtttata                                                            129

<210> SEQ ID NO 36
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 36
attagcagaa agtcaaaagc ctccgaccgg aggcttttga ctaaaacttc ccttggggtt     60
atcattggg                                                             69

<210> SEQ ID NO 37
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 37
ctgtcaccgg atgtgctttc cggtctgatg agtccgtgag gacgaaacag               50

<210> SEQ ID NO 38
<211> LENGTH: 681
<212> TYPE: DNA
<213> ORGANISM: Artificial Sequence
<220> FEATURE:
<223> OTHER INFORMATION: Synthetic Polynucleotide

<400> SEQUENCE: 38
atggcttcct ccgaagacgt tatcaaagag ttcatgcgtt tcaaagttcg tatggaaggt     60
tccgttaacg gtcacgagtt cgaaatcgaa ggtgaaggtg aaggtcgtcc gtacgaaggt    120
acccagaccg ctaaactgaa agttaccaaa ggtggtccgc tgccgttcgc ttgggacatc    180
ctgtccccgc agttccagta cggttccaaa gcttacgtta acacccggc tgacatcccg    240 gactacctga actgtccctt cccggaaggt ttcaaatggg aacgtgttat gaacttcgaa    300
gacggtggtg ttgttaccgt tacccaggac tcctccctgc aagacggtga gttcatctac    360
aaagttaaac tgcgtggtac caacttcccg tccgacggtc cggttatgca gaaaaaaacc    420
atgggttggg aagcttccac cgaacgtatg tacccggaag acggtgctct gaaaggtgaa    480
atcaaaatgc gtctgaaact gaaagacggt ggtcactacg acgctgaagt taaaaccacc    540
```

-continued

```
tacatggcta aaaaaccggt tcagctgccg ggtgcttaca aaaccgacat caaactggac      600
atcacctccc acaacgaaga ctacaccatc gttgaacagt acgaacgtgc tgaaggtcgt      660
cactccaccg gtgcttaata a                                                681

<210> SEQ ID NO 39
<211> LENGTH: 720
<212> TYPE: DNA
<213> ORGANISM: Artificial Sequence
<220> FEATURE:
<223> OTHER INFORMATION: Synthetic Polynucleotide

<400> SEQUENCE: 39
atgcgtaaag gagaagaact tttcactgga gttgtcccaa ttcttgttga attagatggt       60
gatgttaatg ggcacaaatt ttctgtcagt ggagagggtg aaggtgatgc aacatacgga      120
aaacttaccc ttaaatttat ttgcactact ggaaaactac ctgttccatg gccaacactt      180
gtcactactt tcggttatgg tgttcaatgc tttgcgagat acccagatca tatgaaacag      240
catgactttt tcaagagtgc catgcccgaa ggttatgtac aggaaagaac tatattttc       300 aaagatgacg ggaactacaa gacacgtgct gaagtcaagt ttgaaggtga taccttgtt       360 aatagaatcg agttaaaagg tattgatttt aaagaagatg gaaacattct tggacacaaa      420
ttggaataca actataactc acacaatgta tacatcatgg cagacaaaca aaagaatgga      480
atcaaagtta acttcaaaat tagacacaac attgaagatg gaagcgttca actagcagac      540
cattatcaac aaaatactcc aattggcgat ggccctgtcc ttttaccaga caaccattac      600
ctgtccacac aatctgccct ttcgaaagat cccaacgaaa agagagacca catggtcctt      660
cttgagtttg taacagctgc tgggattaca catggcatgg atgaactata caataataa       720
```

ENGINEERING DNA ASSEMBLY IN VIVO AND METHODS OF MAKING AND USING THE REVERSE TRANSCRIPTASE TECHNOLOGY

RELATED APPLICATIONS

This application claims the benefit under 35 U.S.C. § 119(e) of U.S. provisional application No. 61/882,871, filed Sep. 26, 2013, and U.S. provisional application No. 62/013,305, filed Jun. 17, 2014, which are herein incorporated by reference in their entirety.

GOVERNMENT SUPPORT

This invention was made with government support under Grant No. N000014-13-1-0074 awarded by the Office of Naval Research. The government has certain rights in this invention.

BACKGROUND OF THE INVENTION

DNA represents one of the most investigated biological materials because of its ability to store the genetic information of living cells. Over the past few years, the use of the physical properties of nucleic acid has been proposed for nanotechnology applications.[1,2] Self-assembly of artificial DNA-based branched junctions, such as cross-over[3] and paranemic cross-over[4] hybridization patterns, has been utilized as a key element for the creation of nanoarchitectures. This approach has generated double cross-over tiles that include sticky-ends of appropriate complementarity for the self-assembly of 2D, 3D and tube nanostructures.[5-7] Another rapidly-developing paradigm for the self-assembly of DNA nanostructures involves the 2D origami approach.[8] According to this method, a very long viral DNA, e.g., the cyclic M13 phage, is stapled by a many short ssDNAs into the desired structure having dimensions typically around 100× 100 nm. While this method was extended to allow the formation of 3D DNA structures[9-10] utilizing various software packages developed to predict the desired nanostructure, each new DNA scaffold in origami structures was required to be redesigned with a new set of staple DNA strands. This constraint was overcome by the creation of a pool of DNA bricks with the ability to be self-organized into various 3D nanostructures without the viral DNA template.[11] In parallel to nanostructure development, the use of DNA for nanomachineries[12-13] has also been intensively developed, e.g., walker[14-16], tweezers[17-18] and gear[19]. Moreover, the use of catalytic nucleic acid (DNAzyme)[20-21] and the strand displacement process[22-23] has been used for computing, e.g., logic circuits. Various applications have been suggested for this field, such as the use of the DNA nanostructure as scaffolds for the organization of materials[24] and for the synthesis of organic elements.[25-26] The capability to program the arrangement of nanoparticles[27] and to control dynamically their plasmonic properties have been also suggested for applied physics.[28] Few biological applications, such as drug delivery based-DNA nanostructures[29], DNA nanostructures carrying active payloads interacting with the cell-membrane[30-31] or intracellular sensors based on the delivery of DNA tweezers have been suggested.[32] However, the encoded DNA assembly information remains outside the genetic record of the cell thereby losing structural information during cellular division and duplication. Also, the cost to generate such elements at high scale limits industrial applications and the possibility to produce nanostructures requiring long ssDNA (>100 bases) represent an obstacle due to the limitation in oligonucleotide synthesis.

SUMMARY OF THE INVENTION

Aspects of the disclosure relate to a method for synthesizing a single stranded ssDNA oligonucleotide in a cell that expresses a reverse transcriptase and a functional template having a non-coding tRNA structure at the 3' end and a coding RNA sequence at the 5' end, where the non-coding tRNA structure is capable of initiating transcription of the coding RNA sequence using the reverse transcriptase to produce the ssDNA oligonucleotide in the cell. In some embodiments, the ssDNA oligonucleotide is expressed in a bacterial cell, a yeast cell, an insect cell, a mammalian cell, a plant cell or an algal cell. In some embodiments, the bacterial cell is *E. coli*. In some embodiments, the microorganism is a DH10β strain. In some embodiments, the cell lacks intracellular exonuclease activity. In some embodiments, an amplifier is expressed in the cell. In some embodiments the amplifier is MLRT. In some embodiments the cell expresses at least one, two, three, four, five, six, seven, eight, nine, or ten reverse transcriptases. In some embodiments the reverse transcriptase is HIVRT. In some embodiments HIVRT comprises p66 linked to p51. In some embodiments, the p66 domain includes an N-terminal finger, palm and thumb domain. In some embodiments, the non-coding tRNA structure is tRNA$^{Lys}$. In some embodiments, the ssDNA oligonucleotide includes deoxyribonucleotides and ribonucleotides. In some embodiments, the ssDNA oligonucleotide is isolated from the cell. In some embodiments, the ssDNA oligonucleotide is processed to remove the ribonucleotides. In some embodiments, the ssDNA oligonucleotide includes only deoxyribonucleotides. In some embodiments, the ssDNA oligonucleotide is used in the synthesis of a nanostructure. In some embodiments, the ssDNA oligonucleotide is used in a method of DNA origami. In some embodiments, the ssDNA oligonucleotide is 8-200 nucleotides in length. In some embodiments, the ssDNA oligonucleotide is 10-100 nucleotides in length. In some embodiments, the reverse transcriptase is expressed under the control of an inducible promoter. In some embodiments, the functional template is expressed under the control of an inducible promoter.

Other aspects of the disclosure relate to a microorganism having plasmids that confer the ability of the microorganism to synthesize a ssDNA oligonucleotide in vivo where a first plasmid has a first nucleic acid encoding a reverse transcriptase under the control of a first promoter and a second plasmid has a second nucleic acid encoding a functional template under the control of a second promoter where the a functional template has an RNA molecule with a non-coding tRNA structure at the 3' end and a coding RNA sequence at the 5' end where the non-coding tRNA structure is capable of initiating transcription of the coding RNA sequence using the reverse transcriptase to produce a ssDNA oligonucleotide. In some embodiments, the microorganism has a third plasmid with a third nucleic acid encoding a second reverse transcriptase. In some embodiments, the microorganism is selected from the group consisting of a bacterium, a yeast cell, an insect cell, an algal cell and a plant cell. In some embodiments, the second reverse transcriptase is MLRT. In some embodiments, the microorganism lacks intracellular exonuclease activity. In some embodiments, the microorganism is a DH10β strain. In some embodiments, the reverse transcriptase is HIVRT. In some embodiments, the HIVRT comprises p66 linked to p51. In some embodiments, the p66 domain includes an N-terminal finger, palm and thumb domain. In some embodiments, the non-coding tRNA structure is tRNA$^{Lys}$. Other aspects of the disclosure relate to methods for making a nucleic acid nanostructure by synthesizing a set of ssDNA oligonucleotides in a cell and subjecting the set of ssDNA oligonucleotides to conditions to promote DNA-directed self-assembly where the DNA-directed self-assembly produces a nucleic acid nanostructure. In some embodiments, the set of ssDNA oligonucleotides is synthesized in the cell by transforming the cell with at least one first nucleic acid encoding a reverse transcriptase under the control of a first promoter and transforming the cell with at least one second nucleic acid encoding a functional template under the control of a second promoter, where the functional template has an RNA molecule having a non-coding tRNA structure at the 3' end and a coding RNA sequence at the 5' end, where the non-coding tRNA structure is capable of initiating transcription of the coding RNA sequence using the reverse transcriptase to produce the ssDNA oligonucleotide. In some embodiments, the ssDNA oligonucleotides are isolated from the cell and purified. In some embodiments, the cell is transformed with between 1 and 5 additional nucleic acids, each additional nucleic acid encoding an additional functional template under the control of a suitable promoter. In some embodiments, the first promoter is a constitutive promoter and the second promoter is an inducible promoter. In some embodiments the first promoter and second promoter are inducible promoters. In some embodiments the first promoter and second promoter are constitutive promoters. In some embodiments, the second promoter is a constitutive promoter and the first promoter is an inducible promoter. In some embodiments at least one of the additional promoters is an inducible promoter. In some embodiments at least two of the additional promoters is an inducible promoter. In some embodiments the inducible promoter is an arabinose (ara) promoter. In some embodiments, the constitutive promoter is a Lac promoter. In some embodiments the conditions to promote DNA-directed self-assembly involve applying one or more regulators to the cell to promote synthesis of ssDNA oligonucleotide at a time appropriate for adding each ssDNA oligonucleotide to the nanostructure. In some embodiments, the nanostructure is made by DNA origami. In some embodiments the nanostructure is a nanorobot. In some embodiments, there is an additional biomineralization step using the DNA to nucleate, grow and assemble into inorganic material encompassing nanoparticles. In some embodiments, the inorganic material encompassing nanoparticle is a silver nanoparticle. In some embodiments, the biomineralization step is performed in vivo. In some embodiments, the method includes regulating the shape of the nanostructure by adding an external element. In some embodiments the external element is an added nucleic acid, an added small molecule, or a pH change. In some embodiments the added nucleic acid is a long strand DNA molecule. In some embodiments the added small molecule is an aptamer. In some embodiments, the nanostructure includes a functional nucleic acid. In yet another embodiment, the functional nucleic acid is a zinc-finger sequence or an aptamer. It should be appreciated that any of the disclosed nucleic acid nanostructure embodiments may be a DNA-RNA hybrid nanostructure.

Aspects of the disclosure relate to a method of performing multiplex automated genome editing by synthesizing a ssDNA oligonucleotide in a cell with a genome and causing the ssDNA oligonucleotide to integrate into the genome in order to perform multiplex automated genome editing. In some embodiments, the ssDNA oligonucleotide is synthesized in the cell by transforming the cell with at least one nucleic acid encoding a functional template under the control of a first promoter, where the functional template comprises an RNA molecule with a non-coding tRNA structure at the 3' end and a coding RNA sequence at the 5' end, where the non-coding tRNA structure is capable of initiating transcription of the coding RNA sequence using the reverse transcriptase to produce the ssDNA oligonucleotide. In some embodiments, the cell is transformed with a nucleic acid encoding a reverse transcriptase under the control of a second promoter. In some embodiments, the cell is transformed with a nucleic acid encoding a beta protein capable of integrating the ssDNA oligonucleotide into the genome of the cell under the control of a third promoter. In some embodiments, the cell is subjected to a temperature change to cause the ssDNA oligonucleotide to integrate into the genome. In some embodiments, the ssDNA oligonucleotide introduces a mutation of at least one nucleotide into the genome of the cell. In some embodiments, the ssDNA oligonucleotide introduces at least one additional nucleotide into the genome of the cell. In some embodiments, the ssDNA oligonucleotide is designed to remove at least one nucleotide from the genome of the cell.

Aspects of the invention relate a method of modulating gene expression in a cell by synthesizing a DNA oligonucleotide in the cell, where the DNA oligonucleotide is a regulatory oligonucleotide and causes the cell to modulate gene expression with the DNA oligonucleotide. In some embodiments, the DNA oligonucleotide is synthesized in the cell by transforming the cell with at least one nucleic acid encoding a functional template under the control of a first promoter, where the functional template comprises an RNA molecule having a non-coding tRNA structure at the 3' end and a coding RNA sequence at the 5' end, where the non-coding tRNA structure is capable of initiating transcription of the coding RNA sequence using the reverse transcriptase to produce the DNA oligonucleotide. In some embodiments, the cell is transformed with a nucleic acid encoding a reverse transcriptase under the control of a second promoter. In some embodiments, the DNA oligonucleotide is a scaffold capable of binding to at least one DNA binding protein and at least one transcriptional activator protein or transcriptional repressor protein. In some embodiments, the DNA oligonucleotide is an antisense oligonucleotide.

Aspects of the disclosure relate to a_method for promoting altering a biological pathway in a cell by synthesizing a ssDNA oligonucleotide in a cell, where the ssDNA oligonucleotide has at least one protein binding site, and where the ssDNA oligonucleotide alters a biological pathway. In some embodiments, a set of ssDNA oligonucleotides is synthesized in the cell and subjected to conditions to promote DNA-directed self-assembly, where the DNA-directed self-assembly produces a nucleic acid nanostructure and where the nucleic acid nanostructure includes at least two protein binding sites and where a nucleic acid divider separates the at least two protein binding sites. In some embodiments, the protein binding site is a zinc finger binding site. In some embodiments, the ssDNA oligonucleotide is synthesized in the cell by transforming the cell with at least one nucleic acid encoding a reverse transcriptase under the control of a first promoter, and at least one nucleic acid encoding a functional template comprising an RNA molecule having a non-coding tRNA structure at the 3' end and a coding RNA sequence at the 5' end under the control of a second promoter, where the non-coding tRNA structure is capable of initiating transcription of the coding RNA sequence using the reverse transcriptase to produce the ssDNA oligonucleotide. In some embodiments, the cell is transformed with a nucleic acid encoding a chimera of a biosynthetic enzyme and a zinc finger domain. In some embodiments, the biological pathway is altered in the same cell in which the ssDNA oligonucleotide is made. In some embodiments, the ssDNA oligonucleotide or nanostructure made from the set of ssDNA oligonucleotides is isolated from the cell and used to alter a biological pathway in a second cell. In some embodiments, at least two proteins in a biosynthetic pathway can dock to the protein binding sites, and where the altered pathway is a biosynthetic pathway. In some embodiments, the method involves promoting a biosynthetic pathway. In some embodiments, the biosynthetic pathway is a pathway involved in synthesis of a specialty chemical such as a biodegradable plastic, a biofuel, or a therapeutic molecule such as an anticancer agent or an antimicrobial agent. In some embodiments, the method involves altering intracellular signaling pathways. In some embodiments, the method involves altering protein processing. In some embodiments, the protein processing is protein folding, protein degradation, or post-translational modifications. In some embodiments, the cell is a microorganism.

Aspects of the disclosure relate to a kit having a container housing a first plasmid with a first nucleic acid encoding a reverse transcriptase under the control of a first promoter and a container housing a second plasmid having a second nucleic acid encoding a functional template having an RNA molecule with a non-coding tRNA structure at the 3' end and a coding RNA sequence at the 5' end under the control of a second promoter, where the non-coding tRNA structure is capable of initiating transcription of the coding RNA sequence using the reverse transcriptase to produce an ssDNA oligonucleotide.

Aspects of the disclosure relate to a nucleic acid nanostructure having a set of oligonucleotides with of a chimeric DNA-RNA structure, where the set of oligonucleotides is arranged into a three-dimensional structure. In some embodiments, the set of oligonucleotides is composed of identical oligonucleotides. In some embodiments, the set of oligonucleotides is composed of oligonucleotides having two-six different sequences. In some embodiments, the nanostructure includes at least one oligonucleotide that is an all DNA oligonucleotide. In some embodiments, the set of oligonucleotides includes at least two protein binding sites and where a nucleic acid divider separates the at least two protein binding sites. In some embodiments, the nanostructure is a nanorobot. In some embodiments, the nanostructure is a nanotube. In some embodiments, the nanostructure is an inorganic material encompassing nanoparticle. In some embodiments, the nanostructure is a silver nanoparticle. In some embodiments, the nanostructure includes a functional nucleic acid. In some embodiments, the functional nucleic acid is a zinc-finger sequence or an aptamer.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. The details of one or more embodiments of the invention are set forth in the accompanying Detailed Description, Examples, Claims, and Figures.

Other features, objects, and advantages of the invention will be apparent from the description and from the claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows she pipeline for the generation of DNA assembly in vivo using the reverse transcriptase process through the synthesis of ssDNA. FIG. 1B shows the natural HIV reverse transcriptase structural binding site to its engineered synthetic binding site for the activation of the RT process in bacteria. In its natural configuration, the HIV reverse transcriptase (HIVRT) involves the formation of the t-RNA$^{LYS}$-vRNA complex used as the protein binding site (PBS) and the primer for the initiation of the RNA-dependent polymerase. While, the synthetic HIVRT binding site is incorporated into the terminator part of the non-coding RNA reverse transcriptase substrate (RTBS) based on the natural t-RNA$^{LYS}$-vRNA complex. FIG. 1C shows the measurement of terminator strength for variations where different poly-U tails are placed after the hairpin (and corresponding poly-As prior to the hairpins). Various modifications to the hairpin are also tested that either remove a loop or mutate the sequence to remove a bulge (c*). The "no A/U" is the initial version from the native t-RNA$^{LYS}$ and the c* variant is what is referred to as the RTBS part. The knockdown in RFP expression corresponds to the experiments shown in Example 4. To account for different baseline expression levels associated with terminator modifications, the RFP fluorescence is normalizing by the fluorescence measured in the absence of HIVRT. Data shown represent the averages of three independent experiments performed on different days. FIG. 1D shows the scheme for the use of HIVRT to knockdown gene expression. In the absence of HIVRT, the RFP gene can be expressed. When HIVRT is expressed from the constitutive BBa_JE3102 promoter, the RBS is blocked by DNA and RFP cannot be expressed. FIG. 1E shows the percentage of RFP expression in different gene knockdown models. The left set of bars are a control containing a strong terminator (BBa_B0054) and the right set of bars are for the RTBS. The data was measured and processed as in Example 4. FIG. 1F shows a cartoon illustrating the mechanism for the creation of ssDNA in e-coli. The genetic circuit includes two main parts: the RT and its non-coding RNA substrate part (r_oligo). The r_oligo part includes the non-coding RNA terminated by the RTBS part at its 3' end leading to the association of the HIVRT (p66/p51) and the initiation of the RNA-dependent polymerase process. This is followed by the MLRT and HIVRT DNA-dependent polymerase forming a DNA/RNA complex. Finally, the RNAse H activity eliminates the RNA from the DNA/RNA complex releasing the ssDNA as the output of the genetic circuit. FIG. 1G shows a schematic presentation of the genetic circuits studied for the generation of ssDNA (left panel) and their appropriate gel electrophoresis results (right panel). These systems consist of two main parts: the r_oligo part and combinations of RTs. A 189 bases non-coding RNA substrate is engineered on a pLACI inducible promotor (IPTG stimuli) and terminated with the RTBS motif on a p15A plasmid, JEO_0. Combination of RTs are introduced under constitutive promotor (J23102): (i) only the MLRT on a pSC101 origin plasmid, pJEMLRT; (ii) only the p66 on a ColE1 origin plasmid, pJEHIV_1; (iii) the p66 on a ColE1 origin plasmid and the MLRT on a pSC101 origin plasmid, pJEHIV_1 and pJEMLRT, respectively; (iv) the p66 and p51 under a single promotor (J23102) under a ColE1 origin, pJEHIV_2; (v) All the RTs, the p66 and p51 on ColE1 plasmid and the MLRT on a pSC101 plasmid, pJEHIV_2 and pJEMLRT. All the experiment results are ssDNA conjugated to the RTBS, purified from cell grows in the presence of 1 mM IPTG and after incubation with RNAse A (See Example 1). FIGS. 1H and 1I show the r_oligo, p66, p51 and MLRT system (pJEO_0, pJEHIV_2 and pJEMLRT) in the absence/presence of the non-coding RNA substrate, 0 mM and 1 mM IPTG, appropriately: FIG. 1H shows the isolation of the ssDNA_RTBS element under delicate RNAse A condition, FIG. 1I shows the isolation of the ssDNA under robust RNAse A condition removing the RTBS from the ssDNA. FIG. 1J shows the gel electrophoresis results for the isolation of different ssDNA sizes, 189 and 40 bases. The ladder used in all the gel results is 100 bp. All experiments have been repeated at least three times in three different days.

FIG. 2A shows the schematic presentation of the genetic program consisting of three plasmids for the assembly of a DNA nanorod: (1) The oligo plasmid—Four non-coding RNAs (r_oligos) terminated with double terminators (RTBS and B0054) constitutively induce (PROD) and on a p15A plasmid used as the substrates of the RT process, pJEO_4; (2) The initiator plasmid—the HIVRT (p66/p51) constitutively translated (J23102) on a ColE1 origin and mainly use for the initiation of the RNA-dependent polymerase process, pJEHIV_2; (3) The amplifier plasmid—MLRT constitutively induce (J23102) on a pSC101 origin, pJEMLRT. The nanostructure is composed of four ssDNAs, and each single strand forms a double cross-over junction with another strand (10 bp for each cross over less than one helix turn). For example, ssDNA 1 double cross-over ssDNA 3 and 4. FIG. 2B shows a schematic presentation of the genetic circuits controlling the generation of the different DNA motifs, all of them included pJEHIV_3, pJEMLRT and their appropriate oligo plasmid, 1-part pJEO_1, 2-part pJEO_2, 3-part pJEO_3 and 4-part pJEO_4 (left panel). The middle panel shows the gel electrophoresis results of the different assembly according to their appropriate circuits and under IPTG used as the inducer, 0 or 1 mM. The ladder used in all the gel results is 100 bp. The right panel shows the AFM images and their diameter distributions of the different DNA motifs purified from the gel electrophoresis experiments (red square marked on each gel), from a ssDNA (1-part) to the assembly of the fully DNA nanorod based on the double cross-over motifs (4-part). The dimension of the single ssDNA is 19 nm lengths with 1 nm height. The dimension of the double DNA motif is 42 nm lengths with 2 nm height. The 3-part DNA assembly can be visualized with a single "V" at it end while the 4-part have a double "V" at it ends. Bar scale in all the AFM images is 50 nm. All experiments have been repeated at least three times in three different days.

FIG. 3A shows a schematic presentation of the genetic circuit for the generation of a 3-part or a 4-part DNA assembly in a single strain. The r_oligo parts (2) are regulated under pBAD promotor while oligos 1,3 and 4 are constitutively induced, pJEO_5. The HIVRT is regulated under pLacI, and MLRT is constitutively induced under J23102, pJEHIV_3, pJEM-LRT. FIG. 3B shows gel electrophoresis results of the DNA motifs isolate from a single strain, the 3-part DNA motif and the 4-part motif. (0, 0) 0 µM L-Ara, 0 mM IPTG; (1, 0) 1 µM L-ara, 0 mM IPTG; (0, 1) 0 µM L-ara, 1 mM IPTG; (1, 1) 1 µM L-ara, 1 mM IPTG.). All experiments have been repeated at least three times on three different days.

FIG. 4 is a schematic demonstrating an embodiment of the method of the invention related to regulating gene expression.

FIG. 5 is a schematic demonstrating an embodiment of the method of the invention related to regulating gene expression.

FIGS. 6A-E are a schematic demonstrating an embodiment of the method of the invention related to regulating gene expression.

DETAILED DESCRIPTION OF THE INVENTION

DNA nanotechnology is a rapidly-developing research area in nanoscience. It includes the development of DNA nanostructures of different dimensions and their applications for nanoscale machineries and computing. However, the potential to use this technology for in-vivo applications remains a huge challenge and the bioengineering of synthetic pathways for the self-assembly of given ssDNAs within *E. coli* represents a problem yet unsolved. The invention disclosure herein, demonstrates the ability to program genetic circuits for precise self-assembly of DNA nanostructures. For example, a missing element for the activation of eukaryote retrovirus reverse transcriptases in bacteria has been identified and reformulated in a manner that enables highly efficient in vivo DNA production.

Retroviral multifunctional reverse transcriptase (RT) catalyzes the conversion of viral RNA (vRNA) to complementary DNA (cDNA) and their integrase into genomic host organisms.[37] RT processes several enzymatic activities, DNA- and RNA dependent DNA polymerase, cleavage of the RNA from the DNA/RNA complex (RNAse H), strand transfer and strand displacement synthesis.[38–40] As a therapeutic target for HIV-borne disease, RT has been subjected to intensive research, illuminating much of its structural and mechanistic properties.[41] However, retroviral RT pathways in eukaryotes have at least one missing element in bacteria. It has been discovered, according to aspects of the invention, that eukaryotic tRNA$^{Lys}$ is required in bacteria for the interaction of the reverse transcriptase with the vRNA that initiates the polymerase process and that this missing element can be reconstituted in a manner that will allow for the efficient in vivo synthesis of DNA.

Figure 1A:
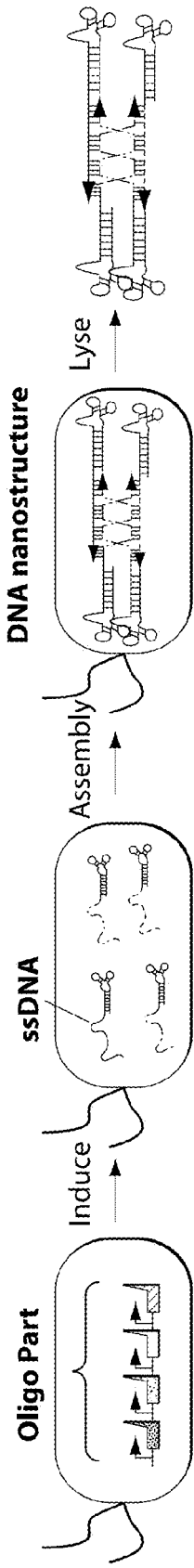
FIGS. 1A-J show the strategy for engineering DNA assembly in vivo and the characterization of the reverse transcriptase process.
Figure 1B:
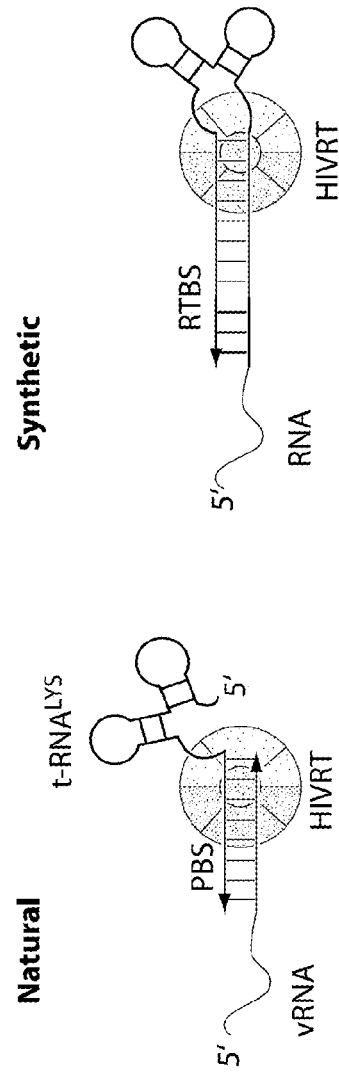

The invention described herein relates to the combination of multiple components from different organisms, eukaryote retrovirus reverse transcriptases and bacteria for the production of oligonucleotides and oligonucleotide assemblies in vivo. An example of these methods is provided schematically in FIG. 1A. Briefly eukaryote t-RNA$^{LYS}$ is conjugated with a terminator region of a non-coding targeted RNA, to produce a new element in this process, referred to herein as a functional template. The functional template serves as a reconstituted replacement for a fundamental missing element in the activation of a reverse transcriptase, such as the HIV reverse transcriptase, process in bacteria (FIG. 1B). The successful utilization of this strategy has allowed for the production of oligonucleotides, which optionally may be further manipulated to cause nucleic acid single strand cross-over assembly for the formation of various DNA nanostructures. As discussed in more detail below, the methods of the invention may be further engineered or manipulated to dictate additional internal and/or external stimuli which will fine tune the in-vivo synthesis of ssDNAs resulting in the dynamic control of the nanostructure shape and/or size and/or constitution.

Aspects of the disclosure relate to methods for producing single stranded DNA (ssDNA) oligonucleotides in a cell. The methods involve expressing at least two elements in a cell. The first element is a reverse transcriptase and the second element is a functional template. The functional template is a conjugate of a eukaryotic t-RNA$^{LYS}$ with a non-coding targeted RNA. Typically the t-RNA$^{LYS}$ is conjugated at the terminator part of the non-coding targeted RNA. The addition of the t-RNA$^{LYS}$ is sufficient to enable the activity of the reverse transcriptase in the cell to produce ssDNA oligonucleotides.

A reverse transcriptase, as used herein, is an enzyme capable of replicating RNA into a complementary DNA or cDNA. Reverse transcription involves copying an RNA template into DNA. The reverse transcriptase may be a naturally occurring reverse transcriptase enzyme, or a variant or fragment thereof that retains the desired enzymatic activity. The invention encompasses the use of any recombinantly engineered synthetic or naturally occurring reverse transcriptase enzyme that has reverse transcriptase activity. In some embodiments a reverse transcriptase is an MMLV reverse transcriptase, an AMV reverse transcriptase, an HIV reverse trascriptase or conservative variants thereof.

In some embodiments, an amplifier is also expressed in the cell. Herein, an amplifier refers to a molecule that increases ssDNA production in a cell. An amplifier may be another reverse transcriptase. For instance, the amplifier may be MLRT. Thus, in some embodiments the cell may be engineered to expresses at least one, two, three, four, five, six, seven, eight, nine, or ten reverse transcriptases or amplifiers. In some embodiments the reverse transcriptase is HIVRT. In some embodiments the HIVRT comprises p66 linked to p51. In some embodiments, the p66 domain includes an N-terminal finger, palm and thumb domain.

The reverse transcriptase acts on the functional template to produce a ssDNA oligonucleotide. The non-coding targeted RNA of the functional template may have any RNA sequence. The RNA sequence may be designed based on the desired properties of the oligonucleotide, using techniques known in the art.

A ssDNA oligonucleotide that is produced by the methods of the invention may be a fully DNA oligonucleotide or a DNA-RNA chimeric oligonucleotide. Herein, oligonucleotides refer to non-circular short single-stranded DNA or RNA molecules. Nucleotide (nt) length is measured by the number of individual nucleotides in a single stranded nucleic acid molecule. In some embodiments the oligonucleotide length is between 2 nt and 1000 nt, 2 nt and 900 nt, 2 nt and 800 nt, 2 nt and 700 nt, 2 nt and 600 nt, 2 nt and 500 nt, 2 nt and 400 nt, 2 nt and 300 nt, 2 nt and 200 nt, 2 nt and 150 nt, 2 nt and 100 nt, 2 nt and 80 nt, 2 nt and 70 nt, 2 nt and 60 nt, 2 nt and 50 nt, 2 nt and 40 nt, 2 nt and 30 nt, 2 nt and 20 nt, 2 nt and 15 nt, 2 nt and 10 nt or 2 nt and 5 nt.

The ssDNA oligonucleotide may be expressed in a variety of cell types, preferably a prokaryote. For instance microorganisms such as bacterial cells and yeast cells, as well as insect cells, mammalian cells, plant cells or algal cells may be used to produce the ssDNA oligonucleotides using the methods. In some embodiments, the bacterial cell is *E. coli*. In some embodiments, the cell is a DH10β strain.

In some embodiments, the cell lacks intracellular exonuclease activity. By reducing or eliminating the exonuclease activity of a cell, the production of the synthetic product may be enhanced. Some cells lacking intracellular exonuclease activity are commercially available. These include, for instance, the DH10β strain. Other types of cells can be manipulated to downregulate this type of intracellular exonuclease activity using routine methods known in the art.

It should be appreciated that bacteria lack the elements necessary to initiate retroviral RT activity and therefore cannot produce a ssDNA oligonucleotide from an RNA transcript. This problem has been solved by engineering a non-coding t-RNA structure at the 3' end of a functional template. In some embodiments the t-RNA structure is tRNA$^{Lys}$. In some embodiments the tRNA structure is any number of tRNA structures capable of initiating transcription using any number of reverse transcriptases. In some embodiments, the reverse transcriptase is expressed under the control of an inducible promoter. In some embodiments, the functional template is expressed under the control of an inducible promoter.

The reverse transcriptase and the functional template are expressed in the cells under the control of a promoter. "Expression" refers to the process of converting genetic information of a polynucleotide into RNA through transcription, which is catalyzed by an enzyme, RNA polymerase, and into protein, through translation of mRNA on ribosomes.

Promoters may be constitutive or inducible. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, Proc. Natl. Acad. Sci. USA, 93:3346-3351 (1996)], the tetracycline-repressible system [Gossen et al, Proc. Natl. Acad. Sci. USA, 89:5547-5551 (1992)], the tetracycline-inducible system [Gossen et al, Science, 268:1766-1769 (1995), see also Harvey et al, Curr. Opin. Chem. Biol., 2:512-518 (1998)], the RU486-inducible system [Wang et al, Nat. Biotech., 15:239-243 (1997) and Wang et al, Gene Ther., 4:432-441 (1997)] and the rapamycin-inducible system [Magari et al, J. Clin. Invest., 100:2865-2872 (1997)]. Still other types of inducible promoters which may be useful in this context are those which are regulated by a specific physiological state, e.g., temperature, acute phase, a particular differentiation state of the cell, or in replicating cells only.

In some embodiments, the cell expresses at least one, two, three, four, five, six, seven, eight, nine, ten, fifteen, twenty or thirty functional templates. The different functional templates may have different properties such as size, sequence, regulatory control. These parameters can be manipulated to regulate the output of the final ssDNA oligonucleotide as well as resultant nanostructures etc.

Once the ssDNA oligonucleotide is produced in the cell it may be used in the cell or isolated from the cell. ssDNA oligonucleotides isolated from a cell may be used for any purpose that ssDNA oligonucleotides are used for. For instance, they may be therapeutic oligonucleotides that can be administered to other cells or in vivo to a subject such as an animal or human. Alternatively they may be used in research or to build structures such as nanostructures or used in a method of DNA origami.

It should be appreciated that the ssDNA oligonucleotides described herein may be designed to produce any matter of nucleic acid based nanostructures. For example, DNA nanostructures can be used as scaffolds for the organization of bioelements. This biomaterial may control metabolic pathways by adding specific binding elements to the nanostructures, such as zinc-finger sequences or aptamers that may be added to the RTBS motif. As DNA can be used to nucleate, grow and assemble inorganic materials, e.g., silver nanoparticles, the potential to use an alternative method for controlling the biomineralization reaction of inorganic materials in vivo is disclosed herein. Additionally, these materials (e.g., silver clusters) exhibit fluorescence properties, and their use for intracellular nanosensors genetically controlled under the synthetic reverse-transcriptase process may be performed. It is possible to dynamically change and control the shape of DNA nanostructures by using an external stimulus[12-13] such as DNA, (e.g., strand displacement process), small molecule (e.g., aptamer) or pH changes (e.g., i-motif). The methods disclosed herein can be used to control dynamically intracellular metabolic processes by engineering the host bacteria to self-assemble DNA nanorobots.

The design of the eukaryotes reverse-transcriptase synthetic pathway for the synthesis of ssDNA through an RNA/DNA complex enables the engineering of a bacterium with information to assemble nanoarchitectures which may facilitate the formation of more complex DNA nanostructures, such as DNA tetrahedron[6] or nanotubes.[7] Moreover, as a bacterium can generate the cyclic M13 phage, its combination with the biological system (RT) may lead to the assembly of DNA origami. Additionally, the system generates unique elements including DNA/RNA hybrids that may be used for the development of novel structural elements.

Aspects of the disclosure relate to methods for making a nucleic acid nanostructure by synthesizing one or more ssDNA oligonucleotides in a cell and subjecting the ssDNA oligonucleotides to conditions that promote DNA-directed self-assembly to produce a nucleic acid nanostructure. In some embodiments a set of oligonucleotides is synthesized in the cell by transforming the cell with at least one first nucleic acid encoding a reverse transcriptase under the control of a first promoter, and transforming the cell with at least one second nucleic acid encoding a functional template under the control of a second promoter where the functional template comprises an RNA molecule having a non-coding tRNA structure at the 3' end and a coding RNA sequence at the 5' end, where the non-coding tRNA structure is capable of initiating transcription of the coding RNA sequence using the reverse transcriptase to produce the ssDNA oligonucleotide. In some embodiments, the ssDNA oligonucleotides are isolated from the cell and purified. In some embodiments, the cell is transformed with between 1 and 5 additional nucleic acids, each additional nucleic acid encoding an additional functional template under the control of a suitable promoter. In some embodiments, the first promoter is a constitutive promoter and the second promoter is an inducible promoter. In some embodiments the first promoter and second promoter are inducible promoters. In some embodiments the first promoter and second promoter are constitutive promoters. In some embodiments, the second promoter is a constitutive promoter and the first promoter is an inducible promoter. In some embodiments at least one of the additional promoters is an inducible promoter. In some embodiments at least two of the additional promoters is an inducible promoter. In some embodiments the inducible promoter is an arabinose (ara) promoter. In some embodiments, the constitutive promoter is a Lac promoter. In some embodiments the conditions to promote DNA-directed self-assembly involve applying one or more regulators to the cell to promote synthesis of ssDNA oligonucleotide at a time appropriate for adding each ssDNA oligonucleotide to the nano structure.

A DNA nanostructure is a structure made from one or more nucleic acids including oligonucleotides and longer nucleic acids and combinations thereof using one or more sticky ends of the nucleic acids to assemble a three dimensional structure driven by programmed base pairing. The term "programmed base pairing" indicates that the sticky ends of the different nucleic acids are designed to ensure interactions of specific nucleic acids through their complementary sticky ends, thus programming the position of the nucleic acid within the structure. A predetermined position indicates that the ultimate position of each nucleic acid in the structure is based on the sequence and position of its sticky ends and the sequence and position of the sticky ends of the other nucleic acid building blocks in the structure, such that the plurality of nucleic acids can only assemble in one specific way.

The methods of the invention can be used (either isolated or within the cell in which it is produced) for the nanofabrication of complex structures and useful devices, essentially of any shape, structure or size.

The nucleic acids used in generating the nanostructures typically have a core and sticky ends for building the structure. The core may include, for instance, 4 arm branch junctions, 3 arm branch junctions, double crossovers, triple crossovers, parallelograms, 8 helix bundles, 6-tube formations, and structures assembled using one or more long strands of nucleic acid that are folded with the help of smaller helper strands. The core may also include protein specific binding sites, as described in more detail below, or other regulatory or non-regulatory elements. The choice of which type of nucleic acid to use is within the level of skill in the art.

Nanostructures may be made for instance by DNA origami techniques, which are well known in the art.

The nanostructure may also be a nanorobot, which can carry out various functions within a cell.

In some embodiments, there is an additional biomineralization step using the DNA to nucleate, grow and assemble into inorganic material encompassing nanoparticles. In some embodiments, the inorganic material encompassing nanoparticle is a silver nanoparticle. In some embodiments, the biomineralization step is performed in vivo. In some embodiments, the method includes regulating the shape of the nanostructure by adding an external element. In some embodiments the external element is an added nucleic acid, an added small molecule, or a pH change. In some embodiments the added nucleic acid is a long strand DNA molecule. In some embodiments the added small molecule is an aptamer. In some embodiments, the nanostructure includes a functional nucleic acid. In yet another embodiment, the functional nucleic acid is a zinc-finger sequence or an aptamer. It should be appreciated that any of the disclosed nucleic acid nanostructure embodiments may be a DNA-RNA hybrid nanostructure.

The invention also encompasses nanostructures made according to the invention. The nanostructures may have the shape size, consistency, components of any known nanostructure but they are made by the in vivo synthesized ssDNA oligonucleotides. In some instances, the nanostructures are made from ssDNA oligonucleotides that are DNA-RNA hybrids, such that the nanostructure has both DNA and RNA components. In some instances the ssDNA oligonucleotides have DNA at one end and RNA at the other end. For instance, sometimes the RNA is at the 5' end and the DNA at the 3' end. These structures may be the building blocks of part or all of the nanostructure. For instance a nanostructure of the invention may have a single chimeric DNA-RNA oligonucleotide or be made from all chimeric DNA-RNA oligonucleotides or any variation there between.

Novel methods for regulating intracellular pathways are a promising direction for synthetic biology. In this aspect, various kinds of scaffolds for the spatial organization of proteins have been demonstrated. For example, plasmid DNA-based zinc-fingers34 and RNA scaffold-based aptamers35 have been produced for controlling intracellular metabolic pathways, e.g., for the production of mevalonate and hydrogen. The use of amino acid interactions for the assembly of peptide structures, such as polypeptide tetrahedron36, has also been intensely investigated. However, it is very difficult to control the exact dimensions of these structures and to prevent their intracellular degradations. Thus, the need to introduce new methods for the assembly of well-defined and predictable nanoelements in-vivo is required.

Thus, it should be appreciated that any one of the described nucleic acid nanostructure embodiments may be used to alter, improve, inhibit or modify a biological process. For example, a nucleic acid molecule may be used as a scaffold for alteration of biosynthetic pathways. Some aspects of the disclosure relate to a method for altering a biological pathway in a cell by synthesizing a ssDNA oligonucleotide in a cell, where the ssDNA oligonucleotide has at least one protein binding site and the ssDNA oligonucleotide alters a biological pathway. In some embodiments, a set of ssDNA oligonucleotides is synthesized in the cell and subjected to conditions to promote DNA-directed self-assembly, where the DNA-directed self-assembly produces a nucleic acid nanostructure and where the nucleic acid nanostructure includes at least two protein binding sites and where a nucleic acid divider separates the at least two protein binding sites.

The DNA oligonucleotides produced according to this embodiment of the invention include one or more protein binding sites in order to provide regulation of proteins within a cell. A number of known protein binding sites may be engineered into the DNA. Some examples of site specific DNA binding domains include but are not limited to a TAL (Transcription Activator-Like Effector) or a zinc finger binding domains. There are numerous different versions of these binding domains. DNA having one or more of these sites can be used to serve, for instance, as a DNA-guided template for assembly of biosynthetic pathways. These types of methods are described, for instance in Conrado et al Nucleic Acids Research, 2012, v. 40, p. 1879-1889. It is also desirable in some instances, to transform the cell with a nucleic acid encoding a chimera of a biosynthetic enzyme and a zinc finger domain. The biological pathway may be altered in the same cell in which the ssDNA oligonucleotide is made. Alternatively, the ssDNA oligonucleotide or nanostructure made from a set of ssDNA oligonucleotides may be isolated from the cell and used to alter a biological pathway in a second cell. In some embodiments, at least two proteins in a biosynthetic pathway can dock to the protein binding sites and where the altered pathway is a biosynthetic pathway. In some embodiments the method involves promoting a biosynthetic pathway. In some embodiments the biosynthetic pathway is a pathway involved in synthesis of a specialty chemical such as a biodegradable plastic, a biofuel, or a therapeutic molecule such as an anticancer agent or an antimicrobial agent. In some embodiments, the method involves altering intracellular signaling pathways. In some embodiments the method involves altering protein processing. In some embodiments, the protein processing is protein folding, protein degradation, or post-translational modifications. In yet other embodiments, the cell is a microorganism.

Figure 8:
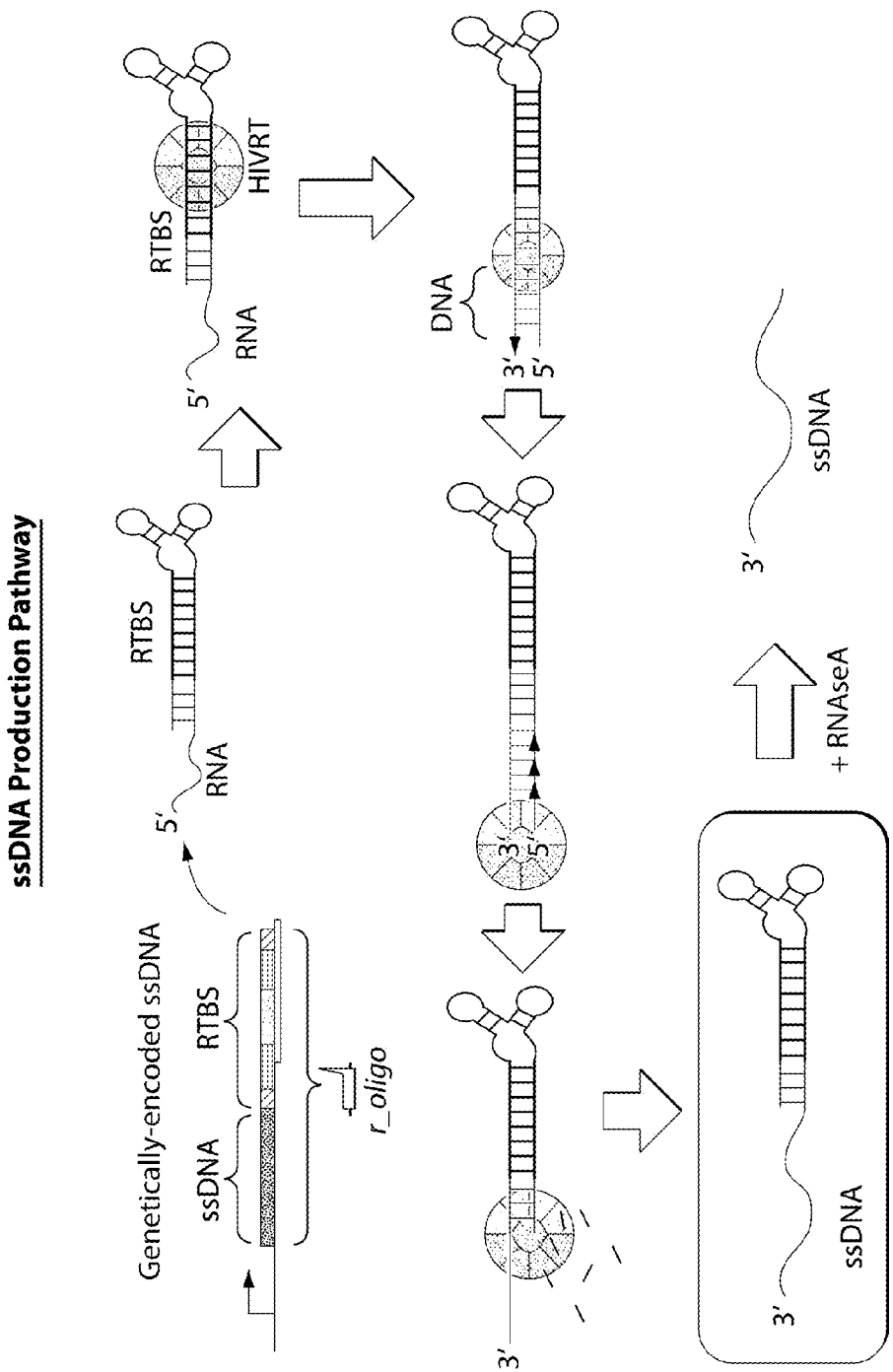
FIG. 8 is a schematic demonstrating an exemplary process of synthesizing ssDNA oligonucleotides in vivo, followed by isolation and digestion to produce a fully DNA oligonucleotide.
Figure 9A:
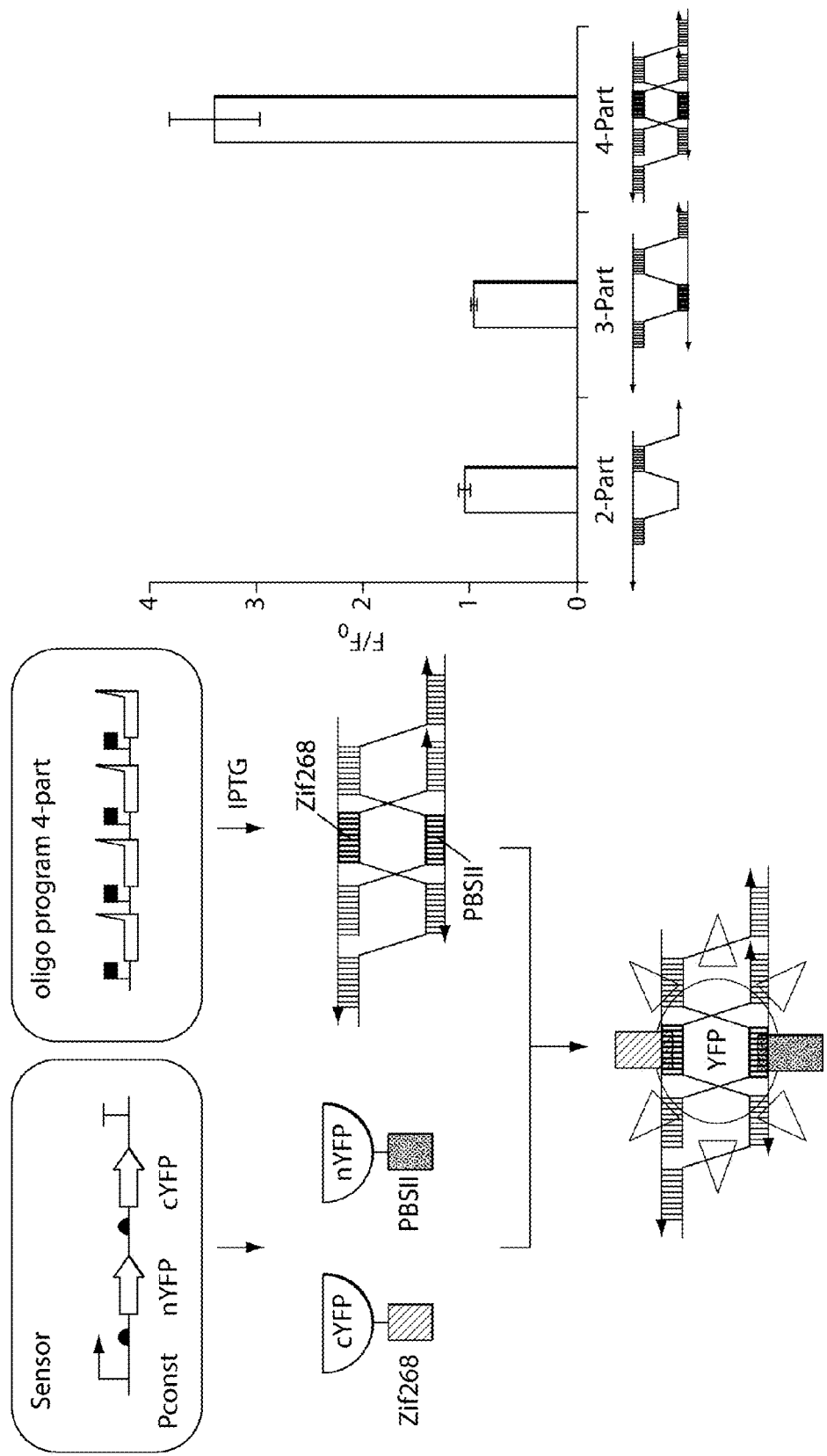
FIGS. 9A-B are a schematic demonstrating a method of the invention related to promoting a biosynthetic pathway.
Figure 9B:
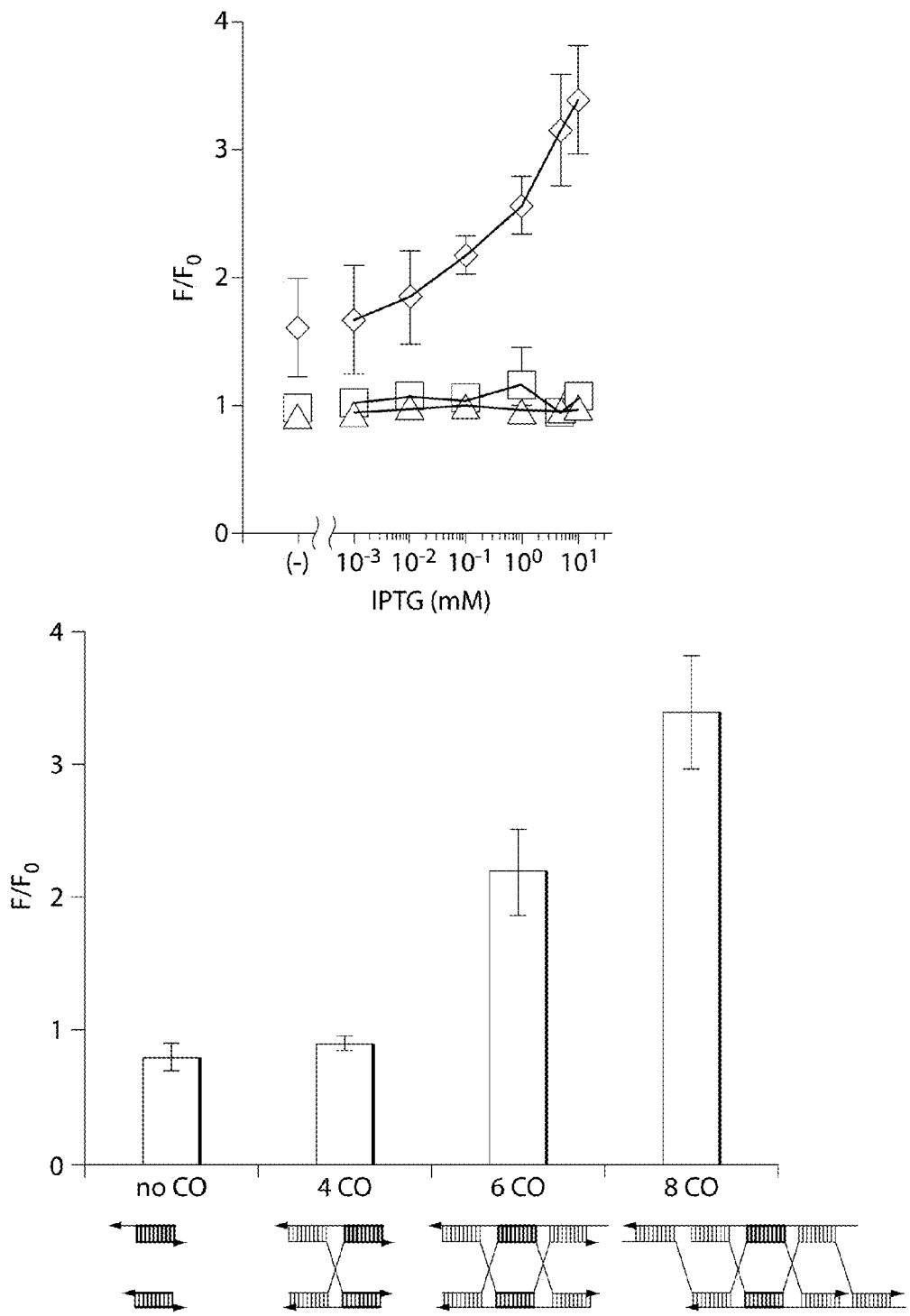
Figure 10:
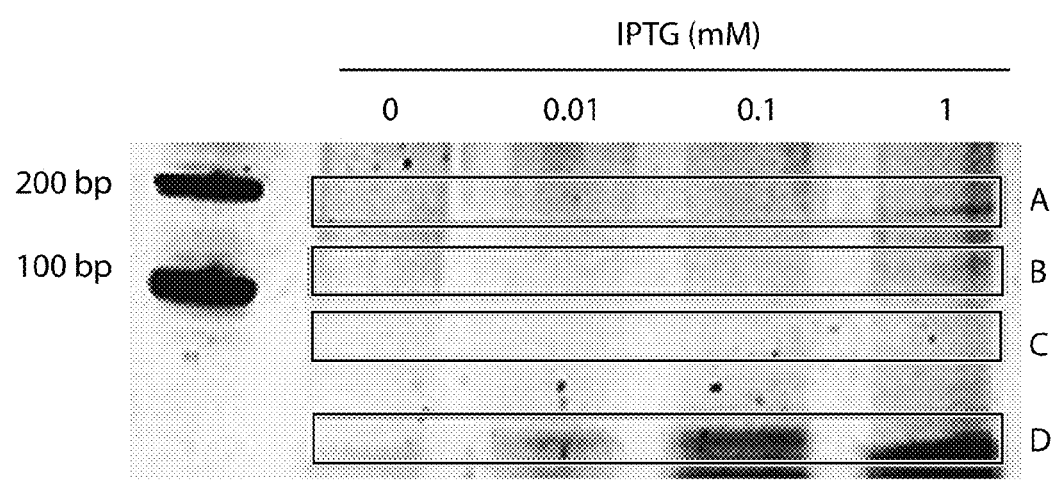
FIG. 10 shows the impact of the induction of HIVRT on the assembly of the 4-part nanowire. The expected location of the ssDNAs (D), 2-part structure (C), 3-part structure (B) and 4-part structure (A) are shown. The plasmids used for this measurement are: pO4, pHIV-pT-p66p51 and pMLRT.
Figure 11:
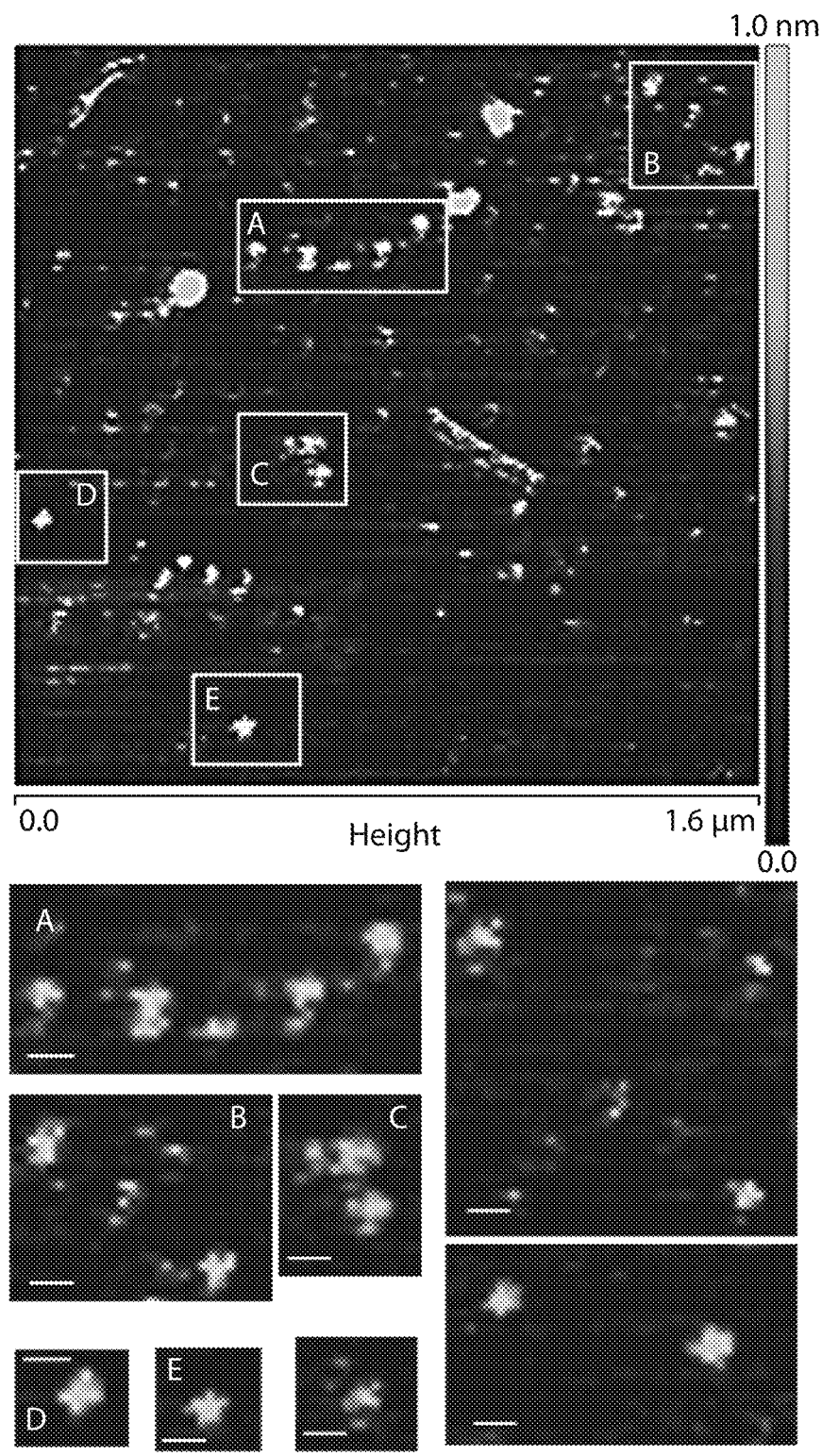
FIG. 11 shows detailed AFM images of the 4-part assembly. These images and those used for FIG. 2 were performed on different days from different starting cultures. The top panel shows large scale AFM image (1.6 µm). The bottom panels zoom into specific structures (scale bar is 50 nm). Letters correspond to regions within the larger image (no letter indicates that the detailed imImages were recorded with AFM tips (Model NSC11, Umasch, USA) and using tapping mode at their resonance frequency. The images were analyzed using NANO Scope analyzing software (Vecco, USA).

In another example the nucleic acid is used to regulate gene expression. This method enables a new mode of gene regulation. Using this technology it is now possible to repress a gene or a set of genes by expressing the functional template (i.e. terminator part, RBTS) and an RT in a cell. It is possible to modulate repression via part selection (for instance RNA secondary structure). Examples of the use of the methods of the invention for regulating gene expression are depicted in FIGS. 4-7. An example of the process of synthesizing ssDNA oligonucleotides in vivo, followed by isolation and digestion to produce a fully DNA oligonucleotide is depicted in FIG. 8. An example of a method related to promoting a biosynthetic pathway is depicted in FIG. 9.

Some aspects of the invention relate to a method of modulating gene expression in a cell by synthesizing a DNA oligonucleotide in the cell where the DNA oligonucleotide is a regulatory oligonucleotide, and causes the cell to modulate gene expression with the DNA oligonucleotide. In some embodiments, the DNA oligonucleotide is an antisense oligonucleotide.

In some embodiments, the DNA oligonucleotide is synthesized in the cell by transforming the cell with at least one nucleic acid encoding a functional template under the control of a first promoter, where the functional template comprises an RNA molecule having a non-coding tRNA structure at the 3' end and a coding RNA sequence at the 5' end, where the non-coding tRNA structure is capable of initiating transcription of the coding RNA sequence using the reverse transcriptase to produce the DNA oligonucleotide. In some embodiments the cell is transformed with a nucleic acid encoding a reverse transcriptase under the control of a second promoter. In some embodiments, the DNA oligonucleotide is a scaffold capable of binding to at least one DNA binding protein and at least one transcriptional activator protein or transcriptional repressor protein.

Aspects of the disclosure relate to a method for performing multiplex automated genome editing (MAGE). Mage is an approach to genome engineering that simultaneously targets many locations on the chromosome for modification in a single cell or across a population of cells. Using allelic replacement, a pool of targeting oligos is repeatedly introduced into a cell. MAGE can successfully introduce new genetic modifications in about 25% of the cell population, creating billions of variants every 3 hours. Not only can MAGE simultaneously modify multiple genomic locations across different length scales (i.e., from single nucleotides to whole genes), it is also possible to tune the amount of sequence change per target. This makes it possible to make specific modifications for specific outcomes or to make high-diversity modifications to explore sequence space. After allelic replacement, cells are assayed for genotype and/or phenotype analysis and the cycle repeats with the subset of cells that contain genomic sequences of interest. The MAGE device can perform up to 50 different genome alterations at nearly the same time, producing combinatorial genomic diversity.

Aspects of the disclosure relate to a method for preforming MAGE by synthesizing a ssDNA oligonucleotide in a cell having a genome and causing the ssDNA oligonucleotide to integrate in to the genome in order to perform MAGE. In some embodiments, the cell is transformed with a nucleic acid encoding a beta protein capable of integrating the ssDNA oligonucleotide into the genome of the cell under the control of a promoter. In some embodiments, the beta protein is red beta protein. In some embodiments, a protein homologous to a beta protein is expressed in the cell. In some embodiments, the cell is subjected to a temperature change to cause the ssDNA oligonucleotide to integrate into the genome. In some embodiments the ssDNA oligonucleotide introduces a mutation of at least one nucleotide into the genome of the cell. In some embodiments, the ssDNA oligonucleotide introduces at least one additional nucleotide into the genome of the cell. In some embodiments, the ssDNA oligonucleotide is designed to remove at least one nucleotide from the genome of the cell.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example 1

Materials and Methods

Strains and Media

*Escherichia coli* strain DH10β (MC1061 F-endA1 recA1 galE15 galK16 nupG rpsL ΔlacX74 Φ80lacZΔM15 araD139 Δ(ara,leu)7697 mcrA Δ(mrr-hsdRMS-mcrBC) λ-) was used for all manipulations and assays except in terminator calculator measurement where DH5α (fhuA2 lac(del)U169 phoA glnV44 Φ80' lacZ(del)M15 gyrA96 recA1 relA1 endA1 thi-1 hsdR17) was used. Cells were grown in LB Miller Broth or Super Optimal Broth (SOB). Ampicillin (100 µg/ml, Affymetrix cat. #11259 5), kanamycin (50 µg/ml, Gold Bio cat. #K-120-5) and/or Spectinomycin (100 µg/ml, MP Biomedicals cat. #021 5899305) were used where appropriate. Isopropyl β-D-1-thiogalactopyranoside (IPTG, Roche cat. #10 745 740 001) or L-arabinose (L-ara, USB Corporation #5328 37 0) inducers were used as inducers for the various constructs. Blue-white screening of colonies resulting from DNA assembly reactions was performed on LB-agar plates (1.5% Bacto agar; VWR cat. #90000-760) supplemented with 0.15 mM IPTG, 60 mg/L 5-bromo-4-chloro-indolyl-β-D-galactopyranoside (Roche cat. #10 745 740 001), and appropriate antibiotics.

DNA Constructs

All DNA sequences are provided in Tables 1-4 and key constructs will be made available via Addgene. The p66 reverse transcriptase part has been order codon optimized according to the codon bias of *Escherichia coli* genes from GeneArt, for its protein and nucleic acid sequence. p51 part represents a short sequence of p66, and then, has been generated from a PCR reaction. The murine leukemia reverse transcriptase gene is not codon optimized. The RTBS part has been order as a Gblock from Integrated DNA technology. The promoter parts, RBS, and terminator parts that entered into the pipeline were themselves constructed using standard cloning techniques including isothermal assembly[53,54] and PCR-ligation[55]. The oligo plasmids (named pJEO_# throughout) have been clone based on the golden gate method[56]. Plasmid maps are provided in FIGS. 12-20 All of the parts used in these oligo plasmids are flanked by sequences "GGAG", "TACT" "AATG", "AGGT", "TACT" and "AATG" into different plasmids (see Example 3 for more details and their plasmid maps). These four-bp sequences correspond to 5'-overhanging single-stranded cohesive ends when digested with restriction enzymes BbsI, and thus, bringing all of the parts into a single desired plasmid. The reaction condition proceeds as follows: a 1:1 concentration ration of the different plasmids (60 ngr for a 2400 bp plasmid) is mixed with 10 U BbsI (New England Biolabs, Ipswich, Mass., cat. #R0539S) and 10 U T4 DNA Ligase (NEB) in a total of 20 µl 1× Promega T4 DNA Ligase Buffer and incubated at 37° C. for 5 hours. Reactions are terminated by incubating at 50° C. for 5 min and 80° C. for 10 min. Constructed plasmids are transformed into DH10β competent cells and prepared for sequence confirmation by sequencing using standard techniques.

The 10 bp sticky regions used for the ssDNAs to build the 4-part nanostructure were designed in the following way. The starting sequence was obtained from the crossover motif[3]. From this starting point, random nucleotides were selected by eye and changed to G or C in order to decrease the hybridization free energy. Each new sequence was tested for secondary structure using NuPack[58] and the IDT oligo analyzer[57] software and problematic sequences were mutated and retested. Using the same software, sequences were analyzed for the possibility to self-dimerize or form undesired hybridization products and potential problems were alleviated by making additional mutations.

Cell Growth and Induction.

All assays for generating ssDNAs and DNA assemblies were performed in *E. coli* DH10β strains using three plasmids (pJEHIV_#, pJEMLRT and pJEO_#). Cells were inoculated in 200 µl Luria-Bertani (LB)-Miller medium (10 g/l tryptone, 5 g/l yeast extract, 10 g/l NaCl, Fisher Scientific) with 100 µg/ml ampicillin, 100 µg/ml Spectinomycin and 50 µg/ml kanamycin in a 96-well plate covered with a breathable membrane (AeraSeal, Excel Scientific) at 37° C., 1000 r.p.m. for 16 h. Overnight culture was diluted 1000-fold by mixing 10 µl culture into 10 ml of LB medium containing the appropriate inducer and incubated at 37° C., 250 r.p.m. for 18 h. After incubation, the desired ssDNAs or DNA assemblies were purified from the overnight culture using the Qiagen RNA purification protocol with a single twist (the columns used during the purification method are QIAquick Spin Columns Mat. No. 1018215). The resulting solution then incubates with RNase A (100 µgr/ml, QIAgen) in the presence of 150 mM NaCl in order to prevent the removal of the RTBS parts and without salt for the assay removing the RTBS part for 10 minutes. Then the appropriate solutions were run into 15% precast polyacrylamide gels in a Tris-borate-EDTA (TBE) buffer solution, that included Tris base (89 mM, pH=7.9), boric acid (89 mM) and EDTA (2 mM). The different samples were mixed with the loading dye, and loaded in the wells of the gel. The gels were run on Mini-PROTEAN Tetra Cell (BIO-RAD #165-8000) under a constant voltage (100 V). After electrophoresis, the gel was stained with SYBR Gold nucleic acid gel stain (Invitrogen) and imaged.

Terminator Strength Experiments.

Assays for terminator strength were performed in *E. coli* DH5α strains. Cells were inoculated in 200 µl Luria-Bertani (LB)-Miller medium (10 g/l tryptone, 5 g/l yeast extract, 10 g/l NaCl, Fisher Scientific) with 100 µg/ml ampicillin in a 96-well plate covered with a breathable membrane (AeraSeal, Excel Scientific) at 37° C., 1,000 r.p.m. for 16 h in a Digital Thermostatic Shaker DTS-4 (Elmi). Overnight culture was diluted 200-fold by mixing 1 µl culture into 199 µl of LB medium containing 10 mM L-arabinose and 100 µg/ml ampicillin. After 3 h of incubation at 37° C. and 1,000 r.p.m., 15 µl of culture was added to 185 µl of 1× PBS with 2 mg/ml kanamycin for flow cytometry.

Flow Cytometry.

Measurements were taken using the LSR Fortessa flow cytometer (BD Biosciences). The voltage gains for each detector were set so that the full dynamic range was used for a control specimen expressing GFP and RFP without any terminators in between: FSC, 700 V; SSC, 241 V; FITC, 407 V; PE-TxRed, 650 V. Compensation was set by measuring cells that express only GFP or RFP. There was no spectral overlap detected from FITC to PE-TxRed. The spectral overlap from PE-TxRed to FITC was 0.11%. Thirty thousand events gated by FSC-H and FSC-W to contain most nonaggregating live cells were collected at 0.5 µl/s sample flow rate under high-throughput mode. Data from FITC and PE-TxRed channels were extracted as the GFP and RFP data.

Flow cytometry data were analyzed using FlowJo 7.6.5 (Tree Star). FSC-A and SSC-A were used to gate live cells containing 50-70% total cells. Data were gated by forward and side scatter. The fluorescence geometric mean of the gated population was calculated, and the mean auto-fluorescence of a 'white cell' control sample was subtracted from the experimental sample's mean. The geometric means in the FITC and PE-TxRed channels were exported as the fluorescence in GFP and RFP.

Fluorescence Assay for RT Activity.

Cells were inoculated in 200 µl LB Miller Broth with antibiotics in a 96-well plate covered with a breathable membrane (AeraSeal, Excel Scientific) at 37° C. at 1,000 rpm (Innova Shaker, Eppendorf) for 16 hrs. Overnight cultures are diluted 200-fold by mixing 1 µl culture into 199 µl of LB medium containing 0.1 mM IPTG, 100 µg/ml spectinomycin and 100 µg/ml ampicillin. After 6 hrs of induction, a 10 µl aliquot of culture is prepared for cytometry by diluting it into 190 μl of 1×PBS with 2 mg/ml kanamycin. The % of RFP expression is calculated by dividing the fluorescence with the expression of HIVRT by that in the absence of HIVRT (cells containing the same plasmid, including inducible system, but lacking the HIVRT genes).

Production and Purification of DNA Nanostructures.

Cells were inoculated in 200 μl LB Miller Broth with antibiotics in a 96-well plate covered with a breathable membrane (AeraSeal, Excel Scientific) at 37° C. and 1000 rpm for 16 h. Overnight culture were then diluted 1000-fold by mixing 10 μl culture into 10 ml of LB Miller Broth containing the appropriate inducer and incubated at 37° C. and 250 rpm for 18 h. After incubation, the DNA nanostructures were purified using the following protocol: 1) Cells were centrifuged at 5000 g for 7 min at 4° C.; 2) The supernatant was removed; 3) Cells were resuspended in 200 μl of TE buffer (10 mM Tris-EDTA) containing 3 mg/mL of Lysozyme; 4) 700 μl of RLT buffer (Qiagen, #79216) was added; 5) The resulting solution was centrifuged at 15000 rpm for 2 min in order to remove the insoluble materials and the supernatant was transferred to a clean tube; 6) 500 μl of 100% ethanol was added to the supernatant; 7) 700 μl of the sample was transferred into a QIAquick Spin Column (Quiagen, #1018215) and centrifuged at 13000 rpm for 15 s; 8) Step 7 was repeated until all the supernatant solution from step 6 has passed through the same column tube (the flow through was discarded after each step); 9) 700 μl of RW1 buffer (Qiagen, #1053394) was added to the collection tube and centrifuge for 15 s at 13000 rpm (the flow through was discarded); 10) 500 μl RPE buffer (Qiagen, #1018013) was pipetted into the column tube and centrifuged for 15 s at 13000 rpm (the flow through was discarded); 11) 500 μl Buffer RPE (Mat. 1018013 Qiagen) was pipetted into the column tube and centrifuge for 2 min at 13000 rpm (the flow through was discarded); 12) The empty column tube was centrifuged for 1 min at 13000 rpm; 13) The column was placed into a clean tube and 50 μl of Elution buffer (Qiagen #19086) was added. 14) The resulting solution was then incubated with RNase A (100 μg/ml, Qiagen) in the presence of 150 mM NaCl[65] to recover the DNA-RNA chimera or without salt to recover just the ssDNA. The purified DNA solutions are then run on a 15% non-denaturing precast polyacrylamide gel (15% Mini-PROTEAN® TBE Precast Gel #456-5053, BIO-RAD) in a Tris-borate-EDTA (TBE) buffer solution, that included Tris base (89 mM, pH=7.9), boric acid (89 mM) and EDTA (2 mM). The different samples were mixed with the loading dye and loaded in the wells of the gel. The gels were run on Mini-PROTEAN Tetra Cell (BIO-RAD #165-8000) under a constant voltage (100 V). After electrophoresis, the gel was stained with SYBR Gold nucleic acid gel stain (Invitrogen) and imaged. The band at the correct size was excised and page purified. The ladder used was 100 bp (New England Biolabs, Mat. N3231L). The gel images were analyzed using ImageJ. All the images have been inverted. The bands have been selected and converted to plot (plots lane function). The different surfaces under the plots (representing the assemblies) have been selected and converted to intensity using the wand tracing tool. The background of the gel intensity have been calculated and subtracted from all the intensities values.

PAGE Purification.

The excised gel slice was incubated in 400 μl RNA Recovery Buffer (ZYMO Research CORP., R1070-1-10) at 65° C. for 15 min. The resulting solution was then placed into a Zymo-Spin IV Column (ZYMO Research CORP., C1007-50) and centrifuged at 10000 rpm for 30 seconds. The flow-through was then transferred into a tube including a 5× volume of buffer PB (QIAgen) and 700 μl of the resulting solution was transferred into QIAquick Spin Columns (QIAgen, Mat. No. 1018215) and centrifuged at 10000 rpm for 30 s. This was repeated until all the solution passes through the column and the flow through was discarded. Then, 750 μl of PE buffer (QIAgen) was added to the column and centrifuged at 10000 rpm for 30 seconds, the flow through discarded, and the empty column centrifuged at 10000 rpm for 1 min to remove residual PE buffer. The column was placed in a clean tube and the DNA was eluted by adding 50 μl of EB buffer (10 mM Tris-C1, pH 8.5) followed by centrifugation at 10000 rpm for 1 min.

Determination of Nanostructure Titer.

The presented titer is the total amount of nanostructures that can be purified from a culture of defined volume and expression time. A 10 ml culture was grown for 18 hours and the DNA nanostructures were purified as described above. The DNA concentration was measured by measuring the absorbance (OD 260) using a ND-1000 Spectrophotometer Nanodrop. The absorbance value was converted to ng/μl using the Nanodrop software. The total weight of the nanostructures was then divided by the culture volume. To determine the total amount of material lost during purification, a control experiment was run by using a synthesized 60 nt oligo (3.2 μg) (ordered from IDT) of known quantity that was then purified.

AFM Assays

Atomic force microscopy (AFM) measurements were performed at room temperature using Dimension 3100 D31005-1 with Nanoscope V (Veeco). AFM images were recorded on freshly cleaved mica surfaces (TED PELLA, Inc., U.S.A.). Samples were prepared by the deposition of a 10 μL of the respective nanostructure solutions in the presence of 10 mM Mg(Ac)$_2$. The dried samples were rinsed with 10 mM Mg(Ac)$_2$ solution, and dried under a stream of air. Images were recorded with AFM tips (Model RTESP, Part MPP-11100-10, BRUKER, USA) using tapping mode at their resonance frequency. The images and distributions were analyzed using NANO Scope analyzing software (Vecco, USA). The nanostructures chosen for the diameter histograms evaluations have been auto-selected and analyzed using NANO Scope analyzing software (Vecco, USA). More specifically, all the particles with a minimum height of 0.5 nm and a maximum of 3 nm have been auto-selected from the AFM images, and added into the histogram results.

Images

Gel Images have been analyzed using ImageJ. The relative intensity (RI) parameter has been calculated as followed: RI=I/Imax, Imax represents the maximum intensity of the appropriate band measured in the gel.

Example 2

Mechanism and Identification of the Reverse Transcriptase

Figure 1C:
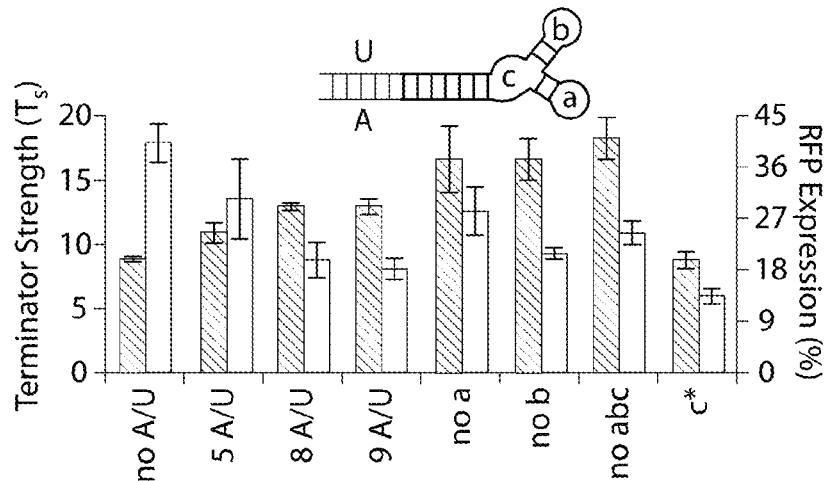
Figure 1D:
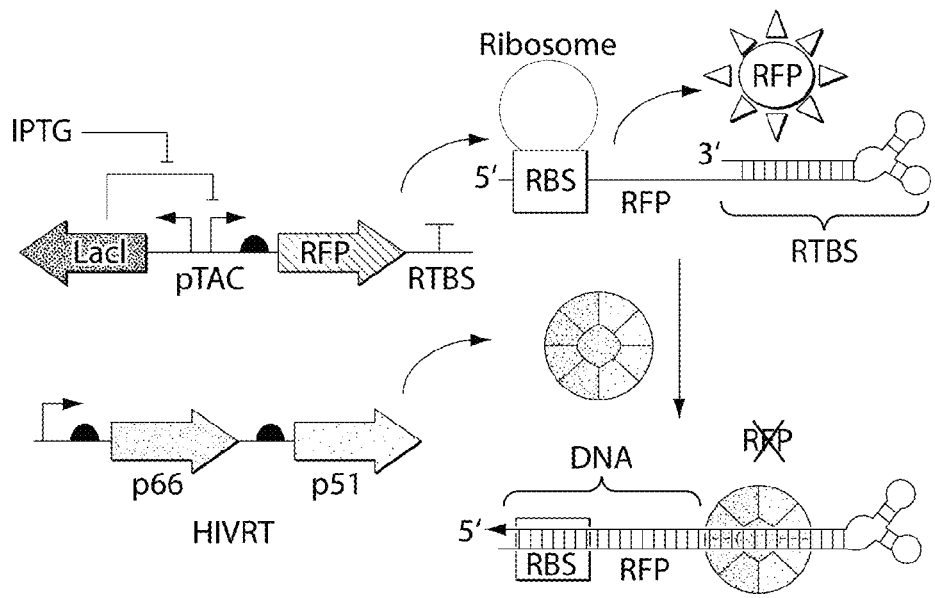
Figure 1E:
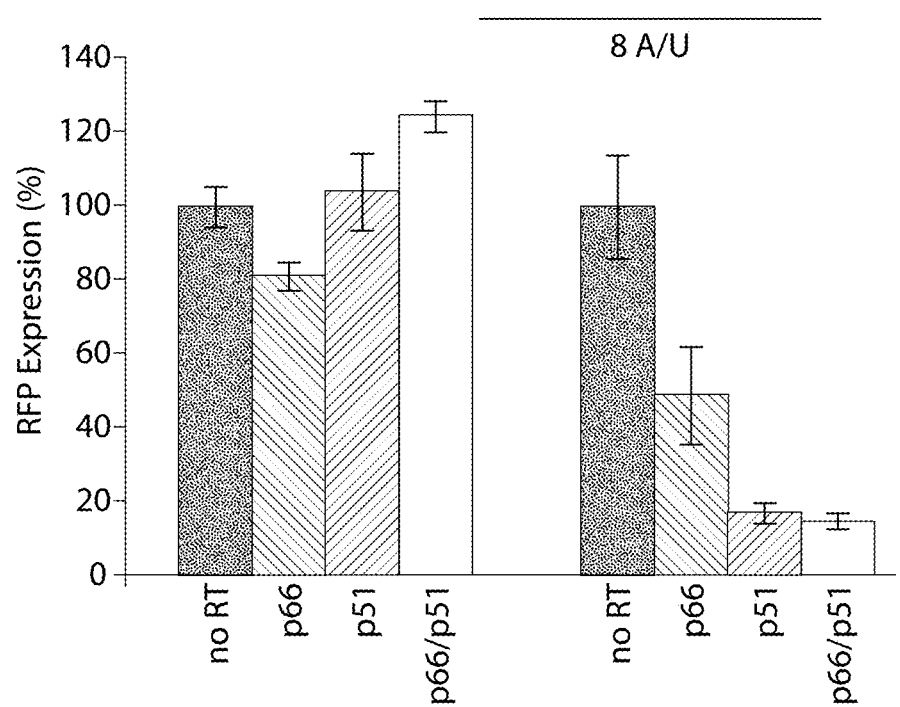
Figure 1F:
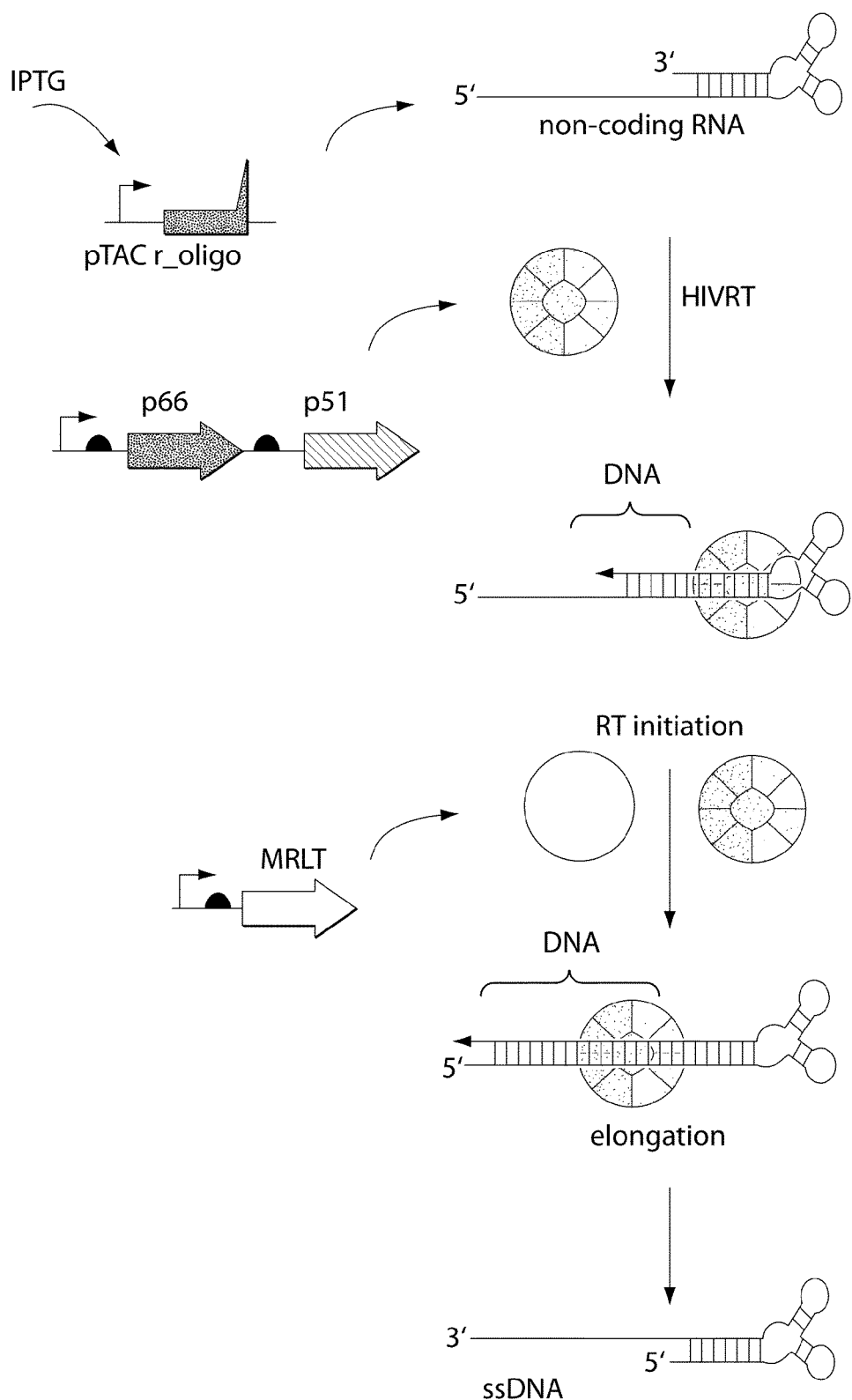

FIG. 1F illustrates the synthetically-engineered pathway for the generation of ssDNA in *E. coli*. The construct consists of two main parts: the reverse transcriptase and a non-coding RNA (ncRNA) used as the template for the RT process. One of the reverse transcriptase used in the system is the HIV reverse transcriptase. The HIV reverse transcriptase is a heterodimer consisting of the p66 and p51 subunits.[45] The p66 includes two parts, the N-terminal polymerase domain (440 residues) containing three subdomains (the finger, the palm and the thumb) and the C-terminal RNase H domain (120 residues). The p66 includes another subdomain (the connection) connecting the hand of the polymerase and the RNase H. This structural motif provides flexibility within this enzyme and facilitates the switching between its various enzymatic activities.[46] The p51 subunit (450 residues) was created by a post-translational modification where the C-terminus of the polyprotein, p66/p66 homodimer, was cleaved while remaining with the polymerase domain of the p66 subunit and lacking the RNAse H activity. While the polymerase domain is included within its sequence, the p51 subunit is mainly responsible for stabilizing the p66 subunit within the vRNA.[47] In order to initiate the RT process through the RNA-dependent polymerase activity, the formation of a precise t-RNA$^{LYS}$/ncRNA is required,[43-44] the protein binding part (PBS), allowing the binding of the HIV-RT to the RNA complex, and also used as the primer. Because the eukaryotes t-RNA$^{LYS}$ element is missing in E. coli, the PBS motif to be the terminator of the non-coding RNA (RTBS) was engineered. This method provides an important advantage, by selectively reverse transcripting only the desired RNA, thus, eliminating the possible cross-talk of a free t-RNA$^{LYS}$ with other intracellular RNAs. The termination straight (TS) of the RTBS was experimentally calculated to be 8.74±0.6 using the terminator calculator[48]. Due to the slow initiation polymerase process of HIV reverse transcriptase,[49] resulting in the inefficiency ssDNA production, the system was introduced to the murine leukemia RT (MLRT, 665 residues) as a DNA-dependent polymerase and RNAse H amplifier. It should be noted that the ssDNA remains conjugated with the RTBS as the final product of the RTs process.

In order to prove the mechanism of the synthetic RT pathway, FIG. 1F, three plasmids were engineered, one for transcripting the r_oligo part under a pLacI promoter and the two others with the RTs (HIV and murine leukemia) each located on a different plasmid and translate under a constitutive promoter. Different reverse transcriptase systems were combined. The ssDNA product was isolated from each system and analyzed it under gel electrophoresis experiments (see Methods for the purification protocol developed). As shown, no ssDNA is produced in the presence of the MLRT alone, which proves the selectivity of the RTBS (t-RNA$^{LYS}$) to the HIV-RT and that the HIV-RT first initiates the RNA-dependent polymerase process. A twofold increase in ssDNA production is observed by the addition of the MLRT to the HIV-RT system demonstrating that the MLRT is used as an amplifier element. The presence of the p51 subunit to the p66-MRT system increases the ssDNA production threefold, due to the higher binding affinity of the p66/p51 complex with the ncRNA substrate[46], and thus, increasing the velocity of the initiation process. Furthermore, by engineering the ncRNA to be transcribed under an inducible promoter, the control of the ssDNA output under external stimulus (IPTG) and more generally under genetic circuits is demonstrated, FIG. 1H. This result proved the specific activation of the RT process on a dictated RNA while unspecific RT processes are not observed. By purifying the product under specific conditions (see experimental section), it was shown that the ssDNA is conjugated with the RTBS motif, FIG. 1I, as a lower shift on the band appear by removing the RTBS from the DNA. Another important capacity needed to be introducing to the system is the possibility to control precisely the length of ssDNA, FIG. 1J. This have been achieved and demonstrated by cloning different sizes of the ncRNA substrates (40 and 189 bases), thus, reverse transcripting different size of ssDNAs. This phenomena overcomes the limitation of in-vitro oligos synthesis (<100 bases), and will enable the assembly of more complex DNA nanostructures in the future. It should be noted that all the experiments have been done in DH1β strain, which lacks the intracellular exonuclease activity, thus, preventing the degradation of the ssDNA.

Example 3

Programming Assembly of DNA Nanostructure in Bacteria

Figure 2A:
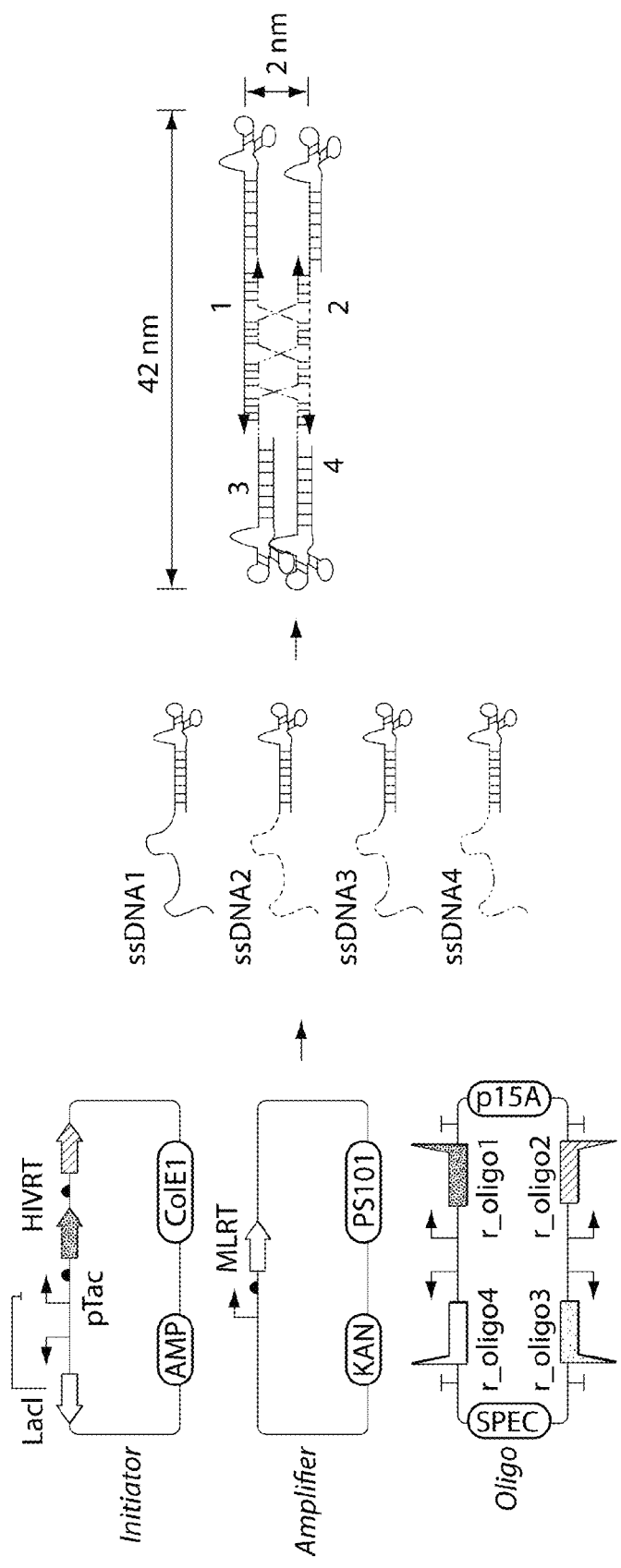
FIGS. 2A-B show genetic circuits programmed by the assembly of a DNA nanorod.
Figure 17:
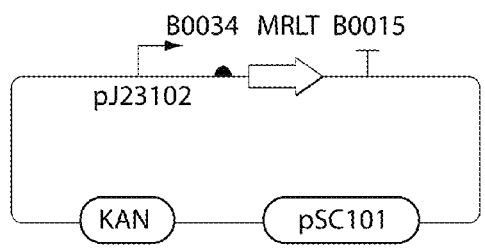
FIG. 17 shows a murine leukemia reverse transcriptase plasmid map. This plasmid is referred to as the "Amplifier" in FIG. 2A. Part sequences are provided in Tables 1-4. Parts beginning with "B" and promoter J23102 are from the Registry of Standard Biological Parts.
Figure 19:
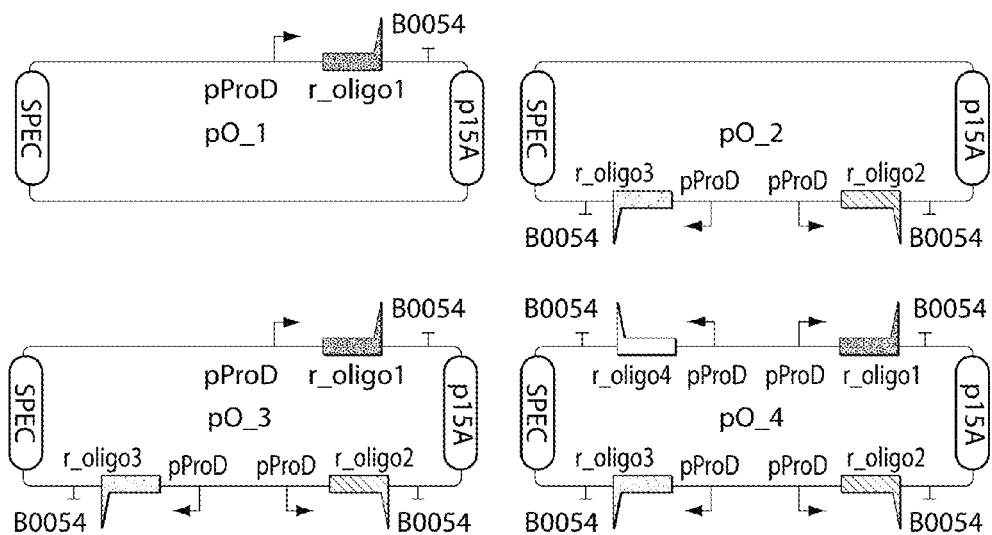
FIG. 19 shows the plasmids used for different combinations of r_oligo genes in FIG. 2. These plasmids are referred to as the "Oligo" in FIG. 2A. Part sequences are provided in Tables 1-4. Parts beginning with "B" are from the Registry of Standard Biological Parts.
Figure 20:
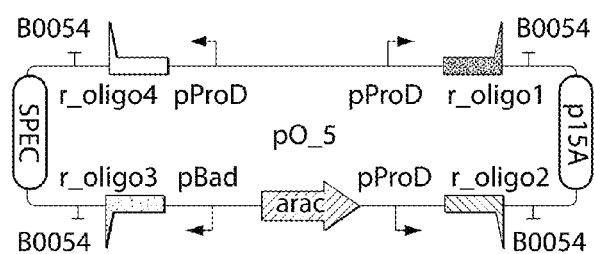
FIG. 20 shows an oligo plasmid map used for the measurements shown in FIG. 21. Part sequences are provided in Tables 1-4. Parts beginning with "B" are from the Registry of Standard Biological Parts.
Figure 21A:
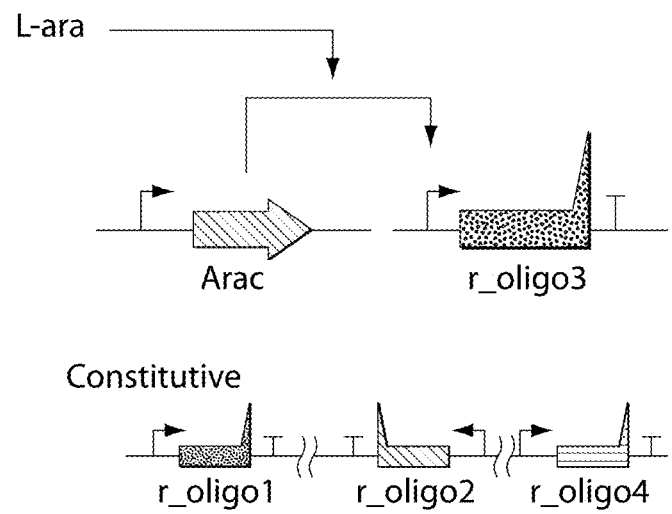
FIGS. 21A-B show the connection to a genetic circuit to switch between 3- and 4-part structures. In 21A, the schematic of the induction of r_oligo3 is shown. The plasmids corresponding to these experiments are: pHIV-pT-p66p51, pO5 and pMLRT. In 21B, gels are shown for different combinations of IPTG and L-arabinose added to the culture media. The regions for the assembly of the 3- and 4-part structures are labelled as X and Y, respectively. The intensity of the gels are quantified (bottom) showing the relative production of the 3- and 4-part structures. The structures were expressed and purified as before (Example 1) under conditions that prevent the removal of the RTBS (RNase A+150 mM NaCl).
Figure 21B:
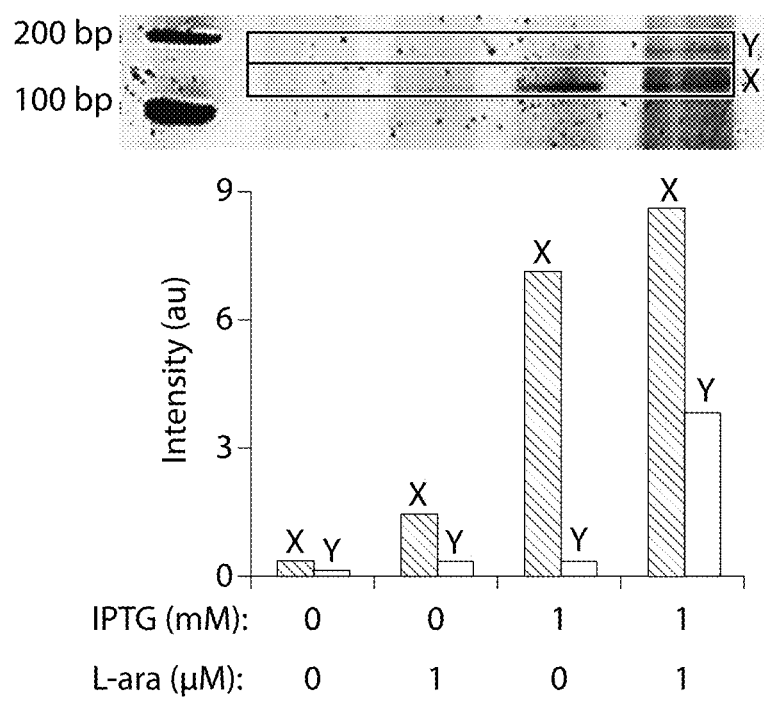

By demonstrating the ability to synthesize ssDNA in-vivo, the study was extended to engineer cells to program self-assembly of DNA nanostructures, (FIGS. 2A, 17 and 19). The engineered-nanostructure is based on the assembly of four ssDNAs (each 40 bases) to form double crossover branched motifs. This is enabled by reverse transcribing four ssDNAs trough the RTs paradigm. In order to prevent the production of undesirable structures, two mainly rules have been implemented into the genetic circuits: (1) similar promoter strength for the transcription of the ncRNAs have been added to prevent effects of stoichiometric DNA assembly; (2)) the r_oligo parts are cloned antiparallel and an additional terminator to the RTBS has been added to these parts in order to increase their termination and to prevent the generation of very long DNAs. In order to prove the assembly process, the HIV-RT was engineered to be regulated under an inducible promoter (LacI) for controlling the concentration of the produced ssDNAs, while constituvely inducing the MLRT. The concentration factor has been previously demonstrated to be important for DNA assembly in-vitro. The oligo plasmid has been decomposed for the reverse transcription of one, two, three and four ssDNAs in order to demonstrate the assembly formation. The resulting nanostructures were isolated from the cells, analyzed under gel electrophoresis, and characterized by AFM, (FIGS. 2B, 10, 11 and 15). It can be seen from the results that bands of different sizes are observed according to the number of r_oligo parts programmed on the plasmid resulting by the DNA nanostructure formation. Also, by controlling the HIVRT under pLACI, it was observed that the assembly is concentration-dependent, >1 mM IPTG a clear higher band is visualized representing the formation of the nanostructure, while the production of the ssDNAs are produced under a lesser amount of inducer ~10 μM, a phenomena usually seen for in vitro assemblies. It should be noted that another undesirable band appeared in all the gels at around 300 bp which does not represent the desired structure. By carefully characterizing it, it was found that this element represents a cDNA (complementary DNA) generated by the RTs process through the ncRNA, since it remains stable under any kind of purification method. The amount of DNA assembly purified from the cell grow through the gel experiment have been evaluated to be 7.5 μgm/L for the 1-part DNA and 2 μgm/L for the 4-part assembly using spectroscopic absorbance measurements (L represent the volume of the media grow, OD 260). It should be noted that a control experiment have been run in order to evaluate the material lost during the purification method to be 90%. The formation of the different assemblies were characterized from a single part to the fully assembly, a 42 nm nanowire (40 bases cross-over motif conjugated to the RTBS 50 bases on each side). The RTBS elements conjugated to the different DNAs were visualized and look as a "V" on one side of the nanowire for the three-part DNA assembly and a double "V" for the four-part DNA assembly. Finally, by analyzing larger AFM areas, the diameter of particle created by a single part system to the 4-part assembly was compared.

Figure 3A:
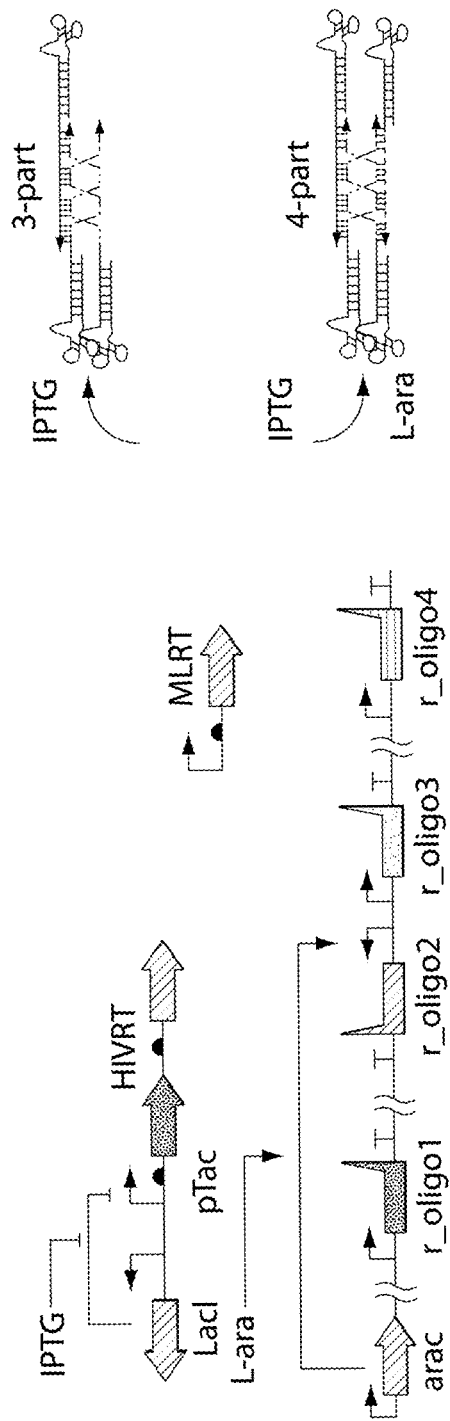
FIGS. 3A-B demonstrate how a genetic circuit regulates the assembly of different DNA motifs in a single strain.
Figure 3B:
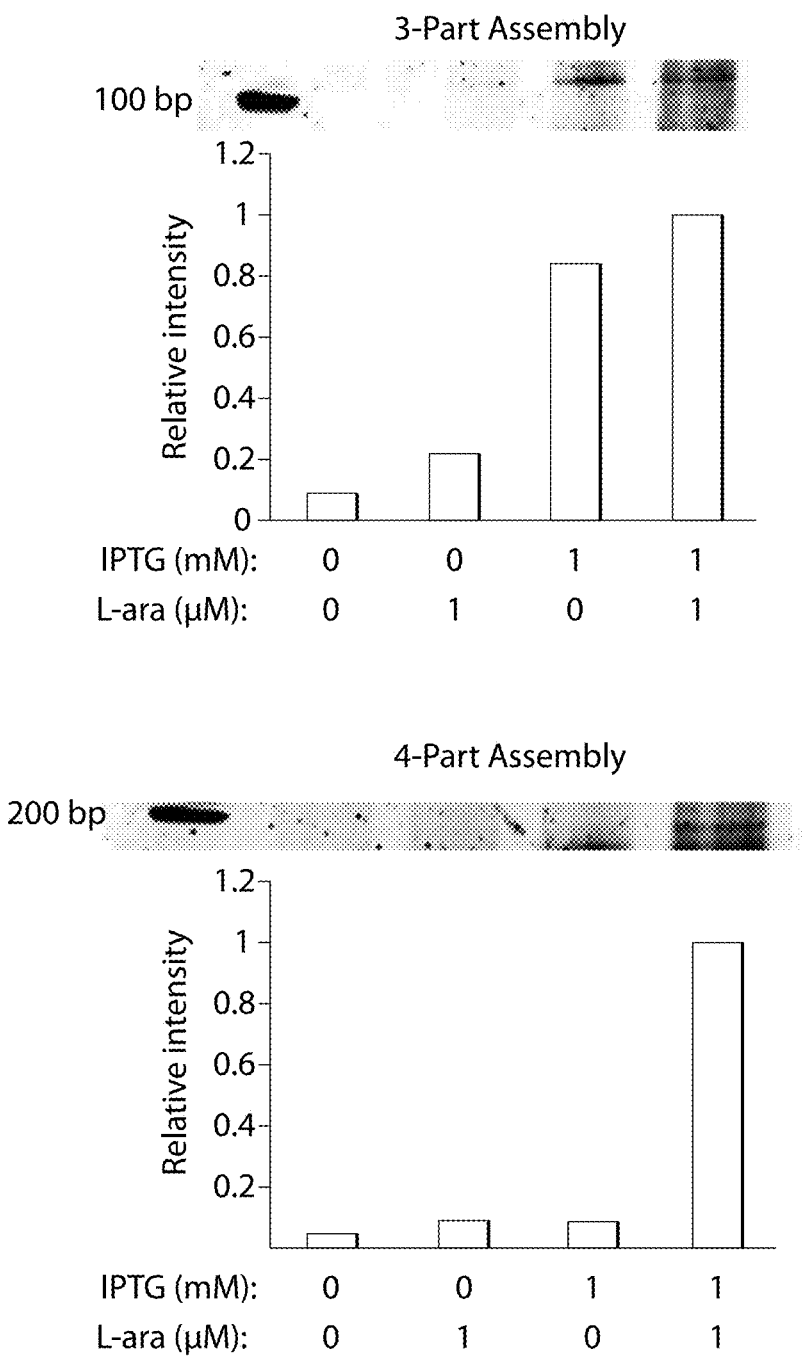
Figure 6A:
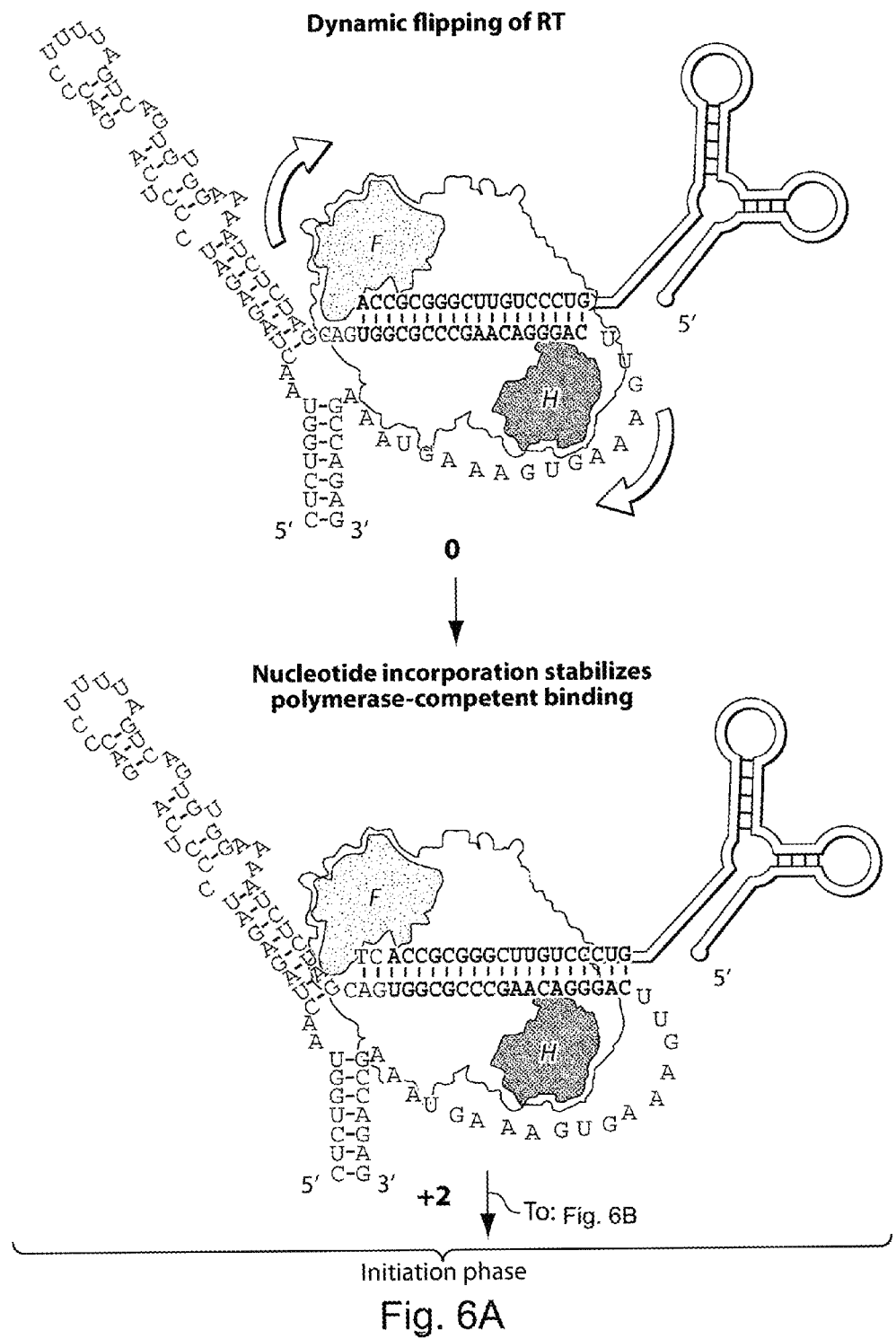
Figure 6B:
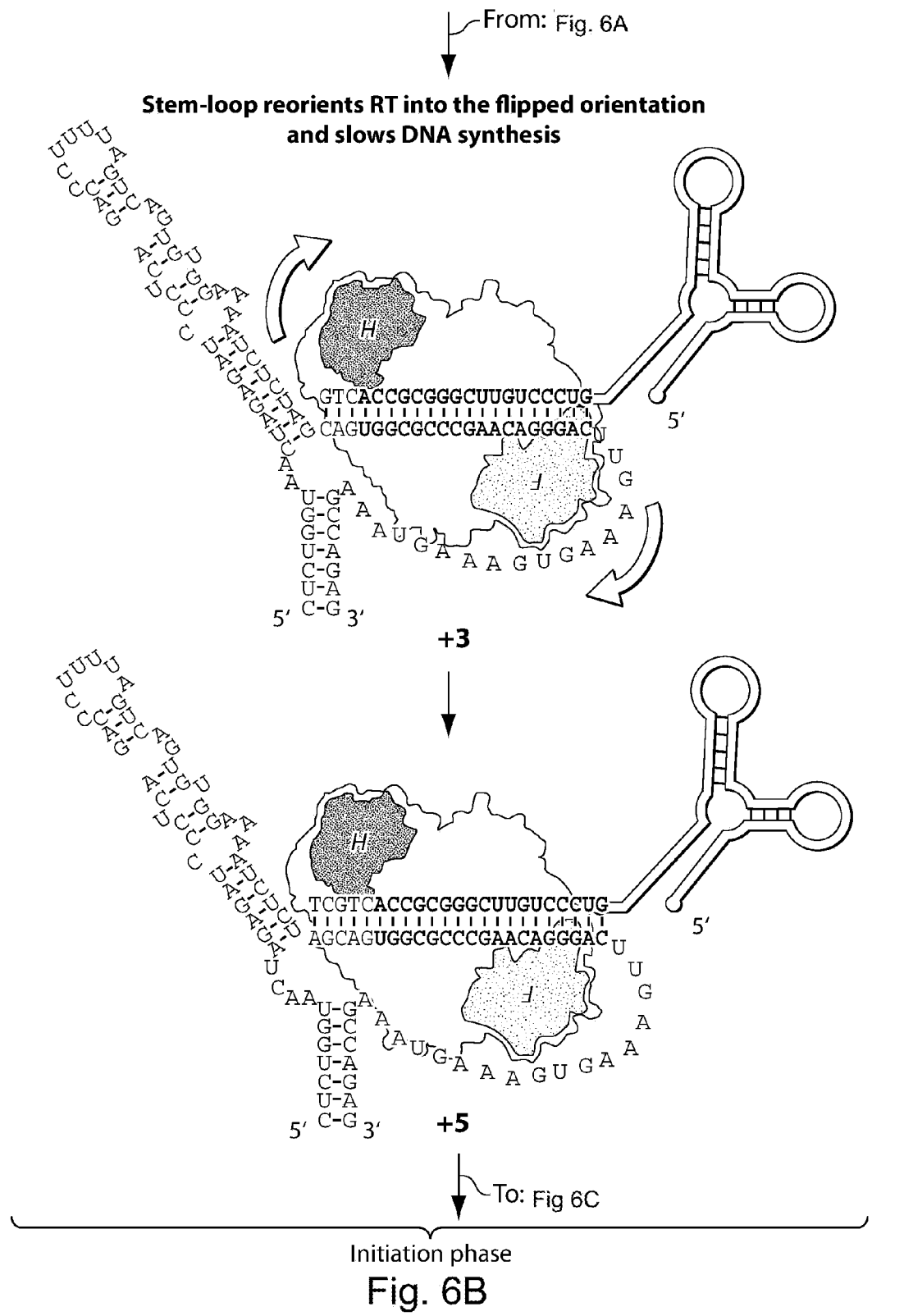
Figure 6C:
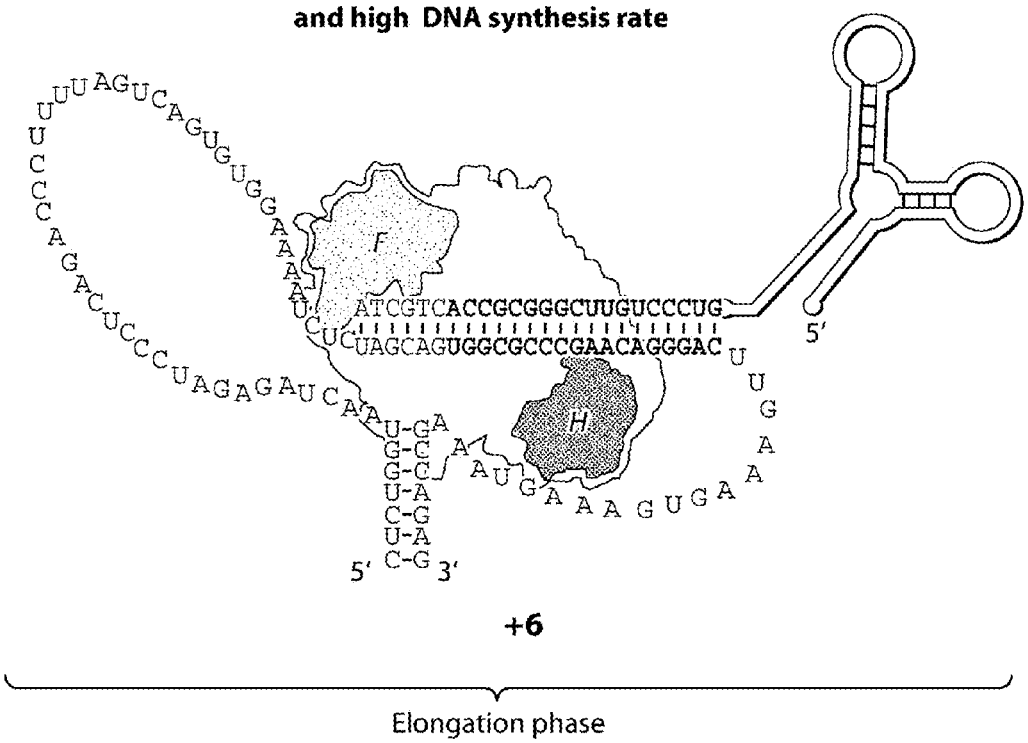
Figure 6D:
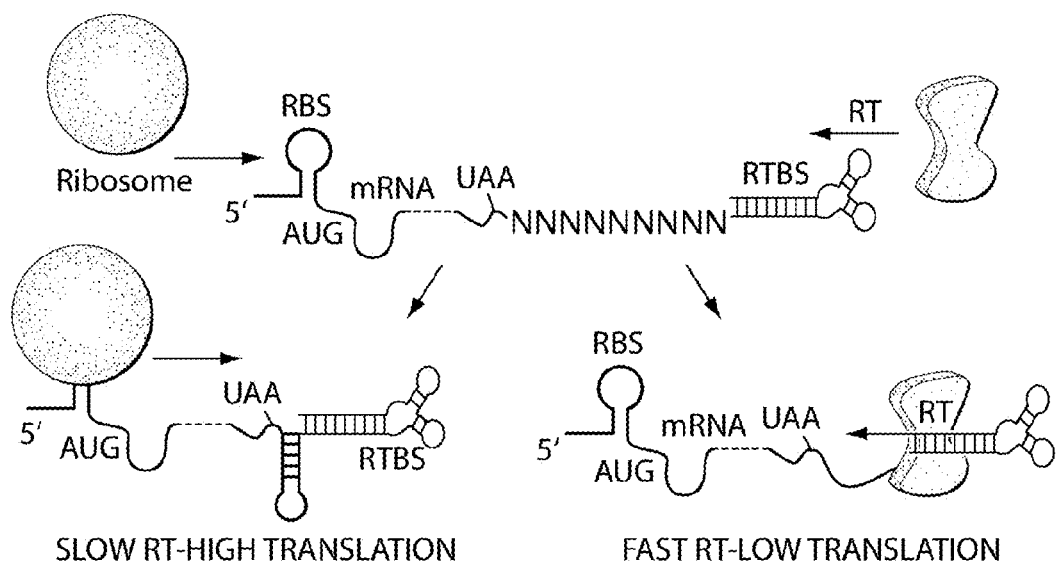
Figure 7:
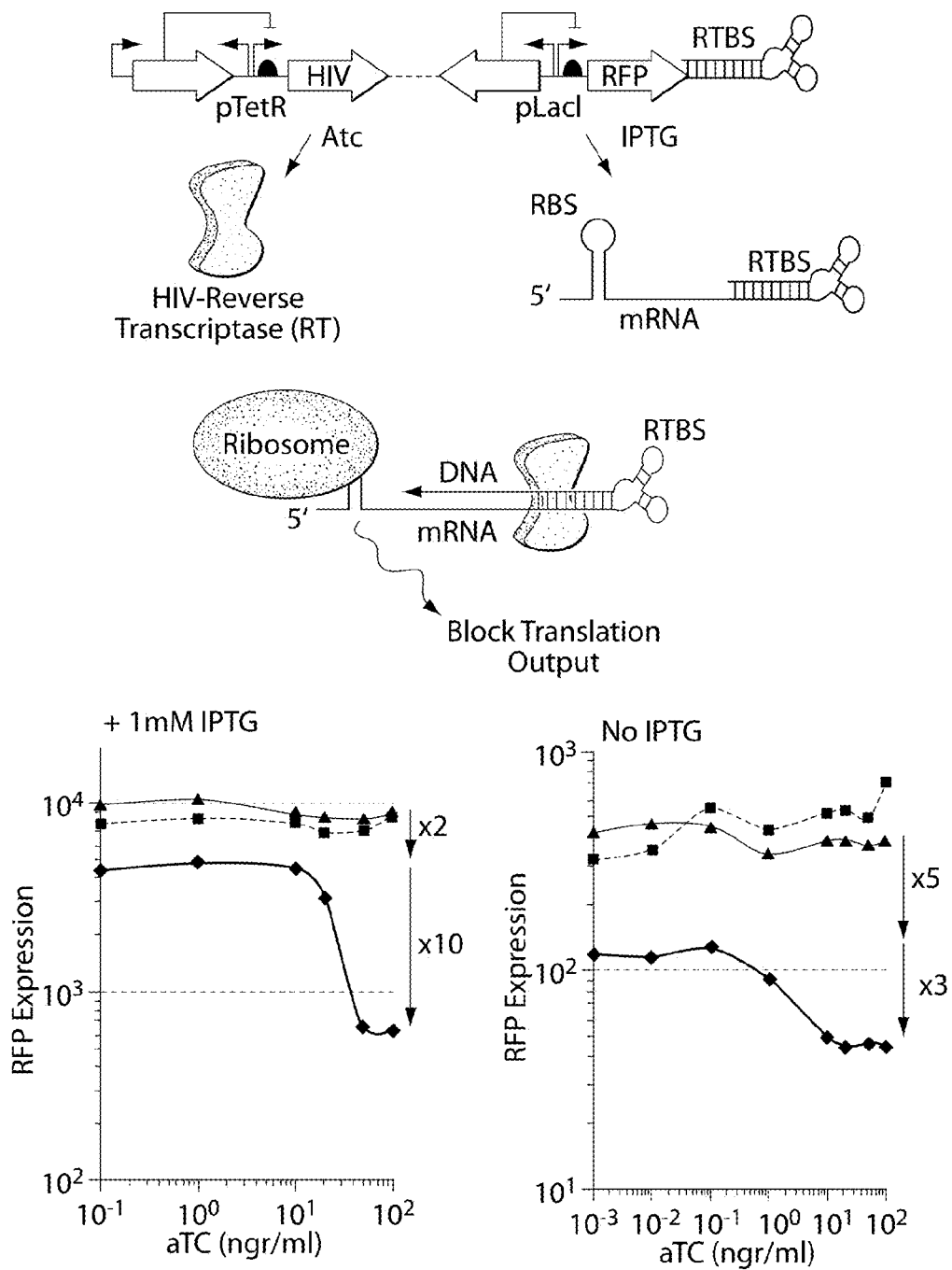
FIG. 7 is a schematic demonstrating an embodiment of the method of the invention related to regulating gene expression.

Furthermore, by adding a second regulator element to the system, the control between different DNA assemblies in a single strain is shown, FIG. 3. The first regulator part controls the RT process by regulating the HIVRT under pLacI (IPTG input). The second regulator part (pBAD) have been added to regulate the transcription of r_oligos parts "2" while remaining r_oligos 1, 3 and 4 constantly transcribed. In the presence of IPTG only, the RT process is activated, leading to the reverse transcription of oligos 1, 3 and 4 following by their assembly (3-part). By adding L-arabinose (L-ara) and remaining IPTG in the system, the reverse transcription of the other oligo "2" proceed resulting in the full assembly of the DNA nanostructure (4-part). It should be noted that this system has been carefully tuned in order to reduce the pLACI leaking effect resulting in fully assembly only in the presence of L-arabinose.

Exemplary nucleic acids of the invention have the following sequences. the invention encompasses the following nucleic acid sequences as well as in isolated and modified formats and related methods of use.

TABLE 1

Gene Sequences of the reverse transcriptases:

P66:
ATGCCGATTAGCCCGATTGAAACCGTTCCGGTTAAACTGAAACCGGGTATGGATG
GTCCGAAAGTTAAACAGTGGCCTCTGACCGAAGAAAAAATCAAAGCACTGGTTG
AAATCTGCACCGAGATGGAAAAAGAAGGCAAAATTAGCAAAATCGGTCCGGAA
AATCCGTATAATACACCGGTTTTTGCCATTAAGAAAAAAGATAGCACCAAATGG
CGCAAACTGGTGGATTTTCGTGAACTGAATAAACGCACCCAGGATTTTTGGGAAG
TTCAGCTGGGTATTCCGCATCCGGCAGGTCTGAAACAGAAAAAAAGCGTTACCG
TTCTGGATGTTGGTGATGCATATTTTAGCGTTCCGCTGGATAAAGATTTCCGTAA
ATATACCGCATTTACCATCCCGAGCATTAATAACGAAACACCGGGTATTCGCTAT
CAGTATAATGTTCTGCCGCAGGGTTGGAAAGGTAGTCCGGCAATTTTTCAGTGTA
GCATGACCAAAATTCTGGAACCGTTTCGTAAACAGAATCCGGATATTGTGATCTA
CCAGTATATGGATGATCTGTATGTTGGTAGCGATCTGGAAATTGGTCAGCATCGT
ACCAAAATTGAAGAACTGCGTCAGCATCTGCTGCGTTGGGGTTTTACCACACCGG
ATAAAAAACATCAGAAAGAACCGCCTTTTCTGTGGATGGGTTATGAACTGCATCC
GGATAAATGGACCGTTCAGCCGATTGTTCTGCCGGAAAAAGATAGCTGGACCGT
TAATGATATTCAGAAACTGGTGGGTAAACTGAATTGGGCAAGCCAGATTTATGCC
GGTATTAAAGTTCGTCAGCTGTGTAAACTGCTGCGTGGCACCAAAGCACTGACCG
AAGTTGTTCCGCTGACAGAAGAAGCAGAACTGGAACTGGCAGAAAATCGTGAAA
TTCTGAAAGAACCGGTTCACGGCGTTTATTATGATCCGAGCAAAGATCTGATTGC
CGAAATTCAGAAACAGGGTCAGGGTCAGTGGACCTATCAGATTTATCAAGAACC
GTTTAAAAACCTGAAAACCGGCAAATATGCACGTATGAAAGGTGCACATACCAA
CGATGTTAAACAGCTGACCGAAGCAGTTCAGAAAATTGCAACCGAAAGCATTGT
GATTTGGGGTAAAACCCCGAAATTCAAACTGCCGATTCAGAAAGAAACCTGGGA
AGCATGGTGGACCGAATATTGGCAGGCAACCTGGATTCCGGAATGGGAATTTGT
TAATACCCCTCCGCTGGTTAAACTGTGGTATCAGCTGGAAAAAGAACCGATTATT
GGTGCCGAAACCTTTTATGTTGATGGTGCAGCCAATCGTGAAACCAAACTGGGTA
AAGCAGGTTATGTTACCGATCGTGGTCGTCAGAAAGTGGTGCCGCTGACCGATAC
CACCAATCAGAAAACCGAACTGCAGGCAATTCATCTGGCACTGCAGGATAGCGG
TCTGGAAGTTAATATTGTTACCGATAGCCAGTATGCCCTGGGTATTATTCAGGCA
CAGCCGGATAAAAGCGAAAGCGAACTGGTTAGCCAGATTATTGAACAGCTGATC
AAAAAAGAAAAAGTGTACCTGGCATGGGTTCCGGCACATAAAGGTATTGGTGGT
AATGAACAGGTTGATGGTCTGGTTAGCGCAGGTATTCGTAAAGTTCTGTAA (SEQ ID NO: 1)

P51:
ATGCCGATTAGCCCGATTGAAACCGTTCCGGTTAAACTGAAACCGGGTATGGATG
GTCCGAAAGTTAAACAGTGGCCTCTGACCGAAGAAAAAATCAAAGCACTGGTTG
AAATCTGCACCGAGATGGAAAAAGAAGGCAAAATTAGCAAAATCGGTCCGGAA
AATCCGTATAATACACCGGTTTTTGCCATTAAGAAAAAAGATAGCACCAAATGG
CGCAAACTGGTGGATTTTCGTGAACTGAATAAACGCACCCAGGATTTTTGGGAAG
TTCAGCTGGGTATTCCGCATCCGGCAGGTCTGAAACAGAAAAAAAGCGTTACCG
TTCTGGATGTTGGTGATGCATATTTTAGCGTTCCGCTGGATAAAGATTTCCGTAA
ATATACCGCATTTACCATCCCGAGCATTAATAACGAAACACCGGGTATTCGCTAT
CAGTATAATGTTCTGCCGCAGGGTTGGAAAGGTAGTCCGGCAATTTTTCAGTGTA
GCATGACCAAAATTCTGGAACCGTTTCGTAAACAGAATCCGGATATTGTGATCTA
CCAGTATATGGATGATCTGTATGTTGGTAGCGATCTGGAAATTGGTCAGCATCGT
ACCAAAATTGAAGAACTGCGTCAGCATCTGCTGCGTTGGGGTTTTACCACACCGG
ATAAAAAACATCAGAAAGAACCGCCTTTTCTGTGGATGGGTTATGAACTGCATCC
GGATAAATGGACCGTTCAGCCGATTGTTCTGCCGGAAAAAGATAGCTGGACCGT
TAATGATATTCAGAAACTGGTGGGTAAACTGAATTGGGCAAGCCAGATTTATGCC
GGTATTAAAGTTCGTCAGCTGTGTAAACTGCTGCGTGGCACCAAAGCACTGACCG
AAGTTGTTCCGCTGACAGAAGAAGCAGAACTGGAACTGGCAGAAAATCGTGAAA
TTCTGAAAGAACCGGTTCACGGCGTTTATTATGATCCGAGCAAAGATCTGATTGC
CGAAATTCAGAAACAGGGTCAGGGTCAGTGGACCTATCAGATTTATCAAGAACC
GTTTAAAAACCTGAAAACCGGCAAATATGCACGTATGAAAGGTGCACATACCAA
CGATGTTAAACAGCTGACCGAAGCAGTTCAGAAAATTGCAACCGAAAGCATTGT
GATTTGGGGTAAAACCCCGAAATTCAAACTGCCGATTCAGAAAGAAACCTGGGA
AGCATGGTGGACCGAATATTGGCAGGCAACCTGGATTCCGGAATGGGAATTTGT
TAATACCCCTCCGCTGGTTAAACTGTGGTATCAGCTGGAAAAAGAACCGATTATT
GGTGCCGAAACCTTTTAA (SEQ ID NO: 2)

TABLE 1 -continued

MLRT:
atgggtcataatcataatcataatcataatcacaacggtggagatgacgatgacaagggtggtcgacaagcttggatccctgc
aggcctcagggcccgatcgatgggaccaatggggcagcccctgcaagtgttgaccctaaatatagaagatgagtatcggctacatga
gacctcaaaagagccagatgtttctctagggtccaaagcctgtctgattttcctcaggcctgggcggaaaccggggcatgggactg
gcagttcgccaagctcctctgatcatacctctgaaagcaacctctaccccgctgtccataaaacaataccccatgtcacaagaagccag
actgggatcaagcccacatacagagactgttggaccagggaatactggtaccctgccagtcccctggaacacgccctgctacc
cgttaagaaaccagggactaatgattataggcctgtccaggatctgagagaagtcaacaagcgggtggaagacatccaccccaccgt
gcccaacccttacaacctcttgagcgggctcccaccgtcccaccagtggtacactgtgcttgatttaaaggatgccttttctgcctgaga
ctccaccccaccagtcagcctctcttcgcctttgagtggagagatccagagatgggaatctcaggacaattgacctggaccagactcc
cacagggtttcaaaaacagtcccaccctgtttgatgaggcactgcacagagacctagcagacttccggatccagcacccagacttgat
cctgctacagtacgtggatgacttactgctggccgccacttctgagctagactgccaacaaggtactcgggccctgttacaaacccctag
ggaacctcgggtatcgggcctcggccaagaaagcccaaatttgccagaaacaggtcaagtatctggggtatcttctaaaagagggtc
agagatggctgactgaggccagaaaagagactgtgatggggcagcctactccgaagaccccctcgacaactaagggagttcctaggg
acggcaggcttctgtcgcctctggatccctgggtttgcagaaatggcagccccccttgtaccctctcaccaaaacggggactctgttttaat
tggggcccagaccaacaaaaggcctatcaagaaatcaagcaagctcttctaactgccccagccctggggttgccagatttgactaagc
cctttgaactctttgtcgacgagaagcagggctacgccaaaggtgtcctaacgcaaaaactgggaccttggcgtcggccggtggccta
cctgtccaaaaagctagaaccagtagcagctgggtggcccctactgccggatggtagcaccattgccgtactgacaaaggatgc
aggcaagctaaccatgggacagccactagtcattctggcccccatgcagtagaggcactagtcaaacaaccccccgaccgctggct
ttccaacgcccggatgactcactatcaggcctgcttttggacacggaccgggtccagttcggaccggtggtagccctgaacccggct
acgctgctcccactgcctgaggaagggctgcaacacaactgccttgatatcctggccgaagcccacggaacccgacccgacctaac
ggaccagccgctcccagacgccgaccacacctggtacaggatggaagcagtcttcttacaagagggacagcgtaaggcgggagct
gcggtgaccaccgagaccgaggtaatctgggctaaagccctgccagccgggacatccgctcagcgggctgaactgatagcactca
cccaggcctaaagatggcagaaggtaagaagctaaatgtttatactgatagccgttatgcttttgctactgcccatatccatgagaaat
atacagaaggcgtgggttgctcacatcagaaggcaaagagatcaaaaataaagacgagatctttaaatga (SEQ ID NO: 3)

RTBS:
AAAAAAAAACGTGGCGCCCGAACAGGGACggataGCTCAGTCGGTAGAGCATCAG
ACTTTTAATCTGAGGGTCCAGGGTTCAAGTCCCTGTTCGGGCGCCACGTTTTTTTT (SEQ ID NO: 4)

Plasmid sequences:

pJEHIV_1:
ttgacagctagctcagtcctaggtactgtgctagctactagtgaaagaggagaaatactagATGCCGATTAGCCCGAT
TGAAACCGTTCCGGTTAAACTGAAACCGGGTATGGATGGTCCGAAAGTTAAACA
GTGGCCTCTGACCGAAGAAAAAATCAAAGCACTGGTTGAAATCTGCACCGAGAT
GGAAAAAGAAGGCAAATTAGCAAATCGGTCCGGAAAATCCGTATAATACACC
GGTTTTTGCCATTAAGAAAAAAGATAGCACCCAAATGGCGCAAACTGGTGGATTTT
CGTGAACTGAATAAACGCACCCAGGATTTTTGGGAAGTTCAGCTGGGTATTCCGC
ATCCGGCAGGTCTGAAACAGAAAAAAAGCGTTACCGTTCTGGATGTTGGTGATG
CATATTTTAGCGTTCCGCTGGATAAAGATTTCCGTAAATATACCGCATTTACCATC
CCGAGCATTAATAACGAAACACCGGGTATTCGCTATCAGTATAATGTTCTGCCGC
AGGGTTGGAAAGGTAGTCCGGCAATTTTTTCAGTGTAGCATGACCAAAATTCTGGA
ACCGTTTCGTAAACAGAATCCGGATATTGTGATCTACCAGTATATGGATGATCTG
TATGTTGGTAGCGATCTGGAAATTGGTCAGCATCGTACCAAAATTGAAGAACTGC
GTCAGCATCTGCTGCGTTGGGGTTTTACCACACCGGATAAAAAACATCAGAAAAG
AACCGCCTTTTCTGTGGATGGGTTATGAACTGCATCCGGATAAATGGACCGTTCA
GCCGATTGTTCTGCCGGAAAAAGATAGCTGGACCGTTAATGATATTCAGAAACTG
GTGGGTAAACTGAATTGGGCAAGCCAGATTATGCCGGTATTAAAGTTCGTCAGC
TGTGTAAACTGCTGCGTGGCACCAAAGCACTGACCGAAGTTGTTCCGCTGACAGA
AGAAGCAGAACTGGAACTGGCAGAAAATCGTGAAATTCTGAAAGAACCGGTTCA
CGGCGTTTATTATGATCCGAGCAAAGATCTGATTGCCGAAATTCAGAAACAGGGT
CAGGGTCAGTGGACCTATCAGATTTATCAAGAACCGTTTAAAAACCTGAAAACC
GGCAAATATGCACGTATGAAAGGTGCACATACCAACGATGTTAAACAGCTGACC
GAAGCAGTTCAGAAAATTGCAACCGAAAGCATTGTGATTTGGGGTAAAACCCCG
AAATTCAAACTGCCGATTCAGAAAGAAACCTGGGAAGCATGGTGGACCGAATAT
TGGCAGGCAACCTGGATTCCGGAATGGGAATTTGTTAATACCCCTCCGCTGGTTA
AACTGTGGTATCAGCTGGAAAAAGAACCGATTATTGGTGCCGAAACCTTTTATGT
TGATGGTGCAGCCAATCGTGAAACCAAACTGGGTAAAGCAGGTTATGTTACCGA
TCGTGGTCGTCAGAAAGTGGTGCCGCTGACCGATACCACCAATCAGAAAACCGA
ACTGCAGGCAATTCATCTGGCACTGCAGGATAGCGGTCTGGAAGTTAATATTGTT
ACCGATAGCCAGTATGCCCTGGGTATTATTCAGGCACAGCCGGATAAAGCGAA
AGCGAACTGGTTAGCCAGATTATTGAACAGCTGATCAAAAAAGAAAAAGTGTAC
CTGGCATGGGTTCCGGCACATAAAGGTATTGGTGGTAATGAACAGGTTGATGGTC
TGGTTAGCGCAGGTATTCGTAAAGTTCTGTAAcgctgatagtgctagtgtagatcgctactagagccag
gcatcaaataaaacgaaaggctcagtcgaaagactgggcctttcgttttatctgttgtttgtcggtgaacgctctctactagagtcacactg
gctcaccttcgggtgggcctttctgcgtttatatactagaagcggccgctgcaggcttcctcgctcactgactcgctgcgctcggtcgttc
ggctgcggcgagcgtatcagctcaatcaaaggcggtaatacggttatccacagaatcaggggataacgcaggaaagaacatgtga
gcaaaaggccagcaaaaggccaggaaccgtaaaaaggccgcgttgctggcgtttttccataggctccgcccccctgacgagcatca
caaaaatcgacgctcaagtcagaggtggcgaaacccgacaggactataaagataccaggcgtttccccctggaagctccctcgtgcg
ctctcctgttccgaccctgccgcttaccggatacctgtccgcctttctcccttcgggaagcgtggcgctttctcatagctcacgctgtaggt
atctcagttcggtgtaggtcgttcgctccaagctgggctgtgtgcacgaaccccccgttcagcccgaccgctgcgccttatccggtaac
tatcgtcttgagtccaacccggtaagacacgacttatcgccactggcagcagccactggtaacaggattagcagagcgaggtatgtag
gcggtgctacagagttcttgaagtggtggcctaactacggctacactagaaggacagtatttggtatctgcgctctgctgaagccagtta
ccttcggaaaaagagttggtagctcttgatccggcaaacaaaccaccgctggtagcggtggtttttttgtttgcaagcagcagattacgc
gcagaaaaaaaggatctcaagaagatcctttgatcttttctacggggtctgacgctcagtggaacgaaaactcacgttaagggattttgg
tcatgagattatcaaaaaggatcttcacctagatccttttaaattaaaaatgaagttttaaatcaatctaaagtatatatgagtaaacttggtct
gacagttaccaatgcttaatcagtgaggcacctatctcagcgatctgtctatttcgttcatccatagttgcctgactccccgtcgtgtagata
actacgatacgggagggcttaccatctggccccagtgctgcaatgataccgcgagacccacgctcaccggctccagatttatcagcaa
taaaccagccagccggaagggccgagcgcagaagtggtcctgcaactttatccgcctccatccagtctattaattgttgccgggaagc
tagagtaagtagttcgccagttaatagtttgcgcaacgttgttgccattgctacaggcatcgtggtgtcacgctcgtcgtttggtatggcttc TABLE 1 -continued attcagctccggttcccaacgatcaaggcgagttacatgatcccccatgttgtgcaaaaaagcggttagctccttcggtcctccgatcgtt
gtcagaagtaagttggccgcagtgttatcactcatggttatggcagcactgcataattctcttactgtcatgccatccgtaagatgcttttct
gtgactggtgagtactcaaccaagtcattctgagaatagtgtatgcggcgaccgagttgctcttgcccggcgtcaatacgggataatac
cgcgccacatagcagaactttaaaagtgctcatcattggaaaacgttcttcgggcgaaaactcttcaaggatcttaccgctgttgagatc
cagttcgatgtaacccactcgtgcacccaactgatcttcagcatcttttttactttcaccagcgtttctgggtgagcaaaaacaggaaggcaa
aatgccgcaaaaaagggaataaggggcgacacggaaatgttgaatactcatactcttcctttttcaatattattgaagcatttatcagggtta
ttgtctcatgagcggatacatatttgaatgtatttagaaaaataaacaaatagggggttccgcgcacatttccccgaaaagtgccacctgac
gtctaagaaaccattattatcatgacattaacctataaaaataggcgtatcacgaggcagaatttcagataaaaaaaatccttagctttcgc
taaggatgatttctggaattcgcggccgcatctagag (SEQ ID NO: 5)

pJEHIV_2:
ttgacagctagctcagtcctaggtactgtgctagctactagtgaaagaggagaaatactagATGCCGATTAGCCCGAT
TGAAACCGTTCCGGTTAAACTGAAACCGGGTATGGATGGTCCGAAAGTTAAACA
GTGGCCTCTGACCGAAGAAAAAATCAAAGCACTGGTTGAAATCTGCACCGAGAT
GGAAAAAGAAGGCAAAATTAGCAAAATCGGTCCGGAAAATCCGTATAATACACC
GGTTTTTGCCATTAAGAAAAAAGATAGCACCCAAATGGCGCAAACTGGTGGATTTT
CGTGAACTGAATAAACGCACCCAGGATTTTTGGGAAGTTCAGCTGGGTATTCCGC
ATCCGGCAGGTCTGAAACAGAAAAAAAGCGTTACCGTTCTGGATGTTGGTGATG
CATATTTTAGCGTTCCGCTGGATAAAGATTTCCGTAAATATACCGCATTTACCATC
CCGAGCATTAATAACGAAACACCGGGTATTCGCTATCAGTATAATGTTCTGCCGC
AGGGTTGGAAAGGTAGTCCGGCAATTTTTCAGTGTAGCATGACCAAAATTCTGGA
ACCGTTTCGTAAACAGAATCCGGATATTGTGATCTACCAGTATATGGATGATCTG
TATGTTGGTAGCGATCTGGAAATTGGTCAGCATCGTACCAAAATTGAAGAACTGC
GTCAGCATCTGCTGCGTTGGGGTTTTACCACACCGGATAAAAAACATCAGAAAG
AACCGCCTTTTCTGTGGATGGGTTATGAACTGCATCCGGATAAATGGACCGTTCA
GCCGATTGTTCTGCCGGAAAAAGATAGCTGGACCGTTAATGATATTCAGAAACTG
GTGGGTAAACTGAATTGGGCAAGCCAGATTTATGCCGGTATTAAAGTTCGTCAGC
TGTGTAAACTGCTGCGTGGCACCAAAGCACTGACCGAAGTTGTTCCGCTGACAGA
AGAAGCAGAACTGGAACTGGCAGAAAATCGTGAAATTCTGAAAGAACCGGTTCA
CGGCGTTTATTATGATCCGAGCAAAGATCTGATTGCCGAAATTCAGAAACAGGGT
CAGGGTCAGTGGACCTATCAGATTTATCAAGAACCGTTTAAAACCTGAAAACC
GGCAAATATGCACGTATGAAAGGTGCACATACCAACGATGTTAAACAGCTGACC
GAAGCAGTTCAGAAAATTGCAACCGAAAGCATTGTGATTTGGGGTAAAACCCCG
AAATTCAAACTGCCGATTCAGAAAGAAACCTGGGAAGCATGGTGGACCGAATAT
TGGCAGGCAACCTGGATTCCGGAATGGGAATTTGTTAATACCCCTCCGCTGGTTA
AACTGTGGTATCAGCTGGAAAAAGAACCGATTATTGGTGCCGAAACCTTTTATGT
TGATGGTGCAGCCAATCGTGAAACCAAACTGGGTAAAGCAGGTTATGTTACCGA
TCGTGGTCGTCAGAAAGTGGTGCCGCTGACCGATACCACCAATCAGAAACCGA
ACTGCAGGCAATTCATCTGGCACTGCAGGATAGCGGTCTGGAAGTTAATATTGTT
ACCGATAGCCAGTATGCCCTGGGTATTATTCAGGCACAGCCGGATAAAAGCGAA
AGCGAACTGGTTAGCCAGATTATTGAACAGCTGATCAAAAAAGAAAAAGTGTAC
CTGGCATGGGTTCCGGCACATAAAGGTATTGGTGGTAATGAACAGGTTGATGGTC
TGGTTAGCGCAGGTATTCGTAAAGTTCTGTAAtactagtgaaagaggagaaatactagATGCCGA
TTAGCCCGATTGAAACCGTTCCGGTTAAACTGAAACCGGGTATGGATGGTCCGAA
AGTTAAACAGTGGCCTCTGACCGAAGAAAAAATCAAAGCACTGGTTGAAATCTG
CACCGAGATGGAAAAAGAAGGCAAAATTAGCAAAATCGGTCCGGAAAATCCGT
ATAATACACCGGTTTTTGCCATTAAGAAAAAAGATAGCACCCAAATGGCGCAAAC
TGGTGGATTTTCGTGAACTGAATAAACGCACCCAGGATTTTTGGGAAGTTCAGCT
GGGTATTCCGCATCCGGCAGGTCTGAAACAGAAAAAAAGCGTTACCGTTCTGGA
TGTTGGTGATGCATATTTTAGCGTTCCGCTGGATAAAGATTTCCGTAAATATACC
GCATTTACCATCCCGAGCATTAATAACGAAACACCGGGTATTCGCTATCAGTATA
ATGTTCTGCCGCAGGGTTGGAAAGGTAGTCCGGCAATTTTTCAGTGTAGCATGAC
CAAAATTCTGGAACCGTTTCGTAAACAGAATCCGGATATTGTGATCTACCAGTAT
ATGGATGATCTGTATGTTGGTAGCGATCTGGAAATTGGTCAGCATCGTACCAAAA
TTGAAGAACTGCGTCAGCATCTGCTGCGTTGGGGTTTTACCACACCGGATAAAAA
ACATCAGAAAGAACCGCCTTTTCTGTGGATGGGTTATGAACTGCATCCGGATAAA
TGGACCGTTCAGCCGATTGTTCTGCCGGAAAAAGATAGCTGGACCGTTAATGATA
TTCAGAAACTGGTGGGTAAACTGAATTGGGCAAGCCAGATTTATGCCGGTATTAA
AGTTCGTCAGCTGTGTAAACTGCTGCGTGGCACCAAAGCACTGACCGAAGTTGTT
CCGCTGACAGAAGAAGCAGAACTGGAACTGGCAGAAAATCGTGAAATTCTGAAA
GAACCGGTTCACGGCGTTTATTATGATCCGAGCAAAGATCTGATTGCCGAAATTC
AGAAACAGGGTCAGGGTCAGTGGACCTATCAGATTTATCAAGAACCGTTTAAAA
ACCTGAAAACCGGCAAATATGCACGTATGAAAGGTGCACATACCAACGATGTTA
AACAGCTGACCGAAGCAGTTCAGAAAATTGCAACCGAAAGCATTGTGATTTGGG
GTAAAACCCCGAAATTCAAACTGCCGATTCAGAAAGAAACCTGGGAAGCATGGT
GGACCGAATATTGGCAGGCAACCTGGATTCCGGAATGGGAATTTGTTAATACCCC
TCCGCTGGTTAAACTGTGGTATCAGCTGGAAAAAGAACCGATTATTGGTGCCGAA
ACCTTTTAAgatcgctactagagccaggcatcaaataaaacgaaaggctcagtcgaaagactgggcctttcgttttatctgttgt
ttgtcggtgaacgctctctactagtcacactggctcaccttcgggtgggcctttctgcgtttatatactagaagcggccgctgcaggct
tcctcgctcactgactcgctgcgctcggtcgttcggctgcggcgagcggtatcagctcactcaaaggcggtaatacggttatccacaga
atcaggggataacgcaggaaagaacatgtgagcaaaaggccagcaaaaggccaggaaccgtaaaaaggccgcgttgctggcgttt
ttccataggctccgcccccctgacgagcatcacaaaaatcgacgctcaagtcagaggtggcgaaacccgacaggactataaagatac
caggcgtttccccctggaagctccctcgtgcgctctcctgttccgaccctgccgcttaccggatacctgtccgcctttctcccttcgggaa
gcgtggcgctttctcatagctcacgctgtaggtatctcagttcggtgtaggtcgttcgctccaagctgggctgtgtgcacgaaccccccg
ttcagcccgaccgctgcgccttatccggtaactatcgtcttgagtccaacccggtaagacacgacttatcgccactggcagcagccact
ggtaacaggattagcagagcgaggtatgtaggcggtgctacagagttcttgaagtggtggcctaactacggctacactagaaggaca
gtatttggtatctgcgctctgctgaagccagttaccttcggaaaaagagttggtagctcttgatccggcaaacaaaccaccgctggtagc
ggtggtttttttgtttgcaagcagcagattacgcgcagaaaaaaaggatctcaagaagatcctttgatcttttctacggggtctgacgctca
gtggaacgaaaactcacgttaagggattttggtcatgagattatcaaaaaggatcttcacctagatccttttaaattaaaaatgaagttttaa
atcaatctaaagtatatatgagtaaacttggtctgacagttaccaatgcttaatcagtgaggcacctatctcagcgatctgtctatttcgttca TABLE 1 -continued tccatagttgcctgactccccgtcgtgtagataactacgatacgggagggcttaccatctggccccagtgctgcaatgataccgcgaga
cccacgctcaccggctccagatttatcagcaataaaccagccagccggaagggccgagcgcagaagtggtcctgcaactttatccgc
ctccatccagtctattaattgttgccgggaagctagagtaagtagttcgccagttaatagtttgcgcaacgttgttgccattgctacaggca
tcgtggtgtcacgctcgtcgtttggtatggcttcattcagctccggttcccaacgatcaaggcgagttacatgatccccatgttgtgcaa
aaaagcggttagctccttcggtcctccgatcgttgtcagaagtaagttggccgcagtgttatcactcatggttatggcagcactgcataat
tctcttactgtcatgccatccgtaagatgcttttctgtgactggtgagtactcaaccaagtcattctgagaatagtgtatgcggcgaccgag
ttgctcttgcccggcgtcaatacgggataataccgcgccacatagcagaactttaaaagtgctcatcattggaaaacgttcttcggggcg
aaaactctcaaggatcttaccgctgttgagatccagttcgatgtaacccactcgtgcacccaactgatcttcagcatcttttactttt caccag
cgtttctgggtgagcaaaaacaggaaggcaaaatgccgcaaaaaagggaataagggcgacacggaaatgttgaatactcatactctt
ccttttt caatattattgaagcatttatcagggttattgtctcatgagcggatacatatttgaatgtatttagaaaaataaacaaatagggg ttc
cgcgcacatttccccgaaaagtgccacctgacgtctaagaaaccattattatcatgacattaacctataaaaataggcgtatcacgaggc
agaatttcagataaaaaaaatccttagctttcgctaaggatgatttctggaattcgcggccgcatctagag (SEQ ID NO: 6)

pJEHIV3:
aaaaataaacaaataggggttccgcgcacatttccccgaaaagtgccacctgacgtctaagaaaaggaatattcagcaatttgcccgtg
ccgaagaaaggcccacccgtgaaggtgagccagtgagttgattgctacgtaatgtcggccaattcgcgctaacttacattaattgcgtt
gcgcTCACTGCCCGCTTTCCAGTCGGGAAACCTGTCGTGCCAGCTGCATTAATGAA
TCGGCCAACGCGCGGGGAGAGGCGGTTTGCGTATTGGGCGCCAGGGTGGTTTTTC
TTTTCACCAGTGAGACTGGCAACAGCTGATTGCCCTTCACCGCCTGGCCCTGAGA
GAGTTGCAGCAAGCGGTCCACGCTGGTTTGCCCCAGCAGGCGAAAATCCTGTTTG
ATGGTGGTTAACGGCGGGATATAACATGAGCTATCTTCGGTATCGTCGTATCCCA
CTACCGAGATATCCGCACCAACGCGCAGCCCGGACTCGGTAATGGCGCGCATTG
CGCCCAGCGCCATCTGATCGTTGGCAACCAGCATCGCAGTGGGAACGATGCCCTC
ATTCAGCATTTGCATGGTTTGTTGAAAACCGGACATGGCACTCCAGTCGCCTTCC
CGTTCCGCTATCGGCTGAATTTGATTGCGAGTGAGATATTTATGCCAGCCAGCCA
GACGCAGACGCGCCGAGACAGAACTTAATGGGCCCGCTAACAGCGCGATTTGCT
GGTGACCCAATGCGACCAGATGCTCCACGCCCAGTCGCGTACCGTCCTCATGGGA
GAAAATAATACTGTTGATGGGTGTCTGGTCAGAGACATCAAGAAATAACGCCGG
AACATTAGTGCAGGCAGCTTCCACAGCAATGGCATCCTGGTCATCCAGCGGATA
GTTAATGATCAGCCCACTGACGCGTTGCGCGAGAAGATTGTGCACCGCCGCTTTA
CAGGCTTCGACGCCGCTTCGTTCTACCATCGACACCACCACGCTGGCACCCAGTT
GATCGGCGCGAGATTTAATCGCCGCGACAATTTGCGACGGCGCGTGCAGGGCCA
GACTGGAGGTGGCAACGCCAATCAGCAACGACTGTTTGCCCGCCAGTTGTTGTGC
CACGCGGTTGGGAATGTAATTCAGCTCCGCCATCGCCGCTTCCACTTTTTCCCGC
GTTTTCGCAGAAACGTGGCTGGCCTGGTTCACCACGCGGGAAACGGTCTGATAA
GAGACACCGGCATACTCTGCGACATCGTATAACGTTACTGGTTTCATATTCACCA
CCCTGAATTGACTCTCTTCCGGGCGCTATCATGCCATACCGCGAAAGGTTTTGCG
CCATTCGATGGCGCGCCGCTTCGTCAGGCCACATAGCTTTCTTGTTCTGATCGGA
ACGATCGTTGGCTGtgttgacaattaatcatcggctcgtataatgtgtggaattgtgagcgctcacaattCTATGGAC
TATGTTTCTGTCACCGGATGTGCTTTCCGGTCTGATGAGTCCGTGAGGACGAAAC
AGtactagtgaaagaggagaaatactagATGCCGATTAGCCCGATTGAAACCGTTCCGGTTAAA
CTGAAACCGGGTATGGATGGTCCGAAAGTTAAACAGTGGCCTCTGACCGAAGAA
AAAATCAAAGCACTGGTTGAAATCTGCACCGAGATGGAAAAAGAAGGCAAAATT
AGCAAAATCGGTCCGGAAAATCCGTATAATACACCGGTTTTTGCCATTAAGAAA
AAAGATAGCACCAAATGGCGCAAACTGGTGGATTTTCGTGAACTGAATAAACGC
ACCCAGGATTTTTGGGAAGTTCAGCTGGGTATTCCGCATCCGGCAGGTCTGAAAC
AGAAAAAAGCGTTACCGTTCTGGATGTTGGTGATGCATATTTTAGCGTTCCGCT
GGATAAAGATTTCCGTAAATATACCGCATTTACCATCCCGAGCATTAATAACGAA
ACACCGGGTATTCGCTATCAGTATAATGTTCTGCCGCAGGGTTGGAAAGGTAGTC
CGGCAATTTTTCAGTGTAGCATGACCAAAATTCTGGAACCGTTTCGTAAACAGAA
TCCGGATATTGTGATCTACCAGTATATGGATGATCTGTATGTTGGTAGCGATCTG
GAAATTGGTCAGCATCGTACCAAAATTGAAGAACTGCGTCAGCATCTGCTGCGTT
GGGGTTTTACCACACCGGATAAAAAACATCAGAAAGAACCGCCTTTTCTGTGGAT
GGGTTATGAACTGCATCCGGATAAATGGACCGTTCAGCCGATTGTTCTGCCGGAA
AAAGATAGCTGGACCGTTAATGATATTCAGAAACTGGTGGGTAAACTGAATTGG
GCAAGCCAGATTTATGCCGGTATTAAAGTTCGTCAGCTGTGTAAACTGCTGCGTG
GCACCAAAGCACTGACCGAAGTTGTTCCGCTGACAGAAGAAGCAGAACTGGAAC
TGGCAGAAAATCGTGAAATTCTGAAAGAACCGGTTCACGGCGTTTATTATGATCC
GAGCAAAGATCTGATTGCCGAAATTCAGAAACAGGGTCAGGGTCAGTGGACCTA
TCAGATTTATCAAGAACCGTTTAAAAACCTGAAACCGGCAAATATGCACGTAT
GAAAGGTGCACATACCAACGATGTTAAACAGCTGACCGAAGCAGTTCAGAAAAT
TGCAACCGAAAGCATTGTGATTTGGGGTAAAACCCCGAAATTCAAACTGCCGATT
CAGAAAGAAACCTGGGAAGCATGGTGGACCGAATATTGGCAGGCAACCTGGATT
CCGGAATGGGAATTTGTTAATACCCCTCCGCTGGTTAAACTGTGGTATCAGCTGG
AAAAAGAACCGATTATTGGTGCCGAAACCTTTTATGTTGATGGTGCAGCCAATCG
TGAAACCAAACTGGGTAAAGCAGGTTATGTTACCGATCGTGGTCGTCAGAAAGT
GGTGCCGCTGACCGATACCACCAATCAGAAAACCGAACTGCAGGCAATTCATCT
GGCACTGCAGGATAGCGGTCTGGAAGTTAATATTGTTACCGATAGCCAGTATGCC
CTGGGTATTATTCAGGCACAGCCGGATAAAAGCGAAAGCGAACTGGTTAGCCAG
ATTATTGAACAGCTGATCAAAAAGAAAAAGTGTACCTGGCATGGGTTCCGGCA
CATAAAGGTATTGGTGGTAATGAACAGGTTGATGGTCTGGTTAGCGCAGGTATTC
GTAAAGTTCTGTAAtactagtgaaagaggagaaatactagATGCCGATTAGCCCGATTGAAACC
GTTCCGGTTAAACTGAAACCGGGTATGGATGGTCCGAAAGTTAAACAGTGGCCT
CTGACCGAAGAAAAAATCAAAGCACTGGTTGAAATCTGCACCGAGATGGAAAAA
GAAGGCAAAATTAGCAAAATCGGTCCGGAAAATCCGTATAATACACCGGTTTTT
GCCATTAAGAAAAAAGATAGCACCAAATGGCGCAAACTGGTGGATTTTCGTGAA
CTGAATAAACGCACCCAGGATTTTTGGGAAGTTCAGCTGGGTATTCCGCATCCGG
CAGGTCTGAAACAGAAAAAAGCGTTACCGTTCTGGATGTTGGTGATGCATATTT
TAGCGTTCCGCTGGATAAAGATTTCCGTAAATATACCGCATTTACCATCCCGAGC
ATTAATAACGAAACACCGGGTATTCGCTATCAGTATAATGTTCTGCCGCAGGGTT TABLE 1 -continued

```
GGAAAGGTAGTCCGGCAATTTTTCAGTGTAGCATGACCAAAATTCTGGAACCGTT
TCGTAAACAGAATCCGGATATTGTGATCTACCAGTATATGGATGATCTGTATGTT
GGTAGCGATCTGGAAATTGGTCAGCATCGTACCAAAATTGAAGAACTGCGTCAG
CATCTGCTGCGTTGGGGTTTTACCACACCGGATAAAAAACATCAGAAAGAACCG
CCTTTTCTGTGGATGGGTTATGAACTGCATCCGGATAAATGGACCGTTCAGCCGA
TTGTTCTGCCGGAAAAAGATAGCTGGACCGTTAATGATATTCAGAAACTGGTGGG
TAAACTGAATTGGGCAAGCCAGATTTATGCCGGTATTAAAGTTCGTCAGCTGTGT
AAACTGCTGCGTGGCACCAAAGCACTGACCGAAGTTGTTCCGCTGACAGAAGAA
GCAGAACTGGAACTGGCAGAAAATCGTGAAATTCTGAAAGAACCGGTTCACGGC
GTTTATTATGATCCGAGCAAAGATCTGATTGCCGAAATTCAGAAACAGGGTCAG
GGTCAGTGGACCTATCAGATTTATCAAGAACCGTTTAAAAACCTGAAAACCGGC
AAATATGCACGTATGAAAGGTGCACATACCAACGATGTTAAACAGCTGACCGAA
GCAGTTCAGAAAATTGCAACCGAAAGCATTGTGATTTGGGGTAAAACCCCGAAA
TTCAAACTGCCGATTCAGAAAGAAACCTGGGAAGCATGGTGGACCGAATATTGG
CAGGCAACCTGGATTCCGGAATGGGAATTTGTTAATACCCCTCCGCTGGTTAAAC
TGTGGTATCAGCTGGAAAAAGAACCGATTATTGGTGCCGAAACCTTTTAAgatcgcta
ctagagccaggcatcaaataaaacgaaaaggctcagtcgaaagactgggcctttcgttttatctgttgtttgtcggtgaacgctctctacta
gagtcacactggctcaccttcgggtgggcctttctgcgtttatatactagaagcggccgctgcaggcttcctcgctcactgactcgctgc
gctcggtcgttcggctgcggcgagcggtatcagctcactcaaaggcggtaatacggttatccacagaatcagggggataacgcaggaa
agaacatgtgagcaaaaggccagcaaaaggccaggaaccgtaaaaaggccgcgttgctggcgtttttccataggctccgcccccct
gacgagcatcacaaaaatcgacgctcaagtcagaggtggcgaaacccgacaggactataaagataccaggcgtttccccctggaag
ctccctcgtgcgctctcctgttccgaccctgccgcttaccggatacctgtccgcctttctcccttcgggaagcgtggcgctttctcatagct
cacgctgtaggtatctcagttcggtgtaggtcgttcgctccaagctgggctgtgtgcacgaaccccccgttcagcccgaccgctgcgc
cttatccggtaactatcgtcttgagtccaacccggtaagacacgacttatcgccactggcagcagccactggtaacaggattagcagag
cgaggtatgtaggcggtgctacagagttcttgaagtggtggcctaactacggctacactagaaggacagtatttggtatctgcgctctgc
tgaagccagttaccttcggaaaaagagttggtagctcttgatccggcaaacaaaccaccgctggtagcggtggttttttttgtttgcaagca
gcagattacgcgcagaaaaaaaggatctcaagaagatcctttgatcttttctacggggtctgacgctcagtggaacgaaaactcacgtt
aagggattttggtcatgagattatcaaaaaggatcttcacctagatccttttaaattaaaaatgaagttttaaatcaatctaaagtatatatga
gtaaacttggtctgacagttaccaatgcttaatcagtgaggcacctatctcagcgatctgtctatttcgttcatccatagttgcctgactccc
cgtcgtgtagataactacgatacgggagggcttaccatctggccccagtgctgcaatgataccgcgagacccacgctcaccggctcc
agatttatcagcaataaaccagccagccggaagggccgagcgcagaagtggtcctgcaactttatccgcctccatccagtctattaatt
gttgccgggaagctagagtaagtagttcgccagttaatagtttgcgcaacgttgttgccattgctacaggcatcgtggtgtcacgctcgtc
gtttggtatggcttcattcagctccggttcccaacgatcaaggcgagttacatgatcccccatgttgtgcaaaaaagcggttagctccttc
ggtcctccgatcgttgtcagaagtaagttggccgcagtgttatcactcatggttatggcagcactgcataattctcttactgtcatgccatc
cgtaagatgcttttctgtgactggtgagtactcaaccaagtcattctgagaatagtgtatgcggcgaccgagttgctcttgcccggcgtca
atacgggataataccgcgccacatagcagaactttaaaagtgctcatcattggaaaacgttcttcggggcgaaaactctcaaggatctta
ccgctgttgagatccagttcgatgtaacccactcgtgcacccaactgatcttcagcatcttttactttcaccagcgtttctgggtgagcaaa
aacaggaaggcaaaatgccgcaaaaaagggaataagggcgacacggaaatgttgaatactcatactcttcctttttcaatattattgaag
catttatcagggttattgtctcatgagcggatacatatttgaatgtatttag (SEQ ID NO: 7)

pJEMLRT:
ttcaggtttgccggctgaaagcgctatttcttccagaattgccatgattttttcccccacgggaggcgtcactggctcccgtgttgtcggcag
ctttgattcgataagcagcatcgcctgtttcaggctgtctatgtgtgactgttgagcgtgaacaagttgtctcaggtgttcaatttcatgttcta
gttgctttgttttactggtttcacctgttctattaggtgttacatgctgttcatctgttacattgtcgatcgttcatggtgaacagctttaaatgca
ccaaaaactcgtaaaagctctgatgtatctatcttttttacaccgttttcatctgtgcatatggacagttttcccttttgatatctaacggtgaaca
gttgttctacttttgtttgttagtcttgatgcttcactgatagatacaagaccatcagatccttcctgtatttagccagtatgttctc
tagtgtggttcgttgttttttgcgtgagccatgagaacgaaccattgagatcatgcttactttgcatgtcactcaaaaattttgcctcaaaactg
gtgagctgaattttttgcagtttaaagcatcgtgtagtgttttttcttagtccgttacgtaggtaggaatctgatgtaatggttgttggtattttgtca
ccattcattttttatctggttgttctcaagttcggttacgagatccatttgtctatctagttcaacttggaaaatcaacgtatcagtcgggcggcc
tcgcttatcaaccaccaattttcatattgctgtaagtgtttaaatctttacttattggtttcaaaaacccatttggttaagcctttttaaactcatgtag
ttatttttcaagcattaacatgaacttaaattcatcaaggctaatctctatatttgccttgtgagttttcttttgtgtagttctttaataaccactcat
aaatcctcatagagtatttgttttcaaaagacttaacatgttccagattatatttttatgaattttttttaactggaaaagataaggcaatatctcttc
actaaaaactaattctaattttttcgcttgagaacttggcatagtttgtccactggaaaatctcaaagcctttaaccaaaggattcctgatttcc
acagttctcgtcatcagctctctggttgcttagctaataccataagcattttccctactgatgttcatcatctgagcgtattggttataagt
gaacgataccgtccgttctttccttgtagggttttcaatcgtggggttgagtagtgccacacagcataaaattagcttggtttcatgctccgt
taagtcatagcgactaatcgctagttcatttgctttgaaaacaactaattcagacatacatctcaattggtctaggtgatttttaatcactataacc
aattgagatgggctagtcaatgataattactagtccttttcctttgagttgtgggtatctgtaaattctgctagaccttctgctggaaaacttgta
aattctgctagaccctctgtaaattccgctagaccctttgtgtgtttttttgtttatattcaagtggttataatttataagaataaagaaagaataaa
aaaagataaaaagaatagatcccagcccgtgtataactcactactttagtcagttccgcagtattacaaaaggatgtcgcaaacgctgtt
tgctcctctacaaaacagaccttaaaaccctcaaaggcttaagtagcaccctcgcaagctcgggcaaatcgctgaatattccttttgtctcc
gaccatcaggcacctgagtcgctgtcttttcgtgacattcagttcgctgcgctcacggctctggcagtgaatgggggtaaatggcacta
caggcgccttttatggattcatgcaaggaaactacccataatacaagaaaagcccgtcacgggcttctcagggcgttttatggcgggtct
gctatgtggtgctatctgactttttgtgtcagcagttcctgccctctgattttccagtctgaccacttcggattatcccgtgacaggtcattc
agactggctaatcacccagtaaggcagcggtatcatcaacaggcttacccgtcttactgtccctagtgcttggattctcaccaataaaa
aacgcccggcggcaaccgagcgttctgaacaaatccagatggagttctgaggtcattactggatctatcaacaggagtccaagcgag
ctctcgaacccagagtcccgctcagaagaactcgtcaagaaggcgatagaaggcgatgcgctgcgaatcgggagcggcgatacc
gtaaagcacgaggaagcggtcagcccattcgccgccaagctcttcagcaatatcacgggtagccaacgctatgtcctgatagcggtc
cgccacacccagccggccacagtcgatgaatccagaaaagcggccattttccaccatgatattcggcaagcaggcatcgccatgggt
cacgacgagatcctcgccgtcgggcatgcgcgccttgagcctggcgaacagttcggctggcgcgagcccctgatgctcttcgtccag
atcatcctgatcgacaagaccggcttccatccgagtacgtgctcgctcgatgcgatgtttcgcttggtggtcgaatgggcaggtagccg
gatcaagcgtatgcagccgccgcattgcatcagccatgatggatactttctcggcaggagcaaggtgagatgacaggagatcctgcc
ccggcacttcgcccaatagcagccagtcccttcccgcttcagtgacaacgtcgagcacagctgcgcaaggaacgcccgtcgtggcc
agccacgatagccgcgctgcctcgtcctgcagttcattcagggcaccggacaggtcggtcttgacaaaaagaaccgggcgcccctg
cgctgacagccggaacacggcggcatcagagcagccgattgtctgttgtgcccagtcatagccgaatagcctctccacccaagcgg
ccggagaacctgcgtgcaatccatcttgttcaatcatgcgaaacgatcctcatcctgtctcttgatcagatcttgatcccctgcgccatca
gatccttggcggcaagaaagccatccagtttactttgcagggcttcccaaccttaccagagggcgccccagctggcaattccgacgtct
aagaaaccattattatcatgacattaacctataaaaataggcgtatcacgaggccctttcgtcttcacctcgagttgacagctagctcagtc
ctaggtactgtgctagcggaattcattaaagaggagaaaggtaccatgggtcataatcataatcataatcataatcataatcacaacggt
gggagatgacgatgacaagggtggtcgacaagcttggatcctgcaggcctcagggccgatcgatgggaccaatggggcagccc
tgcaagtgttgacccctaaatatagaagatgagtatcggctacatgagacctcaaaagagccagatgtttctctagggtccacatggctgt
```

TABLE 1 -continued

```
ctgattttcctcaggcctgggcggaaaccgggggcatgggactggcagttcgccaagctcctctgatcatacctctgaaagcaacctct
accccgtgtccataaaacaataccccatgtcacaagaagccagactggggatcaagccccacatacagagactgttggaccaggg
aatactggtaccctgccagtcccctggaacacgccctgctaccgttaagaaaccagggactaatgattataggcctgtccaggatc
tgagagaagtcaacaagcgggtggaagacatccaccccaccgtgccaaccttacaacctcttgagcgggctcccaccgtcccac
cagtggtacactgtgcttgatttaaaggatgccttttctgcctgagactccaccccaccagtcagcctctcucgcctttgagtggagaga
tccagagatgggaatctcaggacaattgacctggaccagactcccacagggtttcaaaaacagtccaccctgtttgatgaggcactg
cacagagacctagcagacttccggatccagcacccagacttgatcctgctacagtacgtggatgacttactgctggccgccacttctga
gctagactgccaacaaggtactcgggccctgttacaaaccctagggaacctcgggtatcgggcctcggccaagaaagcccaaatttg
ccagaaacaggtcaagtatctggggtatcttctaaaagagggtcagagatggctgactgaggccagaaaagagactgtgatggggca
gcctactccgaagaccccctcgacaactaagggagttcctagggacggcaggcttctgtcgcctctggatccctgggtttgcagaaatg
gcagcccccttgtaccctctcaccaaaacggggactctgtttaattgggggcccagaccaacaaaaggcctatcaagaaatcaagcaag
ctcttctaactgccccagccctgggggttgccagatttgactaagccctttgaactcttttgtcgacgagaagcagggctacgccaaaggtg
tcctaacgcaaaaactgggaccttggcgtcggccggtggcctacctgtccaaaaagctagaccccagtagcagctgggtggccccctt
gcctacggatggtagcagccattgccgtactgacaaaggatgcaggcaagctaaccatgggacagccactagtcattctggcccccc
atgcagtagaggcactagtcaaacaaccccccgaccgctggcttccaacgcccggatgactcactatcaggccttgctttggacac
ggaccgggtccagttcggaccggtggtagccctgaacccggctacgctgctcccactgcctgaggaagggctgcaacacaactgcc
ttgatatcctggccgaagcccacggaaccgaaccgaccttaacggaccagccgctcccagacgccgaccacacctggtacacgga
tggaagcagtctcttacaagagggacagcgtaaggcgggagctgcggtgaccaccgagaccgaggtaatctgggctaaagccctg
ccagccgggacatccgctcagcgggctgaactgatagcactcacccaggccctaaagatggcagaaggtaagaagctaaatgtttat
actgatagccgttatgcttttgctactgcccatatccatggagaaatatacagaaggcgtgggttgctcacatcagaaggcaaagagatc
aaaaataaagacgagatctttaaatgacgctgatagtgctagtgtagatcgctactagagccaggcatcaaataaaacgaaaggctca
gtcgaaagactgggcctttcgtttatctgttgtttgtcggtgaacgctctctactagagtcacactggctcaccttcgggtgggcctttctg
cgtttatatataatataatataaatgtccagacctgcaggcatgcaagcctctagaggcatcaaataaaacgaaaggctcagtcgaaagactggg
cctttcgtntatctgttgtttgtcggtgaacgctctcctgagtaggacaaatccgccgccctagacctagggtacgggttttgctgcccgc
aaacgggctgttctggtgttgctagtttgttatcagaatcgcagatccggc (SEQ ID NO: 8)
``` pJEO_0:

```
tgccacctgacgtctaagaaaaggaatattcagcaatttgcccgtgccgaagaaaggcccacccgtgaaggtgagccagtgagttgat
tgctacgtaatgtcggccaattcgcgctaacttacattaattgcgtTCACTGCCCGCTTTCCAGTCGGGAA
ACCTGTCGTGCCAGCTGCATTAATGAATCGGCCAACGCGCGGGGAGAGGCGGTT
TGCGTATTGGGCGCCAGGGTGGTTTTTCTTTTCACCAGTGAGACTGGCAACAGCT
GATTGCCCTTCACCGCCTGGCCCTGAGAGAGTTGCAGCAAGCGGTCCACGCTGGT
TTGCCCCAGCAGGCGAAAATCTGTTTGATGGTGGTTAACGGCGGGATATAACAT
GAGCTATCTTCGGTATCGTCGTATCCCACTACCGAGATATCCGCACCAACGCGCA
GCCCGGACTCGGTAATGGCGCGCATTGCGCCCAGCGCCATCTGATCGTTGGCAAC
CAGCATCGCAGTGGGAACGATGCCCTCATTCAGCATTTGCATGGTTTGTTGAAAA
CCGGACATGGCACTCCAGTCGCCTTCCCGTTCCGCTATCGGCTGAATTTGATTGC
GAGTGAGATATTTATGCCAGCAGCAGACGCAGACGCGCCAGACAGAACTTA
ATGGGCCCGCTAACAGCGCGATTTGCTGGTGACCCAATGCGACCAGATGCTCCAC
GCCCAGTCGCGTACCGTCCTCATGGGAGAAAATAATACTGTTGATGGGTGTCTGG
TCAGAGACATCAAGAAATAACGCCGGAACATTAGTGCAGGCAGCTTCCACAGCA
ATGGCATCCTGGTCATCCAGCGGATAGTTAATGATCAGCCCACTGACGCGTTGCG
CGAGAAGATTGTGCACCGCCGCTTTACAGGCTTCGACGCCGCTTCGTTCTACCAT
CGACACCACCACGCTGGCACCCAGTTGATCGGCGCGAGATTTAATCGCCGCGAC
AATTTGCGACGGCGCGTGCAGGGCCAGACTGGAGGTGGCAACGCCAATCAGCAA
CGACTGTTTGCCCGCCAGTTGTTGTGCCACGCGGTTGGGAATGTAATTCAGCTCC
GCCATCGCCGCTTCCACTTTTTCCCGCGTTTTCGCAGAAACGTGGCTGGCCTGGTT
CACCACGCGGGAAACGGTCTGATAAGAGACACCGGCATACTCTGCGACATCGTA
TAACGTTACTGGTTTCATATTCACCACCCTGAATTGACTCTCTTCCGGGCGCTATC
ATGCCATACCGCGAAAGGTTTTGCGCCATTCGATGGCGCGCCGCTTCGTCAGGCC
ACATAGCTTTCTTGTTCTGATCGGAACGATCGTTGGCTGtgttgacaattaatcatcggctcgtata
atgtgtggaattgtgagcgctcacaattCTTGGGACTCGTTGTAGCTAGCCTCCTGTCCGGTTCCGT
TAACGGTCACGAGTTCGAAATCGAAGGTGAAGGTGAAGGTCGTCCGTACGAAGG
TACCCAGACCGCTAAACTGAAAGTTACCAAAGGTGGTCCGCTGCCGTTCGCTTGG
GACATCCTGTCCCCGCAGTTCCAGTACGGTTCCAAAGCTTAAAAACGTGGTGCCC
GAACAGGGACGGATCCGCCCGGATAGCTCAGTCGGTAGAGCATCAGACTTTTAA
TCTGAGGGTCCAGGGTTCAAGTCCCTGTTCGGGCGCCACGTTTTTcgctgcaggagtcacta
agggttagttagttagattagcagaaagtcaaaagcctccgaccggaggcttttgactaaaaacttcccttgggggttatcattgggctcac
tcaaaggcggtaatcagataaaaaaaaatccttagctttcgctaagatgatttctagagatggaatagactggatggaggcggata
aagttgcaggaccacttctgcgctcggcccttccggctggctggtttattgctgataaatctggagcggtgagcgtgggtctcgcggt
atcattgcagcactgggcagatggtaagccctcccgtatcgtagttatctacacgacggggagtcaggcaactatggatgaacgaa
atagacagatcgctgagataggtgcctcactgattaagcattggtaactgtcagaccaagttactcatatatactttagattgatttaaaac
ttcattttaattaaaaggatctaggtgaagatcctttttgataatctcatgaccaaaatcccttaacgtgagttttcgttccactgagcgtca
gaccccgtaataagatgatcttcttgagatcgttttggtctgcgcgtaatctcttgctctgaaaacgaaaaaaccgccttgcagggcggtt
ttcgaaggttctctgagctaccaactctttgaaccgaggtaactggcttggaggagcgcagtcaccaaaacttgtccttcagtttagcctt
aaccggcgcatgacttcaagactaactcctctaaatcaattaccagtggctgctgccagtggtgcttttgcatgtctttccgggttggactc
aagacgatagttaccggataaggcgcagcggtcgggactgaacgggggggttcgtgcatacagtcccagcttggagcttggagcttggcgaactgcctacc
cggaactgagtgtcaggcgtggaatgagacaaacgcggccataacagcggaatgacaccggtaaacgaaaggcaggaacagga
gagcgcacgagggagccgcccagggaaacgcctggtatctttatagtcctgtcgggtttcgccaccactgatttgagcgtcagatttcg
tgatgcttgtcagggggcggagcctatgaaaaacggctttgccgcggccctctcacttccctgttaagtatcttcctggcatcttcca
ggaaatctccgccccgttcgtaagcgcattttccgctgcactgcatccgagcgtagcgagtcagtgagcgaggaagcggaa
tatatcctgtatcacatattctgctgacgcaccggtgcagccttttttctcctgccacatgaagcacttcactgacaccctcatcagtgccaa
catagtaagccagtatacactccgctagcgctgaggtctgcctcgtgaagaaggtgttgctgactcataccaggcctgaatcgcccat
catccagccagaaagtgagggagccacggttgatgagagctttgttgtaggtggaccagttggtgattttgaacttttgctttgccacgg
aacggtctgcgttgtcgggaagatgcgtgatctgatcttcaactcagcaaaagttcgatttattcaacaaagccacgttgtgtctcaaaa
tctctgatgttacattgcacaagataaaaatatatcatcatgaacaataaaactgtctgcttacataaacagtaataaagggtgttacta
gaggttgatcggcacgtaagaggttccaactttcaccataatgaaataagatcactaccgggcgtatttttgagttatcgagattttcag
gagctaaggaagctaaaatgagggaagcggtgatcgccgaagtatcgactcaactatcagaggtagttggcgtcatcgagcgccatc
tcgaaccgacgttgctggccgtacatttgtacggctccgcagtggatggcggcctgaagccacacagtgatattgatttgctggttacg
gtgaccgtaaggcttgatgaaacaacgcggcgagctttgatcaacgaccttttggaaacttcggcttcccctggagagagcgagattct
```

TABLE 1 -continued ccgcgctgtagaagtcaccattgttgtgcacgacgacatcattccgtggcgttatccagctaagcgcgaactgcaatttggagaatggc
agcgcaatgacattcttgcaggtatcttcgagccagccacgatcgacattgatctggctatcttgctgacaaaagcaagagaacatagc
gttgccttggtaggtccagcggcggaggaactctttgatccggttcctgaacaggatctatttgaggcgctaaatgaaaccttaacgcta
tggaactcgccgcccgactgggctggcgatgagcgaaatgtagtgcttacgttgtcccgcatttggtacagcgcagtaaccggcaaaa
tcgcgccgaaggatgtcgctgccgactgggcaatggagcgcctgccggcccagtatcagcccgtcatacttgaagctagacaggctt
atcttggacaagaagaagatcgcttggcctcgcgcgcagatcagttggaagaatttgtccactacgtgaaaggcgagatcaccaaggt
agtcggcaaataatactagctccggcaaaaaaacgggcaaggtgtcaccaccctgcccttttctttaaaaccgaaaagattacttcgcg
tt (SEQ ID NO: 9)

pJEO_4:
AGGTcccaatgataaccccaagggaagttttagtcaaaagcctccggtcggaggcttttgactttCTGCTAATCTAACT
AACTAACCCTTAGTGACTCCTGCAGCGAAAAAAAACGTGGCGCCCGAACAGGGA
CTTGAACCCTGGACCCTCAGATTAAAAGTCTGATGCTCTACCGACTGAGCtatccGT
CCCTGTTCGGGCGCCACGTTTTTTTTCGGTGATGTTcagccatagtaGCGGGTGCGccgaat
gctctatttAAAGTTAAACAAAATTATTTGTAGAGGGAAACCGTTGTGGTCTCCCTGAA
TATATTATACGAGCCTTATGCATGCCCGTAAAGTTATCCAGCAACCACTCATAGA
CCTAGGGCAGCAGATAGGGACGACGTGGTGTTAGCTGTGAGcgGCGTGTCATTGG
GGGCTTATACAGGCGTAGACTACAATGGGCCCAACTCACACAGCTAACACCACG
TCGTCCCTATCTGCTGCCCTAGGTCTATGAGTGGTTGCTGGATAACTTTACGGGC
ATGCATAAGGCTCGTATAATATATTCAGGGAGACCACAACGGTTTCCCTCTACAA
ATAATTTTGTTTAACTTTaaataCGGTGATGTTggcgtgctcaaGCGGGTGCGggattgcgcaAA
AAAAAACGTGGCGCCCGAACAGGGACggataGCTCAGTCGGTAGAGCATCAGACTT
TTAATCTGAGGGTCCAGGGTTCAAGTCCCTGTTCGGGCGCCACGTTTTTTTTcgctgc
aggagtcataagggttagttagttagattagcagaaagtcaaaagcctccgaccggaggcttttgactaaaacttcccttggggttatcat
tgggCTCCgctagagatggaatagactggatggaggcggataaagttgcaggaccacttctgcgctcggcccttccggctggctg
gtttattgctgataaatctggagccggtgagcgtgggtctcgcggtatcattgcagcactggggccagatggtaagccctcccgtatcgt
agttatctacacgacggggagtcaggcaactatgatgaacgaaatagacagatcgctgagataggtgcctcactgattaagcattggt
aactgtcagaccaagttactcatatatactttagattgatttaaaacttcattttaatttaaaaggatctaggtgaagatcctttttgataatct
catgaccaaaatccctaacgtgagttttcgttccactgagcgtcagaccccgtaataagatgatcttcttgagatcctttggtctgcgcgt
aatctcttgctctgaaaacgaaaaaccgcctgcagggcggttttttccgaaggttctctgagctaccaactctttcaaccgaggtaactgg
cttgaggagcgcagtcaccaaaacttgtcctttcagtttagcctttaaccggcgcatgacttcaagactaactcctctaaatcaattacca
gtggctgctgccagtggtgcttttgcatgtctttccgggttggactcaagacgatagttaccggataaggcgcagcggtcggactgaac
gggggggttcgtgcatacagtccagcttggagcgaactgcctacccggaactgagtgtcaggcgtggaatgagacaaacgcggccat
aacagcggaatgacaccggtaaaccgaaaggcaggacaggtacactgtagccgtgaagccgcaggggagaacgcctggtatcttt
atagtcctgtcgggtttcgccaccactgatttgagcgtcagatttcgtgatgcttgtcagggggcggagcgtatggaaaaacggctttg
ccgcggccctctcacttccctgttaagtatcttcctggcatcttccaggaaatctccgccccgttcgtaagccatttccgctcgccgcagt
cgaacgaccgagcgtagcgagtcagtgagcgaggaagcggaatatatcctgtatcacatattctgctgacgcaccggtgcagccttttt
tctcctgccacatgaagcacttcactgacaccctcatcagtgccaacatgatacactccgctagcgctgaggtctgcctc
gtgaagaaggtgttgctgactcataccaggcctgaatcgccccatcatccagccagaaagtgagggagccacggttgatgagagctt
gttgtaggtggaccagttggtgattttgaactttttgctttgccacggaacggtctgcgttgtcgggaagatgcgtgatctgatccttcaact
cagcaaaagttcgatttattcaacaaagccacgttgtgtctcaaaatctctgatgttacattgcacaagataaaaatatatcatcatgaaca
ataaaactgtctgcttacataaacagtaataacaaggggtgttactagagGCTTcccaatgataaccccaagggaagttttagtcaaa
agcctccggtcggaggcttttgactttctgctaatctaactaactaactgcagcgAAAAAAAACGTGGCGCCCGAA
CAGGGACTTGAACCCTGGACCCTCAGATTAAAAGTCTGATGCTCTACCGACTGAG
CtatccGTCCCTGTTCGGGCGCCACGTTTTTTTTGCGGCTAgCAgagcattcgggAAAGGTG
TGactatggctgtatttAAAGTTAAACAAAATTATTTGTAGAGGGAAACCGTTGTGGTCTC
CCTGAATATATTATACGAGCCTTATGCATGCCCGTAAAGTTATCCAGCAACCACT
CATAGACCTAGGGCAGCAGATAGGGACGACGTGGTGTTAGCTGTGAGTAATCAC
AGCTCGAGCGCCTTGAATAACATACTCATCTCTATACATTCTCGACACAGCTAAC
ACCACGTCGTCCCTATCTGCTGCCCTAGGTCTATGAGTGGTTGCTGGATAACTTTA
CGGGCATGCATAAGGCTCGTATAATATATTCAGGGAGACCACAACGGTTTCCCTC
TACAAATAATTTTGTTTAACTTTaaataGCGGCTAgCAtgcgcaatccgAAAGGTGTGtgagca
cgccAAAAAAAACGTGGCGCCCGAACAGGGACggataGCTCAGTCGGTAGAGCATCA
GACTTTTAATCTGAGGGTCCAGGGTTCAAGTCCCTGTTCGGGCGCCACGTTTTTTT
Tcgctgcagttagttagttagattagcagaaagtcaaaagcctccgaccggaggcttttgactaaaacttcccttggggttatcattggg
CATTgttgatcgggcacgtaagaggttccaactttcaccataatgaaataagatcactaccgggcgtatttttgagttatcgagattttt
caggagctaaggaagctaaaatgagggaagcggtgatcgccgaagtatcgactcaactatcagaggtagttggcgtcatcgagcgc
catctcgaaccgacgttgctggccgtacatttgtacggctccgcagtggatggcggcctgaagccacacagtgatattgatttgctggtt
acggtgaccgtaaggcttgatgaaacaacgcggcgagcttttgatcaacgaccttttggaaacttcggcttcccctggagagagcgaga
ttctccgcgctgtagaagtcaccattgttgtgcacgacgacatcattccgtggcgttatccagctaagcgcgaactgcaatttggagaat
ggcagcgcaatgacattcttgcaggtatcttcgagccagccacgatcgacattgatctggctatcttgctgacaaaagcaagagaacat
agcgttgccttggtaggtccagcggcggaggaactctttgatccggttcctgaacaggatctatttgaggcgctaaatgaaaccttaacg
ctatggaactcgccgcccgactgggctggcgatgagcgaaatgtagtgcttacgttgtcccgcatttggtacagcgcagtaaccggca
aaatcgcgccgaaggatgtcgctgccgactgggcaatggagcgcctgccggcccagtatcagcccgtcatacttgaagctagacag
gcttatcttggacaagaagaagatcgcttggcctcgcgcgcagatcagttggaagaatttgtccactacgtgaaaggcgagatcacca
aggtagtcggcaaataatactagctccggcaaaaaaacgggcaaggtgtcaccaccctgcccttttctttaaaaccgaaaagattactt
cgcgtt (SEQ ID NO: 10)

pJEO_3:
AGGTcccaatgataaccccaagggaagttttagtcaaaagcctccggtcggaggcttttgactttCTGCTAATCTAACT
AACTAACCCTTAGTGACTCCTGCAGCGGCGTGTCATTGGGGGCTTATACAGGCGT
AGACTACAATGGGCCCAACTCACACAGCTAACACCACGTCGTCCCTATCTGCTGC
CCTAGGTCTATGAGTGGTTGCTGGATAACTTTACGGGCATGCATAAGGCTCGTAT
AATATATTCAGGGAGACCACAACGGTTTCCCTCTACAAATAATTTTGTTTAACTTT
aaataCGGTGATGTTggcgtgctcaaGCGGGTGCGggattgcgcaAAAAAAAACGTGGCGCCCG
AACAGGGACggataGCTCAGTCGGTAGAGCATCAGACTTTTAATCTGAGGGTCCAG
GGTTCAAGTCCCTGTTCGGGCGCCACGTTTTTTTTcgctgcaggagtcataagggttagttagttagatt
agcagaaagtcaaaagcctccgaccggaggcttttgactaaaacttcccttggggttatcattgggCTCCgctagagatggaataga
ctggatggaggcggataaagttgcaggaccacttctgcgctcggcccttccggctggctggtttattgctgataaatctggagccggtg
agcgtgggtctcgcggtatcattgcagcactggggccagatggtaagccctcccgtatcgtagttatctacacgacggggagtcaggc TABLE 1 -continued

```
aactatggatgaacgaaatagacagatcgctgagataggtgcctcactgattaagcattggtaactgtcagaccaagtttactcatatata
ctttagattgatttaaaacttcatttttaatttaaaaggatctaggtgaagatcctttttgataatctcatgaccaaaatcccttaacgtgagtttt
cgttccactgagcgtcagacccctttaataagatgatcttcttgagatcgttttggtctgcgcgtaatctcttgctctgaaaacgaaaaaacc
gccttgcagggcggttttttcgaaggttctctgagctaccaactcttttgaaccgaggtaactggcttggaggagcgcagtcaccaaaactt
gtcctttcagtttagccttaaccggcgcatgacttcaagactaactcctctaaatcaattaccagtggctgctgccagtggtgcttttgcatg
tctttccgggttggactcaagacgatagttaccggataaggcgcagcggtcggactgaacgggggttcgtgcatacagtccagcttg
gagcgaactgcctacccggaactgagtgtcaggcgtggaatgagacaaacgcggccataacagcggaatgacaccggtaaaccga
aaggcaggaacaggagagcgcacgagggagccgccaggggaaacgcctggtatctttatagtcctgtcgggtttcgccaccactga
tttgagcgtcagatttcgtgatgcttgtcagggggcggagcctatggaaaaacggctttgccgcggccctctcacttccctgttaagtat
cttcctggcatcttccaggaaatctccgccccgttcgtaagccatttccgctcgccgcagtcgaacgaccgagcgtagcgagtcagtga
gcgaggaagcggaatatatcctgtatcacatattctgctgacgcaccggtgcagccttttttctcctgccacatgaagcacttcactgaca
ccctcatcagtgccaacatagtaagccagtatacactccgctagcgctgaggtctgcctcgtgaagaaggtgttgctgactcataccag
gcctgaatcgccccatcatccagccagaaagtgagggagccacggttgatgagagctttgttgtaggtggaccagttggtgattttgaa
cttttgctttgccacggaacggtctgcgttgtcgggaagatgcgtgatctgatccttcaactcagcaaaagttcgatttattcaacaaagcc
acgttgtgtctcaaaatctctgatgttacattgcacaagataaaaatatatcatcatgaacaataaaactgtctgcttacataaacagtaata
caagggggtgtttactagagGCTTcccaatgataaccccaagggaagttttagtcaaaagcctccggtcggaggcttttgactttctgc
taatctaactaactaactgcagcgAAAAAAAACGTGGCGCCCGAACAGGGACTTGAACCCTGG
ACCCTCAGATTAAAAGTCTGATGCTCTACCGACTGAGCtatccGTCCCTGTTCGGGC
GCCACGTTTTTTTTGCGGCTAgCAgagcattcgggAAAGGTGTGactatggctgtatttAAAGTTA
AACAAAATTATTTGTAGAGGGAAACCGTTGTGGTCTCCCTGAATATATTATACGA
GCCTTATGCATGCCCGTAAAGTTATCCAGCAACCACTCATAGACCTAGGGCAGCA
GATAGGGACGACGTGGTGTTAGCTGTGAGTAATCACAGCTCGAGCGCCTTGAAT
AACATACTCATCTCTATACATTCTCGACACAGCTAACACCACGTCGTCCCTATCT
GCTGCCCTAGGTCTATGAGTGGTTGCTGGATAACTTTACGGGCATGCATAAGGCT
CGTATAATATATTCAGGGAGACCACAACGGTTTCCCTCTACAAATAATTTTGTTT
AACTTTaaataGCGGCTAgCAtgcgcaatccgAAAGGTGTGtgagcacgccAAAAAAAACGTGG
CGCCCGAACAGGGACggataGCTCAGTCGGTAGAGCATCAGACTTTTAATCTGAGG
GTCCAGGGTTCAAGTCCCTGTTCGGGCGCCACGTTTTTTTTcgctgcagttagttagttagattag
cagaaagtcaaaagcctccgaccggaggcttttgactaaaaacttcccttggggttatcattgggCATTgttgatcgggcacgtaaga
ggttccaacttttcaccataatgaaataagatcactaccgggcgtatttttttgagttatcgagattttcaggagctaaggaagctaaaatgag
ggaagcggtgatcgccgaagtatcgactcaactatcagaggtagttggcgtcatcgagcgccatctcgaaccgacgttgctggccgta
catttgtacggctccgcagtggatggcggcctgaagccacacagtgatattgatttgctggttacggtgaccgtaaggcttgatgaaac
aacgcggcgagctttgatcaacgaccttttggaaacttcggcttccctggagagagcgagattctccgcgctgtagaagtcaccattg
ttgtgcacgacgacatcattccgtggcgttatccagctaagcgcgaactgcaatttggagaatggcagcgcaatgacattcttgcaggt
atcttcgagccagccacgatcgacattgatctggctatcttgctgacaaaagcaagagaacatagcgttgccttggtaggtccagcggc
ggaggaactctttgatccggttcctgaacaggatctatttgaggcgctaaatgaaaccttaacgctatggaactcgccgcccgactggg
ctggcgatgagcgaaatgtagtgcttacgttgtcccgcatttggtacagcgcagtaaccggcaaaatcgcgccgaaggatgtcgctgc
cgactgggcaatggagcgcctgccggcccagtatcagcccgtcatacttgaagctagacagcgttatcttggacaagaagaagatcg
cttggcctcgcgcgcagatcagttggaagaattgtccactacgtgaaaggcgagatcaccaaggtagtcggcaaataatactagctc
cggcaaaaaaaacgggcaaggtgtcaccaccctgcccttttttctttaaaaccgaaaagattacttcgcgtt (SEQ ID NO: 11)
``` pJE0_2:
```
AGGTgctagagatggaatagactggatggaggcggataaagttgcaggaccacttctgcgctcggccctttccggctggctggttta
ttgctgataaatctggagccggtgagcgtgggtctcgcggtatcattgcagcactggggccagatggtaagccctcccgtatcgtagtt
atctacacgacggggagtcaggcaactatggatgaacgaaatagacagatcgctgagataggtgcctcactgattaagcattggtaac
tgtcagaccaagtttactcatatatactttagattgatttaaaacttcatttttaatttaaaaggatctaggtgaagatcctttttgataatctcatg
accaaaatcccttaacgtgagttttcgttccactgagcgtcagacccctttaataagatgatcttcttgagatcgttttggtctgcgcgtaatct
cttgctctgaaaacgaaaaaaccgccttgcagggcggttttttcgaaggttctctgagctaccaactcttttgaaccgaggtaactggcttg
gaggagcgcagtcaccaaaacttgtcctttcagtttagccttaaccggcgcatgacttcaagactaactcctctaaatcaattaccagtgg
ctgctgccagtggtgcmtgcatgtctttccgggttggactcaagacgatagttaccggataaggcgcagcggtcggactgaacgggg
ggttcgtgcatacagtccagcttggagcgaactgcctacccggaactgagtgtcaggcgtggaatgagacaaacgcggccataaca
gcggaatgacaccggtaaaccgaaaggcaggaacaggagagcgcacgagggagccgccaggggaaacgcctggtatctttatag
tcctgtcgggtttcgccaccactgatttgagcgtcagatttcgtgatgcttgtcagggggcggagcctatggaaaaacggctttgccgc
ggccctctcacttccctgttaagtatcttcctggcatcttccaggaaatctccgccccgttcgtaagccatttccgctcgccgcagtcgaa
cgaccgagcgtagcgagtcagtgagcgcgaggaagcggaatatatcctgtatcacatattctgctgacgcaccggtgcagccttttttctc
ctgccacatgaagcacttcactgacaccctcatcagtgccaacatagtaagccagtatacactccgctagcgctgaggtctgcctcgt
aagaaggtgttgctgactcataccaggcctgaatcgccccatcatccagccagaaagtgagggagccacggttgatgagagctttgtt
gtaggtggaccagttggtgattttgaacttttgctttgccacggaacggtctgcgttgtcgggaagatgcgtgatctgatccttcaactcag
caaaagttcgatttattcaacaaagccacgttgtgtctcaaaatctctgatgttacattgcacaagataaaaatatatcatcatgaacaataa
aactgtctgcttacataaacagtaatacaagggggtgtttactagagGCTTcccaatgataaccccaagggaagttttagtcaaaagcc
tccggtcggaggcttttgactttctgctaatctaactaactaactgcagcgAAAAAAAACGTGGCGCCCGAACAG
GGACTTGAACCCTGGACCCTCAGATTAAAAGTCTGATGCTCTACCGACTGAGCtatc
cGTCCCTGTTCGGGCGCCACGTTTTTTTTGCGGCTAgCAgagcattcgggAAAGGTGTGac
tatggctgtatttAAAGTTAAACAAAATTATTTGTAGAGGGAAACCGTTGTGGTCTCCCTG
AATATATTATACGAGCCTTATGCATGCCCGTAAAGTTATCCAGCAACCACTCATA
GACCTAGGGCAGCAGATAGGGACGACGTGGTGTTAGCTGTGAGTAATCACAGCT
CGAGCGCCTTGAATAACATACTCATCTCTATACATTCTCGACACAGCTAACACCA
CGTCGTCCCTATCTGCTGCCCTAGGTCTATGAGTGGTTGCTGGATAACTTTACGG
GCATGCATAAGGCTCGTATAATATATTCAGGGAGACCACAACGGTTTCCCTCTAC
AAATAATTTTGTTTAACTTTaaataGCGGCTAgCAtgcgcaatccgAAAGGTGTGtgagcacgcc
AAAAAAAACGTGGCGCCCGAACAGGGACggataGCTCAGTCGGTAGAGCATCAGA
CTTTTAATCTGAGGGTCCAGGGTTCAAGTCCCTGTTCGGGCGCCACGTTTTTTTTcg
ctgcagttagttagttagattagcagaaagtcaaaagcctccgaccggaggcttttgactaaaaacttcccttggggttatcattgggCA
TTgttgatcgggcacgtaagaggttccaacttttcaccataatgaaataagatcactaccgggcgtatttttttgagttatcgagattttcag
gagctaaggaagctaaaatgagggaagcggtgatcgccgaagtatcgactcaactatcagaggtagttggcgtcatcgagcgccatc
tcgaaccgacgttgctggccgtacatttgtacggctccgcagtggatggcggcctgaagccacacagtgatattgatttgctggttacg
gtgaccgtaaggcttgatgaaacaacgcggcgagctttgatcaacgaccttttggaaacttcggcttcccctggagagagcgagattct
ccgcgctgtagaagtcaccattgttgtgcacgacgacatcattccgtggcgttatccagctaagcgcgaactgcaatttggagaatggc
agcgcaatgacattcttgcaggtatcttcgagccagccacgatcgacattgatctggctatcttgctgacaaaagcaagagaacatagc
gttgccttggtaggtccagcggcggaggaactctttgatccggttcctgaacaggatctatttgaggcgctaaatgaaaccttaacgcta
```

TABLE 1 -continued tggaactcgccgcccgactgggctggcgatgagcgaaatgtagtgcttacgttgtcccgcatttggtacagcgcagtaaccggcaaaa
tcgcgccgaaggatgtcgctgccgactgggcaatggagcgcctgccggcccagtatcagcccgtcatacttgaagctagacaggctt
atcttggacaagaagaagatcgcttggcctcgcgcgcagatcagttggaagaatttgtccactacgtgaaaggcgagatcaccaaggt
agtcggcaaataatactagctccggcaaaaaaacgggcaaggtgtcaccaccctgcccttttctttaaaaccgaaaagattacttcgcg
tt (SEQ ID NO: 12)

pJE0_1:
accctgccctttttctttaaaaccgaaaagattacttcgcgtttgccacctgacgtctaagaaCACAGCTAACACCACGT
CGTCCCTATCTGCTGCCCTAGGTCTATGAGTGGTTGCTGGATAACTTTACGGGCA
TGCATAAGGCTCGTATAATATATTCAGGGAGACCACAACGGTTTCCCTCTACAAA
TAATTTTGTTTAACTTTtgcgcaatccgAAAGGTGTGtgagcacgccAAAAAAAAACGTGGC
GCCCGAACAGGGACggataGCTCAGTCGGTAGAGCATCAGACTTTTAATCTGAGGG
TCCAGGGTTCAAGTCCCTGTTCGGGCGCCACGTTTTTTTTTcgctgcagttaggagtcataagggtt
agttagattagcagaaagtcaaaagcctccgaccggaggcttttgactaaaacttcccttggggttatcattggggctcactcaaaggcg
gtaatcagataaaaaaaatcctagctttcgctaaggatgatttctgctagagatggaatagactggatggaggcggataaagttgcagg
accacttctgcgctcggcccttccggctggctggtttattgctgataaatctggagccggtgagcgtgggtctcgcggtatcattgcagc
actggggcagatggtaagccctcccgtatcgtagttatctacacgacgggggagtcaggcaactatggatgaacgaaatagacagat
cgctgagataggtgcctcactgattaagcattggtaactgtcagaccaagtttactcatatatactttagattgatttaaaacttcatttttaatt
taaaaggatctaggtgaagatccttttgataatctcatgaccaaaatcccttaacgtgagttttcgttccactgagcgtcagaccccttaat
aagatgatcttcttgagatcgttttggtctgcgcgtaatctcttgctctgaaaacgaaaaaaccgccttgcagggcggtttttcgaaggttct
ctgagctaccaactctttgaaccgagggtaactggcttggaggagcgcagtcaccaaaacttgtccttttcagtttagccttaaccggcgca
tgacttcaagactaactcctcaaatcaattaccagtggctgctgccagtggtgcttttgcatgtctttccgggttggactcaagacgatag
ttaccggataaggcgcagcggtcggactgaacggggggttcgtgcatacagtccagcttggagcgaactgcctacccggaactgag
tgtcaggcgtggaatgagacaaacgcggccataacagcggaatgacaccggtaaaccgaaaggcaggaacaggagagcgcacg
agggagccgccagggaaacgcctggtatctttatagtcctgtcgggtttcgccaccactgatttgagcgtcagatttcgtgatgcttgtc
agggggcggagcctatgaaaaacggctttgccgcggccctctcacttccctgttaagtatcttcctggcatcttccaggaaatctcc
gccccgttcgtaagccatttccgctcgccgcagtcgaacgaccgagcgtagcgagtcagtgagcgaggaagcggaatatatcctgta
tcacatattctgctgacgcaccggtgcagccttttttctcctgccacatgaagcacttcactgacacccctcatcagtgccaacatagtaag
ccagtatacactccgctagcgctgaggtctgcctcgtgaagaaggtgttgctgactcataccaggcctgaatcgccccatcatccagcc
agaaagtgagggagccacggttgatgagagctttgttgtaggtggaccagttggtgattttgaacttttgcttttgcccacggaacggtctg
cgttgtcgggaagatgcgtgatctgatccttcaactcagcaaaagttcgatttattcaacaaagccacgttgtgtctccaaaatctctgatgtt
acattgcacaagataaaaatatatcatcatgaacaataaaactgtctgcttcatataaacagtaatacaagggggtgtttactagaggttgatc
gggcacgtaagaggttccaactttcaccataatgaaataagatcactaccgggcgtattttttgagttatcgagattttcaggagctaagg
aagctaaaatgagggaagcggtgatcgccgaagtatcgactcaactatcagaggtagttggcgtcatcgagcgccatctcgaaccga
cgttgctggccgtacatttgtacgcctccgcagtggatggcggcctgaagccacacagtgatattgatttgctggttacggtgaccgtaa
ggcttgatgaaacaacgcggcgagctttgatcaacgaccttttggaaacttcggcttcccctggagagagcgagattctccgcgctgta
gaagtcaccattgttgtgcacgacgacatcattccgtggcgttatccagctaagcgcgaactgcaatttggagaatggcagcgcaatga
cattcttgcaggtatcttcgagccagccacgatcgacattgatctggctatcttgctgacaaaagcaagagaacatagcgttgccttggta
ggtccagcggcggaggaactctttgatccggttcctgaacaggatctatttgaggcgctaaatgaaaccttaacgctatggaactcgcc
gcccgactgggctggcgatgagcgaaatgtagtgcttacgttgtcccgcatttggtacagcgcagtaaccggcaaaatcgcgccgaa
ggatgtcgctgccgactgggcaatggagcgcctgccggcccagtatcagcccgtcatacttgaagctagacaggcttatcttggacaa
gaagaagatcgcttggcctcgcgcgcagatcagttggaagaatttgtccactacgtgaaaggcgagatcaccaaggtagtcggcaaa
taatactagctccggcaaaaaaacgggcaaggtgtcaccaccctgcccttttctttaaaaccgaaaagattacttcgcgtt (SEQ ID NO: 13)

pJE0_5
AGGTcccaatgataaccccaagggaagttttagtcaaaagcctccggtcggaggcttttgactttCTGCTAATCTAACT
AACTAACCCTTAGTGACTCCTGCAGCGAAAAAAAACGTGGCGCCCGAACAGGGA
CTTGAACCCTGGACCCTCAGATTAAAAGTCTGATGCTCTACCGACTGAGCtatccGT
CCCTGTTCGGGCGCCACGTTTTTTTTCGGTGATGTTcagccatagtaGCGGGTGCGccgaat
gctcggagaaacagtagagagttgcgataaaaagcgtcaggtaggatccgctaatctatgatgataaaaatgctatggcatagcaaagt
gtgacgccgtgcaaataatcaatgtAGcgGCGTGTCATTGGGGGCTTATACAGGCGTAGACTACA
ATGGGCCCAACTCACACAGCTAACACCACGTCGTCCCTATCTGCTGCCCTAGGTC
TATGAGTGGTTGCTGGATAACTTTACGGGCATGCATAAGGCTCGTATAATATATT
CAGGGAGACCACAACGGTTTCCCTCTACAAATAATTTTGTTTAACTTTaaatacGGTT
GATGTTggcgtgctcaaGCGGGTGCGggattgcgcaAAAAAAAAACGTGGCGCCCGAACAGG
GACggataGCTCAGTCGGTAGAGCATCAGACTTTTAATCTGAGGGTCCAGGGTTCA
AGTCCCTGTTCGGGCGCCACGTTTTTTTTCgctgcaggagtcataagggttagttagttagattagcagaaa
gtcaaaagcctccgaccggaggcttttgactaaaacttcccttggggttatcattgggCTCCgctagagatggaatagactggatgg
aggcggataaagttgcaggaccacttctgcgctcggcccttccggctggctggtttattgctgataaatctggagccggtgagcgtggg
tctcgcggtatcattgcagcactggggcagatggtaagccctcccgtatcgtagttatctacacgacgggggagtcaggcaactatgg
atgaacgaaatagacagatcgctgagataggtgcctcactgattaagcattggtaactgtcagaccaagtttactcatatatactttagatt
gatttaaaacttcatttttaatttaaaaggatctaggtgaagatccttttgataatctcatgaccaaaatcccttaacgtgagttttcgttccac
tgagcgtcagacccctaataagatgatcttcttgagatcgttttggtctgcgcgtaatctcttgctctgaaaacgaaaaaaccgccttgca
gggcggtttttcgaaggttctctgagctaccaactctttgaaccgaggtaactggcttggaggagcgcagtcaccaaaacttgtccttca
gtttagccttaaccggcgcatgacttcaagactaactcctcaaatcaattaccagtggctgctgccagtggtgcttttgcatgtctttccgg
gttggactcaagacgatagttaccggataaggcgcagcggtcggactgaacgggggttcgtgcatacagtccagcttggagcgaa
ctgcctacccggaactgagtgtcaggcgtggaatgagacaaacgcggccataacagcggaatgacaccggtaaaccgaaaggcag
gaacaggagagcgcacgagggagccgccagggaaacgcctggtatctttatagtcctgtcgggtttcgccaccactgatttgagcg
tcagatttcgtgatgcttgtcagggggcggagcctatgaaaaacggctttgccgcggccctctcacttccctgttaagtatcttcctgg
catcttccaggaaatctccgccccgttcgtaagccatttccgctcgccgcagtcgaacgaccgagcgtagcgagtcagtgagcgagg
aagcggaatatatcctgtatcacatattctgtatcacatattctgctgacgcaccggtgcagccttttttctcctgccacatgaagcacttcactgacacccctcat
cagtgccaacatagtaagccagtatacactccgctagcgctgaggtctgcctcgtgaagaaggtgttgctgactcataccaggcctga
atcgccccatcatccagccagaaagtgagggagccacggttgatgagagctttgttgtaggtggaccagttggtgattttgaacttttgct
ttgccacggaacggtctgcgttgtcgggaagatgcgtgatctgatccttcaactcagcaaaagttcgatttattcaacaaagccacgttgt
gtctcaaaatctctgatgttacattgcacaagataaaaatatatcatcatgaacaataaaactgtctgcttcatataaacagtaatacaaggg
gtgtttactagagGCTcccaatgataaccccaagggaagttttagtcaaaagcctccggtcggaggcttttgactttctgctaatcta
actaactaactgcagcgAAAAAAAAACGTGGCGCCCGAACAGGGACTTGAACCCTGGACCC
TCAGATTAAAAGTCTGATGCTCTACCGACTGAGCtatccGTCCCTGTTCGGGCGCCA
CGTTTTTTTTGCGGCTAgcAgagcattcgggAAAGGTGTGactatggctgtatttAAAGTTAAACA
AAATTATTTGTAGAGGGAAACCGTTGTGGTCTCCCTGAATATATTATACGAGCCT TABLE 1 -continued

```
TATGCATGCCCGTAAAGTTATCCAGCAACCACTCATAGACCTAGGGCAGCAGAT
AGGGACGACGTGGTGTTAGCTGTGAGTAtactagagtttatgacaacttgacggctacatcattcactttttcttc
acaaccggcacggaactcgctcgggctggccccggtgcattttttaaataccccgcgagaaatagagttgatcgtcaaaaccaacattg
cgaccgacggtggcgataggcatccgggtggtgctcaaaagcagcttcgcctggctgatacgttggtcctcgcgccagcttaagacg
ctaatccctaactgctggcggaaaagatgtgacagacgcgacggcgacaagcaaacatgctgtgcgacgctggcgatatcaaaattg
ctgtctgccaggtgatcgctgatgtactgacaagcctcgcgtacccgattatccatcggtggatggagcgactcgttaatcgcttccatg
cgccgcagtaacaattgctcaagcagatttatcgccagcagctccgaatagcgccttcccctttgcccggcgttaatgatttgcccaaa
caggtcgctgaaatgcggctggtgcgcttcatccgggcgaaagaaccccgtattggcaaatattgacggccagttaagccattcatgc
cagtaggcgcgcggacgaaagtaaacccactggtgataccattcgcgagcctccggatgacgaccgtagtgatgaatctctcctggc
gggaacagcaaaatatcacccggtcggcaaacaaattctcgtccctgattttttcaccacccctgaccgcgaatggtgagattgagaat
ataacctttcattcccagcggtcggtcgataaaaaaatcgagataaccgttggcctcaatcggcgttaaacccgccaccagatgggcat
taaacgagtatcccggcagcaggggatcattttgcgcttcagccatactttttcatactcccgccattcagagaagaaaccaattgtccata
ttgcatcagacattgccgtcactgcgtcttttactggctcttctcgctaaccaaaccggtaaccccgcttattaaaagcattctgtaacaaa
gcgggaccaaagccatgacaaaaacgcgtaacaaaagtgtctataatcacggcagaaaagtccacattgattatttgcacggcgtcac
actttgctatgccatagcattttttatccataagattagcggatcctacctgacgcttttttatcgcaactctctactgtttctccGCGGCTA
gCAtgcgcaatccgAAAGGTGTGtgagcacgccAAAAAAAACGTGGCGCCCGAACAGGGACg
gataGCTCAGTCGGTAGAGCATCAGACTTTTAATCTGAGGGTCCAGGGTTCAAGTC
CCTGTTCGGGCGCCACGTTTTTTTTcgctgcagttagttagttagattagcagaaagtcaaaagcctccgaccgg
aggcttttgactaaaacttcccttggggttatcattgggCATTgttgatcgggcacgtaagaggttccaactttcaccataatgaaataa
gatcactaccgggcgtattttttgagttatcgagattttcaggagctaaggaagctaaaatgagggaagcggtgatcgccgaagtatcg
actcaactatcagaggtagttggcgtcatcgagcgccatctcgaaccgacgttgctggccgtacatttgtacggctccgcagtggatgg
cggcctgaagccacacagtgatattgatttgctggttacggtgaccgtaaggcttgatgaaacaacgcggcgagctttgatcaacgacc
ttttggaaacttcggcttcccctggagagagcgagattctccgcgctgtagaagtcaccattgttgtgcacgacgacatcattccgtggc
gttatccagctaagcgcgaactgcaatttggagaatggcagcgcaatgacattcttgcaggtatcttcgagccagccacgatcgacatt
gatctggctatcttgctgacaaaagcaagagaacatagcgttgccttggtaggtccagcggcggaggaactctttgatccggttcctga
acaggatctatttgaggcgctaaatgaaaccttaacgctatggaactcgccgcccgactgggctggcgatgagcgaaatgtagtgctta
cgttgtcccgcatttggtacagcgcagtaaccggcaaaatcgcgccgaaggatgtcgctgccgactgggcaatggagcgcctgccg
gcccagtatcagcccgtcatacttgaagctagacaggcttatcttggacaagaagaagatcgcttggcctcgcgcgcagatcagttgg
aagaatttgtccactacgtgaaaggcgagatccaccaaggtagtcggcaaataatactagctccggcaaaaaaacgggcaaggtgtca
ccaccctgcccttttctttaaaaccgaaaagattacttcgcgtt (SEQ ID NO: 14)
```

REFERENCES

1. Seeman, N. C. Nucleic Acid Junctions and Lattices. J. Theor. Biol. 1982, 99, 237-24.
2. Pinheiro, A. V., Han, D., Shih, W. M. & Yan H. Challenges and opportunities for structural DNA nanotechnology. *Nature Nanotech.* 6, 763-772 (2011)
3. Fu, T. J.; Seeman, N. C. DNA Double-crossover Molecules. Biochemistry 1993, 32, 3211-3220.
4. Li, X. J.; Yang, X. P.; Qi, J.; Seeman, N. C. Antiparallel DNA Double Crossover Molecules As Components for Nanoconstruction. J. Am. Chem. Soc. 1996, 118, 6131-6140.
5. Winfree, E.; Liu, F.; Wenzler, L. A.; Seeman, N. C. Design and Self-assembly of Two-dimensional DNA Crystals. Nature 1998, 394, 539-544.
6. Goodman, R. P.; Schaap, I. A. T.; Tardin, C. F.; Erben, C. M.; Berry, C. M.; Schmidt, C. F.; Turberfield, A. J. Rapid Chiral Assembly of Rigid DNA Building Blocks for Molecular Nanofabrication. Science 2005, 310, 1661-1665.
7. Le, J. D.; Pinto, Y.; Seeman, N. C.; Musier-Forsyth, K.; Taton, T. A.; Kiehl, K. A. DNA-Templated Self-Assembly of Metallic Nanocomponent Arrays on a Surface. Nano Lett. 2004, 4, 2343-2347.
8. Rothemund, P. W. K. Folding DNA to Create Nanoscale Shapes and Patterns. Nature 2006, 440, 297-302.
9. Douglas, S. M.; Dietz, H.; Liedl, T.; Hogberg, B.; Graf, F.; Shih, W. M. Self-Assembly of DNA into Nanoscale Three-Dimensional Shapes. Nature 2009, 459, 414-418.
10. Han, D.; Pal, S.; Nangreave, J.; Deng, Z.; Liu, Y.; Yan, H., DNA Origami with Complex Curvatures in Three-Dimensional Space. Science 332, 343-346 (2011).
11. Y. Ke, L. Ong, W. Shih, P. Yin Three-dimensional structures self-assembled from DNA bricks Science 338, 1177-1183 (2012).
12. Bath, J. & Turberfield, A. J. DNA nanomachines. Nat. Nanotech. 2, 275-284 (2007).
13. Krishnan, Y. & Simmel, F. C. Nucleic acid based molecular devices. Angew. Chem. Int. Ed. 50, 3124-3156 (2011).
14. Shin, J. S.; Pierce, N. A. A Synthetic DNA Walker for Molecular Transport. J. Am. Chem. Soc. 2004, 126, 10834-10835.
15. Omabegho, T., Sha, R. & Seeman, N. C. A bipedal DNA Brownian motor with coordinated legs. Science 324, 67-71 (2009).
16. Wang, Z. G., Elbaz, J. & Willner, I. DNA machines: bipedal walker and stepper. Nano Lett. 11, 304-309 (2011).
17. Yurke, B.; Turberfield, A. J.; Mills, A. P., Jr.; Simmel, F. C.; Neumann, J. L. A DNA-Fuelled Molecular Machine made of DNA. Nature 2000, 406, 605-608.
18. Elbaz, J., Wang, Z. G., Orbach, R. & Willner, I. pH-stimulated concurrent mechanical activation of two DNA 'tweezers'. A 'SETRESET' logic gate system. Nano Lett. 9, 4510-4514 (2009).
19. Tian, Y. & Mao, C. D. Molecular gears: a pair of DNA circles continuously rolls against each other. J. Am. Chem. Soc. 126, 11410-11411 (2004).
20. Elbaz, J. et al. DNA computing circuits using libraries of DNAzyme subunits. Nat. Nanotech. 5, 417-422 (2010).
21. Renjun Pei, Elizabeth Matamoros, Manhong Liu, Darko Stefanovic, and Milan N. Stojanovic Training a molecular automaton to play a game. *Nature Nanotechnology* 773-777 (2010).
22. Seelig, G., Soloveichik, D., Zhang, D. Y. & Winfree, E. Enzyme-free nucleic acid logic circuits. Science 314, 1585-1588 (2006).
23. Qian, L. L. & Winfree, E. Scaling Up Digital Circuit Computation with DNA Strand Displacement Cascades *Science* 332, 1196-1201 (2011).
24. Mastroianni, A. J.; Claridge, S. A. & Alivisatos, A. P. Pyramidal and chiral groupings of gold nanocrystals assembled using DNA scaffolds. J. Am. Chem. Soc. 131, 8455-8459 (2009).
25. He, Y., Liu, D. R. Autonomous Multistep Organic Synthesis in a Single Isothermal Solution Mediated by a DNA Walker. *Nat. Nanotech.* 5, 778-782 (2010).

26. Niels V. Voigt et al. Single-molecule chemical reactions on DNA origami. *Nature Nanotechnology* 200-203 (2010).
27. Gu, H. Z., Chao, J., Xiao, S. J. & Seeman, N. C. A proximity-based programmable DNA nanoscale assembly line. *Nature* 465, 202-205 (2010).
28. Elbaz, J., Cecconello, A., Fan, Z., Govorov, A. O., Willner, I. Powering the programmed nanostructure and function of gold nanoparticles with catenated DNA machines. *Nat. Commun.* dx.doi.org/10.1038/ncomms3000.
29. Lee et al Molecularly self-assembled nucleic acid nanoparticles for targeted in vivo siRNA delivery *Nature Nanotech.* 7, 389-393 (2012).
30. Douglas, S. M., Bachelet, I. & Church, G. M. A Logic-Gated Nanorobot for Targeted Transport of Molecular Payloads. *Science* 335, 831-834 (2012).
31. Yaniv Amir et al. Universal computing by DNA origami robots in a living animal. *Nature Nanotechnology* 353-357 (2014).
32. Modi, S.; Swetha, M. G.; Goswami, D.; Gupta, G. D.; Mayor, S.; Krishnan, Y. A DNA Nanomachine that Maps Spatial and Temporal pH Changes Inside Living Cells. *Nat. Nanotechnol.* 2009, 4, 325-330.
33. Lin, C., Rinker, S., Wang, X., Liu, Y., C. Seeman, N. C. Yan, H. In vivo cloning of artificial DNA nanostructures. *Proc. Natl. Acad. Sci. U.S.A.* 105, 17626-17631 (2008).
34. Conrado, R. J. et al DNA-guided assembly of biosynthetic pathways promotes improved catalytic efficiency. *Nucl. Acids Res* 40, 1879-1889 (2012).
35. Delebecque, C. J., Lindner, A. B., Silver, P. A. & Aldaye, F. A. Organization of Intracellular Reactions with Rationally Designed RNA Assemblies *Science* 333, 470-474 (2011).
36. Helena Gradišar et al. Design of a single-chain polypeptide tetrahedron assembled from coiled-coil segments. *Nature Chemical Biology* 362-366 (2013).
37. Telesnitsky, A.; Goff, S. P. Reverse transcriptase and the generation of retroviral DNA *Retroviruses*, 121-160 (1997).
38. Baltimore, D. Viral RNA-dependent DNA polymerase: RNA-dependent DNA polymerase in virions of RNA tumour viruses. *Nature* 226, 1209-1211 (1970).
39. Temin, A. M. & Mizutani, S. Viral RNA-dependent DNA polymerase: RNA-dependent DNA polymerase in virions of Rous sarcoma virus. *Nature* 226, 1211-1213 (1970).
40. Leis, J. P., Berkower, I. & Hurwitz, J. RNA-dependent DNA polymerase activity of RNA tumor viruses. 5. Mechanism of action of ribonuclease H isolated from avian myeloblastosis virus and *Escherichia coli*. Proc. Natl Acad. Sci. USA 70, 466-470 (1973).
41. A. Jacobo-Molina et al., Crystal structure of human immunodeficiency virus type 1 reverse transcriptase complexed with double-stranded DNA at 3.0 A resolution shows bent DNA. *Proc. Natl. Acad. Sci. U.S.A.* 90, 6320 (1993).
42. Freeman W M, Walker S J, Vrana K E "Quantitative RT-PCR: pitfalls potential". *BioTechniques* 26,112-122, (1999).
43. Aiyar, A., Cobrinik, D., Ge, Z., Kung, H. J. & Leis, J. Interaction between retroviral U5 RNA and the TC loop of the tRNATrp primer is required for efficient initiation of reverse transcription. *J. Virol.* 66, 2464-2472 (1992).
44. Kleiman L. tRNALys3: The Primer tRNA for Reverse Transcription in HIV-1. *IUBMB Life*, 53, 107-114 (2002).
45. Arnold, e., et al Structure of HIV-1 reverse transcriptase/DNA complex at 7 A resolution showing active site locations. *Nature*. 357, 85-89 (1992).
46. Elio A. Abbondanzieri et al. Dynamic binding orientations direct activity of HIV reverse transcriptase. *Nature* 184-189 (2008).
47. Harris, D., Lee, R., Misra, H. S., Pandey, P. K., and Pandey, V. N. The p51 subunit of human immunodeficiency virus type 1 reverse transcriptase is essential in loading the p66 subunit on the template primer, Biochemistry 37, 5903-5908 (1998).
48. Lanchy, J. M., Ehresmann, C., Le Grice, S. F., Ehresmann, B., Marquet, R. Binding and kinetic properties of HIV-1 reverse transcriptase markedly differ during initiation and elongation of reverse transcription. EMBO J. 15, 7178-7187 (1996).
49. Ying-Ja Chen et al. Characterization of 582 natural and synthetic terminators and quantification of their design constraints. *Nature Methods* 659-664 (2013).
50. Petty, J. T.; Zheng, J.; Hud, N. V.; Dickson, R. M. DNA-Templated Ag Nanocluster Formation *J. Am. Chem. Soc.*, 126, 5207-5212 (2004).
51. Tae Nam, K., Lee, Y. J., Krauland, E. M., Kottmann, S. T., Belcher A. M. Peptide-Mediated Reduction of Silver Ions on Engineered Biological Scaffolds ACS Nano 2, 1480-1486 (2008).
52. Gwinn, E. G.; O'Neill, P.; Guerrero, A. J.; Bouwmeester, D.; Fygenson, D. K. Sequence-Dependent Fluorescence of DNA-Hosted Silver Nanoclusters Adv. Mater. 20, 279-283 (2008).
53. Gibson, D. G., et al. Enzymatic assembly of DNA molecules up to several hundred kilobases. Nat. Methods 6:343-345 (2009).
54. Gibson, D. G., Smith, H. O., Hutchison III, C. A., Venter, J. C., & Merryman, C. Chemical synthesis of the mouse mitochondrial genome. Nat. Methods 7, 901-903 (2010).
55. Moon, T. S., Lou, C., Tamsir, A., Stanton, B. C., & Voigt, C. A. Genetic programs constructed from layered logic gates in single cells. Nature 491, 249-253 (2012).
56. Engler, C., Kandzia, R., & Marillonnet, S. (2008) A one pot, one step, precision cloning method with high throughput capability. PLoS ONE 3:e3647 doi:10.1371/journal.pone.0003647.
57. PrimerQuest® program, IDT, Coralville, USA. Retrieved 12 Dec., 2012. http://www.idtdna.com/Scitools.
58. J. N. Zadeh, C. D. Steenberg, J. S. Bois, B. R. Wolfe, M. B. Pierce, A. R. Khan, R. M. Dirks, N. A. Pierce. NUPACK: analysis and design of nucleic acid systems. *J Comput Chem*, 32, 170-173, 2011.

Example 4

Genetic Encoding of DNA Nanostructures and their Self-Assembly in Living Bacteria It is shown that 4 ssDNAs can be expressed in *E. coli* and assembled into a crossover junction that forms a 45 nm nanostructure. Each ssDNA (40-189 nt) is encoded by a gene that is transcribed into non-coding RNA containing a 3'-hairpin (RTBS). RTBS recruits HIV reverse transcriptase (HIVRT), which nucleates DNA synthesis and is aided in elongation by murine leukemia reverse transcriptase (MLRT). Genetic circuits can switch the structure by changing which ssDNAs are expressed. Genetically encoding DNA nanostructures provides a route for their bio-manufacturing and for applications in living cells.

Here, a method that enables a ssDNA to be encoded as a gene (r_oligo) that is expressed as a non-coding RNA (ncRNA) that is enzymatically converted to ssDNA is presented. This conversion is performed naturally by retroviruses, which have RNA genomes that need to be converted to DNA prior to integrating into the host genome[37]. The enzyme responsible is reverse transcriptase (RT), which has several roles, including functioning as a DNA- and RNA-dependent DNA polymerase, as an RNAase that cleaves the RNA from the DNA:RNA complex, and to catalyze strand transfer and displacement synthesis[38-40]. The mechanism of RTs has been a subject of intensive research because it is a therapeutic target for HIV[41] and is commonly used in molecular biology to quantify transcript abundance (RT-PCR)[42]. However, it has not been possible to functionally express these eukaryotic retroviral RTs in bacteria. This may be due to a lack of eukaryotic t-RNA$^{LYS}$, which is required for binding to the RT at the protein binding site (PBS) and recruiting it to viral RNA to initiate polymerization (FIG. 1B)[43,44].

Figure 12:
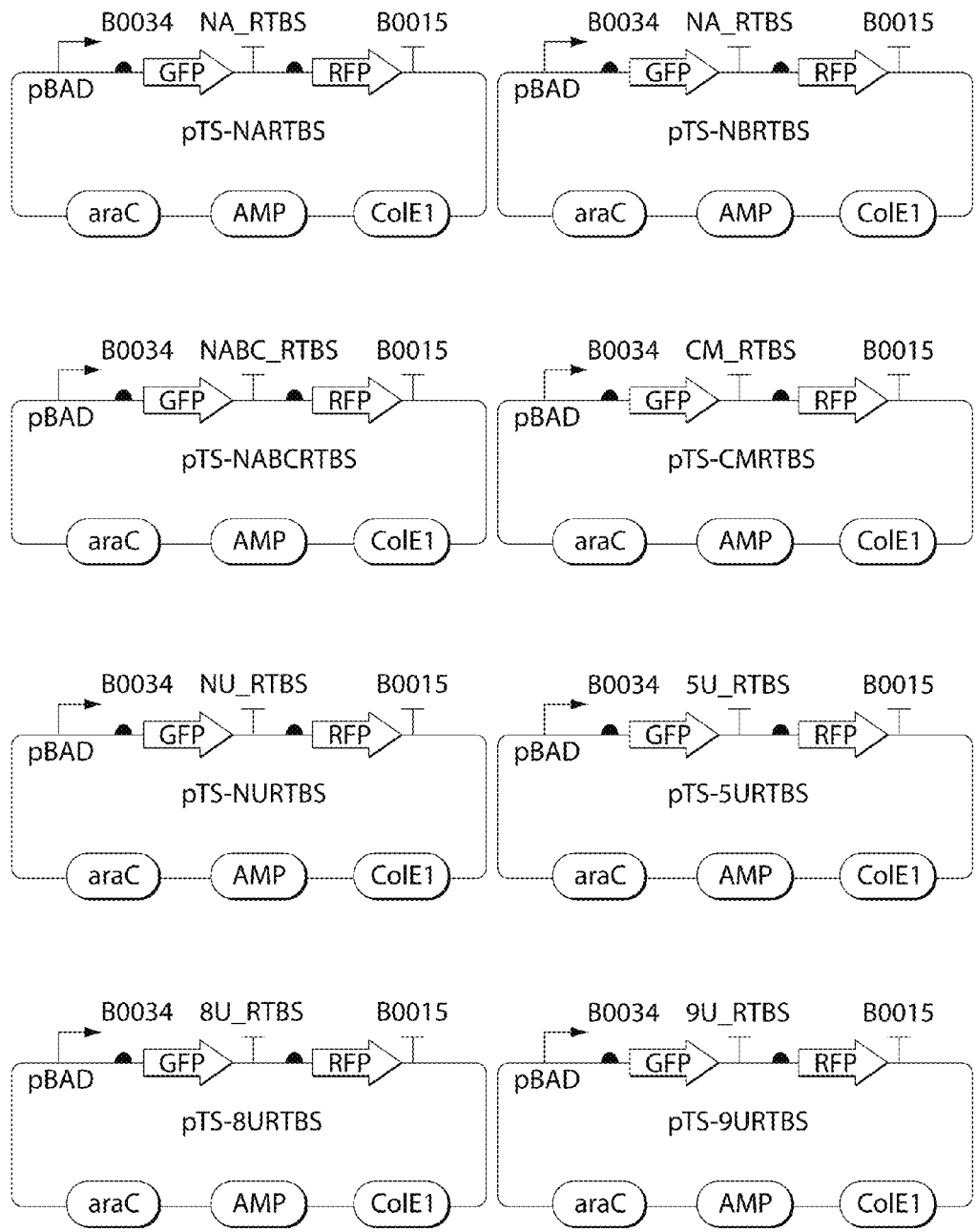
FIG. 12 shows the RTBS terminator strength (Ts) measurement plasmid maps. All these plasmids have been used for the terminator strength experiments shown in FIG. 1D. Part sequences are provided in Tables 1-4. Parts beginning with "B" are from the Registry of Standard Biological Parts. The RTBS variants are named as in Table 1.
Figure 13:
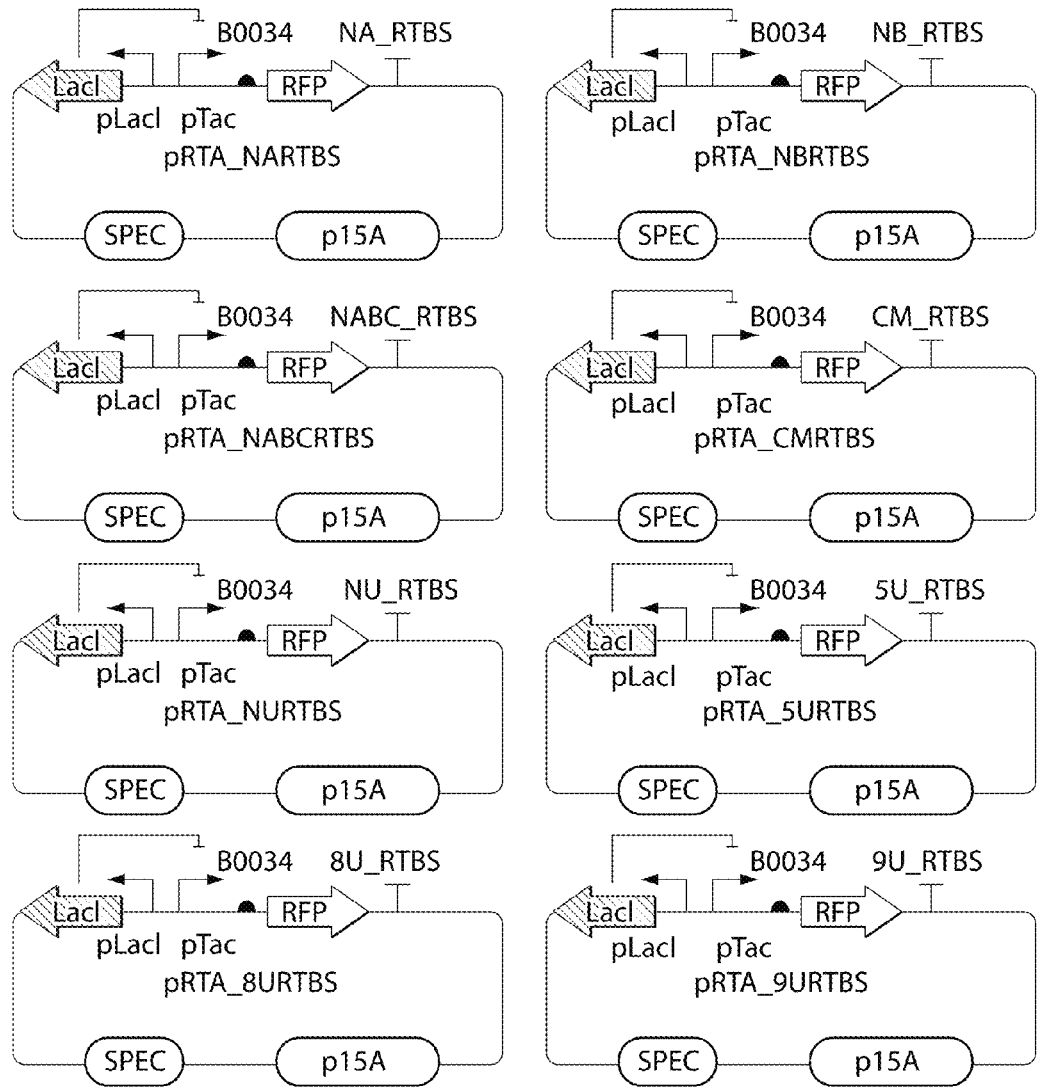
FIG. 13 shows HIV reverse transcriptase activity measurements plasmid maps. All these plasmids have been used for the HIV reverse transcriptase activity measurements shown in FIG. 1(D-E) Part sequences are provided in Tables 1-4. Parts beginning with "B" are from the Registry of Standard Biological Parts. The RTBS variants are named as in Table 1.

It was observed that when t-RNA$^{LYS}$ binds to the 3' end of the vRNA that the two molecules would create a single non-coding RNA if the 3'-end of the vRNA were covalently bound to the 5'-end of the tRNA (FIG. 1B). The challenge is that the ncRNA would have to precisely end after the PBS with the last nucleotide forming a basepair in order for HIVRT to begin DNA polymerization. Using a mathematical model for guidance[45], it was hypothesized that the hairpin of the t-RNA could function as a transcriptional terminator, which was confirmed experimentally (FIG. 1C). Various mutations were made to hairpin that were predicted by the model (e.g., adding a poly-U and modifying the hairpin loops) and tested for increased termination strength ($T_S$). Next, the ability for the hairpins to recruit HIVRT when fused to the 3'-end of the ncRNA was tested. To do this, an assay was developed based on the capability of HIVRT to block translation by polymerizing DNA across a ribosome binding site (RBS) (FIGS. 1D, 12 and 13). This causes a knockdown of expression when red fluorescent protein (RFP) is encoded on the RNA. The hairpins were screened and one with a mutation to close a bulge (C*) and add 8 A/U bp was chosen (referred to as RTBS), which co-optimizes termination efficiency as well as the recruitment of HIVRT. RTBS sequences are shown in Table 2 below. An important advantage of fusing the recognition hairpin to the ncRNA is that the RT will only transcribe the desired RNA(s), thus eliminating the potential for crosstalk with free t-RNA$^{LYS}$ and other intracellular RNAs.

Figure 14:
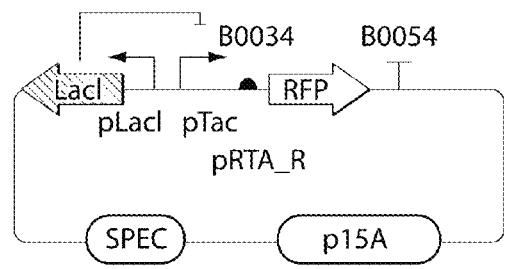
FIG. 14 shows a HIV reverse transcriptase control measurements plasmid map. The control uses the strong BBa_B0054 terminator, as opposed to an RTBS part containing the HIVRT recognition hairpin. This plasmid has been for data shown in FIG. 1E. Part sequences are provided in Tables 1-4. Parts beginning with "B" are from the Registry of Standard Biological Parts.
Figure 15:
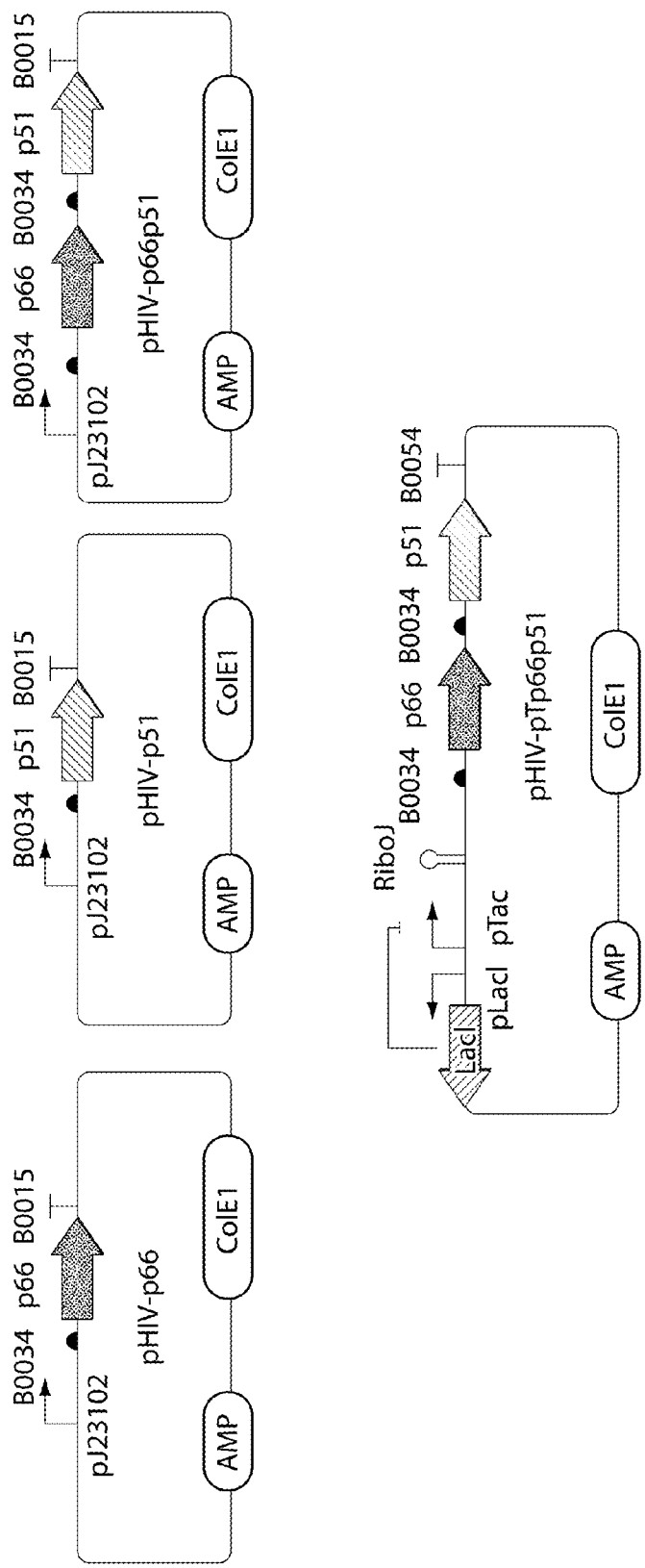
FIG. 15 shows HIV reverse transcriptase plasmid maps. The plasmids (pHIV-p66, pHIV-p51 and pHIV-p66p51) have been used for data shown in FIG. 1, while plasmid pHIV-pTp66p51 has been used for data shown in FIGS. 2, 10 and 21 and is referred to the "initiator" plasmid. Part sequences are provided in Tables 1-4. Parts beginning with "B" and promoter J23102 are from the Registry of Standard Biological Parts.
Figure 16:
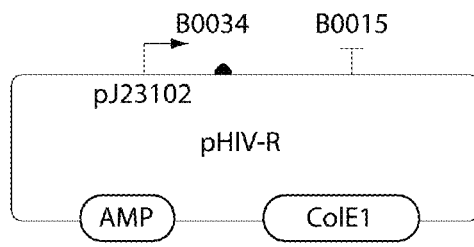
FIG. 16 shows a HIV reverse transcriptase control plasmid map. This plasmid is identical to that used to express the HIVRT genes and is used as a control. Parts beginning with "B" and promoter J23102 are from the Registry of Standard Biological Parts.

HIVRT is a heterodimer composed of the p66 and p51 subunits[37]. The p66 subunit has three domains: a polymerase, a linker, and an RNAse[38-40]. In the context of the virus, the p51 subunit is created by a post-translational mechanism where the C-terminus of a p66/p66 homodimer is cleaved to remove the RNAse H domain. The p51 subunit contains a polymerase domain, but is mainly responsible for stabilizing the p66 subunit when bound to the viral RNA[46]. Using the RFP assay, the requirement that both of the subunits be expressed, where they encoded as separate genes and codon optimized for E. coli (Example 1) was tested. In this assay, either subunit or both together are able to knock-down RFP expression (FIGS. 1E and 14).

Figure 1G:
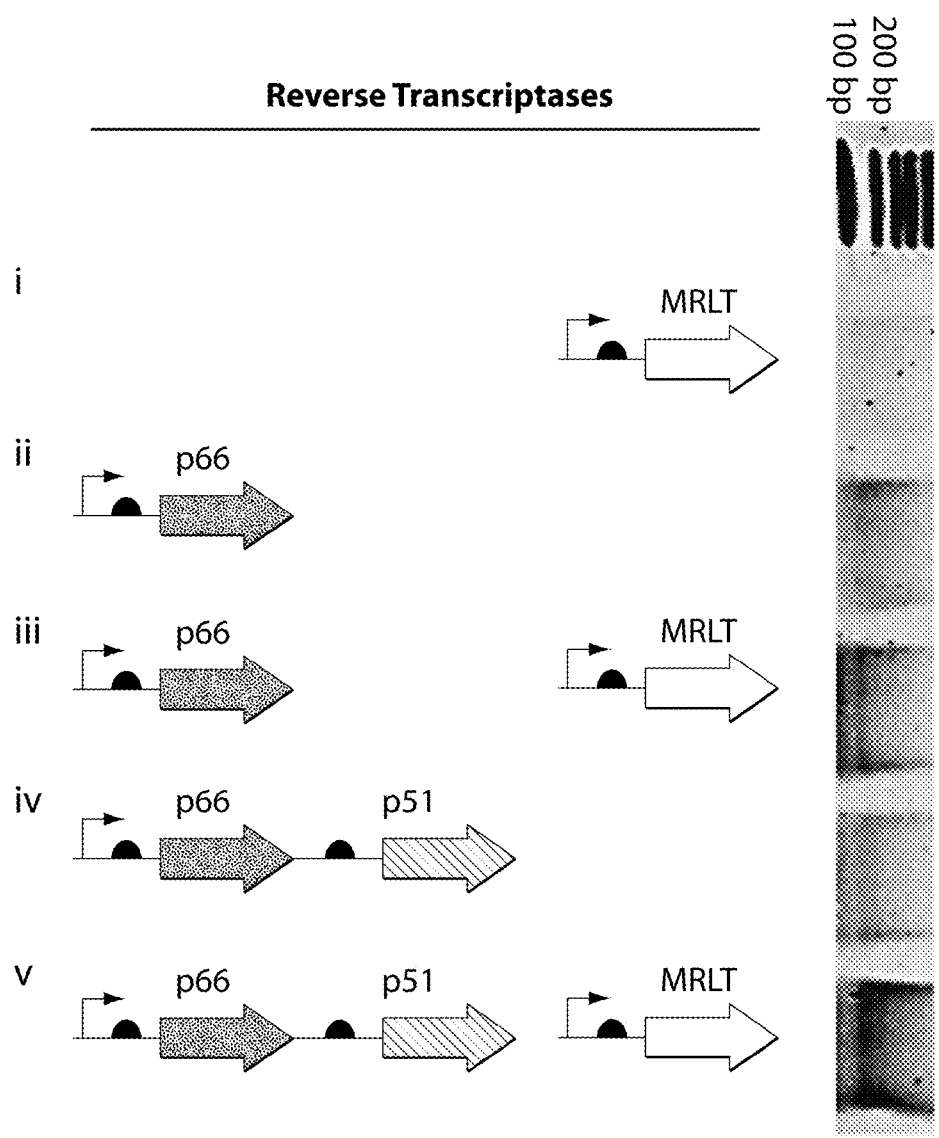
Figure 18:
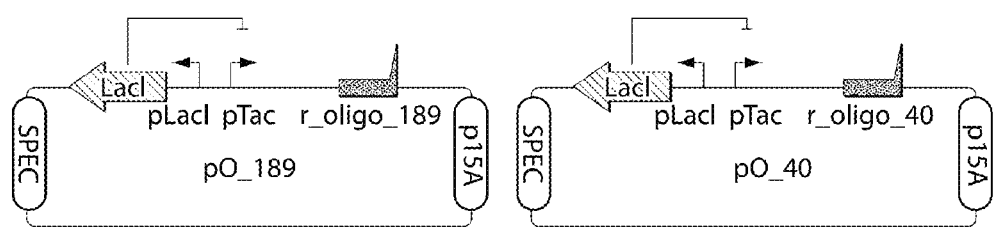
FIG. 18 shows the plasmids used for different combinations of r_oligo genes in FIG. 1. Part sequences are provided in Tables 1-4. Parts beginning with "B" are from the Registry of Standard Biological Parts. r_oligo_###; ### represents the number of nucleotides included in the ssDNA.

The HIVRT subunits were then tested for the ability to produce ssDNA in cells (FIGS. 1F and 18). The r_oligo gene containing 189 nt ssDNA sequence and RTBS is placed under pTAC control so that it can be induced with IPTG. A purification protocol was developed to isolate DNA products from lysed cells, which can be visualized using non-denaturing gel electrophoresis (Example 1). All ssDNA production experiments are performed in the cloning strain E. coli DH10β, which lacks the intracellular exonuclease activity, thus preventing the degradation of ssDNA. The expression of the p66 subunit alone is sufficient to observe a slight band at the correct length (FIGS. 1G and 18). The co-expression of the p51 subunit increases the production of the ssDNA because the p66/p51 complex has a higher affinity to the ncRNA substrate[46]. HIVRT is known to be slow as a DNA polymerase because it performs this function through multiple association and dissociation events and individual turnovers (versus a continuous progression)[47,48]. To increase production, a second RT from murine leukemia virus (MLRT), which is a DNA-dependent polymerase with strong RNAse H activity[49] was introduced. The MLRT gene is expressed under the control of a constitutive promoter from a separate plasmid (Example 1). The expression of MLRT alone is unable to produce the ssDNA because of the HIVRT specificity of RTBS (FIG. 1G). When co-expressed with p66 or p66/p51, strong bands are observed. The expres-

TABLE 2

RTBSs sequences

| Name[a] | Sequence |
|---|---|
| NA_RTBS | AAAAAAAACGUGGCGCCCGAACAGGGACGGAUCCGCCCGGAUAAUCAGACUUUUAAUCUGAGGGUC CAGGGUUCAAGUCCCUGUUCGGGCGCCACGUUUUUUUU (SEQ ID NO: 15) |
| NB_RTBS | AAAAAAAACGUGGCGCCCGAACAGGGACGGAUCCGCCCGGAUAGCUCAGUCGGUAGAGCAUCAGAC UUUUAAUCUGAGUCCCUGUUCGGGCGCCACGUUUUUUU3 (SEQ ID NO: 16) |
| NABC_RTBS | AAAAAAAACGUGGCGCCCGAACAGGGACUCGUGGAAUGUCCCUGUUCGGGCGCCACGUUUUUUUU (SEQ ID NO: 17) |
| C*_RTBS | AAAAAAAACGUGGCGCCCGAACAGGGACGGAUAGCUCAGUCGGUAGAGCAUCAGACUUUUAAUCUG AGGGUCCAGGGUUCAAGUCCCUGUUCGGGCGCCACGUUUUUUUU (SEQ ID NO: 18) |
| NU_RTBS | AAAAAAAACGUGGCGCCCGAACAGGGACGGAUCCGCCCGGAUAGCUCAGUCGGUAGAGCAUCAGAC UUUUAAUCUGAGGGUCCAGGGUUCAAGUCCCUGUUCGGGCGCCACG (SEQ ID NO: 19) |
| 5U_RTBS | AAAAACGUGGCGCCCGAACAGGGACGGAUCCGCCCGGAUAGCUCAGUCGGUAGAGCAUCAGACUUU UAAUCUGAGGGUCCAGGGUUCAAGUCCCUGUUCGGGCGCCACGUUUUU (SEQ ID NO: 20) |
| 8U_RTBS | AAAAAAAACGUGGCGCCCGAACAGGGACGGAUCCGCCCGGAUAGCUCAGUCGGUAGAGCAUCAGAC UUUUAAUCUGAGGGUCCAGGGUUCAAGUCCCUGUUCGGGCGCCACGUUUUUUUU (SEQ ID NO: 21) |
| 9U_RTBS | AAAAAAAACGUGGCGCCCGAACAGGGACGGAUCCGCCCGGAUAGCUCAGUCGGUAGAGCAUCAGA CUUUUAAUCUGAGGGUCCAGGGUUCAAGUCCCUGUUCGGGCGCCACGUUUUUUUUU (SEQ ID NO: 22) |

[a]The sequences shown the different RTBSs (ribonucteotides) used to this study (XX_RTBS, XX represents the modification made on the RTBS).

sion of all three genes enhances the production of the ssDNA 8-fold over p66 alone and 3-fold over both expressions of p66 and MLRT.

Figure 1H:
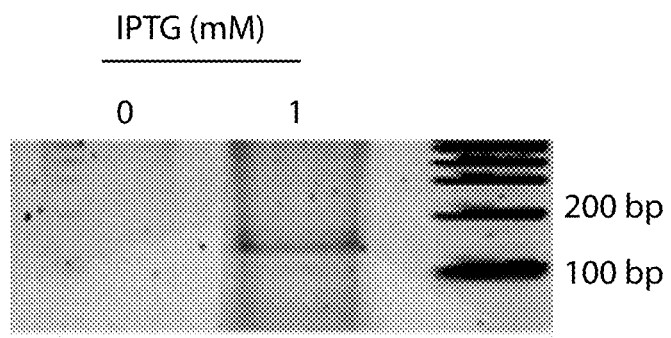
Figure 1I:
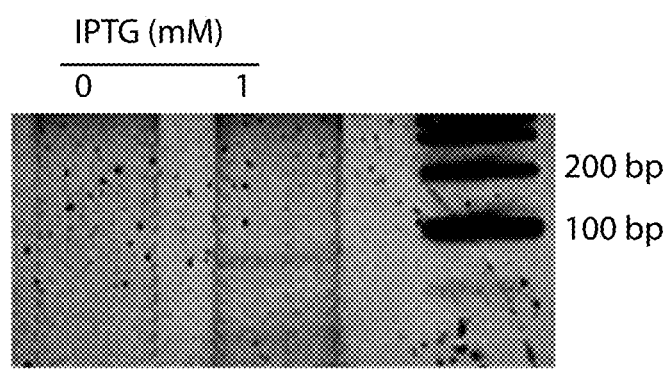
Figure 1J:
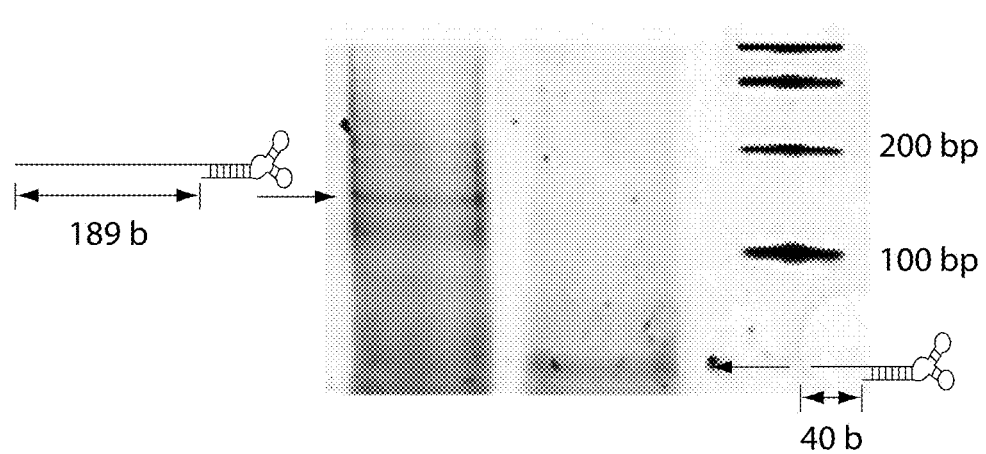

The r_oligo1 gene is under the control of the pTAC promoter; thus, it can be induced by IPTG and no ssDNA product is observed in the absence of inducer (FIGS. 1H and 1I). Being able to induce ssDNA production is important when using genetic circuits to control their expression to build more complex structures. This also shows that the ssDNA requires r_oligo expression and is not a byproduct of a nonspecific RT process. After purification, the RTBS motif was removed through the addition of RNase A in the absence of salt, leaving just the ssDNA (FIGS. 1I and 1I). Finally, the production of ssDNA with two lengths (40 and 189 nt), representing a typical range of chemically synthesized oligonucleotides was demonstrated (FIGS. 1J and 1I). Table 3 shows ssDNA representative ssDNA sequences:

carefully selecting sequences that do not generate undesired secondary structures and assemblies (Example 1). The remaining 5 nt part (TTTAT) at the 3'-end is optional and is added to eliminate the possibility of the RT from continuing to function as a polymerase on the DNA nanostructure by preventing the hybridization of the last 3' base. The RNA hairpins were not cleaved in order to aid visualization by atomic force microscopy (AFM) and distinguish shapes associated with different combinations of oligos. Different structures can be visualized due to the flexibility caused by the nick that forms at the junction between the hairpin and the dsDNA of the structure.

Figure 2B:
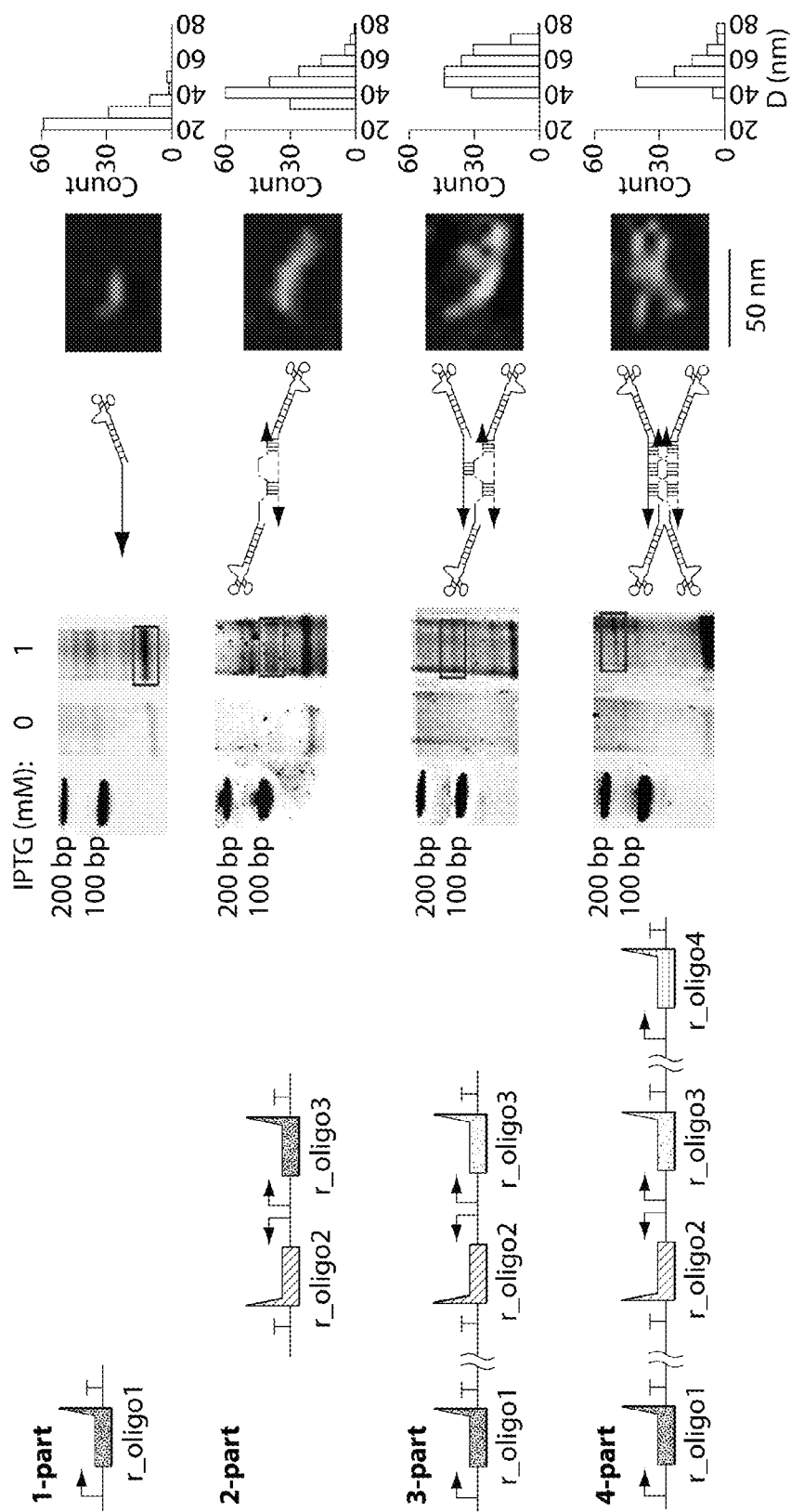

Different versions of the oligo plasmid were constructed to express 1, 2, 3, or all 4 ssDNAs (FIG. 2B). The ssDNAs were expressed and analyzed using non-denaturing gel electrophoresis (Example 1). In all cases, no bands were observed in the absence of IPTG (no HIVRT is expressed).

TABLE 3 ssDNAs sequences

| Name[a] | Sequence |
|---|---|
| r_oligo189 | 5' TAAGCTTTGGAACCGTACTGGAACTGCGGGGACAGGATGTCCCAAGCGAACGGCAGCGGACCAC CTTTGGTAACTTTCAGTTTAGCGGTCTGGGTACCTTCGTACGGACGACCTTCACCTTCACCTTCGA TTTCGAACTCGTGACCGTTAACGGAACCGGACAGGAGG CTAGCTACAACGAGTCCCAAG 3' (SEQ ID NO: 23) |
| r_oligo40 | 5' AACGGAACCGGACAGGAGGCTAGCTACAACGAGTCCCAAG 3' (SEQ ID NO: 24) |
| r_oligo1 | 5' TGCGCAATCCCGCACCCGCTTGAGCACGCCAACATCACCGTATTT 3' (SEQ ID NO: 25) |
| r_oligo2 | 5' GCGGCTAGCAGAGCATTCGGGAAAGGTGTGACTATGGCTGTATTT 3' (SEQ ID NO: 26) |
| r_oligo3 | 5' GGCGTGCTCACACACCTTTCGGATTGCGCATGCTAGCCGCTATTT 3' (SEQ ID NO: 27) |
| r_oligo4 | 5' CGGTGATGTTCAGCCATAGTAGCGGGTGCGCCGAATGCTCTATTT 3' (SEQ ID NO: 28) |

[a]The sequences represent the reverse transcribed ssDNAs included in the r_oligo parts.

A genetic system was developed to express multiple ssDNAs so that they can assemble to form a nanostructure (FIG. 2A). An initiator plasmid controls the expression of both genes for HIVRT under IPTG inducible control on a medium copy ColE1 origin. A second amplifier plasmid contains MLRT, which is constitutively expressed at low copy (psc101). Finally, all of the r_oligo genes are carried on a third p15a origin plasmid. Each gene is controlled with the same strong constitutive promoter (proD[50]) in order to keep the stoichiometry close to unity. The absolute concentrations and their ratios have been previously shown to be important for DNA assembly in vitro[4-7]. The selection of constitutive promoters of different strength would enable different ratios of ssDNAs to be produced; the only requirement is that the +1 transcription start site be precise[51] so that additional nucleotides do not appear on the 3' end of the ssDNA. To reduce the potential impact of transcriptional readthrough, strong terminators (BBa_B0054) are placed after each r_oligo gene and they are encoded in alternating orientations.

Four ssDNAs were designed to assemble into a nanostructure that is 45 nm long and 2 nm wide that is based on the crossover branched motif (FIG. 2A). This motif is a fundamental architectural unit core to many nanostructures[4-11] representing different topologies and scales, ranging from 10 nm tetrahedra[5] to 100 nm origami[8]. The motif is built using four 45 nt ssDNAs, each of which includes four 10-base sticky binding regions that connect the strands. The sequences of this region were selected based on seed sequences from the literature and expanding on them while When 1 mM IPTG is added, bands appear and their length shifts depending on how many ssDNAs are expressed. When ssDNA1 (45 nt) is expressed alone, the only base paired region is in the RNA hairpin (34 bp), and a strong band is observed at the correct length. When both ssDNA2 and ssDNA3 are expressed, this leads to several bands, including one at ~90 bp. This shifts up to ~110 bp when ssDNA1 is co-expressed with them. Finally, this shifts to ~170 bp when all four ssDNAs were co-expressed. Note that the ssDNAs were only designed to form the complete 4-part nanostructure. When only 2 or 3 are expressed, there are additional bands that form on the gel corresponding to alternate structures and these are almost eliminated when all four are expressed. Using a control experiment, we estimated that 90% of the material produced in vivo is lost during purification and recovery. Not accounting for this loss, the titers range from 7.5 μg/L when only ssDNA1 is expressed to 2 μg/L for the 4-part crossover junction calculated based on spectroscopic absorbance measurements (Example 1).

The nanostructures were purified and visualized using tapping AFM (Example 1). The nick between the RTBS and the dsDNA allows for flexibility and these results in a "V" in the structure that simplifies the quantification of the final and intermediate structures. Representative structures are show in FIG. 2B along with an automated analysis of the images that quantifies all of the structures that are above the height of a DNA strand. The length of ssDNA1, including the RTBS, is expected to be 28 nm and indeed the structures observed by AFM are almost exactly this length. When ssDNA2 and ssDNA3 are co-expressed, the average length is 45 nm as expected and a number of boomerang shaped structures are observed. The expression of the third ssDNA1 leads to the observation of "Y" shaped structures and a widening of the average length, possibly due to non-specific structures or aggregation, which also corresponds to appearance of additional bands on the gel. The expression of all four ssDNAs forms "X" shaped structures and the size distribution peaks at 45 nm with a narrower distribution than observed for the intermediate structures.

Connecting the expression of different r_oligo genes to synthetic genetic circuits enables the DNA structure to be changed in response to environmental conditions or as part of a larger program to build a composite material or supermolecular assembly. To this end, the r_oligo3 gene was placed under the control of an arabinose-inducible promoter (pBAD) and the remaining genes (r_oligo1, 2, and 4) under constitutive control so that they are always expressed (Example 1, FIGS. 21, 15, 16 and 20). Precise knowledge of the +1 transcription start site[52] so that additional nucleotides are not added to the 5'-UTR that would be reverse transcribed as ssDNA is important. The structure that is formed can be changed through the addition of arabinose. In its absence, only the 3-part assembly is observed. With 1 μM L-arabinose, r_oligo3 is expressed and the complete crossover junction is formed.

TABLE 4

Promoter, RBS, terminator, riboJ, RFP and GFP sequences

| Name[a,b] | Sequence |
|---|---|
| BBa_J23102 | 5' TTGACAGCTAGCTCAGTCCTAGGTACTGTGCTAGC 3' (SEQ ID NO: 29) |
| PROD | 5' CACAGCTAACACCACGTCGTCCCTATCTGCTGCCCTAGGTCTATGAGTGGTTGCTGGATAACTT TACGGGCATGCATAAGGCTCGTATAATATATTCAGGGAGACCACAACGGTTTCCCTCTACAAATAA TTTTGTTTAACTTT 3' (SEQ ID NO: 30) |
| pLacI | 5' GCGGCGCGCCATCGAATGGCGCAAAACCTTTCGCGGTATGGCATGATAGCGCCCGGAAGAGAGT CAATTCAGGGTGGTGAAT 3' (SEQ ID NO: 31) |
| pTac | 5' TGTTGACAATTAATCATCGGCTCGTATAATGTGTGGAATTGTGAGCGCTCACAATT 3' (SEQ ID NO: 32) |
| LacI | 5' ATGAAACCAGTAACGTTATACGATGTCGCAGAGTATGCCGGTGTCTCTTATCAGACCGTTTCCC GCGTGGTGAACCAGGCCAGCCACGTTTCTGCGAAAACGCGGGAAAAAGTGGAAGCGGCGATGGCGG AGCTGAATTACATTCCCAACCGCGTGGCACAACAACTGGCGGGCAAACAGTCGTTGCTGATTGGCG TTGCCACCTCCAGTCTGGCCCTGCACGCGCCGTCGCAAATTGTCGCGGCGATTAAATCTCGCGCCG ATCAACTGGGTGCCAGCGTGGTGGTGTCGATGGTAGAACGAAGCGGCGTCGAAGCCTGTAAAGCGG CGGTGCACAATCTTCTCGCGCAACGCGTCAGTGGGCTGATCATTAACTATCCGCTGGATGACCAGG ATGCCATTGCTGTGGAAGCTGCCTGCACTAATGTTCCGGCGTTATTTCTTGATGTCTCTGACCAGA CACCCATCAACAGTATTATTTTCTCCCATGGAGACGGTACGCGACTGGGCGTGGAGCATCTGGTCG CATTGGGTCACCAGCAAATCGCGCTGTTAGCGGGCCCATTAAGTTCTGTCTCGGCGCGTCTGCGTC TGGCTGGCTGGCATAAATATCTCACTCGCAATCAAATTCAGCCGATAGCGGAACGGGAAGGCGACT GGAGTGCCATGTCCGGTTTTCAACAAACCATGCAAATGCTGAATGAGGGCATCGTTCCCACTGCGA TGCTGGTTGCCAACGATCAGATGGCGCTGGGCGCAATGCGCGCCATTACCGAGTCCGGGCTGCGCG TTGGTGCGGATATCTCGGTAGTGGGATACGACGATACCGAAGATAGCTCATGTTATATCCCGCCGT TAACCACCATCAAACAGGATTTTCGCCTGCTGGGGCAAACCAGCGTGGACCGCTTGCTGCAACTCT CTCAGGGCCAGGCGGTGAAGGGCAATCAGCTGTTGCCAGTCTCACTGGTGAAAAGAAAAACCACCC TGGCGCCCAATACGCAAACCGCCTCTCCCCGCGCGTTGGCCGATTCATTAATGCAGCTGGCACGAC AGGTTTCCCGACTGGAAAGCGGGCAGTGAgcgcaacgcaattaatgtaagttagcgcgaattggcc gac 3' (SEQ ID NO: 33) |
| pBAD-araC (I0500) | 5' AGTTATGACAACTTGACGGCTACATCATTCACTTTTTCTTCACAACCGGCACGGAACTCGCTCG GGCTGGCCCCGGTGCATTTTTTAAATACCCGCGAGAAATAGAGTTGATCGTCAAAACCAACATTGC GACCGACGGTGGCGATAGGCATCCGGGTGGTGCTCAAAAGCAGCTTCGCCTGGCTGATACGTTGGT CCTCGCGCCAGCTTAAGACGCTAATCCCTAACTGCTGGCGGAAAAGATGTGACAGACGCGACGGCG ACAAGCAAACATGCTGTGCGACGCTGGCGATATCAAAATTGCTGTCTGCCAGGTGATCGCTGATGT ACTGACAAGCCTCGCGTACCCGATTATCCATCGGTGGATGGAGCGACTCGTTAATCGCTTCCATGC GCCGCAGTAACAATTGCTCAAGCAGATTTATCGCCAGCAGCTCCGAATAGCGCCCTTCCCCTTGCC CGGCGTTAATGATTTGCCCAAACAGGTCGCTGAAATGCGGCTGGTGCGCTTCATCGGGCGAAAGA ACCCCGTATTGGCAAATATTGACGGCCAGTTAAGCCATTCATGCCAGTAGGCGCGCGGACGAAAGT AAACCCACTGGTGATACCATTCGCGAGCCTCCGGATGACGACCGTAGTGATGAATCTCTCCTGGCG GGAACAGCAAAATATCACCCGGTCGGCAAACAAATTCTCGTCCCTGATTTTTCACCACCCCCTGAC CGCGAATGGTGAGATTGAGAATATAACCTTTCATTCCCAGCGGTCGGTCGATAAAAAAATCGAGAT AACCGTTGGCCTCAATCGGCGTTAAACCCGCCACCAGATGGGCATTAAACGAGTATCCCGGCAGCA GGGGATCATTTTGCGCTTCAGCCATACTTTTCATACTCCCGCCATTCAGAGAAGAAACCAATTGTC CATATTGCATCAGACATTGCCGTCACTGCGTCTTTTACTGGCTCTTCTCGCTAACCAAACCGGTAA CCCCGCTTATTAAAGCATTCTGTAACAAAGCGGGACCAAAGCCATGACAAAAACGCGTAACAAAA GTGTCTATAATCACGGCAGAAAAGTCCACATTGATTATTTGCACGGCGTCACACTTTGCTATGCCA TAGCATTTTTATCCATAAGATTAGCGGATCCTACCTGACGCTTTTTATCGCAACTCTCTACTGTTT CTCC 3' (SEQ ID NO: 34) |
| BBa_B0015 (Terminator) | 5' CCAGGCATCAAATAAAACGAAAGGCTCAGTCGAAAGACTGGGCCTTTCGTTTTATCTGTT GTTTGTCGGTGAACGCTCTCTACTAGAGTCACACTGGCTCACCTTCGGGTGGGCCTTTCTGCG TTTATA 3' (SEQ ID NO: 35) |
| BBa_B0054 (Terminator) | 5' ATTAGCAGAAAGTCAAAAGCCTCCGACCGGAGGCTTTTGACTAAAACTTCCCTTGGGGTTATCA TTGGG 3' (SEQ ID NO: 36) |
| RiboJ | 5' CTGTCACCGGATGTGCTTTCCGGTCTGATGAGTCCGTGAGGACGAAACAG 3' (SEQ ID NO: 37) |

TABLE 4 -continued

Promoter, RBS, terminator, riboJ, RFP and GFP sequences

| Name[a,b] | Sequence |
|---|---|
| RFP | 5' ATGGCTTCCTCCGAAGACGTTATCAAAGAGTTCATGCGTTTCAAAGTTCGTATGGAAGGTTCCG<br>TTAACGGTCACGAGTTCGAAATCGAAGGTGAAGGTGAAGGTCGTCCGTACGAAGGTACCCAGACCG<br>CTAAACTGAAAGTTACCAAAGGTGGTCCGCTGCCGTTCGCTTGGGACATCCTGTCCCCGCAGTTCC<br>AGTACGGTTCCAAAGCTTACGTTAAACACCCGGCTGACATCCCGGACTACCTGAAACTGTCCTTCC<br>CGGAAGGTTTCAAATGGGAACGTGTTATGAACTTCGAAGACGGTGGTGTTGTTACCGTTACCCAGG<br>ACTCCTCCCTGCAAGACGGTGAGTTCATCTACAAAGTTAAACTGCGTGGTACCAACTTCCCGTCCG<br>ACGGTCCGGTTATGCAGAAAAAAACCATGGGTTGGGAAGCTTCCACCGAACGTATGTACCCGGAAG<br>ACGGTGCTCTGAAAGGTGAAATCAAAATGCGTCTGAAACTGAAAGACGGTGGTCACTACGACGCTG<br>AAGTTAAAACCACCTACATGGCTAAAAAACCGGTTCAGCTGCCGGGTGCTTACAAAACCGACATCA<br>AACTGGACATCACCTCCCACAACGAAGACTACACCATCGTTGAACAGTACGAACGTGCTGAAGGTC<br>GTCACTCCACCGGTGCTTAATAA 3' (SEQ ID NO: 38) |
| GFP | 5' ATGCGTAAAGGAGAAGAACTTTTCACTGGAGTTGTCCCAATTCTTGTTGAATTAGATGGTGATG<br>TTAATGGGCACAAATTTTCTGTCAGTGGAGAGGGTGAAGGTGATGCAACATACGGAAAACTTACCC<br>TTAAATTTATTTGCACTACTGGAAAACTACCTGTTCCATGGCCAACACTTGTCACTACTTTCGGTT<br>ATGGTGTTCAATGCTTTGCGAGATACCCAGATCATATGAAACAGCATGACTTTTTCAAGAGTGCCA<br>TGCCCGAAGGTTATGTACAGGAAAGAACTATATTTTTCAAAGATGACGGGAACTACAAGACACGTG<br>CTGAAGTCAAGTTTGAAGGTGATACCCTTGTTAATAGAATCGAGTTAAAAGGTATTGATTTTAAAG<br>AAGATGGAAACATTCTTGGACACAAATTGGAATACAACTATAACTCACACAATGTATACATCATGG<br>CAGACAAACAAAAGAATGGAATCAAAGTTAACTTCAAAATTAGACACAACATTGAAGATGGAAGCG<br>TTCAACTAGCAGACCATTATCAACAAAATACTCCAATTGGCGATGGCCCTGTCCTTTTACCAGACA<br>ACCATTACCTGTCCACACAATCTGCCCTTTCGAAAGATCCCAACGAAAAGAGAGACCACATGGTCC<br>TTCTTGAGTTTGTAACAGCTGCTGGGATTACACATGGCATGGATGAACTATACAAATAATAA 3'<br>(SEQ ID NO: 39) |

Each RFP and GFP genes start with a 3 nucteotide-start codon and end with a 3 nucteotide-stop codon pLacI, pTac and LacI sequences are based on the pEXT20 plasmid(addgene)

REFERENCES

1. N. C. Seeman Nucleic Acid Junctions and Lattices. *J. Theor. Biol.* 99, 237-24 (1982).
2. T. J. Fu, N. C. Seeman DNA Double-crossover Molecules. *Biochemistry* 32, 3211-3220 (1993).
3. X. J. Li, X. P. Yang, J. Qi, N. C. Seeman Antiparallel DNA Double Crossover Molecules As Components for Nanoconstruction. *J. Am. Chem. Soc.* 118, 6131-6140 (1996).
4. E. Winfree, F. Liu, L. A. Wenzler, N. C. Seeman Design and Self-assembly of Two-dimensional DNA Crystals. *Nature* 394, 539-544 (1998)
5. R. P. Goodman et al Rapid Chiral Assembly of Rigid DNA Building Blocks for Molecular Nanofabrication. *Science* 310, 1661-1665 (2005).
6. P. Yin et al Programming DNA tube circumferences *Science* 321, 824-826 (2008).
7. Y. He et al. Hierarchical self-assembly of DNA into symmetric supramolecular polyhedra. *Nature* 452, 198-201 (2008).
8. P. W. K. Rothemund Folding DNA to Create Nanoscale Shapes and Patterns. *Nature* 440, 297-302 (2006).
9. Y. Ke, L. Ong, W. Shih, P. Yin Three-dimensional structures self-assembled from DNA bricks *Science* 338, 1177-1183 (2012).
10. S. M. Douglas, H. Dietz, T. Liedl, B. Hogberg, F. Graf, W. M. Shih Self-Assembly of DNA into Nanoscale Three-Dimensional Shapes. *Nature* 459, 414-418 (2009).
11. D. Han, S. Pal, J. Nangreave, Z. Deng, Y. Liu, H. Yan DNA Origami with Complex Curvatures in Three-Dimensional Space. *Science* 332, 343-346 (2011).
12. J. Bath, A. J. Turberfield DNA nanomachines. *Nat. Nanotech.* 2, 275-284 (2007).
13. Y. Krishnan, F. C. Simmel Nucleic acid based molecular devices. *Angew. Chem. Int. Ed.* 50, 3124-3156 (2011).
14. J. S. Shin, N. A. Pierce A Synthetic DNA Walker for Molecular Transport. *J. Am. Chem. Soc.* 126, 10834-10835 (2004).
15. T. Omabegho, R. Sha, N. C. Seeman A bipedal DNA Brownian motor with coordinated legs. *Science* 324, 67-71 (2009).
16. Z. G. Wang, J. Elbaz, I. Willner DNA machines: bipedal walker and stepper. *Nano Lett.* 11, 304-309 (2011).
17. B. Yurke, A. J. Turberfield, A. P. Mills Jr., F. C. Simmel, J. L. Neumann A DNA-Fuelled Molecular Machine made of DNA. *Nature* 406, 605-608 (2000).
18. J. Elbaz, Z. G. Wang, R. Orbach, I. Willner pH-stimulated concurrent mechanical activation of two DNA 'tweezers'. A 'SETRESET' logic gate system. *Nano Lett.* 9, 4510-4514 (2009).
19. Y. Tian, C. D. Mao Molecular gears: a pair of DNA circles continuously rolls against each other. *J. Am. Chem. Soc.* 126, 11410-11411 (2004).
20. J. Elbaz et al DNA computing circuits using libraries of DNAzyme subunits. *Nat. Nanotech.* 5, 417-422 (2010).
21. R. Pei, E. Matamoros, M. Liu, D. Stefanovic, M. N. Stojanovic Training a molecular automaton to play a game. *Nat. Nanotech.* 5, 773-777 (2010).
22. G. Seelig, D. Soloveichik, D. Y. Zhang, E. Winfree Enzyme-free nucleic acid logic circuits. *Science* 314, 1585-1588 (2006).
23. L. L. Qian, E. Winfree Scaling Up Digital Circuit Computation with DNA Strand Displacement Cascades *Science* 332, 1196-1201 (2011).
24. Y. Jiang, B. Li, X. Chen, A. D. Ellington Coupling two different nucleic acid circuits in an enzyme-free amplifier. *Molecules* 17, 13211-13220. (2012).
25. A. J. Mastroianni, S. A. Claridge, A. P Alivisatos Pyramidal and chiral groupings of gold nanocrystals assembled using DNA scaffolds. *J. Am. Chem. Soc.* 131, 8455-8459 (2009).
26. Y. He, D. R. Liu Autonomous Multistep Organic Synthesis in a Single Isothermal Solution Mediated by a DNA Walker. *Nat. Nanotech.* 5, 778-782 (2010).
27. N. V. Voigt et al. Single-molecule chemical reactions on DNA origami. *Nat. Nanotech.* 5, 200-203 (2010).

28. H. Z. Gu, J. Chao, S. J. Xiao, N. C. Seeman A proximity-based programmable DNA nanoscale assembly line. *Nature* 465, 202-205 (2010).
29. J. Elbaz, A. Cecconello, Z. Fan, A. 0. Govorov, I. Willner Powering the programmed nanostructure and function of gold nanoparticles with catenated DNA machines. *Nat. Commun.* dx.doi.org/10.1038/ncomms3000.
30. S. Modi, M. G. Swetha, D. Goswami, G. D. Gupta, S. Mayor, Y. Krishnan A DNA Nanomachine that Maps Spatial and Temporal pH Changes Inside Living Cells. *Nat. Nanotech.* 4, 325-330 (2009).
31. H. Lee et al Molecularly self-assembled nucleic acid nanoparticles for targeted in vivo siRNA delivery *Nature Nanotech.* 7, 389-393 (2012).
32. S. M. Douglas, I. Bachelet, G. M. Church A Logic-Gated Nanorobot for Targeted Transport of Molecular Payloads. *Science* 335, 831-834 (2012).
33. A. Yaniv et al. Universal computing by DNA origami robots in a living animal. *Nat. Nanotech.* 9, 353-357 (2014).
34. P. A. Carr, G. M. Church Genome engineering. *Nat. Biotech.* 27, 1151-1162 (2009).
35. C. Lin, S. Rinker, X. Wang, Y. C. Liu, N. C. Seeman, H. Yan In vivo cloning of artificial DNA nanostructures. *Proc. Natl. Acad. Sci. U.S.A.* 105, 17626-17631 (2008).
36. C. Ducani, K. Corinna, M. Moshe, W. Shih, B. Högberg Enzamatic production of 'monoclonal stoichiometric' single-stranded DNA oligonucleotides. *Nat. Methods* 10, 647-652 (2013).
37. A. Telesnitsky, S. P. Goff, Reverse transcriptase and the generation of retroviral DNA *Retroviruses*, 121-160 (1997).
38. D. Baltimore Viral RNA-dependent DNA polymerase: RNA-dependent DNA polymerase in virions of RNA tumour viruses. *Nature* 226, 1209-1211 (1970).
39. A. M. Temin, S. Mizutani, Viral RNA-dependent DNA polymerase: RNA-dependent DNA polymerase in virions of Rous sarcoma virus. *Nature* 226, 1211-1213 (1970).
40. J. P. Leis, I. Berkower, J. Hurwitz, RNA-dependent DNA polymerase activity of RNA tumor viruses. 5. Mechanism of action of ribonuclease H isolated from avian myeloblastosis virus and *Escherichia coli*. *Proc. Natl Acad. Sci. USA* 70, 466-470 (1973).
41. A. Jacobo-Molina et al., Crystal structure of human immunodeficiency virus type 1 reverse transcriptase complexed with double-stranded DNA at 3.0 A resolution shows bent DNA. *Proc. Natl. Acad. Sci. U.S.A.* 90, 6320-6324 (1993).
42. W. M. Freeman, S. J. Walker, K. E. Vrana "Quantitative RT-PCR: pitfalls potential". *BioTechniques* 26,112-122, (1999).
43. A. Aiyar, D. Cobrinik, Z. Ge, H. J. Kung, J. Leis, Interaction between retroviral U5 RNA and the TC loop of the tRNATrp primer is required for efficient initiation of reverse transcription. *J. Virol.* 66, 2464-2472 (1992).
44. L. Kleiman, tRNALys3: The Primer tRNA for Reverse Transcription in HIV-1. IUBMB *Life*, 53, 107-114 (2002).
45. C. Ying-Ja et al. Characterization of 582 natural and synthetic terminators and quantification of their design constraints. *Nat. Methods* 10, 659-664 (2013).
46. D. Harris, R. Lee, H. S. Misra, P. K. Pandey, V. N. Pandey, The p51 subunit of human immunodeficiency virus type 1 reverse transcriptase is essential in loading the p66 subunit on the template primer, *Biochemistry* 37, 5903-5908 (1998).
47. E. A. Abbondanzieri et al. Dynamic binding orientations direct activity of HIV reverse transcriptase. *Nature* 453, 184-189 (2008).
48. J. M. Lanchy, C. Ehresmann, S. F. Le Grice, B. Ehresmann, R. Marquet, R. Binding and kinetic properties of HIV-1 reverse transcriptase markedly differ during initiation and elongation of reverse transcription. *EMBO J.* 15, 7178-7187 (1996).
49. D. Lim et al Crystal Structure of the Moloney Murine Leukemia Virus RNase H Domain. *J. VIROL* 80, 8379-8389 (2006).
50. J. H. Davis, A. J. Rubin, R. T. Sauer, Design, construction and characterization of a set of insulated bacterial promoters. *Nucleic Acids Res.* 39, 1131-1141 (2011).
51. V. K. Mutalik et al Precise and reliable gene expression via standard transcription and translation initiation elements. *Nat. Methods* 10, 354-360 (2013).
52. R. Heim, A. Cubitt, R. Y. Tsien, Improved green fluorescence. *Nature* 373, 663-664 (1995).
53. K. Deisseroth, Optogenetics and psychiatry: applications, challenges, and opportunities. *Biol Psychiatry*. 71, 1030-1032 (2012).
54. H. Wang et al. Programming cells by multiplex genome engineering and accelerated evolution. *Nature* 460, 894-898 (2009).
55. R. J. Conrado et al DNA-guided assembly of biosynthetic pathways promotes improved catalytic efficiency. *Nucl. Acids Res.* 40, 1879-1889 (2012).
56. C. J. Delebecque, A. B. Lindner, P. A. Silver, F. A. Aldaye, Organization of Intracellular Reactions with Rationally Designed RNA Assemblies *Science* 333, 470-474 (2011).
57. J. E. Dueber et al Synthetic protein scaffolds provide modular control over metabolic flux. *Nat. Biotechnol.* 27, 753-759 (2009)
58. T. O. Yeates, M. C. Thompson, T. A. Bobik, The protein shells of bacterial microcompartment organelles. *Curr. Opin. Struct. Biol.* 21, 223-231 (2011).
59. O. I Wilner et al Enzyme cascades activated on topologically programmed DNA scaffolds. *Nat. Nanotech.* 4, 249-254.
60. A. D. Ellington, J. W. Szostak In vitro selection of RNA molecules that bind specific ligands. *Nature* 346, 818-822 (1990).
61. L. Chen, L. Cai, X. Zhang, A. Rich, Crystal structure of a four-stranded intercalated DNA: d(C4) *Biochemistry* 33, 13540 1994.
62. C. Engler, R. Kandzia, S. Marillonnet A one pot, one step, precision cloning method with high throughput capability. *PLoS ONE* doi:10.1371/journal.pone.0003647 (2008).
63. J. N. Zadeh, C. D. Steenberg, J. S. Bois, B. R. Wolfe, M. B. Pierce, A. R. Khan, R. M. Dirks, N. A. Pierce. NUPACK: analysis and design of nucleic acid systems. *J Comput Chem*, 32, 170-173, 2011.
64. PrimerQuest® program, IDT, Coralville, USA. Retrieved 12 Dec., 2012. http://www.idtdna.com/Scitools.
65. F. M. Ausubel et al Current Protocols in Molecular Biology (vol. 1, John Wiley).

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one or all of the group members are present in, employed in or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for synthesizing a single stranded DNA (ssDNA) oligonucleotide in a cell, comprising: expressing a reverse transcriptase in the cell and expressing in the cell a functional template comprising a tRNA structure is fused to a terminator or 3' end of a non-coding RNA sequence, wherein the tRNA structure is capable of initiating transcription of the non-coding RNA sequence using the reverse transcriptase to produce the ssDNA oligonucleotide in the cell, wherein the cell is a bacteria, wherein the bacteria lacks intracellular exonuclease, and wherein the ssDNA oligonucleotide is 8-200 nucleotides in length.

2. A method for synthesizing a single stranded DNA (ssDNA) oligonucleotide in a cell, comprising: expressing a reverse transcriptase in the cell and expressing in the cell a functional template comprising a tRNA structure is fused to a terminator or 3' end of a non-coding RNA sequence, wherein the tRNA structure is capable of initiating transcription of the coding RNA sequence using the reverse transcriptase to produce the ssDNA oligonucleotide in the cell, wherein the cell lacks intracellular exonuclease, further comprising expressing a second reverse transcriptase in the cell.

3. The method of claim 2, wherein the second reverse transcriptase is MLRT.

4. The method of claim 1, wherein the reverse transcriptase is HIVRT.

5. The method of claim 4, wherein the HIVRT comprises p66 linked to p51.

6. The method of claim 5, wherein the p66 domain includes an N-terminal finger, palm and thumb domain.

7. The method of claim 1, wherein the tRNA structure is tRNA$^{Lys}$.

8. The method of claim 1, wherein the ssDNA oligonucleotide includes deoxyribonucleotides and ribonucleotides.

9. The method of claim 1, further comprising isolating the ssDNA oligonucleotide from the cell.

10. The method of claim 9, wherein ssDNA oligonucleotide is processed to remove the ribonucleotides.

11. The method of claim 1, wherein the ssDNA oligonucleotide includes only deoxyribonucleotides.

12. The method of claim 1, wherein the ssDNA oligonucleotide is used in the synthesis of a nanostructure.

13. The method of claim 1, further comprising using the ssDNA oligonucleotide in a method of DNA origami.

14. The method of claim 1, wherein the ssDNA oligonucleotide is 10-100 nucleotides in length.

15. The method of claim 1, wherein the reverse transcriptase is expressed under the control of an inducible promoter.

* * * * *